(12) United States Patent
Yamada et al.

(10) Patent No.: US 7,922,651 B2
(45) Date of Patent: Apr. 12, 2011

(54) ULTRASONIC TREATMENT APPARATUS, ENDOSCOPE APPARATUS, AND TREATMENT METHOD

(75) Inventors: Norihiro Yamada, Tokyo (JP); Yoshio Onuki, Tokyo (JP); Mitsumasa Okada, Tokyo (JP); Akihito Sadamasa, Aomori (JP); Kiyoshi Miyake, Saitama (JP); Masayuki Iwasaka, Tokyo (JP)

(73) Assignees: Olympus Corporation (JP); Olympus Medical Systems Corporation (JP)

( * ) Notice: Subject to any disclaimer, the term of this patent is extended or adjusted under 35 U.S.C. 154(b) by 1295 days.

(21) Appl. No.: 11/492,668

(22) Filed: Jul. 25, 2006

(65) Prior Publication Data
US 2007/0038157 A1   Feb. 15, 2007

Related U.S. Application Data

(63) Continuation of application No. PCT/JP2005/013831, filed on Jul. 28, 2005.

(30) Foreign Application Priority Data

Nov. 4, 2004 (JP) ................................ 2004-321328
Nov. 4, 2004 (JP) ................................ 2004-321329

(51) Int. Cl.
*A61B 1/00* (2006.01)
(52) U.S. Cl. ............ 600/104; 606/46; 604/22; 600/437; 600/459
(58) Field of Classification Search .................. 600/437, 600/459; 606/32–52; 604/22
See application file for complete search history.

(56) References Cited

U.S. PATENT DOCUMENTS

| 5,188,102 | A |   | 2/1993 | Idemoto et al. | 128/24 |
| 5,391,144 | A |   | 2/1995 | Sakurai et al. | 604/22 |
| 5,578,031 | A | * | 11/1996 | Wilk et al. | 606/49 |
| 5,741,271 | A | * | 4/1998 | Nakao et al. | 606/114 |
| 6,086,583 | A | * | 7/2000 | Ouchi | 606/41 |
| 6,251,110 | B1 |   | 6/2001 | Wampler | 606/49 |
| 6,319,260 | B1 | * | 11/2001 | Yamamoto | 606/113 |
| 6,387,109 | B1 |   | 5/2002 | Davison et al. | 606/169 |
| 6,569,178 | B1 | * | 5/2003 | Miyawaki et al. | 606/169 |
| 6,582,419 | B1 | * | 6/2003 | Schoon et al. | 606/1 |
| 6,669,690 | B1 |   | 12/2003 | Okada et al. | 606/40 |
| 6,838,194 | B2 | * | 1/2005 | Huang et al. | 428/690 |
| 2003/0225332 | A1 |   | 12/2003 | Okada et al. | 600/439 |

FOREIGN PATENT DOCUMENTS

JP        62-22643 A        1/1987

(Continued)

OTHER PUBLICATIONS

Microfilm of the Specification and drawings annexed to the request of Japanese Utility Model Application No. 162432/1982 (Laid-open No. 68512/1984) (Mochida Pharmaceutical Co., Ltd) May 9, 1984, Description: p. 4, line 4 to 10; Fig 1.

(Continued)

*Primary Examiner* — Matthew J Kasztejna
(74) *Attorney, Agent, or Firm* — Ostrolenk Faber LLP

(57) ABSTRACT

An ultrasonic treatment apparatus includes a sheath which has an opening at a distal-end thereof; an ultrasonic transducer which is connected to the sheath, the ultrasonic transducer being able to generate ultrasonic vibration which is of treatment energy; an ultrasonic power supply unit which supplies electric power for driving the ultrasonic transducer; a treatment unit which is connected to the ultrasonic transducer, the treatment unit transmitting the ultrasonic vibration to a living tissue; and a high-frequency power supply unit which supplies high-frequency current which is of the treatment energy to the treatment unit.

4 Claims, 91 Drawing Sheets

FOREIGN PATENT DOCUMENTS

| | | |
|---|---|---|
| JP | 63-281639 | 11/1988 |
| JP | 08-299355 | 11/1996 |
| JP | 10-225460 | 8/1998 |
| JP | 2000-254140 A | 9/2000 |
| JP | 2000-312681 | 11/2000 |
| JP | 2001-029353 A | 2/2001 |
| JP | 2003-339731 | 12/2003 |
| JP | 2004-000336 | 1/2004 |

OTHER PUBLICATIONS

Hiroyuki Ono and Tetusya INUI. Jun. 1, 2003 "Insulation-tipped electrsurgical knife (IT KNIFE)" and art and a point of digestive organs endoscopical therapy P.100-P.105.

Takushi Gotoda and Hiroyuki Ono of National Cancer Center "Basic techique of insuldation-Tipped Electrosurgical knife (IT KNIFE)" An endoscopical therapy of the gullet/a stomach p. 134-p. 137.

International Search Report PCT/JP2005/013831 dated Oct. 28, 2005 (Japanese Patent Office).

Japanese Office Action issued Jan. 19, 2010 in corresponding Japanese Patent Application No. 2006-542253.

English translation of Japanese Office Action issued Jan. 19, 2010 in connection with corresponding Japanese Patent Application No. 2006-542253.

\* cited by examiner

FIG.69
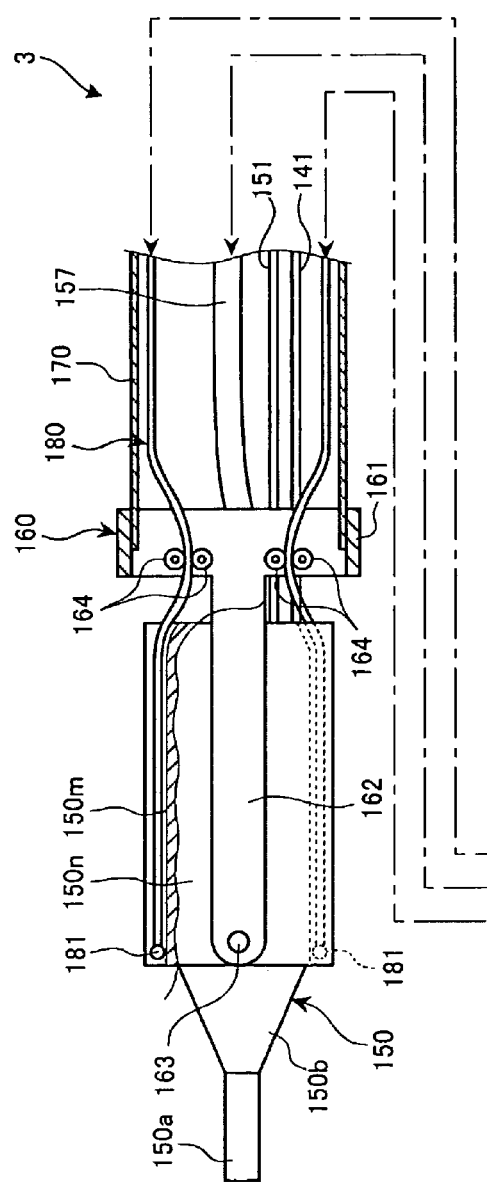
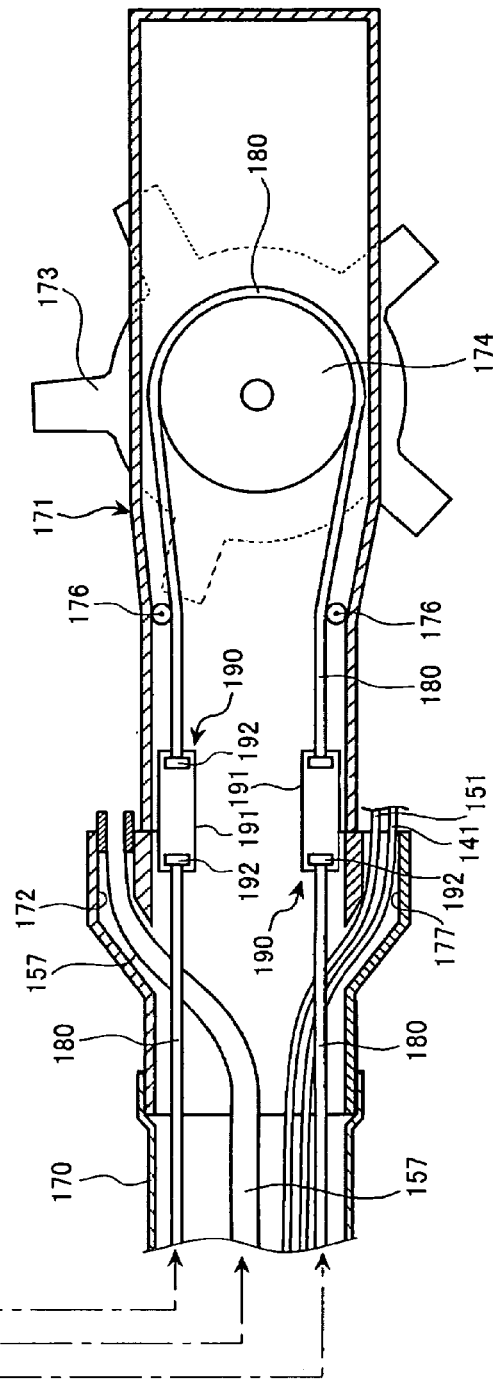

ULTRASONIC TREATMENT APPARATUS, ENDOSCOPE APPARATUS, AND TREATMENT METHOD

CROSS-REFERENCE TO RELATED APPLICATIONS

This application is a continuation of PCT international application Ser. No. PCT/JP2005/013831 filed Jul. 28, 2005 which designates the United States, incorporated herein by reference, and which claims the benefit of priority from Japanese Patent Applications Nos. 2004-321328 and 2004-321329 both filed Nov. 4, 2004, incorporated herein by reference.

BACKGROUND OF THE INVENTION

1. Field of the Invention

The present invention relates to an ultrasonic treatment apparatus, an endoscope apparatus, and a treatment method therefor. The ultrasonic treatment apparatus and the endoscope apparatus include a portion to be inserted into a body cavity of a subject for observation of a living tissue or for incision and coagulation of the living tissue in the body cavity, for example.

2. Description of the Related Art

Some conventional treatment apparatuses include an electrode knife which protrudes from a flexible electrically-insulating tube, and the electrode knife is provided with a high-frequency knife at a protruding end thereof. The high-frequency knife has an insulating chip which is larger in diameter than the knife itself. In the high-frequency knife, when a living tissue such as a mucosa is incised by the electrode knife with the use of a high-frequency current, the insulating chip prevents the electrode knife from cutting through the a lower-layer of the living tissue which should not be incised, and the insulating chip also prevents unnecessary cauterization. The conventional treatment apparatus as described above is described, for example, in Japanese Patent Application Laid-Open (JP-A) No. H8-299355.

SUMMARY OF THE INVENTION

An ultrasonic treatment apparatus according to one aspect of the present invention includes a sheath which has an opening at a distal end thereof; an ultrasonic transducer which is connected to the sheath, the ultrasonic transducer being able to generate ultrasonic vibration which is of treatment energy; an ultrasonic power supply unit which supplies electric power for driving the ultrasonic transducer; a treatment unit which is connected to the ultrasonic transducer, the treatment unit transmitting the ultrasonic vibration to a living tissue; and a high-frequency power supply unit which supplies a high-frequency current which is of the treatment energy to the treatment unit.

An endoscope apparatus according to another aspect of the present invention includes an ultrasonic treatment apparatus, a flexible insertion unit, and an observation unit. The ultrasonic treatment apparatus includes; a sheath which has an opening at a distal end thereof, an ultrasonic transducer which is connected to the sheath, the ultrasonic transducer being able to generate ultrasonic vibration which is of treatment energy, an ultrasonic power supply unit which supplies electric power for driving the ultrasonic transducer, a treatment unit which is connected to the ultrasonic transducer, the treatment unit transmitting the ultrasonic vibration to a living tissue, and a high-frequency power supply unit which supplies a high-frequency current which is of the treatment energy to the treatment unit. In the flexible insertion unit, the sheath can be arranged. The observation unit is provided inside the insertion unit, and the observation unit is able to observe an outside from a distal end of the insertion unit.

A treatment method according to still another aspect of the present invention includes an insertion process of inserting an insertion unit of an endoscope apparatus into a subject. The endoscope apparatus includes an ultrasonic treatment apparatus, the flexible insertion unit, and an observation unit. The ultrasonic treatment apparatus includes a sheath which has an opening at a distal end thereof, an ultrasonic transducer which is connected to the sheath, the ultrasonic transducer being able to generate ultrasonic vibration which is of treatment energy, an ultrasonic power supply unit which supplies electric power for driving the ultrasonic transducer, a treatment unit which is connected to the ultrasonic transducer, the treatment unit transmitting the ultrasonic vibration to a living tissue, and a high-frequency power supply unit which supplies a high-frequency current which is of the treatment energy to the treatment unit. In the flexible insertion unit, the sheath can be arranged. The observation unit is provided inside the insertion unit, and is able to observe an outside from a distal end of the insertion unit. The treatment method further includes an arrangement process of arranging a treated site of a subject in a visual field of the observation unit; a marking process of performing marking of surrounding tissue of the treated site with the ultrasonic treatment apparatus; an injection process of inserting a tube into the insertion unit of the endoscope apparatus to inject a local injection solution into a lower portion of the treated site through the tube; an incision and dissection process of incising and dissecting a living tissue including the treated site with the ultrasonic treatment apparatus, the living tissue being raised by the injection of the local injection solution; and a hemostatic process of performing hemostasis with the ultrasonic treatment apparatus when bleeding is generated in the incision and dissection process.

An ultrasonic treatment apparatus according to still another aspect of the present invention includes a sheath which has an opening at a distal end thereof; an ultrasonic transducer which is connected to the sheath, the ultrasonic transducer being able to generate ultrasonic vibration which is of treatment energy; an ultrasonic power supply unit which supplies electric power for driving the ultrasonic transducer; a treatment unit which has a hollow shaped portion, the treatment unit being connected to the ultrasonic transducer, the treatment unit transmitting the ultrasonic vibration and applying a high-frequency current to a living tissue; a high-frequency power supply unit which supplies the high-frequency current which is of the treatment energy to the treatment unit; and a tube which has a passageway communicated with the hollow shaped portion, the tube being connected to the hollow shaped portion.

An endoscope apparatus according to still another aspect of the present invention includes an ultrasonic treatment apparatus, a flexible insertion unit, and an observation unit. The ultrasonic treatment apparatus includes a sheath which has an opening at a distal end thereof, an ultrasonic transducer which is connected to the sheath, the ultrasonic transducer being able to generate ultrasonic vibration which is of treatment energy, an ultrasonic power supply unit which supplies electric power for driving the ultrasonic transducer, a treatment unit which has a hollow shaped portion, the treatment unit being connected to the ultrasonic transducer, the treatment unit transmitting the ultrasonic vibration and applying a high-frequency current to a living tissue, a high-frequency power supply unit which supplies the high-frequency current which is of the treatment energy to the treatment unit, and a tube which has a passageway communicated with the hollow shaped portion, the tube being connected to the hollow shaped portion. In the flexible insertion unit, the sheath can be arranged. The observation unit is provided inside the insertion unit, and is able to observe an outside from a distal end of the insertion unit.

A treatment method according to still another aspect of the present invention includes an insertion process of inserting an insertion unit of an endoscope apparatus into a subject. The endoscope apparatus includes an ultrasonic treatment apparatus, a flexible insertion unit, and an observation unit. The ultrasonic treatment apparatus includes a sheath which has an opening at a distal end thereof, an ultrasonic transducer which is connected to the sheath, the ultrasonic transducer being able to generate ultrasonic vibration which is of treatment energy, an ultrasonic power supply unit which supplies electric power for driving the ultrasonic transducer, a treatment unit which has a hollow shaped portion, the treatment unit being connected to the ultrasonic transducer, the treatment unit transmitting the ultrasonic vibration and applying a high-frequency current to a living tissue, a high-frequency power supply unit which supplies the high-frequency current which is of the treatment energy to the treatment unit, and a tube which has a passageway communicated with the hollow shaped portion, the tube being connected to the hollow shaped portion. In the flexible insertion unit, the sheath can be arranged. The observation unit is provided inside the insertion unit, and is able to observe an outside from a distal end of the insertion unit. The treatment method further includes an arrangement process of arranging a treated site of a subject in a visual field of the observation unit; a spreading process of spreading a coloring agent through the tube from the hollow shaped portion to the treated site; a marking process of performing marking of surrounding tissue of the treated site with the ultrasonic treatment apparatus; an injection process of injecting a local injection solution through the tube from the hollow shaped portion to a lower portion of the treated site; an incision and dissection process of incising and dissecting a living tissue including the treated site with the ultrasonic treatment apparatus, the living tissue being raised by the injection of the local injection solution; and a hemostatic process of performing hemostasis with the ultrasonic treatment apparatus when bleeding is generated in the incision and dissection process.

An ultrasonic treatment apparatus according to still another aspect of the present invention includes a sheath which has an opening at a distal end thereof; an ultrasonic transducer which is connected to the sheath, the ultrasonic transducer being able to rotate in a circumferential direction of the sheath, the ultrasonic transducer being able to generate ultrasonic vibration which is of treatment energy; a treatment unit which has a distal-end surface portion, the distal-end surface portion moving to treat a treated site in a subject in at least two directions, the treatment unit being connected to the ultrasonic transducer, the treatment unit transmitting the ultrasonic vibration to a living tissue; and an operating unit which rotatably operates the ultrasonic transducer and the treatment unit with respect to the sheath.

An ultrasonic treatment apparatus according to still another aspect of the present invention includes a sheath which has an opening at a distal end thereof; an ultrasonic transducer which is connected to the sheath, the ultrasonic transducer being able to rotate in a circumferential direction of the sheath, the ultrasonic transducer being able to generate ultrasonic vibration which is of treatment energy; a treatment unit which has a hollow shaped portion and a distal-end surface portion, the distal-end surface portion moving to treat a treated site in a subject in at least two directions, the treatment unit being connected to the ultrasonic transducer, the treatment unit transmitting the ultrasonic vibration to a living tissue; a tube which has a passageway communicated with the hollow shaped portion, the tube being connected to the hollow shaped portion; and an operating unit which rotatably operates the ultrasonic transducer and the treatment unit with respect to the sheath.

An endoscope apparatus according to still another aspect of the present invention includes an ultrasonic treatment apparatus, a flexible insertion unit, and an observation unit. The ultrasonic treatment apparatus includes a sheath which has an opening at a distal end thereof, an ultrasonic transducer which is connected to the sheath, the ultrasonic transducer being able to rotate in a circumferential direction of the sheath, the ultrasonic transducer being able to generate ultrasonic vibration which is of treatment energy, a treatment unit which has a distal-end surface portion, the distal-end surface portion moving to treat a treated site in a subject in at least two directions, the treatment unit being connected to the ultrasonic transducer, the treatment unit transmitting the ultrasonic vibration to a living tissue, and a high-frequency power supply unit which supplies high-frequency current which is of the treatment energy to the treatment unit, and an operating unit which rotatably operates the ultrasonic transducer and the treatment unit with respect to the sheath. In the flexible insertion unit, the sheath can be arranged. The observation unit is provided inside the insertion unit, and is able to observe an outside from a distal end of the insertion unit.

An endoscope apparatus according to still another aspect of the present invention includes an ultrasonic treatment apparatus, a flexible insertion unit, and an observation unit. The ultrasonic treatment apparatus includes a sheath which has an opening at a distal end thereof, an ultrasonic transducer which is connected to the sheath, the ultrasonic transducer being able to rotate in a circumferential direction of the sheath, the ultrasonic transducer being able to generate ultrasonic vibration which is of treatment energy, a treatment unit which has a hollow shaped portion and a distal-end surface portion, the distal-end surface portion moving to treat a treated site in a subject in at least two directions, the treatment unit being connected to the ultrasonic transducer, the treatment unit transmitting the ultrasonic vibration to a living tissue, a tube which has a passageway communicated with the hollow shaped portion, the tube being connected to the hollow shaped portion, and a high-frequency power supply unit which supplies a high-frequency current which is of the treatment energy to the treatment unit, and an operating unit which rotatably operates the ultrasonic transducer and the treatment unit with respect to the sheath. In the flexible insertion unit, the sheath can be arranged. The observation unit is provided inside the insertion unit, and is able to observe an outside from a distal end of the insertion unit.

A treatment method according to still another aspect of the present invention includes an insertion process of inserting an insertion unit of an endoscope apparatus into a subject. The endoscope apparatus includes an ultrasonic treatment apparatus, a flexible insertion unit, and an observation unit. The ultrasonic treatment apparatus includes a sheath which has an opening at a distal end thereof, an ultrasonic transducer which is connected to the sheath, the ultrasonic transducer being able to rotate in a circumferential direction of the sheath, the ultrasonic transducer being able to generate ultrasonic vibration which is of treatment energy, a treatment unit which has a distal-end surface portion, the distal-end surface portion moving to treat a treated site in a subject in at least two directions, the treatment unit being connected to the ultrasonic transducer, the treatment unit transmitting the ultrasonic vibration to a living tissue, and an operating unit which rotatably operates the ultrasonic transducer and the treatment unit with respect to the sheath. In the flexible insertion unit, the sheath can be arranged. The observation unit is provided inside the insertion unit, and is able to observe an outside from a distal end of the insertion unit. The treatment method further includes an arrangement process of arranging a treated site of the subject in a visual field of the observation unit; a marking process of performing marking of surrounding tissue of the treated site with the ultrasonic treatment apparatus; an injection process of inserting a tube into the insertion unit of the endoscope apparatus to inject a local injection solution into a lower portion of the treated site through the tube; a rotation process of causing the operating unit to rotate the ultrasonic transducer and the treatment unit with respect to the sheath to set the distal-end surface portion such that treatment can be performed in a desired direction to a treated site of the subject; an incision and dissection process of incising and dissecting a living tissue including the treated site with the ultrasonic treatment apparatus, the living tissue being raised by the injection of the local injection solution; and a hemostatic process of performing hemostasis with the ultrasonic treatment apparatus when bleeding is generated in the incision and dissection process.

A treatment method according to still another aspect of the present invention includes an insertion process of inserting an insertion unit of an endoscope apparatus into a subject. The endoscope apparatus includes an ultrasonic treatment apparatus, a flexible insertion unit, and an observation unit. The endoscope apparatus includes a sheath which has an opening at a distal end thereof, an ultrasonic transducer which is connected to the sheath, the ultrasonic transducer being able to rotate in a circumferential direction of the sheath, the ultrasonic transducer being able to generate ultrasonic vibration which is of treatment energy, a treatment unit which has a hollow shaped portion and a distal-end surface portion, the distal-end surface portion moving to treat a treated site in a subject in at least two directions, the treatment unit being connected to the ultrasonic transducer, the treatment unit transmitting the ultrasonic vibration to a living tissue, a tube which has a passageway communicated with the hollow shaped portion, the tube being connected to the hollow shaped portion, and an operating unit which rotatably operates the ultrasonic transducer and the treatment unit with respect to the sheath. In the flexible insertion unit, the sheath can be arranged. The observation unit is provided inside the insertion unit, and is able to observe an outside from a distal end of the insertion unit. The treatment method further includes an arrangement process of arranging a treated site of the subject in a visual field of the observation unit; a spreading process of spreading a coloring agent through the tube from the hollow shaped portion to the treated site; a marking process of performing marking of surrounding tissue of the treated site with the ultrasonic treatment apparatus; an injection process of injecting a local injection solution through the tube from the hollow shaped portion to a lower portion of the treated site; a rotation process of causing the operating unit to rotate the ultrasonic transducer and the treatment unit with respect to the sheath to set the distal-end surface portion such that treatment can be performed in a desired direction to the treated site of the subject; an incision and dissection process of incising and dissecting the living tissue including the treated site with the ultrasonic treatment apparatus, the living tissue being raised by the injection of the local injection solution; and a hemostatic process of performing hemostasis with the ultrasonic treatment apparatus when bleeding is generated in the incision and dissection process.

A treatment method according to still another aspect of the present invention includes an insertion process of inserting an insertion unit of an endoscope apparatus into a subject. The endoscope apparatus includes an ultrasonic treatment apparatus, a flexible insertion unit, and an observation unit. The ultrasonic treatment apparatus includes a sheath which has an opening at a distal end thereof, an ultrasonic transducer which is connected to the sheath, the ultrasonic transducer being able to rotate in a circumferential direction of the sheath, the ultrasonic transducer being able to generate ultrasonic vibration which is of treatment energy, an ultrasonic power supply unit which supplies electric power for driving the ultrasonic transducer, a treatment unit which has a distal-end surface portion, the distal-end surface portion moving to treat a treated site in a subject in at least two directions, the treatment unit being connected to the ultrasonic transducer, the treatment unit transmitting the ultrasonic vibration to a living tissue, a high-frequency power supply unit which supplies high-frequency current which is of treatment energy to the treatment unit, and an operating unit which rotatably operates the ultrasonic transducer and the treatment unit with respect to the sheath. In the flexible insertion unit, the sheath can be arranged. The observation unit is provided inside the insertion unit, and is able to observe an outside from a distal end of the insertion unit. The treatment method further includes an arrangement process of arranging a treated site of the subject in a visual field of the observation unit; a marking process of performing marking of surrounding tissue of the treated site with the ultrasonic treatment apparatus; an injection process of inserting a tube into the insertion unit of the endoscope apparatus to inject a local injection solution into a lower portion of the treated site through the tube; a rotation process of causing the operating unit to rotate the ultrasonic transducer and the treatment unit with respect to the sheath to set the distal-end surface portion such that treatment can be performed in a desired direction to the treated site of the subject; an incision and dissection process of incising and dissecting the living tissue including the treated site with the ultrasonic treatment apparatus, the living tissue being raised by the injection of the local injection solution; and a hemostatic process of performing hemostasis with the ultrasonic treatment apparatus when bleeding is generated in the incision and dissection process.

A treatment method according to still another aspect of the present invention includes an insertion process of inserting an insertion unit of an endoscope apparatus into a subject. The endoscope apparatus includes an ultrasonic treatment apparatus, a flexible insertion unit, and an observation unit. The ultrasonic treatment apparatus includes a sheath which has an opening at a distal end thereof, an ultrasonic transducer which is connected to the sheath, the ultrasonic transducer being able to rotate in a circumferential direction of the sheath, the ultrasonic transducer being able to generate ultrasonic vibration which is of treatment energy, an ultrasonic power supply unit which supplies electric power for driving the ultrasonic transducer, a treatment unit which has a hollow shaped portion and a distal-end surface portion, the distal-end surface portion moving to treat a treated site in a subject in at least two directions, the treatment unit being connected to the ultrasonic transducer, the treatment unit transmitting the ultrasonic vibration to a living tissue, a high-frequency power supply unit which supplies high-frequency current which is of treatment energy to the treated site, a tube which has a passageway communicated with the hollow shaped portion, the tube being connected to the hollow shaped portion, and an operating unit which rotatably operates the ultrasonic transducer and the treatment unit with respect to the sheath. In the flexible insertion unit, the sheath can be arranged. The observation unit is provided inside the insertion unit, and is able to observe an outside from a distal end of the insertion unit. The treatment method further includes an arrangement process of arranging a treated site of the subject in a visual field of the observation unit; a spreading process of spreading a coloring agent through the tube from the hollow shaped portion to the treated site; a marking process of performing marking of surrounding tissue of the treated site with the ultrasonic treatment apparatus; an injection process of injecting a local injection solution through the tube from the hollow shaped portion to a lower portion of the treated site; a rotation process of causing the operating unit to rotate the ultrasonic transducer and the treatment unit with respect to the sheath to set the distal-end surface portion such that treatment can be performed in a desired direction to the treated site of the subject; an incision and dissection process of incising and dissecting a living tissue including the treated site with the ultrasonic treatment apparatus, the living tissue being raised by the injection of the local injection solution; and a hemostatic process of performing hemostasis with the ultrasonic treatment apparatus when bleeding is generated in the incision and dissection process.

An ultrasonic treatment apparatus according to still another aspect of the present invention includes a sheath which has an opening at a distal end thereof; an ultrasonic transducer which is connected to the sheath, the ultrasonic transducer being able to generate ultrasonic vibration which is of treatment energy; and a treatment unit which is connected to the ultrasonic transducer, the treatment unit transmitting the ultrasonic vibration to a living tissue.

An endoscope apparatus according to still another aspect of the present invention includes an ultrasonic treatment apparatus, a flexible insertion unit, and an observation unit. The ultrasonic treatment apparatus includes a sheath which has an opening at a distal end thereof, an ultrasonic transducer which is connected to the sheath, the ultrasonic transducer being able to generate ultrasonic vibration which is of treatment energy, and a treatment unit which is connected to the ultrasonic transducer, the treatment unit transmitting the ultrasonic vibration to a living tissue. In the flexible insertion unit, the sheath can be arranged. The observation unit is provided inside the insertion unit, and is able to observe an outside from a distal end of the insertion unit.

A treatment method according to still another aspect of the present invention includes an insertion process of inserting an insertion unit of an endoscope apparatus into a subject. The endoscope apparatus includes an ultrasonic treatment apparatus, an insertion unit, and an observation unit. The ultrasonic treatment apparatus includes a sheath which has an opening at a distal end thereof, an ultrasonic transducer which is connected to the sheath, the ultrasonic transducer being able to generate ultrasonic vibration which is of treatment energy, and a treatment unit which is connected to the ultrasonic transducer, the treatment unit transmitting the ultrasonic vibration to a living tissue. In the flexible insertion unit, the sheath can be arranged. The observation unit is provided inside the insertion unit, and is able to observe an outside from a distal end of the insertion unit. The treatment method further includes an arrangement process of arranging a treated site of a subject in a visual field of the observation unit; a marking process of performing marking of surrounding tissue of the treated site with the ultrasonic treatment apparatus; an injection process of inserting a tube into the insertion unit of the endoscope apparatus to inject a local injection solution into a lower portion of the treated site through the tube; an incision and dissection process of incising and dissecting the living tissue including the treated site with the ultrasonic treatment apparatus, the living tissue being raised by the injection of the local injection solution; and a hemostatic process of performing hemostasis with the ultrasonic treatment apparatus when bleeding is generated in the incision and dissection process.

An ultrasonic treatment apparatus according to still another aspect of the present invention includes a sheath which has an opening at a distal end thereof; an ultrasonic transducer which is connected to the sheath, the ultrasonic transducer being able to generate ultrasonic vibration which is of treatment energy; a treatment unit which has a hollow shaped portion, the treatment unit being connected to the ultrasonic transducer, the treatment unit transmitting the ultrasonic vibration and applying the high-frequency current to a living tissue; and a tube which has a passageway communicated with the hollow shaped portion, the tube being connected to the hollow shaped portion.

An endoscope apparatus according to still another aspect of the present invention includes an ultrasonic treatment apparatus, an insertion unit, and an observation unit. The ultrasonic treatment apparatus includes a sheath which has an opening at a distal end thereof, an ultrasonic transducer which is connected to the sheath, the ultrasonic transducer being able to generate ultrasonic vibration which is of treatment energy, a treatment unit which has a hollow shaped portion, the treatment unit being connected to the ultrasonic transducer, the treatment unit transmitting the ultrasonic vibration and applying a high-frequency current to a living tissue, and a tube which has a passageway communicated with the hollow shaped portion, the tube being connected to the hollow shaped portion. In the flexible insertion unit, the sheath can be arranged. The observation unit is provided inside the insertion unit, and is able to observe an outside from a distal end of the insertion unit.

The treatment method according to still another aspect of the present invention includes an insertion process of inserting an insertion unit of an endoscope apparatus into a subject. The endoscope apparatus includes an ultrasonic treatment apparatus, an insertion unit, and an observation unit. Then ultrasonic treatment apparatus includes a sheath which has an opening at a distal end thereof, an ultrasonic transducer which is connected to the sheath, the ultrasonic transducer being able to generate ultrasonic vibration which is of treatment energy, a treatment unit which has a hollow shaped portion, the treatment unit being connected to the ultrasonic transducer, the treatment unit transmitting the ultrasonic vibration to a living tissue, and a tube which has a passageway communicated with the hollow shaped portion, the tube being connected to the hollow shaped portion. In the flexible insertion unit, the sheath can be arranged. The observation unit is provided inside the insertion unit, and is able to observe an outside from a distal end of the insertion unit. The treatment method further includes an arrangement process of arranging a treated site of a subject in a visual field of the observation unit; a spreading process of spreading a coloring agent through the tube from the hollow shaped portion to the treated site; a marking process of performing marking of surrounding tissue of the treated site with the ultrasonic treatment apparatus; an injection process of injecting a local injection solution through the tube from the hollow shaped portion to a lower portion of the treated site; an incision and dissection process of incising and dissecting the living tissue including the treated site with the ultrasonic treatment apparatus, the living tissue being raised by the injection of the local injection solution; and a hemostatic process of performing hemostasis with the ultrasonic treatment apparatus when bleeding is generated in the incision and dissection process.

An endoscope apparatus according to still further aspect of the present invention includes an ultrasonic treatment apparatus, an insertion unit, and an observation unit. The ultrasonic treatment apparatus includes a sheath which has an opening at a distal end thereof, an ultrasonic transducer which is connected to the sheath, the ultrasonic transducer being able to rotate in a circumferential direction of the sheath, the ultrasonic transducer being able to generate ultrasonic vibration which is of treatment energy, a treatment unit which has a hollow shaped portion and a distal-end surface portion, the distal-end surface portion moving to be treated in at least two directions with respect to a treated site in a subject, the treatment unit being connected to the ultrasonic transducer, the treatment unit transmitting the ultrasonic vibration to a living tissue, a tube which has a passageway communicated with the hollow shaped portion, the tube being connected to the hollow shaped portion, and an operating unit which rotatably operates the ultrasonic transducer and the treatment unit with respect to the sheath. In the flexible insertion unit, the sheath can be arranged. The observation unit is provided inside the insertion unit, and is able to observe an outside from a distal end of the insertion unit.

A treatment method according to still another aspect of the present invention includes an insertion process of inserting an insertion unit of an endoscope apparatus into a subject. The endoscope apparatus includes an ultrasonic treatment apparatus, an insertion unit, and an observation unit. The ultrasonic treatment apparatus includes a sheath which has an opening at a distal end thereof, an ultrasonic transducer which is connected to the sheath, the ultrasonic transducer being able to rotate in a circumferential direction of the sheath, the ultrasonic transducer being able to generate ultrasonic vibration which is of treatment energy, a treatment unit which has a distal-end surface portion, the distal-end surface portion moving to be treated in at least two directions with respect to a treated site in a subject, the treatment unit being connected to the ultrasonic transducer, the treatment unit transmitting the ultrasonic vibration to a living tissue, and an operating unit which rotatably operates the ultrasonic transducer and the treatment unit with respect to the sheath. In the flexible insertion unit, the sheath can be arranged. The observation unit is provided inside the insertion unit, and is able to observe an outside from a distal end of the insertion unit. The treatment method further includes an arrangement process of arranging a treated site of the subject in a visual field of the observation unit; a marking process of performing marking of surrounding tissue of the treated site with the ultrasonic treatment apparatus; an injection process of inserting a tube into the insertion unit of the endoscope apparatus to inject a local injection solution into a lower portion of the treated site through the tube; a rotation process of causing the operating unit to rotate the ultrasonic transducer and the treatment unit with respect to the sheath to set the distal-end surface portion such that treatment can be performed in a desired direction to the treated site of the subject; an incision and dissection process of incising and dissecting the living tissue including the treated site with the ultrasonic treatment apparatus, the living tissue being raised by the injection of the local injection solution; and a hemostatic process of performing hemostasis with the ultrasonic treatment apparatus when bleeding is generated in the incision and dissection process.

A treatment method according to still another aspect of the present invention includes an insertion process of inserting an insertion unit of an endoscope apparatus into a subject. The endoscope apparatus includes an ultrasonic treatment apparatus, an insertion unit, and an observation unit. The ultrasonic treatment apparatus includes a sheath which has an opening at a distal end thereof, an ultrasonic transducer which is connected to the sheath, the ultrasonic transducer being able to rotate in a circumferential direction of the sheath, the ultrasonic transducer being able to generate ultrasonic vibration which is of treatment energy, a treatment unit which has a hollow shaped portion and a distal-end surface portion, the distal-end surface portion moving to be treated in at least two directions with respect to a treated site in a subject, the treatment unit being connected to the ultrasonic transducer, the treatment unit transmitting the ultrasonic vibration to a living tissue, a tube which has a passageway communicated with the hollow shaped portion, the tube being connected to the hollow shaped portion, and an operating unit which rotatably operates the ultrasonic transducer and the treatment unit with respect to the sheath. In the flexible insertion unit, the sheath can be arranged. The observation unit is provided inside the insertion unit, and is able to observe an outside from a distal end of the insertion unit. The treatment method further includes an arrangement process of arranging a treated site of the subject in a visual field of the observation unit; a spreading process of spreading a coloring agent through the tube from the hollow shaped portion to the treated site; a marking process of performing marking of surrounding tissue of the treated site with the ultrasonic treatment apparatus; an injection process of injecting a local injection solution through the tube from the hollow shaped portion to a lower portion of the treated site; a rotation process of causing the operating unit to rotate the ultrasonic transducer and the treatment unit with respect to the sheath to set the distal-end surface portion such that treatment can be performed in a desired direction to the treated site of the subject; an incision and dissection process of incising and dissecting the living tissue including the treated site with the ultrasonic treatment apparatus, the living tissue being raised by the injection of the local injection solution; and a hemostatic process of performing hemostasis with the ultrasonic treatment apparatus when bleeding is generated in the incision and dissection process.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 69 is a partial sectional side view of the ultrasonic treatment apparatus according to a twelfth embodiment in which an ultrasonic transducer can be oscillated;

FIG. 113A is a top view of a distal-end treatment unit of a sixth modification of the thirteenth embodiment of the present invention;

FIG. 113B is a front elevational view of the distal-end treatment unit of the sixth modification of the thirteenth embodiment of the present invention;

FIG. 114A is a top view of a distal-end treatment unit of a seventh modification of the thirteenth embodiment of the present invention;

FIG. 114B is a front elevational view of the distal-end treatment unit of the seventh modification of the thirteenth embodiment of the present invention;

FIG. 115A is a top view of a distal-end treatment unit of an eighth modification of the thirteenth embodiment of the present invention;

FIG. 115B is a front elevational view of the distal-end treatment unit of the eighth modification of the thirteenth embodiment of the present invention;

FIG. 116A is a top view of a distal-end treatment unit of an ninth modification of the thirteenth embodiment of the present invention;

FIG. 116B is a front elevational view of the distal-end treatment unit of the ninth modification of the thirteenth embodiment of the present invention;

FIG. 117A is a top view of a distal-end treatment unit of a tenth modification of the thirteenth embodiment of the present invention;

FIG. 117B is a front elevational view of the distal-end treatment unit of the tenth modification of the thirteenth embodiment of the present invention;

FIG. 118A is a top view of a distal-end treatment unit of an eleventh modification of the thirteenth embodiment of the present invention;

FIG. 118B is a front elevational view of the distal-end treatment unit of the eleventh modification of the thirteenth embodiment of the present invention;

Figure 119A:
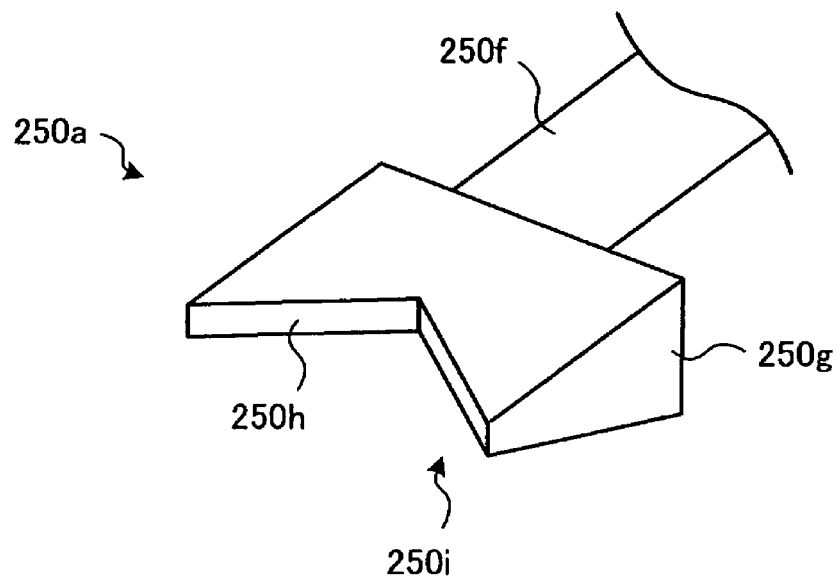
Figure 119B:
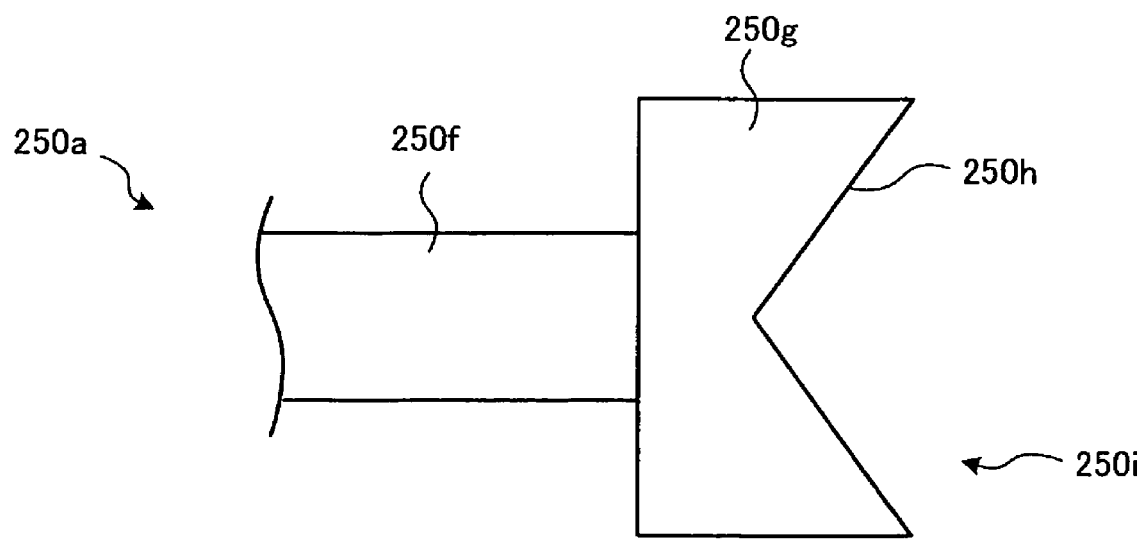
Figure 119C:
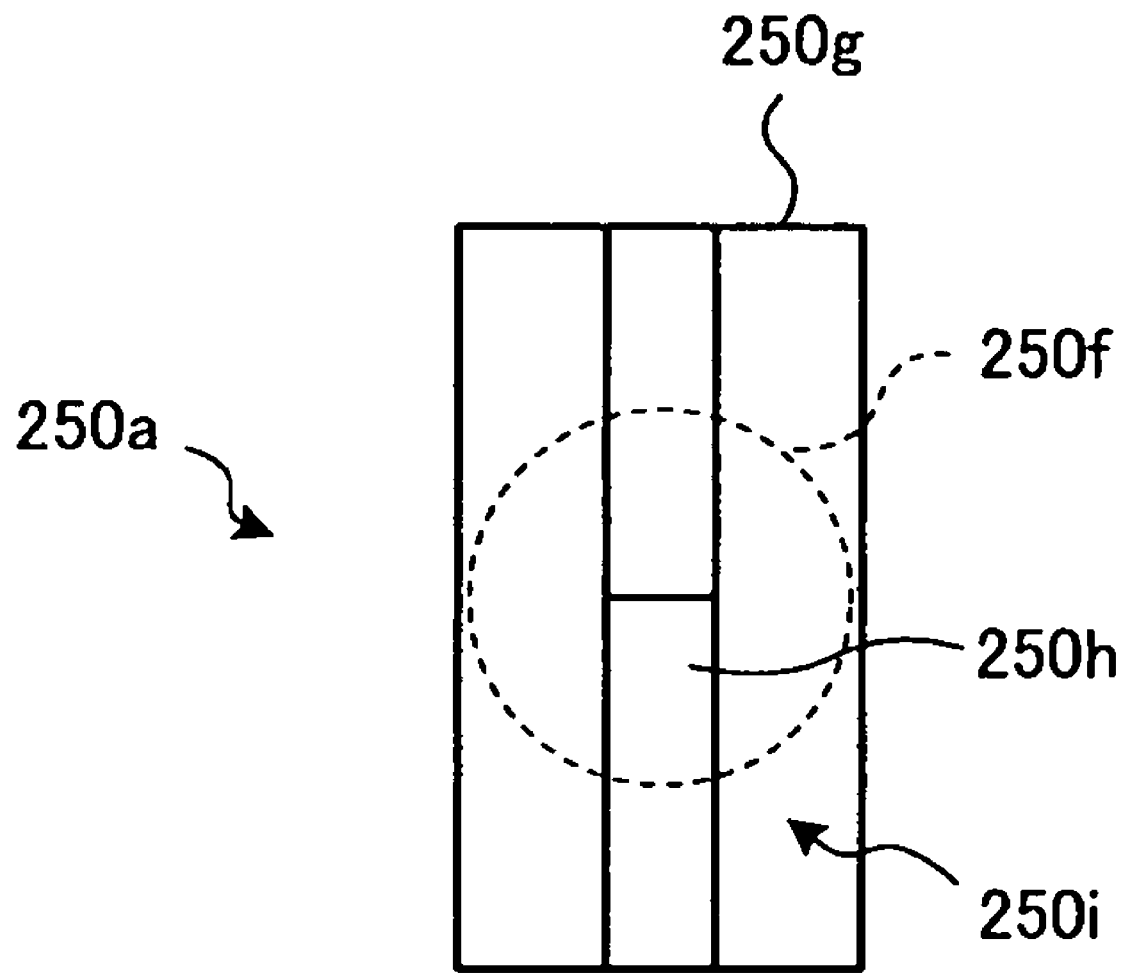
Figure 120A:
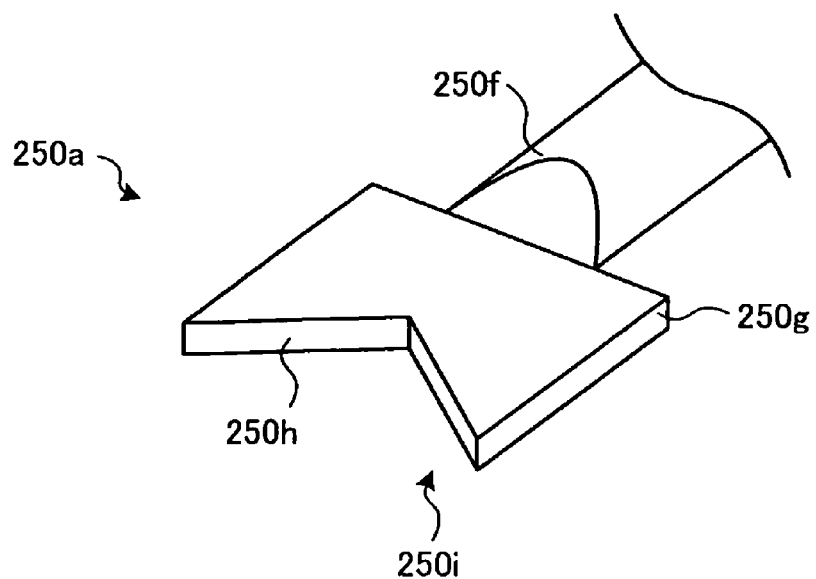
Figure 120B:
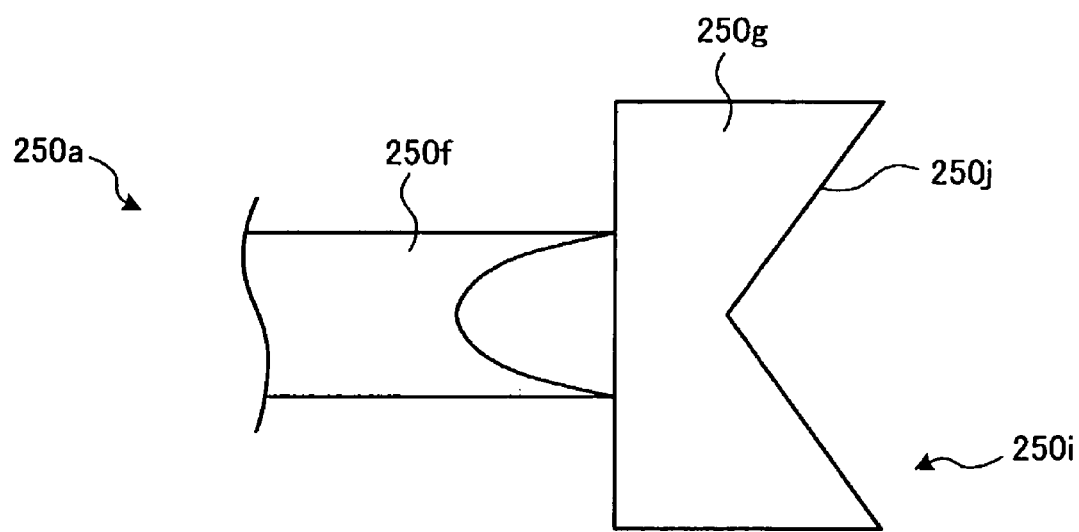
Figure 120C:
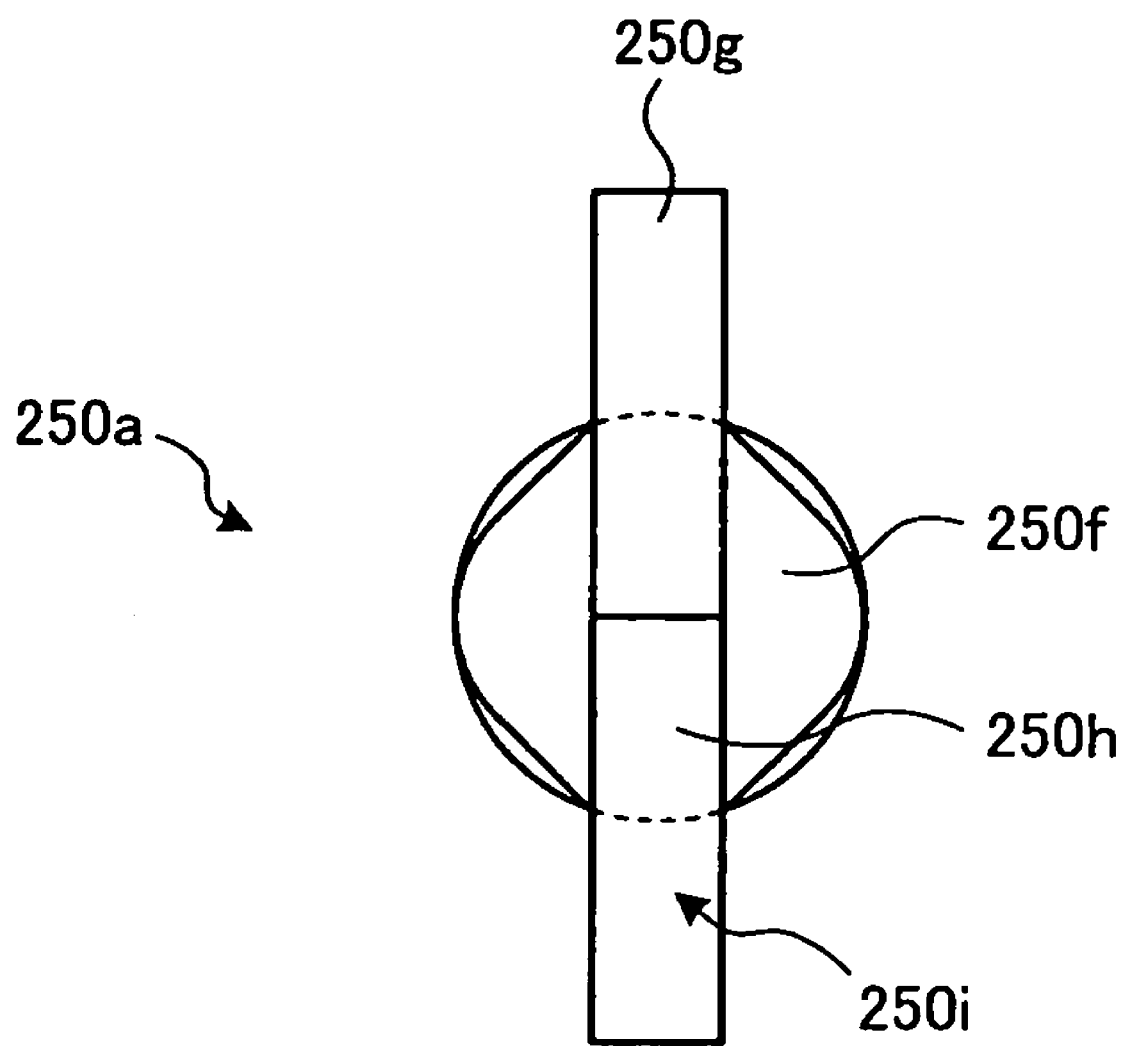
Figure 121:
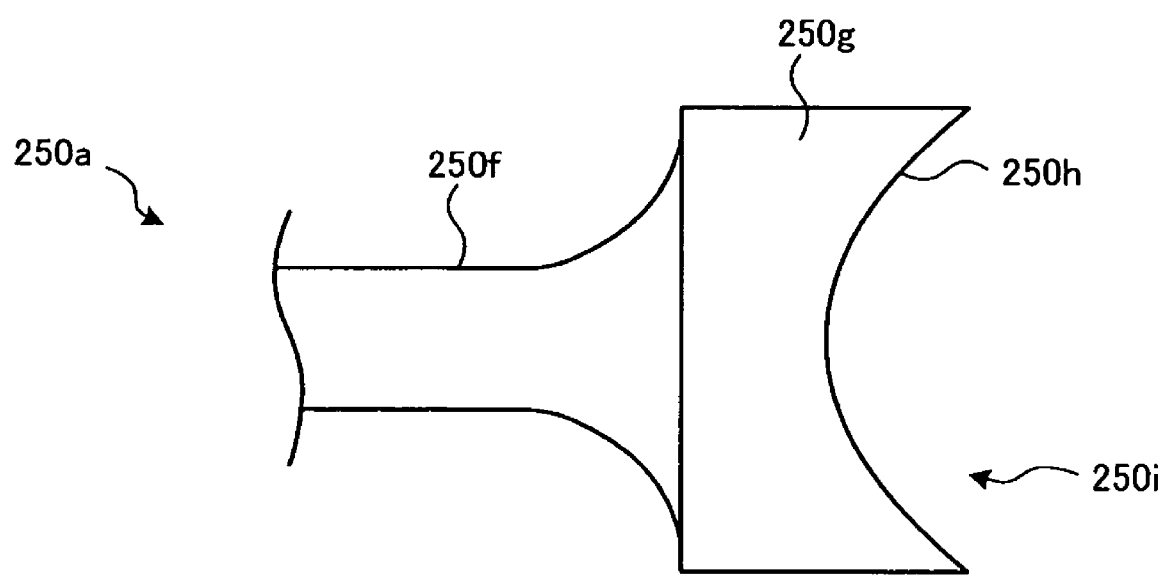
Figure 122A:
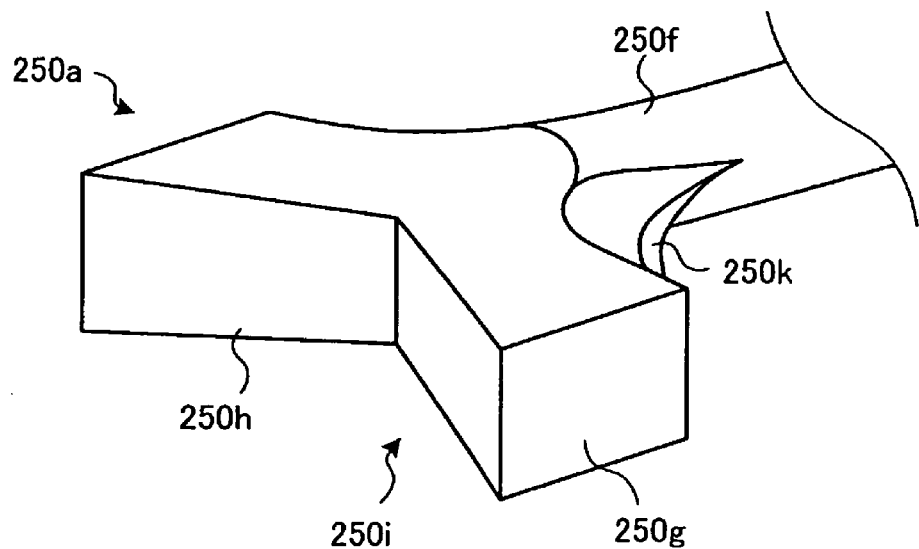
Figure 122B:
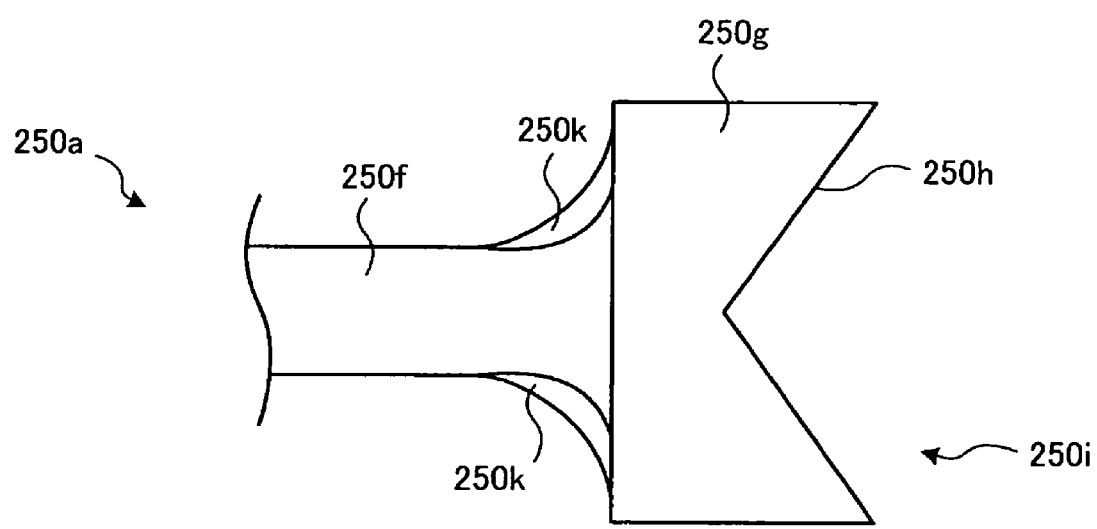
Figure 123A:
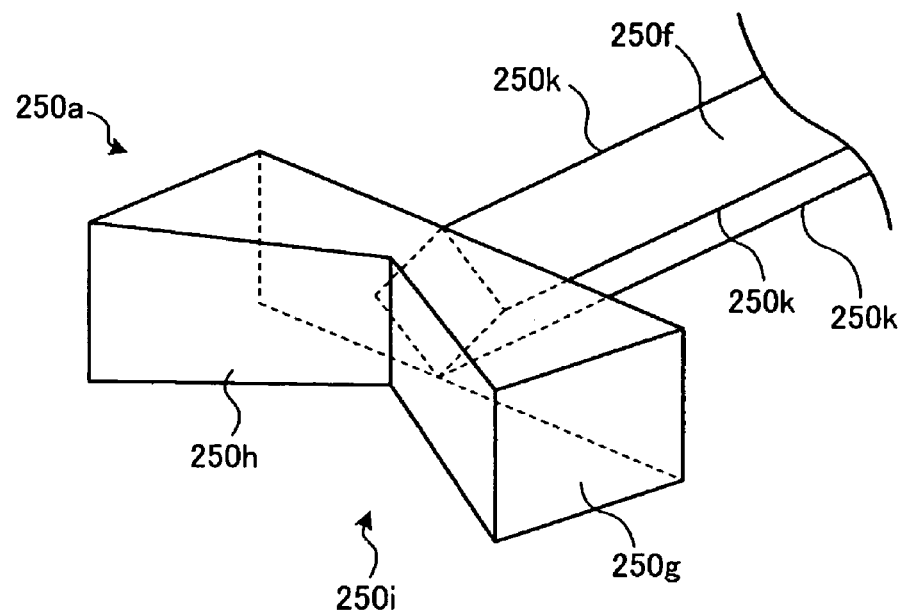
Figure 123B:
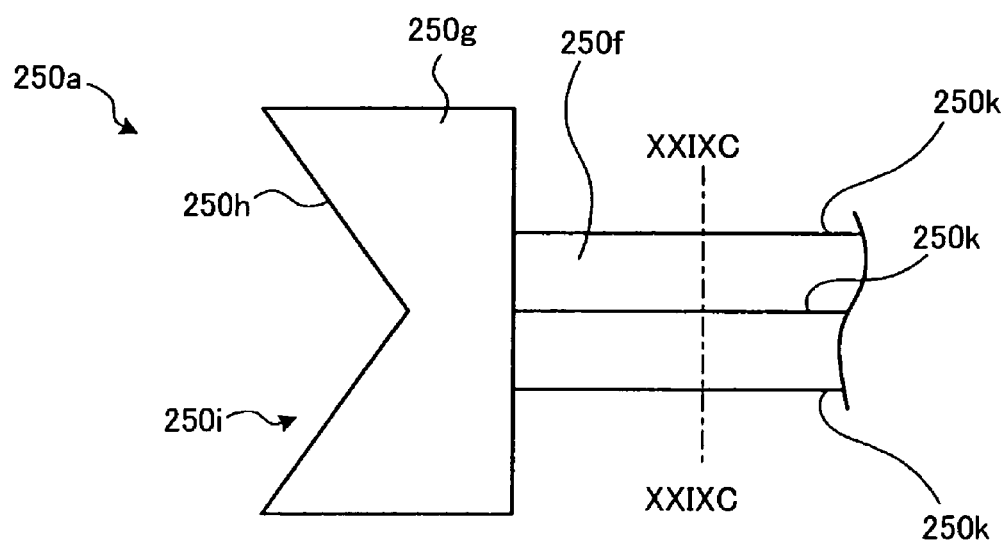
Figure 123C:
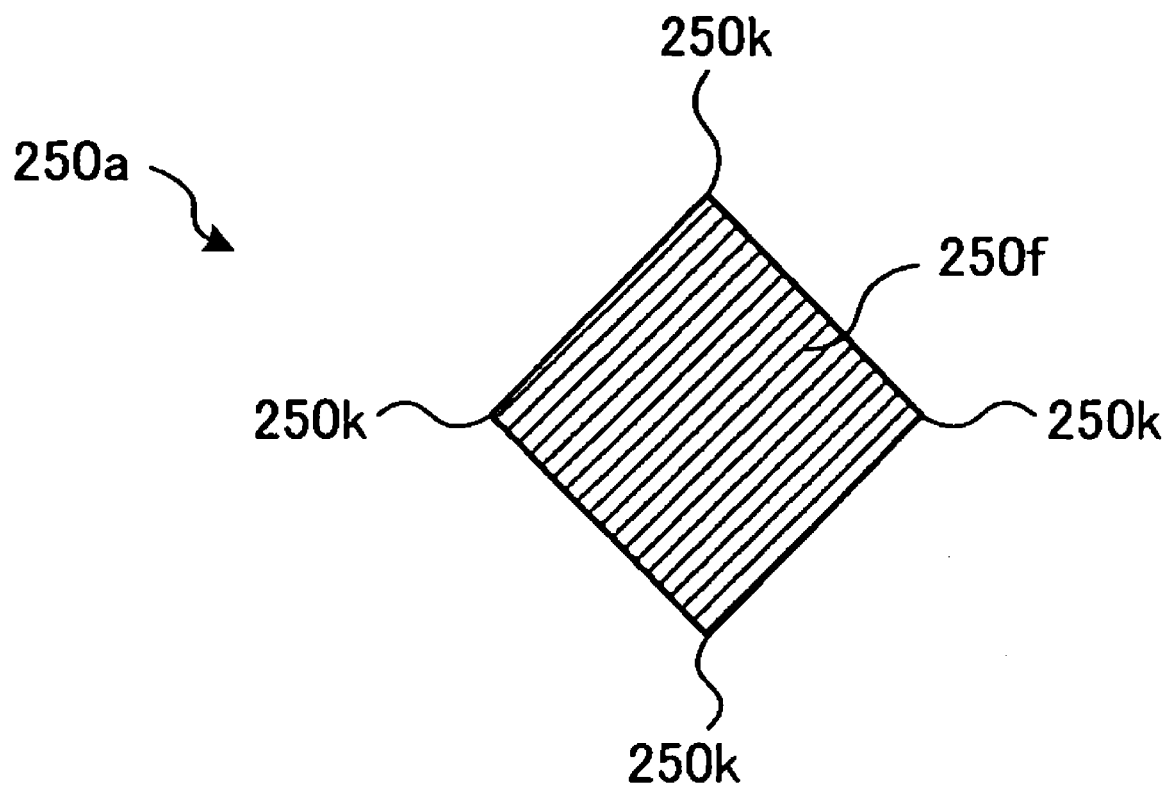
Figure 124A:
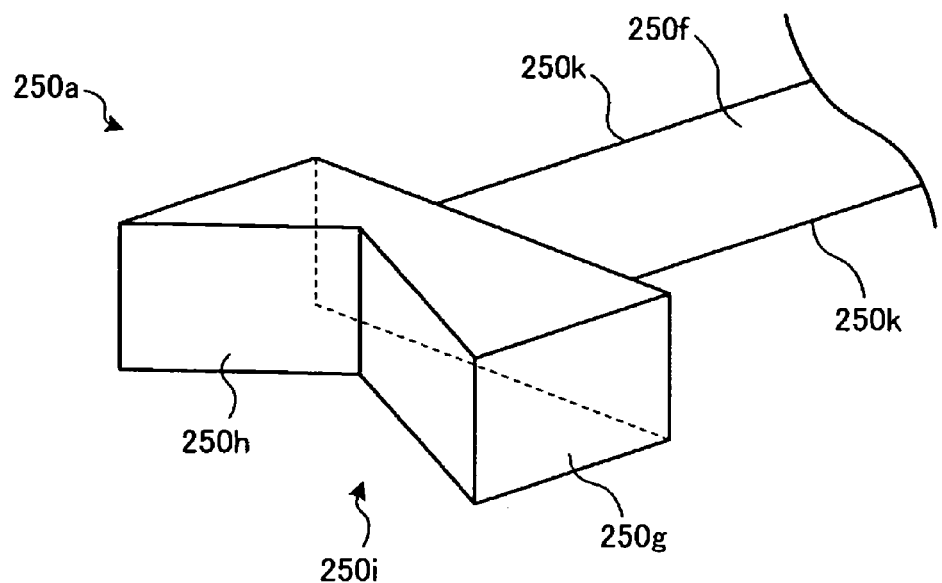
Figure 124B:
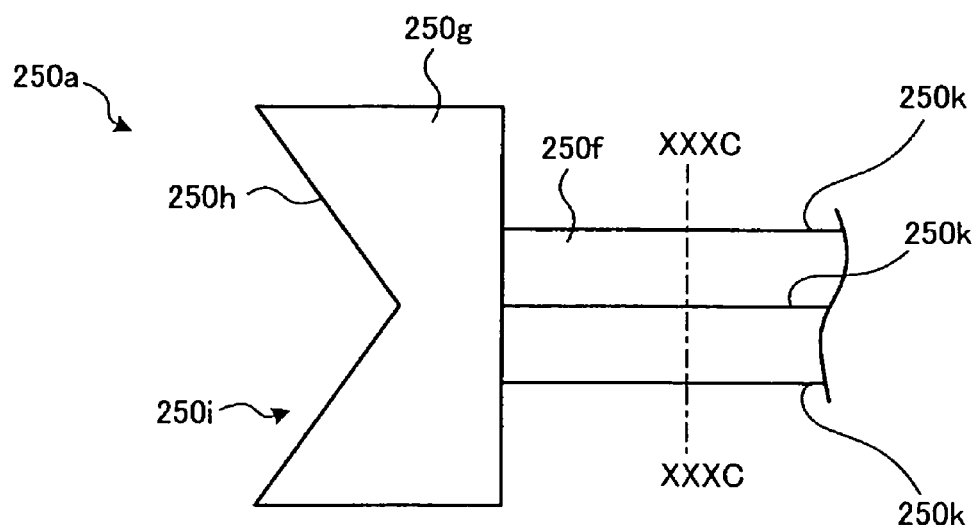
Figure 124C:
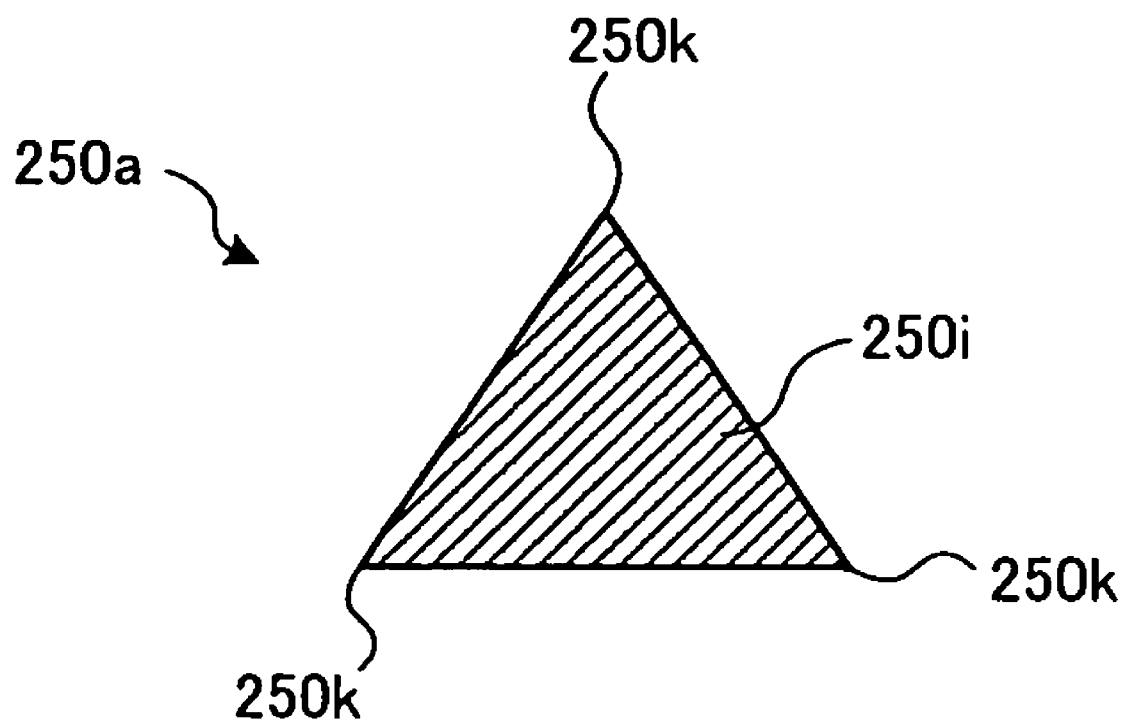
Figure 125:
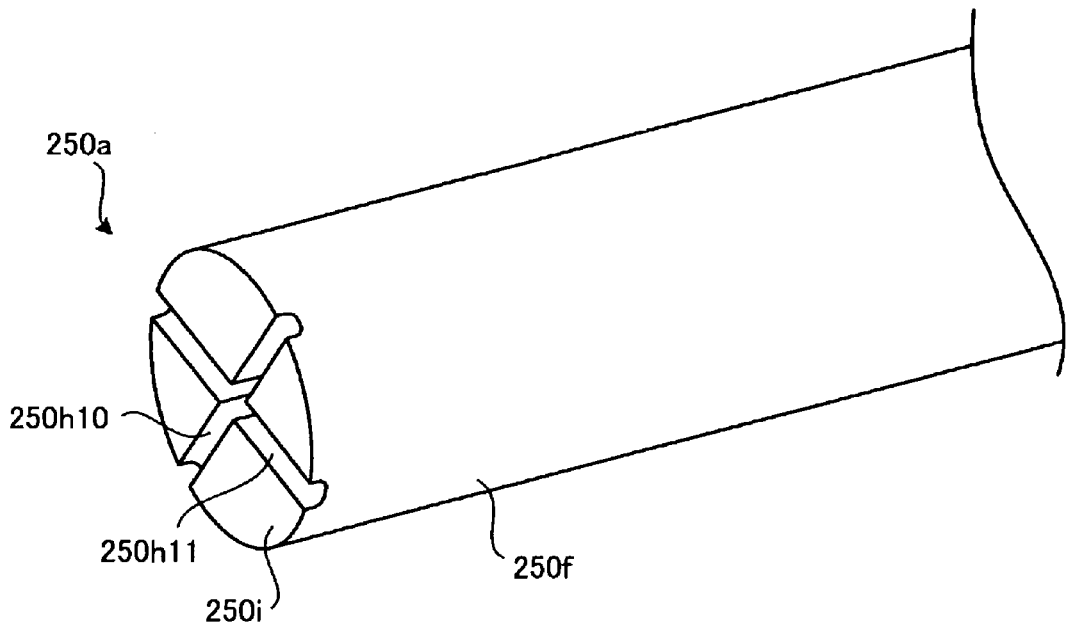
Figure 126:
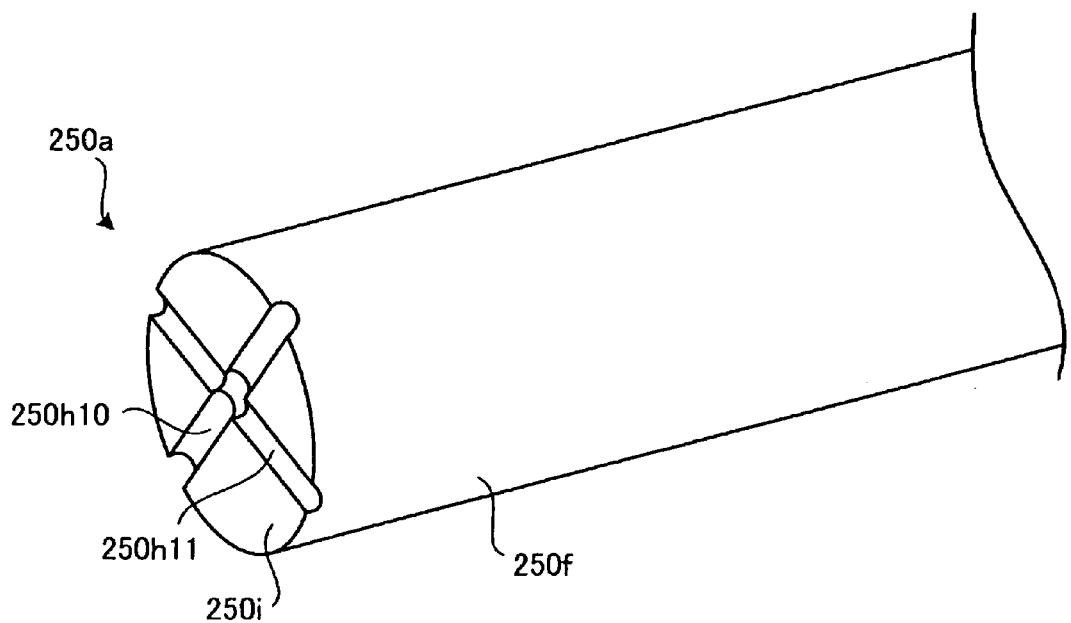
Figure 127:
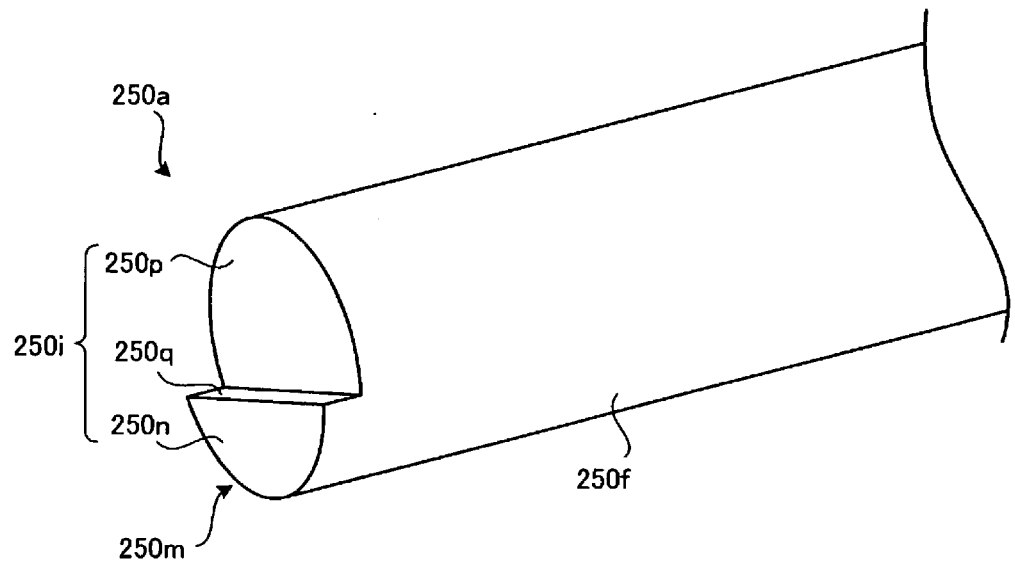
Figure 128:
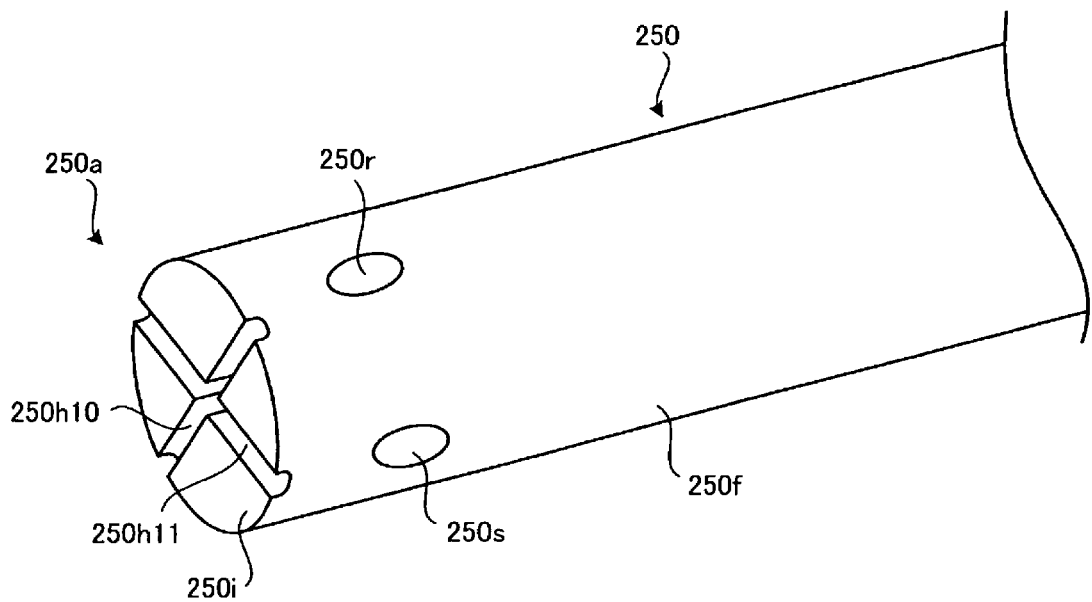
Figure 129:
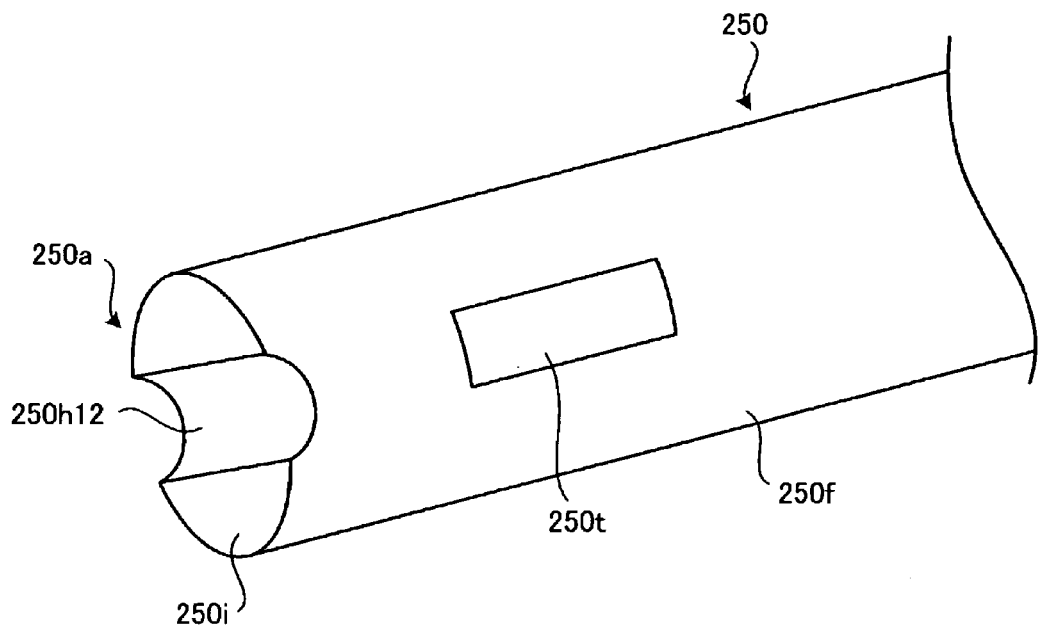
Figure 130:
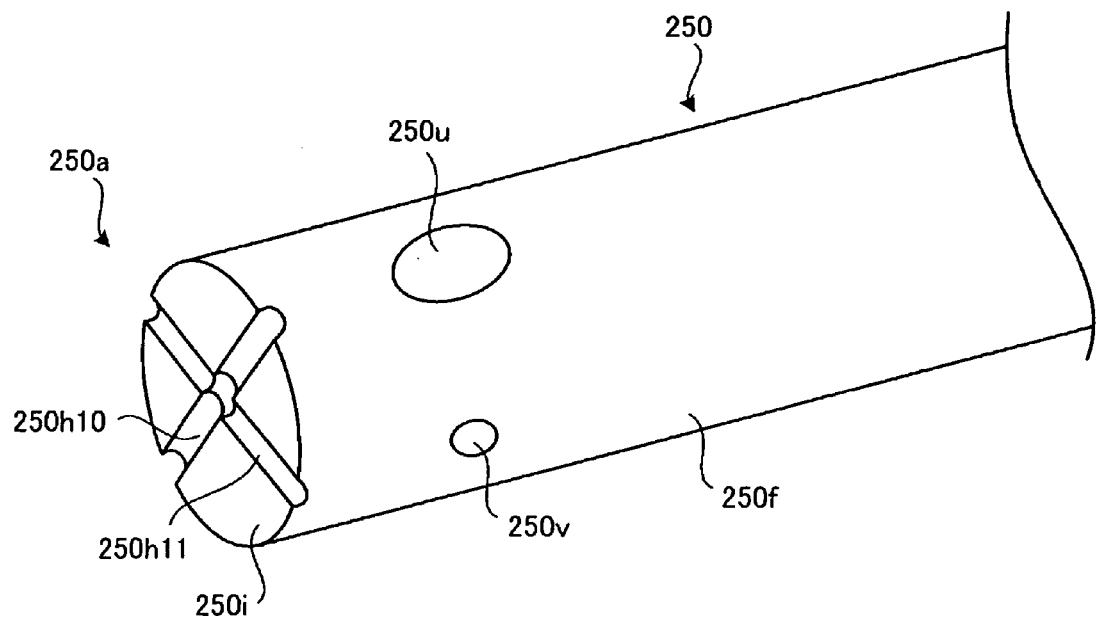

FIG. 119A is a perspective view of a distal-end treatment unit of a twelfth modification of the thirteenth embodiment of the present invention;

FIG. 119B is a top view showing the distal-end treatment unit of the twelfth modification of the thirteenth embodiment of the present invention;

FIG. 119C is a front elevational view of the distal-end treatment unit of the twelfth modification of the thirteenth embodiment of the present invention;

FIG. 120A is a perspective view of a distal-end treatment unit of a thirteenth modification of the thirteenth embodiment of the present invention;

FIG. 120B is a top view of the distal-end treatment unit of the thirteenth modification of the thirteenth embodiment of the present invention;

FIG. 120C is a front elevational view of the distal-end treatment unit of the thirteenth modification of the thirteenth embodiment of the present invention;

FIG. 121 is a top view of the distal-end treatment unit of the fourteenth modification of the thirteenth embodiment of the present invention;

FIG. 122A is a perspective view of a distal-end treatment unit of a fifteenth modification of the thirteenth embodiment of the present invention;

FIG. 122B is a top view of the distal-end treatment unit of the fifteenth modification of the thirteenth embodiment of the present invention;

FIG. 123A is a perspective view of a distal-end treatment unit of a sixteenth modification of the thirteenth embodiment of the present invention;

FIG. 123B is a top view of the distal-end treatment unit of the sixteenth modification of the thirteenth embodiment of the present invention;

FIG. 123C is a horizontal sectional view of the distal-end treatment unit of the sixteenth modification of the thirteenth embodiment of the present invention taken on line XXIXC-XXIXC of FIG. 123B;

FIG. 124A is a perspective view of a distal-end treatment unit of a seventeenth modification of the thirteenth embodiment of the present invention;

FIG. 124B is a top view of the distal-end treatment unit of the seventeenth modification of the thirteenth embodiment of the present invention;

FIG. 124C is a horizontal sectional view of the distal-end treatment unit of the seventeenth modification of the thirteenth embodiment of the present invention taken on line XXXC-XXXC of FIG. 123B;

FIG. 125 is a perspective view of a distal-end treatment unit of an eighteenth modification of the thirteenth embodiment of the present invention;

FIG. 126 is a perspective view of a distal-end treatment unit of a nineteenth modification of the thirteenth embodiment of the present invention;

FIG. 127 is a perspective view of a distal-end treatment unit of a twentieth modification of the thirteenth embodiment of the present invention;

FIG. 128 is a perspective view of a distal-end treatment unit of a twenty-first modification of the thirteenth embodiment of the present invention;

FIG. 129 is a perspective view of a distal-end treatment unit of a twenty-second modification of the thirteenth embodiment of the present invention; and FIG. 130 is a perspective view of a distal-end treatment unit of a twenty-third modification of the thirteenth embodiment of the present invention.

DETAILED DESCRIPTION OF THE PREFERRED EMBODIMENTS

Exemplary embodiments of an ultrasonic treatment apparatus, an endoscope apparatus, and a treatment method according to the present invention will be described in detail below with reference to FIGS. 1 to 130. The present invention is not limited to the embodiments, and various changes and modifications could be made without departing from the scope of the present invention.

Figure 2:
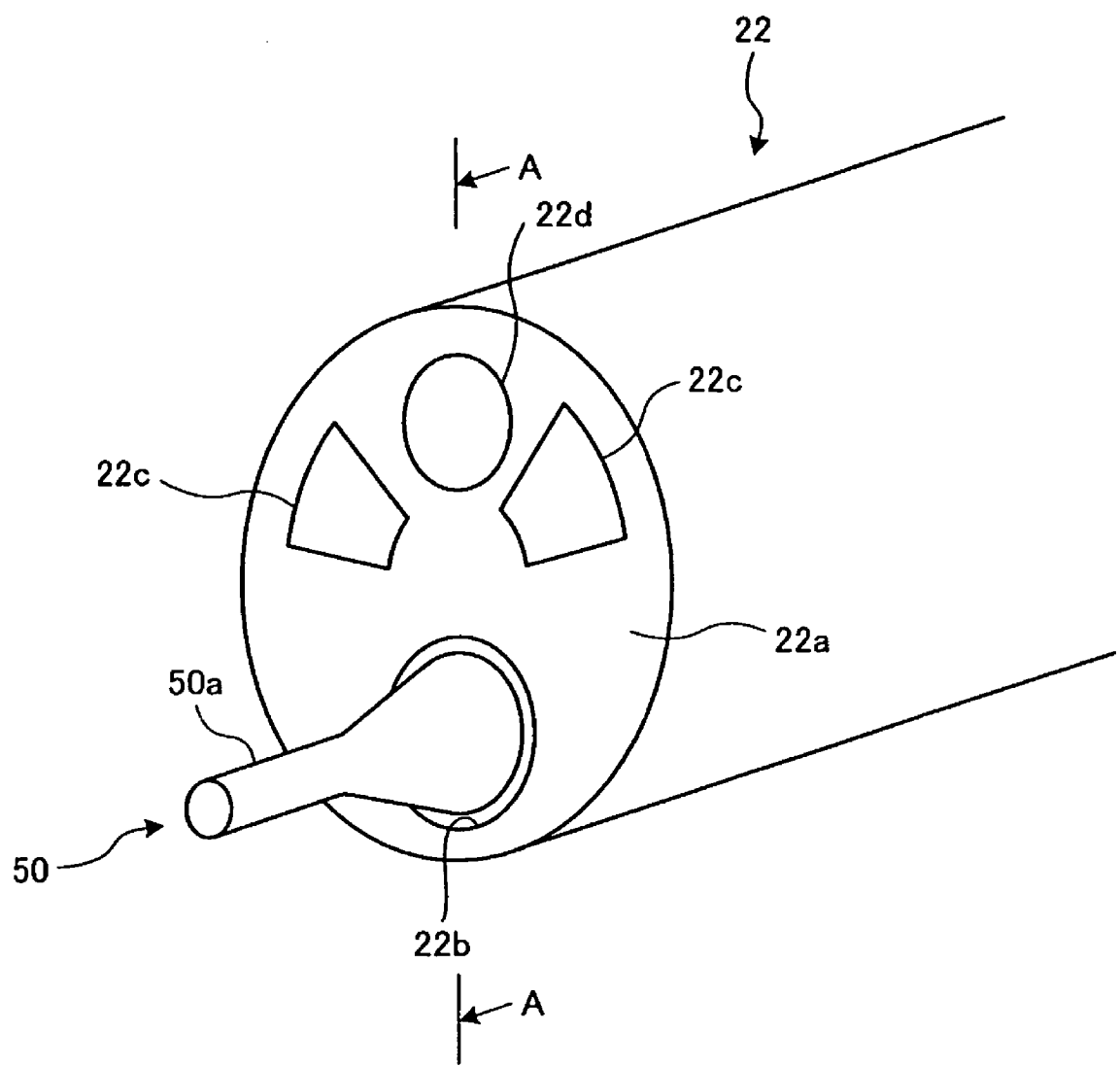
FIG. 2 is a perspective view of a distal-end portion of an insertion unit shown in FIG. 1 according to a first embodiment.
Figure 3:
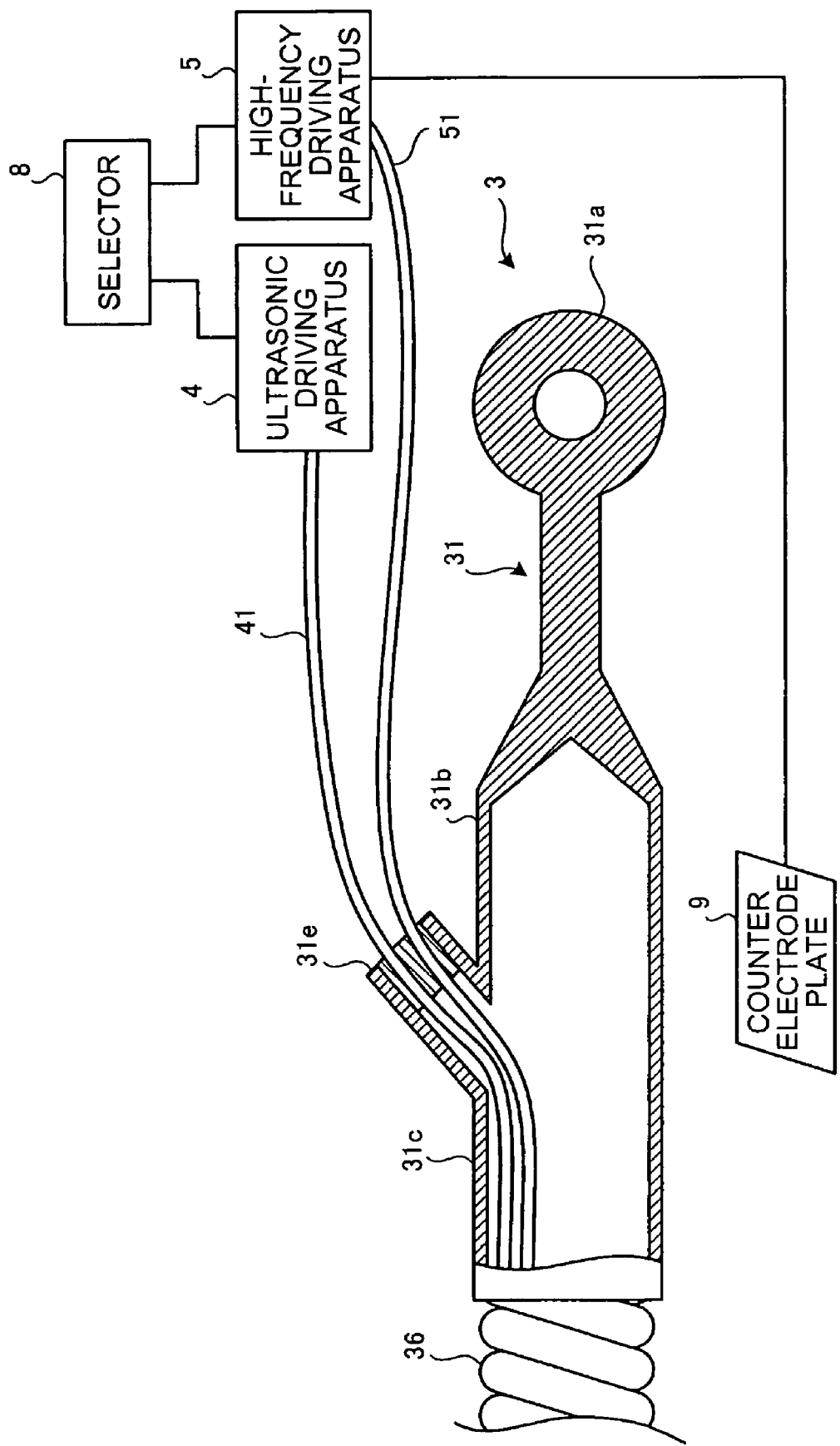
FIG. 3 is a sectional side view of an operating unit shown in FIG. 1.
Figure 4:
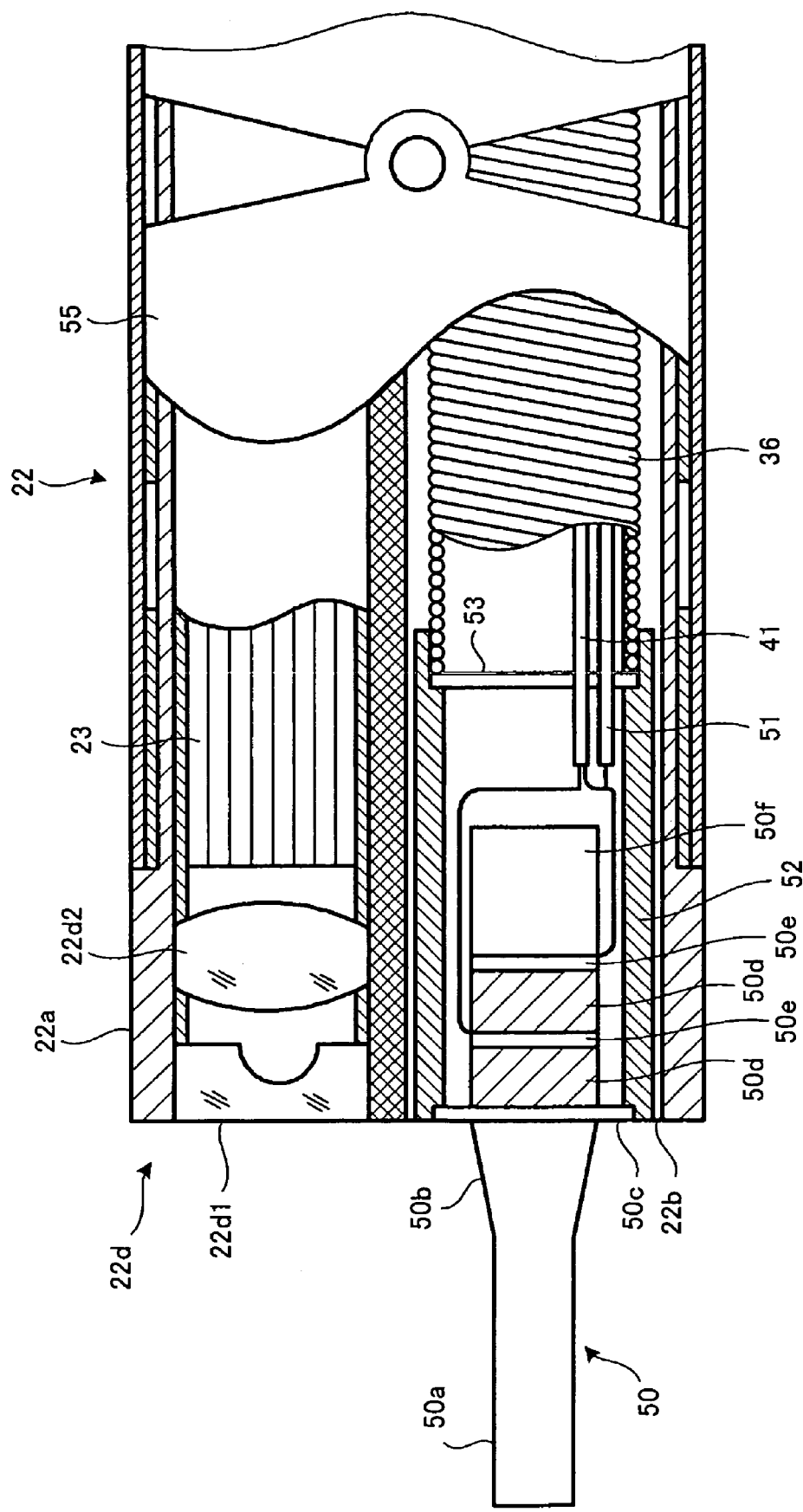
FIG. 4 is a sectional view of the insertion unit taken on line A-A of FIG. 2.

A first embodiment of the present invention will be described below with reference to FIGS. 1 to 4. FIG. 1 is a schematic diagram of an endoscope apparatus 1 which includes an ultrasonic treatment apparatus having a first exemplary configuration according to the present invention. FIG. 2 is a perspective view of a distal-end portion of an insertion unit shown in FIG. 1 according to a first embodiment. FIG. 3 is a sectional side view of an operating unit shown in FIG. 1. FIG. 4 is a sectional view of the insertion unit taken on line A-A of FIG. 2. In these drawings, the endoscope apparatus 1 includes a videoscope 2, an ultrasonic treatment apparatus 3, an ultrasonic driving apparatus 4, and a high-frequency driving apparatus 5. The videoscope 2 is connected to a light source apparatus (not shown) and a display apparatus (not shown). The ultrasonic driving apparatus 4 is an ultrasonic power supply unit which supplies electric power to the ultrasonic treatment apparatus 3. The high-frequency driving apparatus 5 is a high-frequency power supply unit which supplies current to the ultrasonic treatment apparatus 3. The ultrasonic treatment apparatus 3 and the ultrasonic driving apparatus 4 are connected to each other via an electric power line 41, and the ultrasonic treatment apparatus 3 and the high-frequency driving apparatus 5 are connected to each other via an electric current line 51.

The videoscope 2 includes a scope operating unit 21 and a thin, cylindrical insertion unit 22. The scope operating unit 21 is provided on a proximal-end side of the insertion unit 22. The insertion unit 22 is provided in a lower portion of the scope operating unit 21, and the insertion unit 22 is inserted into a subject. A flexible universal cord 21a is connected to a side face of the scope operating unit 21 to connect the scope operating unit 21 and the light source apparatus or display apparatus. A bending operation knob 21b is projected from the side face of the scope operating unit 21 at a different position from the position of the universal cord 21a. A distal-end of the insertion unit 22 is controlled so as to bend through the manipulation of the bending operation knob 21b.

A grip unit 21c is provided in the scope operating unit 21 so that an operator can grip the grip unit 21c to hold and fix the videoscope 2. In the scope operating unit 21, a forceps insertion port 21d is projected on the side where the insertion unit 22 is attached. A pair of forceps which is of the ultrasonic treatment apparatus 3 according to the present invention is inserted into the forceps insertion port 21d. In FIG. 1, the ultrasonic treatment apparatus 3 is inserted into the forceps insertion port 21d, and an operating unit 31 attached at one end of a flexible sheath 36 is projected from the forceps insertion port 21d.

The insertion unit 22 inserted into the subject includes a hard distal-end portion 22a, a bending unit, and a flexible pipe. The distal-end portion 22a is provided at the distal-end of the insertion unit 22, the bending unit is caused to perform the bending action by operating the scope operating unit 21, and the flexible pipe has flexibility. These units are configured to be aligned linearly. As shown in FIG. 2, a channel 22b is formed in the distal-end portion 22a of the insertion unit 22, and an ultrasonic transducer 50 of the ultrasonic treatment apparatus 3 is provided inside the channel 22b in a projectable manner. The distal-end portion 22a of the insertion unit 22 includes two lighting windows 22c, one observation window 22d, and an image guide fiber 23. The lighting window 22c includes a lighting system fixed to the distal end, the observation window 22d includes an observation system lens, and one end of the image guide fiber 23 is fixed to the observation window 22d. The lighting window 22c, the observation window 22d, and the image guide fiber 23 are provided as components of an observation unit. The other end of the image guide fiber 23 provided in the insertion unit 22 is connected to the light source apparatus through the universal cord 21a.

One end of a lightguide fiber provided in the insertion unit 22 is provided in the lighting window 22c, and the other end is connected to the light source apparatus through the inside of the universal cord 21a. An outside, e.g., a treated site (living tissue) which is a treatment target in the body cavity is illuminated with the illumination light emitted from the light source apparatus from the lighting window of the distal-end portion 22a through the lightguide fiber. The observation system lens includes, e.g., two lenses 22d1 and 22d2, takes in the light reflected from the treated site in the body cavity, and emits the light to an image guide fiber 23. The reflected light emitted from the observation system lens is sent through the image guide fiber 23 to the display apparatus located on the other end, and an image of the treated site is displayed on the display apparatus to allow the operator to observe the treated site.

Figure 1:
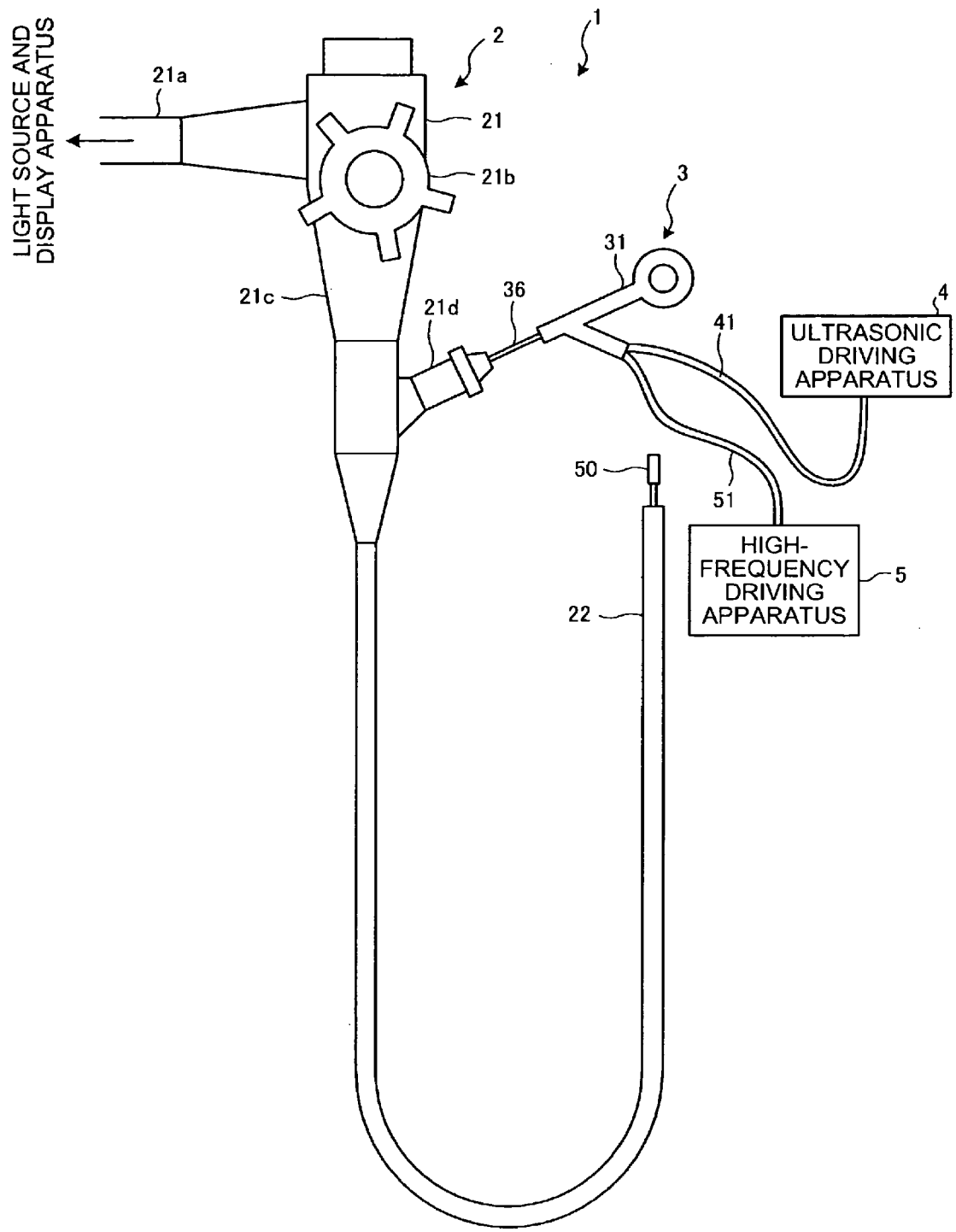
FIG. 1 is a schematic diagram of an endoscope apparatus which includes an ultrasonic treatment apparatus having a first exemplary configuration according to the present invention.

The ultrasonic treatment apparatus 3 includes the operating unit 31 that has a bifurcated configuration shown in FIG. 1, the ultrasonic transducer 50 that is provided at the distal end as shown in the sectional view of FIG. 4, the electric power line 41 that supplies the electric power to the ultrasonic transducer 50, the electric current line 51 that supplies the electric current to the ultrasonic transducer 50, a cylindrical cover 52 that fixes the ultrasonic transducer 50, a partition 53 that keeps a later-described piezoelectric element and an electrode of the ultrasonic transducer 50 watertight, and the flexible sheath 36 through which the electric power line 41 and the electric current line 51 are inserted and which is connected to the hard cover 52 at one end. The partition 53 is arranged in a coupling portion between the cover 52 and the flexible sheath 36. The other end of the flexible sheath 36, in which one piece of wire is wound in a spiral manner, is connected to the operating unit 31. The operator manually inserts or draws the flexible sheath 36 into or from the videoscope 2 to retractably move the flexible sheath 36 in the insertion unit 22. For example, the flexible sheath 36 is inserted into the videoscope 2 through the forcep insertion port 21d. The flexible sheath 36 is moved toward a direction of the distal-end portion 22a in the channel of the insertion unit 22, so that the ultrasonic transducer 50 and a part of the cover 52 are projected from the distal-end portion 22a, and the treatment is performed with the electric cautery in which the ultrasonic vibration or high-frequency current of the ultrasonic transducer 50 is utilized. The flexible sheath 36 is moved toward the direction of the operating unit 31 in the channel of the insertion unit 22 to store the ultrasonic transducer 50 and cover 52 in the distal-end portion 22a.

The ultrasonic transducer 50 is made of an electrically conductive material such as titanium. The ultrasonic transducer 50 includes a cylindrical distal-end treatment unit 50a which has a hollow structure, a horn 50b that transmits the ultrasonic vibration to the distal-end treatment unit 50a, a flange 50c that fixes the ultrasonic transducer 50 to the cover 52, a piezoelectric element 50d that generates the ultrasonic vibration, an electrode 50e which is connected to the electric power line 41 and supplies an electric signal to the piezoelectric element 50d, and a backing plate 50f. The ultrasonic driving apparatus 4 supplies an electric power signal to the piezoelectric element 50d through the electric power line 41 and the operating unit 31. The piezoelectric element 50d receives the electric power signal to generate e.g., the ultrasonic vibration having a frequency of 100 kHz. The generated ultrasonic vibration passes through the drawn-shape horn 50b to enlarge vibration amplitude, and the ultrasonic vibration is transmitted to the distal-end treatment unit 50a. The flange 50c is provided at a node position of the vibration, and the flange 50c is fixed to an end portion of the cover 52.

The electric current line 51 is connected to the electrode 50e, and a counter electrode plate 9, which is paired with the electrode 50e, is connected to the high-frequency driving apparatus 5. A current signal supplied from the high-frequency driving apparatus 5 is passed between the distal-end treatment unit 50a and the counter electrode plate 9 through a human body, which allows the ultrasonic treatment apparatus 3 to function as the electric cautery having, e.g., a frequency of 350 kHz. The ultrasonic treatment apparatus 3 includes a selector 8. The operator can select the treatments with the electric cautery, in which the ultrasonic vibration or high-frequency current is utilized, by the selector 8. The selector 8 is connected to the ultrasonic driving apparatus 4 and the high-frequency driving apparatus 5 to enable the selection of the supply of the electric power and/or the supply of the electric current. Hereinafter the electric power signal and the current signal are collectively referred to as electric signal, and the electric power line and the electric current line are collectively referred to as electric signal line. In the first embodiment, the frequency of the ultrasonic vibration is set at 100 kHz, and the frequency of the electric cautery is set at 350 kHz. However, the present invention is not limited to the first embodiment. For example, the frequencies may be selected from a range where resonance is not generated between the frequencies of the ultrasonic vibration and electric cautery.

As shown in FIG. 3, the operating unit 31 includes a substantially cylindrical operating unit main body 31a, a ring unit 31b provided at one end of the operating unit main body 31a, and a bifurcated joint unit 31c provided at the other end of the operating unit main body 31a to enable insertion of the electric signal lines 41 and 51 from the driving apparatus 4 and 5 into the flexible sheath 36. The operating unit 31 can also include an instruction button as the selector 8 for providing an instruction of selecting the supply of the electric power and/or the supply of the electric current from the driving apparatus 4 or 5.

As described above, the electric signal lines 41 and 51 are inserted from the driving port 31e, made to bend in the joint unit 31c, and pass through the inside of the flexible sheath 36 to be connected to the ultrasonic transducer 50 provided at the distal end of the insertion unit 22. This enables the electric signal to be supplied to the ultrasonic transducer 50.

The endoscope apparatus 1 includes a bending block 55 in the insertion unit 22 near the distal-end portion 22a. The bending block 55 is connected to the bending operation knob 21b, and the bending operation knob 21b is operated to enable the distal end of the insertion unit 22 of the endoscope apparatus 1 to be bent. The endoscope apparatus 1 includes a compact soft endoscope, for example, in which the insertion unit 22 has the flexibility.

Figure 5:
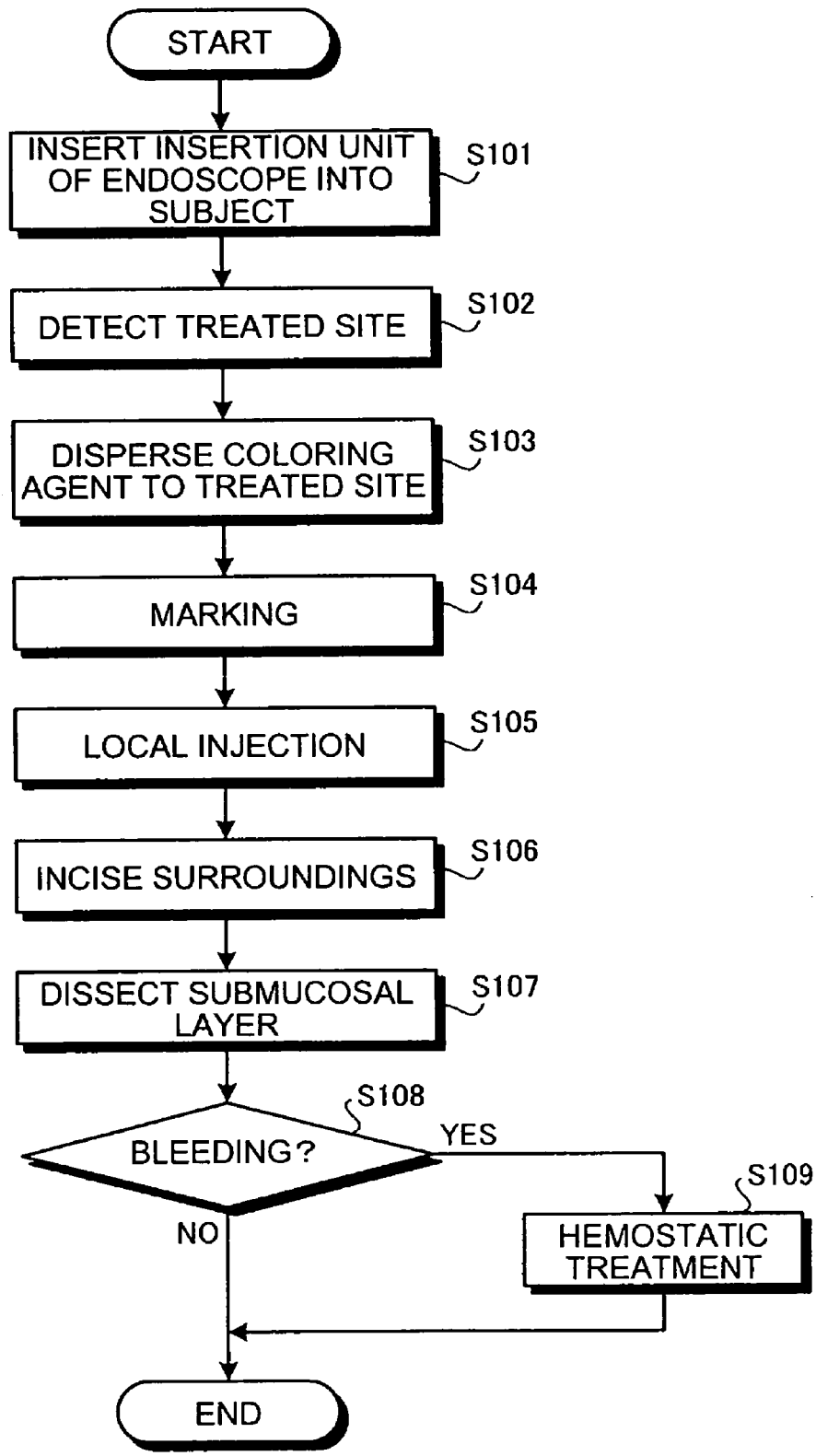
FIG. 5 is a flowchart of a treatment procedure of the ultrasonic treatment apparatus shown in FIG. 1.

A treatment action of the ultrasonic treatment apparatus will be described with reference to FIG. 5 to FIG. 14. FIG. 5 is a flowchart of a treatment procedure of the ultrasonic treatment apparatus shown in FIG. 1 and FIG. 6 to FIG. 14 shows each process of the treatment procedure in an incision operation.

In these drawings, the insertion unit 22 of the endoscope apparatus 1 is inserted into the subject (Step 101), and a treated site B to be treated is arranged within a visual field and detected by the observation unit (Step 102). In an initial state, instead of the ultrasonic treatment apparatus 3, a tube 10 is inserted into the insertion unit 22 from the forceps insertion port 21d. A cylinder (not shown) in which a coloring agent is injected is attached to the tube 10, and the inserted tube 10 is projected to the outside from the distal end of the insertion unit 22.

Figure 6:
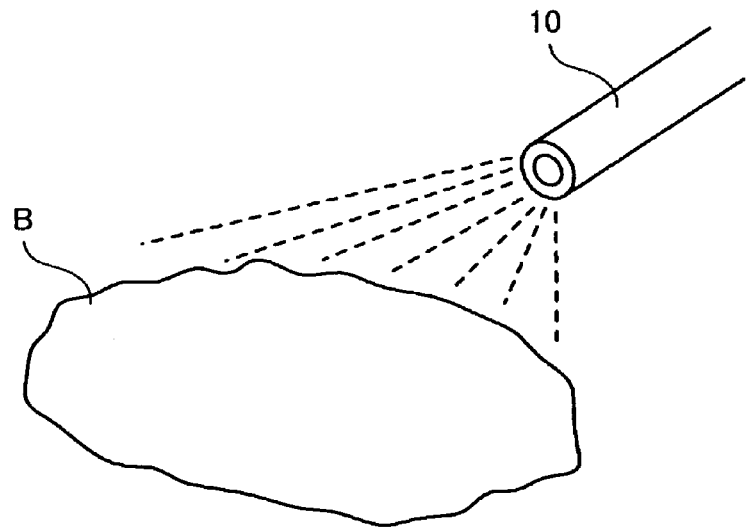
FIG. 6 shows how a coloring agent is spread from the distal-end portion shown in FIG. 2.

When the treated site is detected, the distal-end portion 22a of the insertion unit 22 is brought close to the treated site, and at the same time, the coloring agent filled in the cylinder is dispersed to the treated site B from the distal end of the tube 10 projected from the distal end of the insertion unit 22 as shown in FIG. 6 (Step 103).

Figure 7:
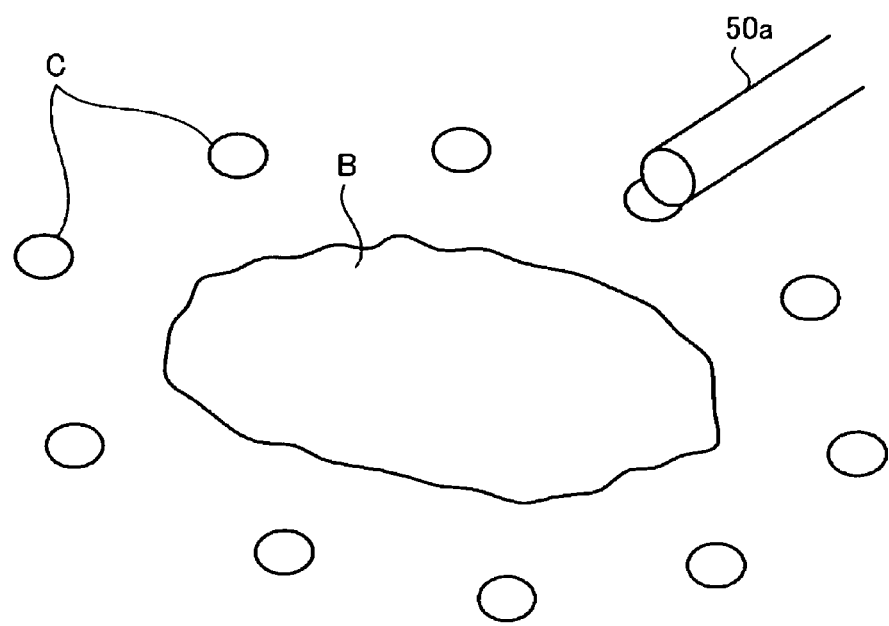
FIG. 7 shows how a marking is performed by the distal-end portion shown in FIG. 2.

Then, the tube 10 is taken out from the insertion unit 22 of the endoscope apparatus 1, instead the ultrasonic treatment apparatus 3 is inserted into the insertion unit 22 from the forceps insertion port 21d, and the current signal is supplied from the high-frequency driving apparatus 5 to the electrode 50e of the ultrasonic transducer 50 through the electric current line 51. This enables the distal-end treatment unit 50a to function as the electric cautery. As shown in FIG. 7, recognizable markings C are formed by cauterizing the living tissue around the colored treated site B using the distal-end treatment unit 50a having a function of the electric cautery (Step 104).

Figure 8:
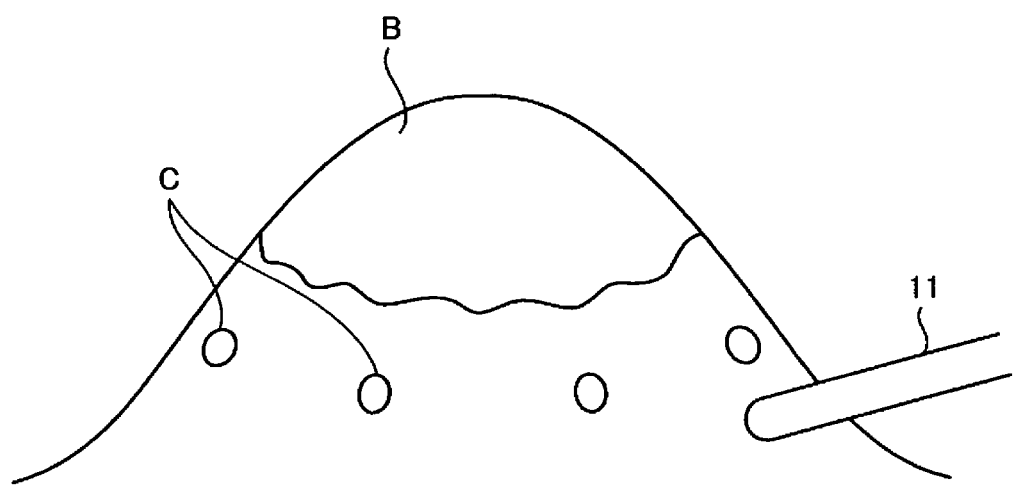
FIG. 8 shows how a local injection is performed by the distal-end portion shown in FIG. 2.

Then, the ultrasonic treatment apparatus 3 is taken out again from the insertion unit 22 of the endoscope apparatus 1, and instead the tube and an injection needle 11 attached at the distal end thereof are inserted into the insertion unit 22 from the forceps insertion port 21d. The cylinder (not shown) is attached to the tube, and a local injection solution (such as a physiological salt solution or Glyceol) is injected in the cylinder. As shown in FIG. 8, the distal end of the distal-end treatment unit 50a is inserted into the lower portion of the treated site B from the outside of the markings C, the local injection solution is injected from the tube, and the living tissue including the treated site B is raised (Step 105).

Figure 9:
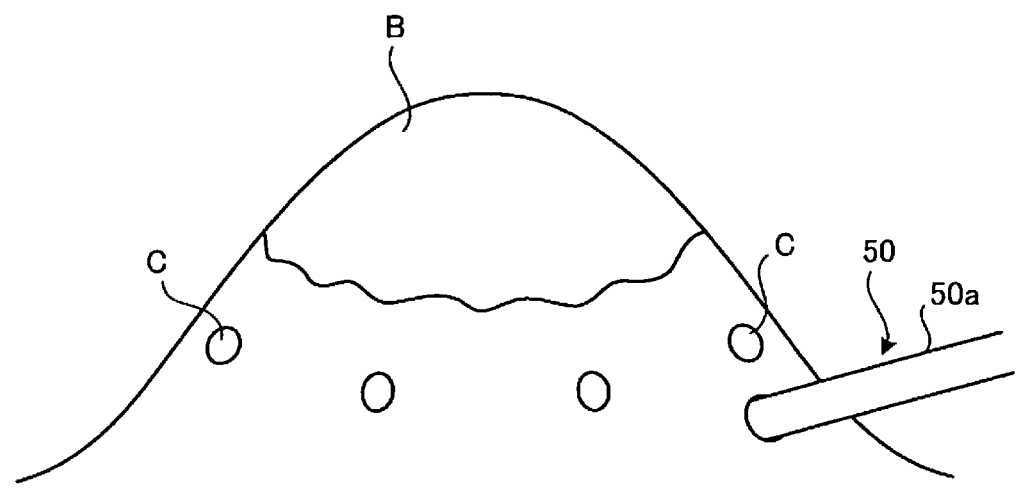
FIG. 9 shows how a periphery of a living tissue is incised by the distal-end portion shown in FIG. 2.
Figure 10:
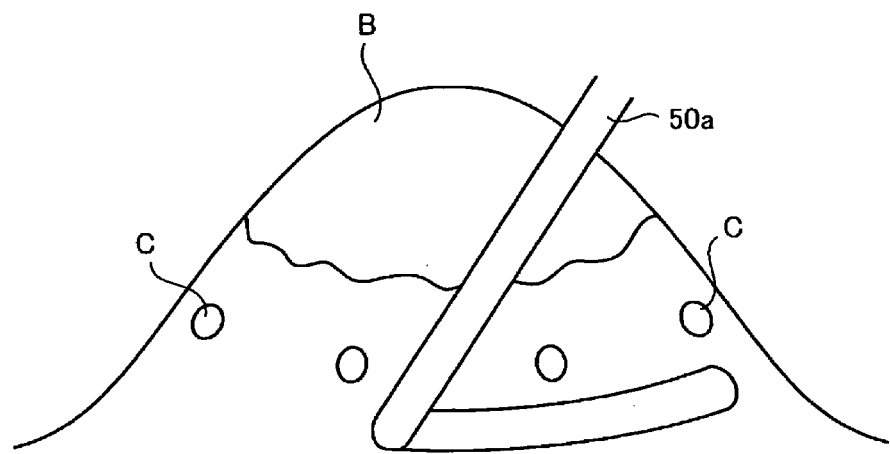
FIG. 10 shows how a periphery of a living tissue is incised by the distal-end portion shown in FIG. 2.
Figure 11:
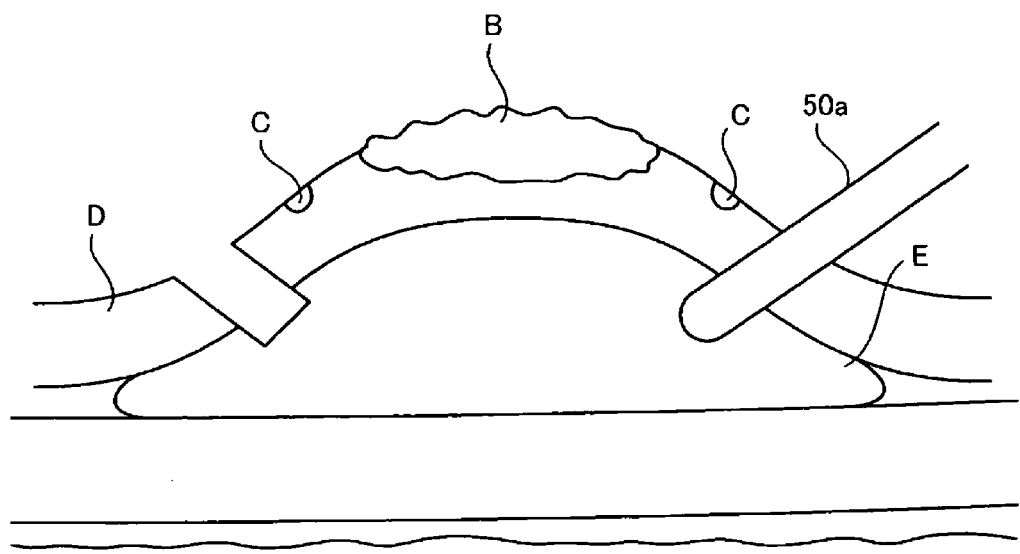
FIG. 11 shows how a periphery of a living tissue is incised by the distal-end portion shown in FIG. 2.
Figure 12:
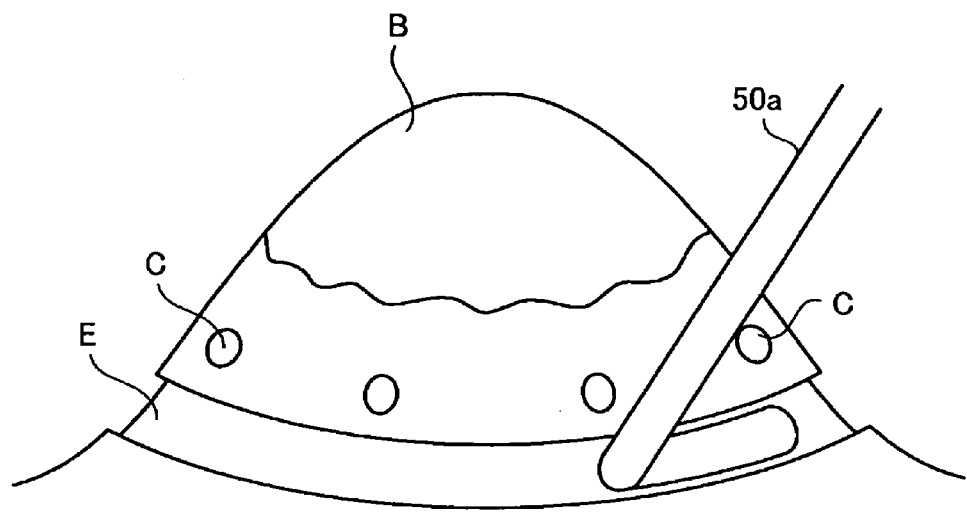
FIG. 12 shows how a submucosal tissue is ablated by the distal-end portion shown in FIG. 2.
Figure 13:
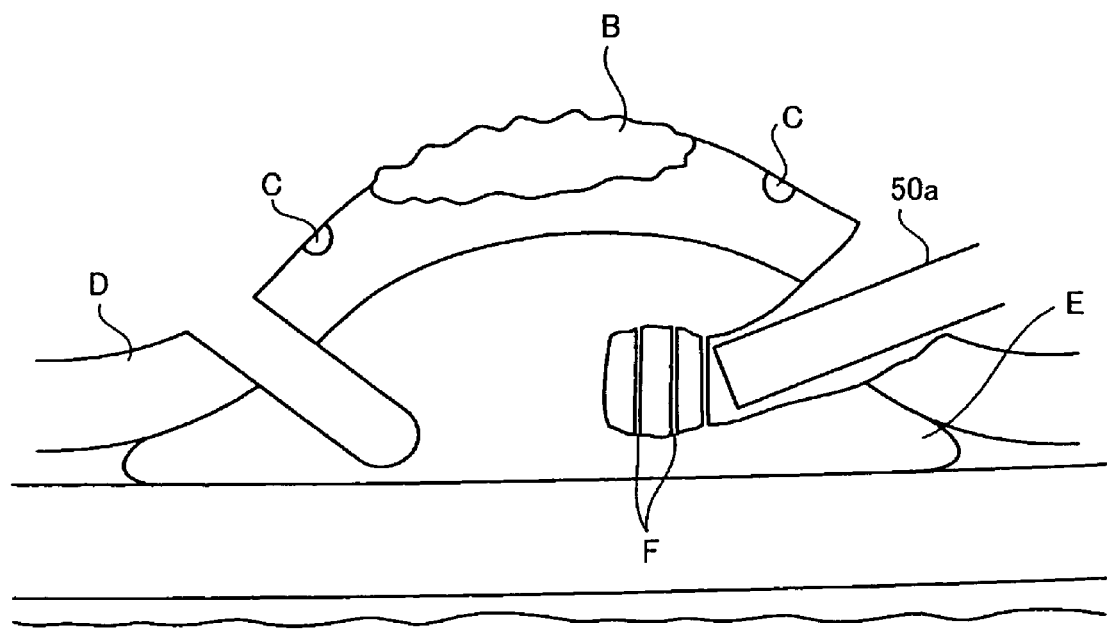
FIG. 13 shows how a submucosal tissue is ablated by the distal-end portion shown in FIG. 2.
Figure 14:
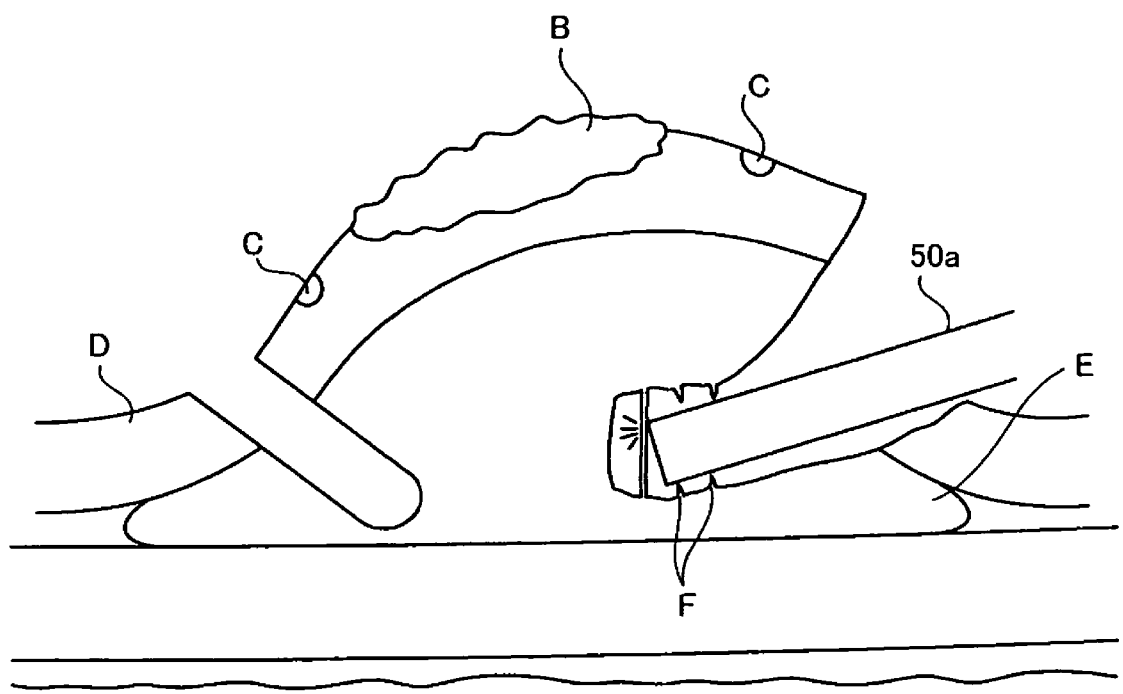
FIG. 14 shows how a submucosal tissue is ablated by the distal-end portion shown in FIG. 2.

Then, the tube 10 is taken out from the insertion unit 22 of the endoscope apparatus 1, instead the ultrasonic treatment apparatus 3 is inserted into the insertion unit 22 from the forceps insertion port 21d to generate the ultrasonic vibration, the surroundings of the living tissue (mucosa D) raised by the distal-end treatment unit 50a are incised as shown in FIG. 9 to FIG. 11, and the mucosa D is incised over all circumferences (Step 106). Further, in the first embodiment, a submucosal layer E existing below the mucosa D is peeled off as shown in FIG. 12 (Step 107). In this case, as shown in FIG. 13, the submucosal layer E is crushed into a jelly-like substance by the ultrasonic treatment. For a fiber F and a blood vessel shown in FIG. 13 and FIG. 14, the tissue having high elasticity is easily cut while hemostasis is performed by selecting the electric cautery function to cauterize and cut the fiber F and the blood vessel.

In the case of bleeding (Step 108), the hemostastic treatment is performed using the electric cautery function (Step 109). In order to recover the cut tissue specimen, instead of the ultrasonic treatment apparatus 3, for example a pair of grip forceps (not shown) is inserted from the forceps insertion port 21d into the channel 22b of the distal-end portion 22a, and the tissue specimen can be taken out while being gripped by the grip forceps.

Although the ultrasonic vibration function and the electric cautery function are individually driven in the first embodiment, the present invention is not limited to the first embodiment. For example, in the process of dissecting the submucosal layer, either or both of the ultrasonic vibration function and the electric cautery function may simultaneously be driven according to the treatment process.

Thus, in the first embodiment, the ultrasonic treatment apparatus includes the treatment unit having both the ultrasonic vibration function and the electric cautery function, the surroundings of the living tissue are incised to crush the living tissue by the ultrasonic vibration, and other incisions are performed by selecting any of the functions. Therefore, the heat damage of the tissue specimen to be cut off is prevented to obtain the proper tissue specimen, so that work necessary to cut the surroundings can be decreased as compared with the conventional art.

In the first embodiment, the distal-end treatment unit 50a of the ultrasonic transducer 50 has the hollow structure, so that a diameter of the distal-end treatment unit can be made smaller. Accordingly, in the case where the ultrasonic treatment apparatus is caused to function as the electric cautery, the current density is increased to efficiently generate the heat of the distal-end treatment unit, which allows the improvement of the operability.

Generally, for the electric cautery function, it is desirable that the current density be concentrated on one point. Therefore, the electric cautery is brought into point contact with the treated site, and the treated site is incised by the generated heat. In the first embodiment, since the distal-end treatment unit 50a of the ultrasonic transducer 50 is formed in the cylindrical hollow structure, an area is remarkably small in the distal-end portion of the distal-end treatment unit 50a, and the ultrasonic treatment apparatus can function as the electric cautery while functioning as the ultrasonic vibration, even when the distal-end portion is caused to abut against the treated site. However, sometimes it is necessary that the further effects be obtained as the ultrasonic vibration and the electric cautery.

Figure 15:
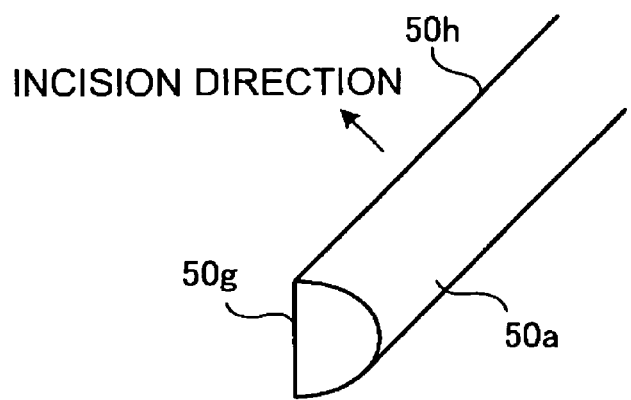
FIG. 15 is a perspective view of the distal-end portion of the insertion unit shown in FIG. 1 having a first exemplary configuration according to a second embodiment.

Therefore, in the second embodiment, as shown in a first exemplary configuration shown in FIG. 15 of the distal-end portion of the insertion unit, a sharp unit 50h having a sharp angle is formed at a tangential line between an outer periphery of the distal-end treatment unit 50a and a cut unit 50g by providing a cut-out portion in a part of the distal-end treatment unit 50a in a longitudinal direction. In the second embodiment, the treated site is incised with the use of the sharp unit 50h. That is, when the sharp unit 50h is orientated toward the incision direction to incise the mucosa D or submucosal layer E (for example, see FIG. 11) which is of the treated site by the electric cautery function, the sharp unit 50h having the high current density comes into linear contact with the treated site, and the treated site can be well incised by the generated heat.

In the case where the ultrasonic vibration function is used, similarly, when the sharp unit 50h is orientated toward the incision direction to incise the treated site by the ultrasonic vibration, the ultrasonically vibrating sharp unit 50h comes into contact with the treated site, and the treated site can be well incised. Therefore, in addition to the effects of the first embodiment, usability of the ultrasonic treatment apparatus can be improved.

Figure 16:
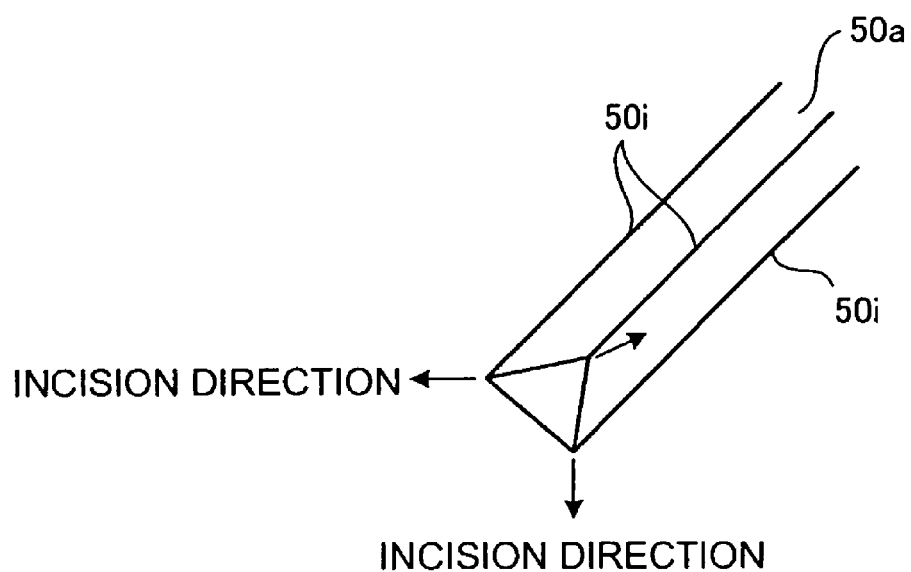
FIG. 16 is a perspective view of the distal-end portion of the insertion unit shown in FIG. 1 having a second exemplary configuration according to the second embodiment.

FIG. 16 is a perspective view of the distal-end portion of the insertion unit shown in FIG. 1 having a second exemplary configuration according to the second embodiment. In FIG. 16, the distal-end treatment unit 50a of the ultrasonic transducer 50 is formed by a triangle pole having a solid structure, and three sharp units 50i having angles sharper than that of the sharp unit 50h are formed in the tangential lines between the sides. In the second embodiment, the incision can be performed with the sharp units 50i orientated toward the three directions using the ultrasonic vibration function and the electric cautery function, and the usability of the ultrasonic treatment apparatus can be further improved as compared with the first example.

In the second embodiment, since the incision is performed with the sharp units 50i having angles sharper than that of the sharp unit 50h, the treated site can be incised further rapidly and securely.

Figure 17:
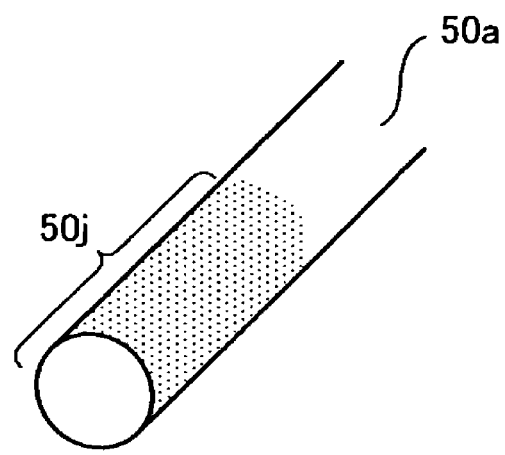
FIG. 17 is a perspective view of the distal-end portion of the insertion unit shown in FIG. 1 having a third exemplary configuration according to the second embodiment.

FIG. 17 is a perspective view of the distal-end portion of the insertion unit shown in FIG. 1 having a third exemplary configuration according to the second embodiment. In FIG. 17, similarly to the first embodiment, the distal-end treatment unit 50a of the ultrasonic transducer 50 is formed in the cylindrical solid structure. However, the third example differs from the first embodiment in that a roughened surface portion 50j which is formed in the roughened shape is provided on the outer peripheral surface.

An average interval between concavity and convexity in the roughened surface portion 50j is determined by the vibration amplitude of the ultrasonic transducer 50. For example, in the normal ultrasonic transducer, the vibration amplitude depends on a size thereof, and the vibration amplitude is about 0.3 mm at the maximum, and about 0.003 mm at the minimum. Therefore, in the second embodiment, the average interval between concavity and convexity in the roughened surface portion 50j is preferably set slightly smaller than the vibration amplitude, e.g., in the range of 0.002 mm to 0.2 mm.

Accordingly, in the second embodiment, when the roughened surface portion 50j is brought into contact with the treated site to perform the incision by the ultrasonic vibration, the vibration is transmitted to the distal-end treatment unit 50a to enhance friction between the roughened surface portion 50j and the treated site, which allows the treated site to be better incised as compared with the first embodiment.

Figure 18:
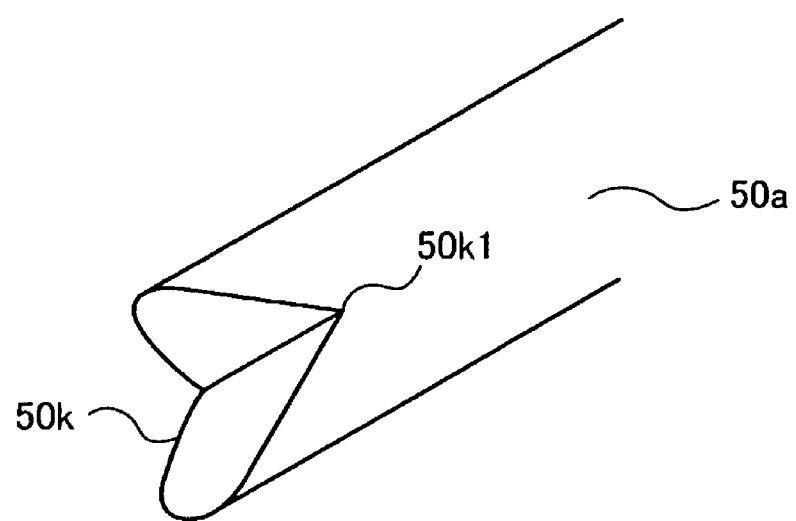
FIG. 18 is a perspective view of the distal-end portion of the insertion unit shown in FIG. 1 having a fourth exemplary configuration according to the second embodiment.

FIG. 18 is a perspective view of the distal-end portion of the insertion unit shown in FIG. 1 having a fourth exemplary configuration according to the second embodiment. In the drawings, similarly to the first embodiment, the distal-end treatment unit 50a of the ultrasonic transducer 50 is formed in the cylindrical shape having the solid structure. However, the fourth example differs from the first embodiment in that a rectangular opening 50k having a mouth angle 50k1 is provided at the distal end of the distal-end treatment unit 50a.

In the second embodiment, when the mucosa D or submucosal layer E (for example, see FIG. 11) which is the treated site is hooked by the mouth angle 50k1 to perform the ultrasonic vibration function or the electric cautery function, the treated site can better be incised as compared with the first embodiment.

Figure 19:
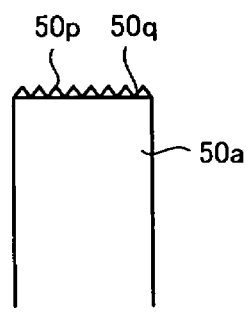
FIG. 19 is a side view of the distal-end portion of the insertion unit shown in FIG. 1 having a fifth exemplary configuration according to the second embodiment.

FIG. 19 is a side view of the distal-end portion of the insertion unit shown in FIG. 1 having a fifth exemplary configuration according to the second embodiment. In FIG. 19, similarly to the first embodiment, the distal-end treatment unit 50a of the ultrasonic transducer 50 is formed in the cylindrical shape having the solid structure. However, the fifth example differs from the first embodiment in that the distal end of the distal-end treatment unit 50a is formed in a sawtooth shape including plural convex portions 50p and concave portions 50q.

In the second embodiment, when the convex portions 50P and the concave portions 50q are caused to abut against the treated site to perform the ultrasonic vibration function and the electric cautery function, the distal-end treatment unit 50a is never moved from the treated site, so that the treated site can be incised at the optimum position.

Although the plural convex portions 50P and concave portions 50q are provided in the distal-end treatment unit in the second embodiment, the present invention is not limited to the second embodiment. For example, a pair of convex portion and concave portion may be provided, and only the convex portion or the concave portion may be provided in the distal-end treatment unit. In the case where only the convex portion or the concave portion is provided, the convex portion or the concave portion is preferably provided near the center of the distal end.

Figure 20:
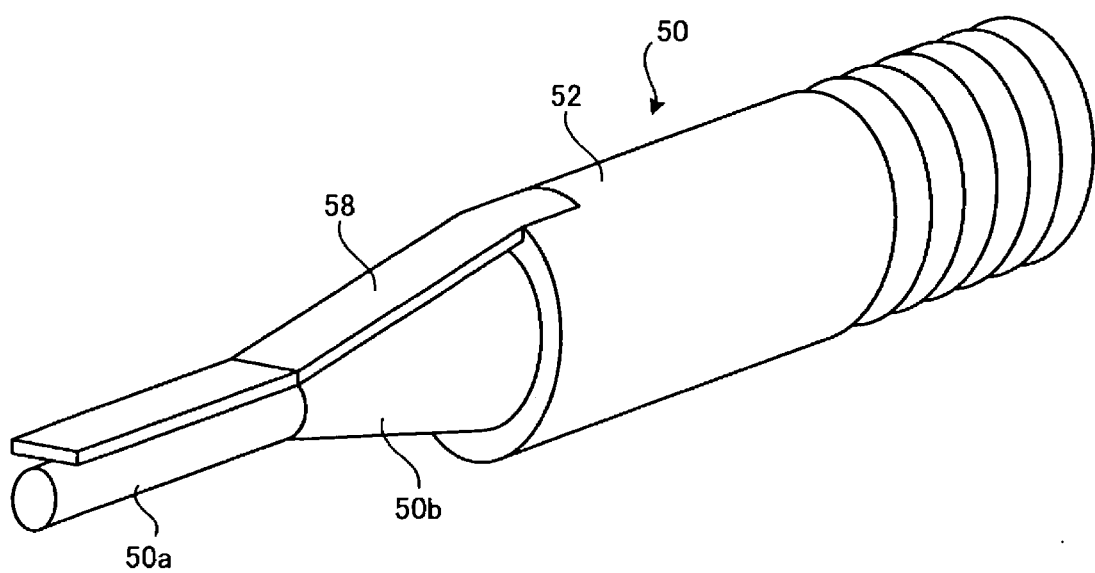
FIG. 20 is a perspective view of the distal-end portion of the insertion unit shown in FIG. 1 having a first exemplary configuration according to a third embodiment.

A third embodiment of the present invention will be described below. FIG. 20 is a perspective view of the distal-end portion of the insertion unit shown in FIG. 1 having a first exemplary configuration according to the third embodiment. A flat plate 58 is provided in the third embodiment. The flat plate 58 is fixed to the end portion of the cover 52, and the flat plate 58 is formed in the longitudinal direction of the ultrasonic transducer 50 while having a predetermined clearance between the distal-end treatment unit 50a and horn 50b. For example, the flat plate 58 is made of a Teflon (registered trademark) material. For example, the clearance between the flat plate 58 and the distal-end treatment unit 50a is set such that the mucosa D can be sandwiched between the flat plate 58 and the distal-end treatment unit 50a.

Figure 21:
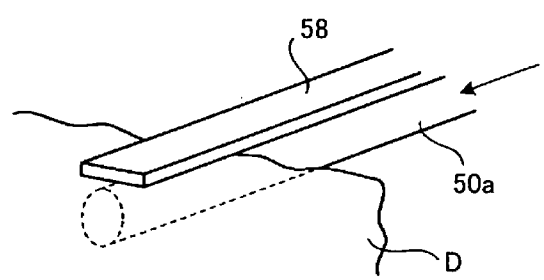
FIG. 21 is a perspective view for explaining a usage condition of the distal-end portion shown in FIG. 20.
Figure 22:
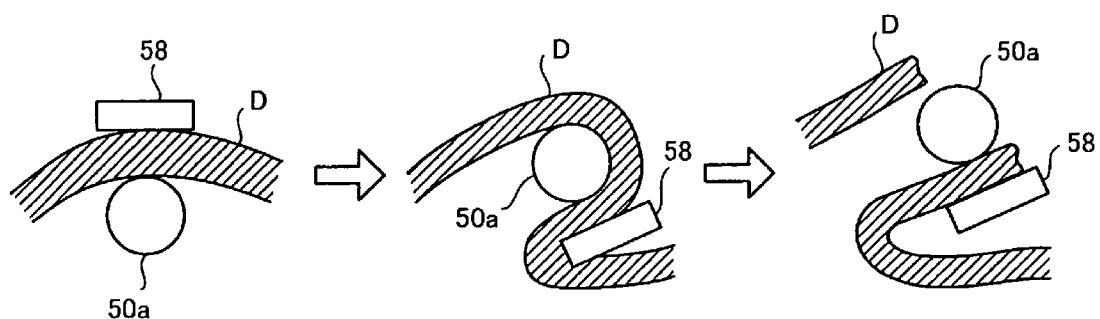
FIG. 22 is a front view for explaining the usage condition of the distal-end portion shown in FIG. 20.

In the third embodiment, the mucosa D is sandwiched between the distal-end treatment unit 50a and the flat plate 58 as shown in a perspective view of FIG. 21, and the ultrasonic treatment apparatus is twisted in a circumferential direction of the distal-end treatment unit 50a while the ultrasonic vibration is applied as shown in FIG. 22. Therefore, the mucosa D is entangled with the distal-end treatment unit 50a and flat plate 58 to apply tension to the mucosa D, which allows the mucosa D to be cut.

In the third embodiment, since the mucosa D sandwiched between the distal-end treatment unit 50a and the flat plate 58 is cut by twisting the mucosa, the mucosa can be incised more easily in addition to the effects of the first embodiment.

Figure 23:
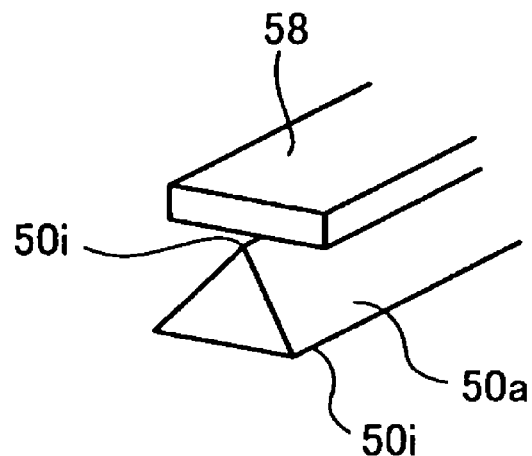
FIG. 23 is a perspective view of the distal-end portion of the insertion unit shown in FIG. 1 having a second exemplary configuration according to a third embodiment.
Figure 24:
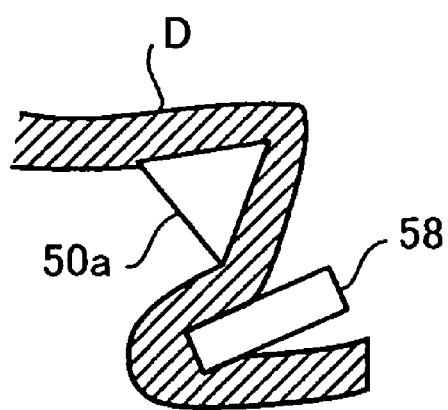
FIG. 24 is a front view for explaining a usage condition of the distal-end portion shown in FIG. 23.

FIG. 23 is a perspective view of the distal-end portion of the insertion unit shown in FIG. 1 having a second exemplary configuration according to a third embodiment. FIG. 24 is a front view for explaining a usage condition of the distal-end portion shown in FIG. 23. In the drawings, the distal-end treatment unit 50a formed by the triangle pole having the solid structure shown in FIG. 16 and the flat plate 58 shown in FIG. 20 are combined in the third embodiment.

In the third embodiment, the mucosa D is sandwiched and twisted between the flat plate 58 and the distal-end treatment unit 50a in which the sharp units 50i are formed, and the tension is further applied to the mucosa D. Therefore, the mucosa D can be cut, and the mucosa can be incised still more easily as compared with the first example.

A fourth embodiment of the present invention will be described below. Because the incision of the treated site has a directional property in the above embodiments, it is necessary that the flexible sheath 36 transmit a torque precisely. Therefore, the configuration of the flexible sheath 36 which precisely transmits the torque will be described in the fourth embodiment.

Figure 25:
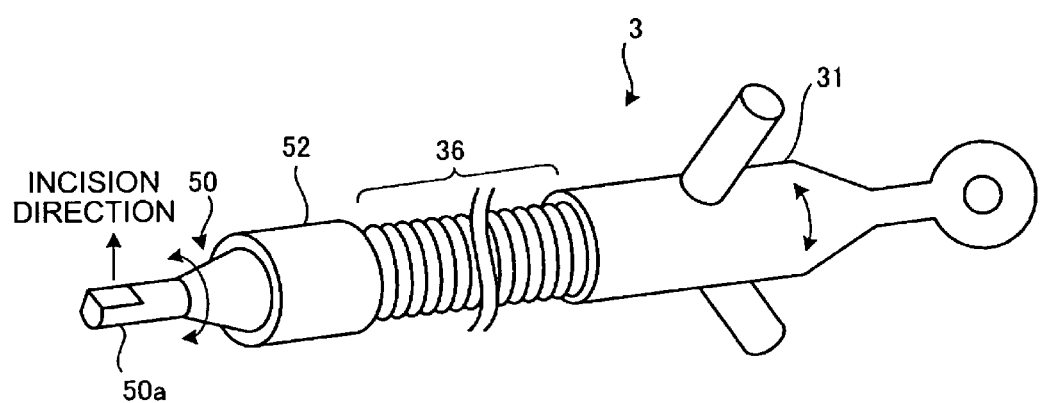
FIG. 25 is a perspective view of the ultrasonic treatment apparatus shown in FIG. 1 according to a fourth embodiment.
Figure 26:
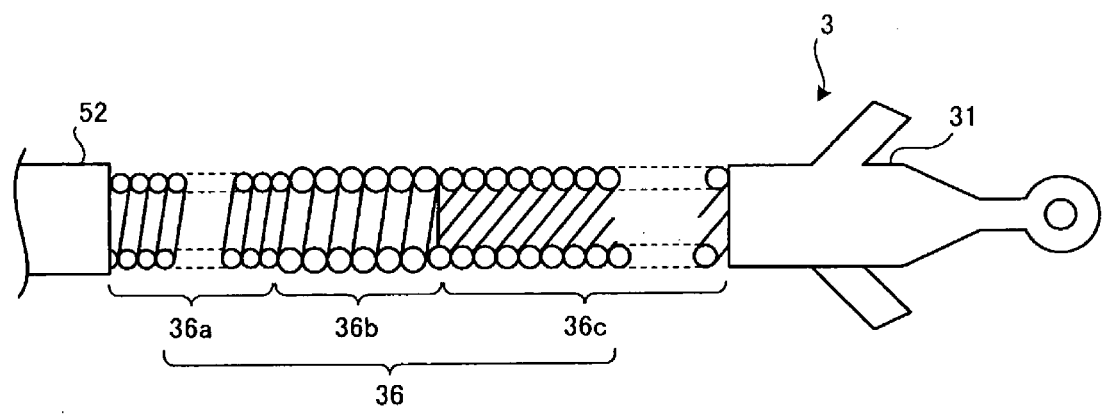
FIG. 26 is a sectional side view of a flexible sheath portion shown in FIG. 25.

FIG. 25 is a perspective view of the ultrasonic treatment apparatus shown in FIG. 1 according to the fourth embodiment. FIG. 26 is a sectional side view of the flexible sheath 36 portion shown in FIG. 25. In FIG. 25, in the fourth embodiment, the flexible sheath 36 is formed by three components, and the components are connected to one another while working with one another. That is, the flexible sheath 36 includes a sheath 36a which is connected to the cover 52 and formed by one strip of coil, a sheath 36b which is connected to the sheath 36a, and formed by one strip of coil whose element-wire diameter is larger than that of the sheath 36a, and sheath 36c which is connected to the sheath 36b and the operating unit 31, and formed by one apparent coil in which plural strips, e.g., three to five strips of coils are collectively wound.

For example, the sheaths 36a and 36b are formed by the right-handed coils, and the sheath 36c is formed by the left-handed coil. The element-wire diameter of the coil of the sheath 36c is formed smaller than the element-wire diameter of the coil of the sheath 36a. Therefore, spring force of the coil of the sheath 36c is strengthened to eliminate clearance, and transmission power of the torque is increased. The torque is transmitted to the sheath 36a having the smaller diameter through the sheath 36b having the larger diameter, and thereby the torque of the sheath 36c is precisely transmitted to the distal-end treatment unit 50a of the ultrasonic transducer 50.

Thus, the fourth embodiment includes the sheath which has three components, and the different components of the sheath are combined and used. Therefore, the torque from the operating unit 31, e.g., the torque of clockwise rotation or the torque of counterclockwise rotation is precisely transmitted to the distal-end treatment unit 50a through the sheath, so that the treated site can be well incised precisely.

Figure 27:
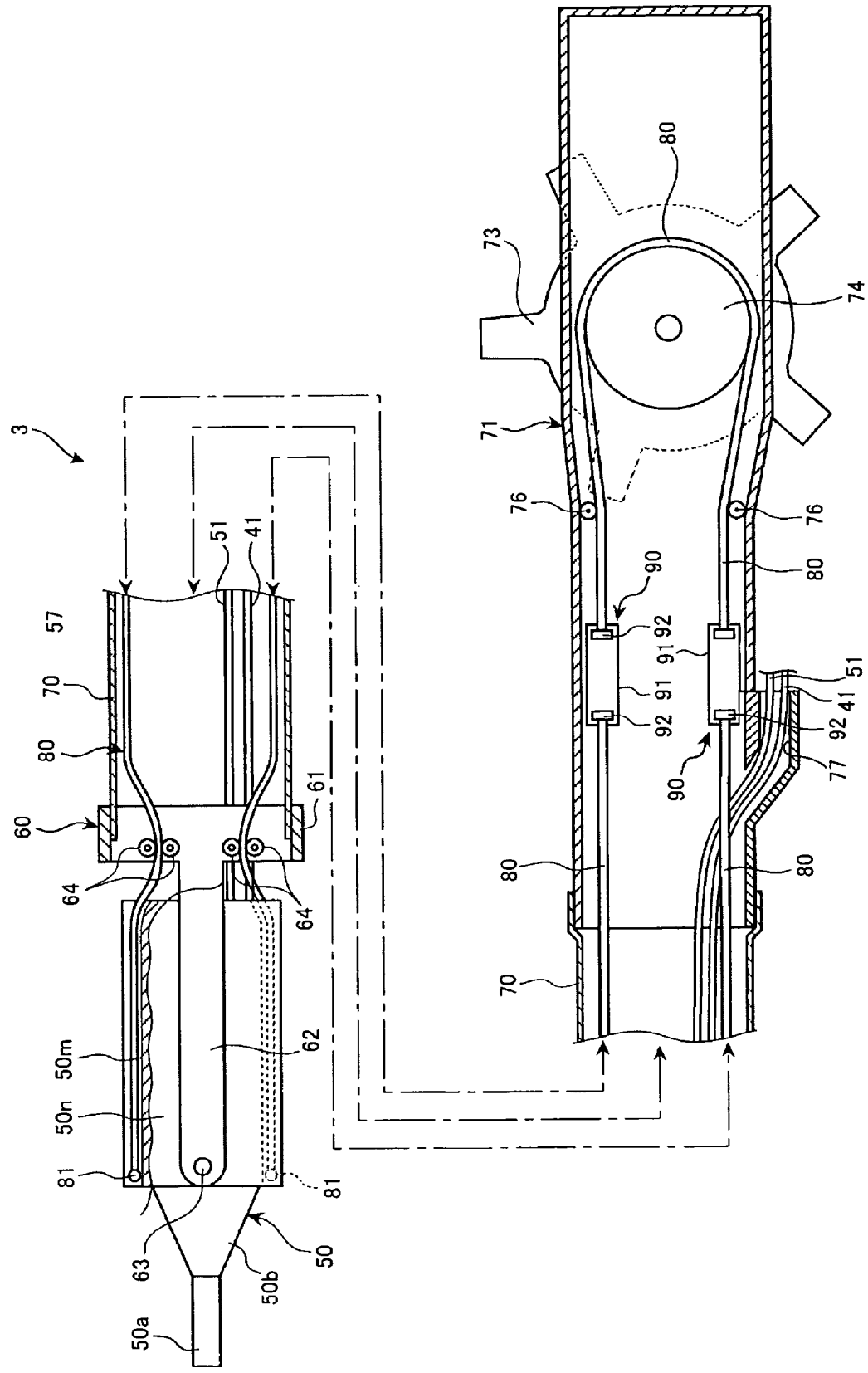
FIG. 27 is a partial sectional side view of the ultrasonic treatment apparatus according to a fifth embodiment in which an ultrasonic transducer can be oscillated.
Figure 28:
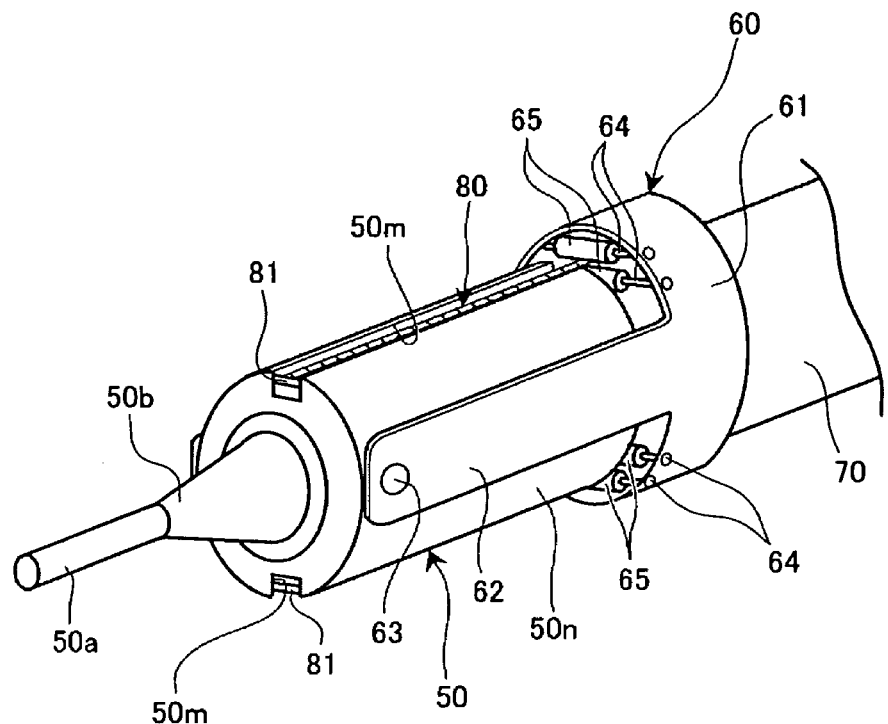
FIG. 28 is a perspective view of a distal-end portion of the ultrasonic treatment apparatus shown in FIG. 27.
Figure 29:
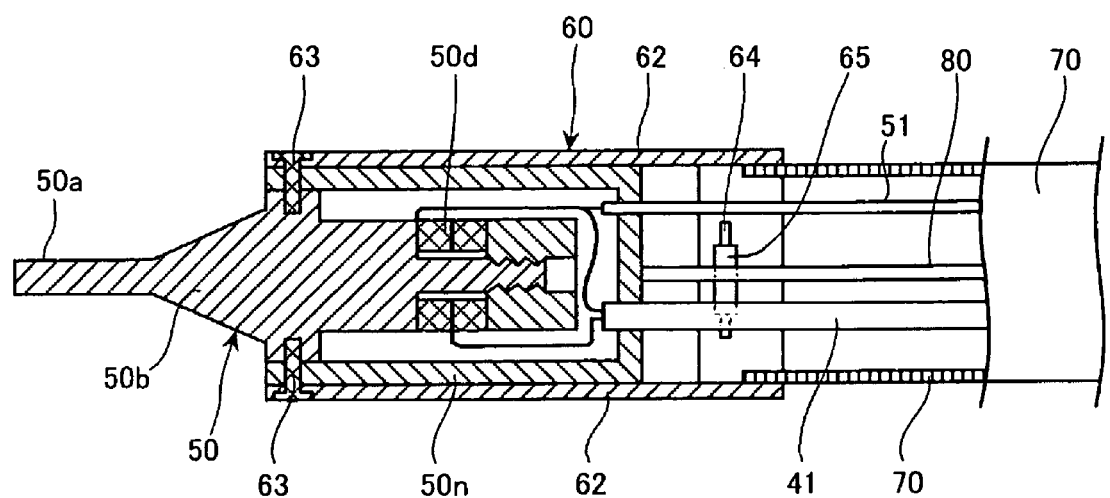
FIG. 29 is a sectional side view of the distal-end portion of the ultrasonic treatment apparatus shown in FIG. 28.
Figure 30:
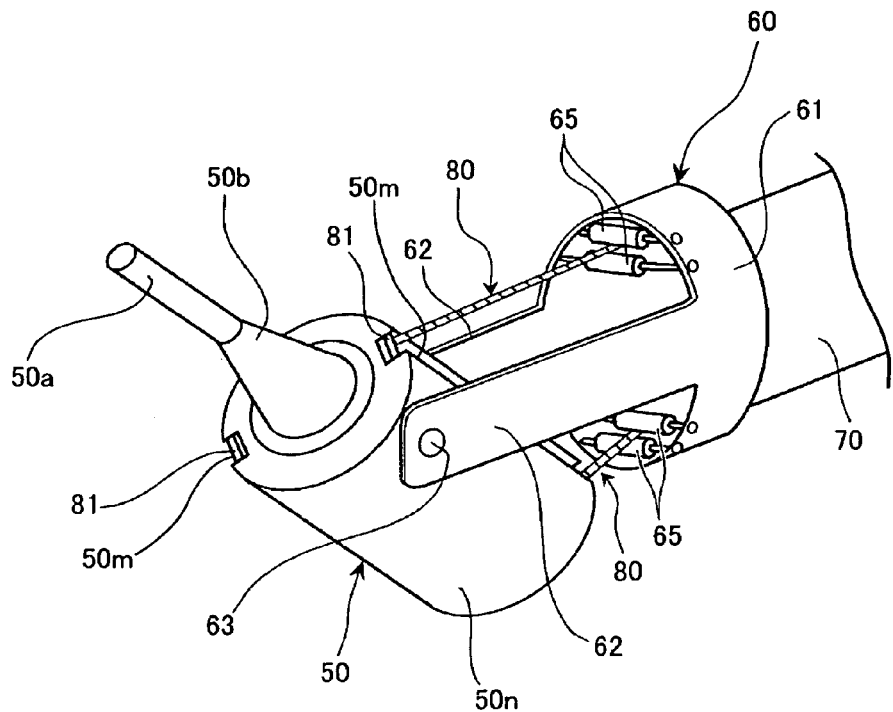
FIG. 30 is a perspective view of the ultrasonic transducer shown in FIG. 28 in an open state.

A fifth embodiment will be described below. FIG. 27 is a partial sectional side view of the ultrasonic treatment apparatus according to the fifth embodiment in which an ultrasonic transducer can be oscillated. FIG. 28 is a perspective view of a distal-end portion of the ultrasonic treatment apparatus shown in FIG. 27. FIG. 29 is a sectional side view of the distal-end portion shown in FIG. 28. FIG. 30 is a perspective view of the ultrasonic transducer shown in FIG. 28 in an open state. An oscillating mechanism of the ultrasonic transducer is substantially similar to that disclosed in Japanese Patent Application Laid-Open No. 2004-122868, and the oscillating mechanism will be described below.

In these drawings, the ultrasonic treatment apparatus 3 includes the ultrasonic transducer 50, a support cover 60, the electric power line 41 and electric current line 51, a sheath 70, and an operating wire 80.

The ultrasonic transducer 50 is arranged at the distal end of the ultrasonic treatment apparatus 3, the piezoelectric element 50d is provided at the back of the horn 50b, and the distal-end treatment unit 50a having the solid structure is provided in front of the horn 50b. The ultrasonic transducer 50 includes a cylinder 50n at the back of the horn 50b, and the cylinder 50n accommodates the piezoelectric element 50d. In FIG. 30, in the ultrasonic transducer 50, wire grooves 50m are formed along the longitudinal direction at upper and lower portions of the cylinder 50n respectively.

The support cover 60 is attached to the end portion of the sheath 70. As shown in FIG. 28, two support arms 62 extending in a forward direction of a cylindrical unit 61 are provided in the support cover 60, and the distal end of the support arm 62 is attached to the cylinder 50n by a support pin 63. The cylindrical unit 61 is formed by guide means for guiding the operating wire 80, and each of two sets of wire guides 65 are supported by a pin 64 and provided respectively at an upper and lower portions of the cylindrical unit 61.

At this point, the support pin 63 is attached to the cylinder 50n between the two wire grooves 50m of the outer periphery of the cylinder 50n while being located at the node position of the ultrasonic vibration. Therefore, the support cover 60 suppresses the influence of the ultrasonic vibration to the minimum, and the support cover 60 rotatably supports the ultrasonic transducer 50 around the support pin 63. As shown in FIG. 7, the two pairs of wire guides 65 provided in the upper and lower portions respectively are provided at the positions shifted toward the side of the support arm 62 with respect to the extending direction of the wire groove 50m. Therefore, the ultrasonic transducer 50 can effectively be rotated by the tension of the operating wire 80. The support pin 63 may be placed through the horn 50b. Instead of the support pin 63, two protrusions are provided at the node position of the ultrasonic vibration in the horn 50b, and the support cover 60 may support the ultrasonic transducer 50 using the protrusions.

As shown in FIG. 27, the electric signal lines 41 and 51 extend from the cylinder 50n, the electric signal lines 41 and 51 are guided to the outside from a leading port 77 of an operating unit 71 through the sheath 70, and end portions of the electric signal lines 41 and 51 are connected to the ultrasonic driving apparatus and high-frequency driving apparatus (not shown) respectively.

As shown in FIG. 27, in the sheath 70, the operating unit 71 is provided at one end, and the support cover 60 is attached at the other end. The end portion of the sheath 70 is fixed to the support cover 60 or the operating unit 71 by laser welding or a bonding agent.

The operating unit 71 is a portion which the operator grips by hand to operate the ultrasonic treatment apparatus 3. As shown in FIG. 27, in the operating unit 71, the leading port 77 of the electric signal lines 41 and 51 is provided near the coupling portion with the sheath 70. An operating dial 73 is provided at a substantially intermediate position of the outer surface in the operating unit 71, and a pulley 74 coaxial with the operating dial 73 is provided inside the operating unit 71. The operating dial 73 is rotated clockwise or counterclockwise to move the operating wire 80 along the longitudinal direction, which allows the ultrasonic transducer 50 to rotate about a support pin 63. The operating dial 73 includes a knob (not shown) which fixes the operating dial 73 to the operating unit 71 to hold the ultrasonic transducer 50 at a desired rotation position. When the knob is rotated in one direction, the knob loosens to release the fixation of the operating dial 73 to the operating unit 71. Therefore, the ultrasonic transducer 50 can freely be rotated with respect to the support cover 60. When the knob is rotated in the other direction, the knob tightens to fix the operating dial 73 to the operating unit 71. Therefore, the ultrasonic transducer 50 is held so as not to rotate with respect to the support cover 60. Guide rollers 76 are provided at appropriate positions inside the operating unit 71. The guide roller 76 guides the movement of the operating wire 80 along the longitudinal direction in association with the rotation of the operating dial 73.

In the operating wire 80, relaxation removers 90 are provided near the pulley 74 of the operating unit 71. The operating wire 80 is entrained about the pulley 74 at the midpoint thereof, both ends of the operating wire 80 are coupled to the outside of the ultrasonic transducer 50, and the operating wire 80 is arranged along the longitudinal direction in the sheath 70. At this point, the both ends of the operating wire 80 are arranged in the wire grooves 50m formed in the cylinder 50n, and the both ends are coupled to the node positions in the ultrasonic vibration outside the cylinder 50n by wire pins 81. Therefore, the ultrasonic vibration generated by the ultrasonic transducer 50 is never transmitted to the operating wire 80, and energy loss of the ultrasonic transducer 50 is suppressed.

The relaxation remover 90 is one which absorbs relaxation or tension of the operating wire 80 when the operating dial 73 is rotated. In the relaxation remover 90, a latching unit 92 having a large diameter is accommodated in a case 91. The latching unit 92 latches the end portion of the operating wire 80. For example, in FIG. 27, when the operating dial 73 is rotated clockwise, the upper-side operating wire 80 is pulled and tensed by the pulley 74 while the lower-side operating wire 80 is relaxed in the operating unit 71. Therefore, assuming that the state shown in FIG. 27 is set at a reference, in the ultrasonic transducer 50, as shown in FIG. 30, the distal end of the distal-end treatment unit 50a is orientated obliquely upward, and the rear portion of the cylinder 50n is lowered. When the operating dial 73 is rotated, the relaxation remover 90 absorbs the relaxation or the tension of the operating wire 80 so as not to entangle the operating wire 80, and thereby the ultrasonic transducer 50 is smoothly rotated counterclockwise. When the operating dial 73 is rotated counterclockwise, the lower-side operating wire 80 is pulled and tensed by the pulley 74 while the upper-side operating wire 80 is relaxed in the operating unit 71. Therefore, contrary to the state shown in FIG. 30, the distal end of the distal-end treatment unit 50a is orientated obliquely downward, and the rear portion of the cylinder 50n is lifted.

Figure 31:
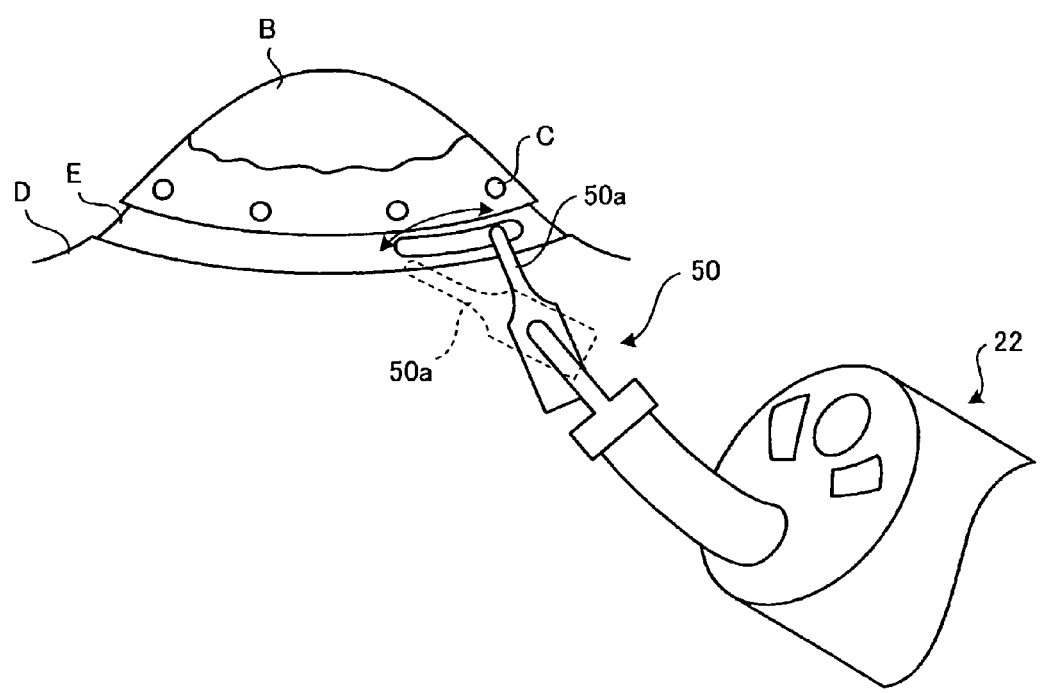
FIG. 31 is shows how the incision is performed by the ultrasonic treatment apparatus shown in FIG. 30.

When the ultrasonic treatment apparatus 3 having the above configuration is used for the incision of the treated site, e.g., the submucosal layer E, the same effects as the first embodiment are obtained, and the ultrasonic transducer 50 can perform the oscillating action as shown in FIG. 31 to perform the incision operation simply and rapidly. Therefore, the tissue specimen can be extracted more rapidly.

Figure 32:
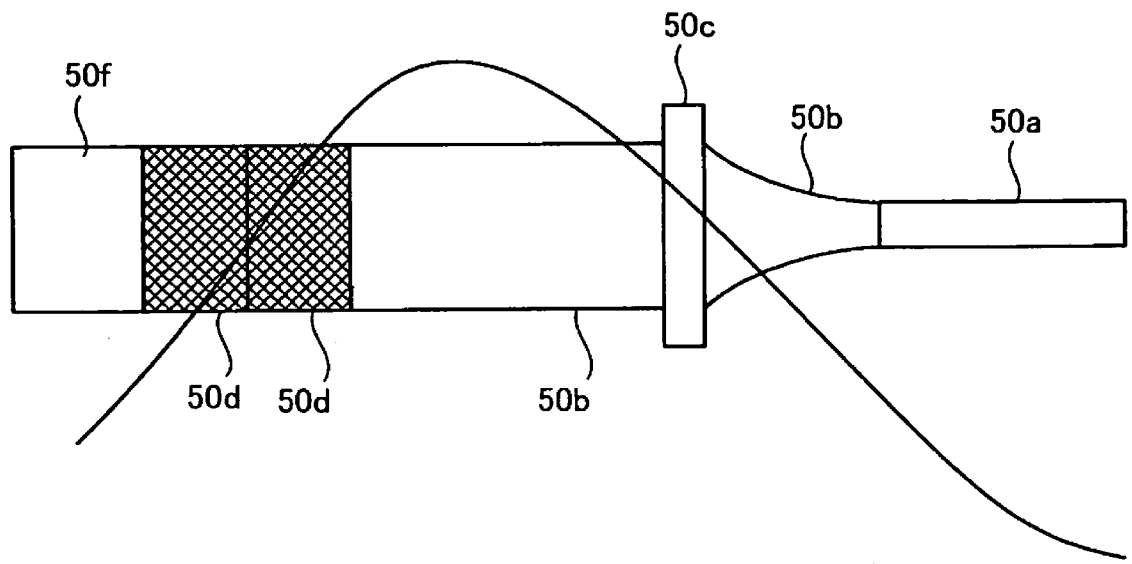
FIG. 32 is a side view of a ultrasonic transducer.

Sometimes the compact soft endoscope is used at frequencies of, e.g., 100 kHz, 150 kHz, and 200 kHz. In the case of the frequency of 100 kHz, the amplitude is set in the range of 16 to 40 μm. In the case of the frequency of 150 kHz, the amplitude is set in the range of 12 to 30 μm. In the case of the frequency of 200 kHz, the amplitude is set in the range of 8 to 20 μm. As shown in FIG. 32, the amplitude is set such that the distal-end portion of the distal-end treatment unit 50a comes to an antinode of the amplitude, and the flange 50c comes to the node of the amplitude.

Figure 33:
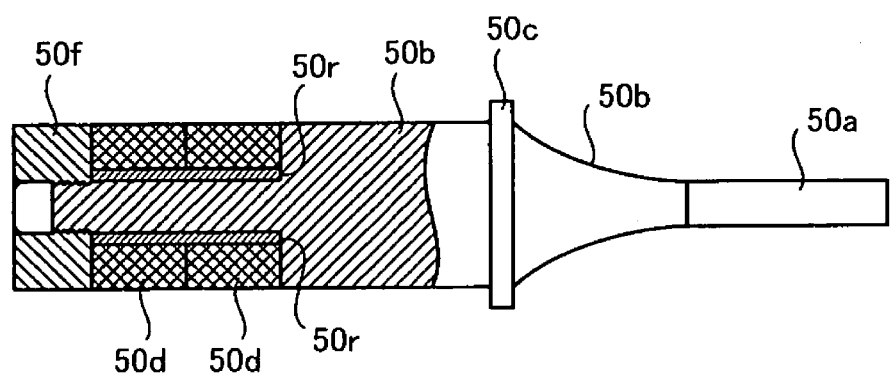
FIG. 33 is a partial sectional side view of the ultrasonic transducer shown in FIG. 32.

In FIG. 33, in the ultrasonic transducer 50, the horn 50b and the backing plate 50f are made of, e.g., a titanium alloy (Ti-6Al-4V), duralumin, or stainless steel to improve acoustic impedance. The piezoelectric element 50d is formed by, e.g., an electrostrictive strain element (PZT) which is strained when the voltage is applied. An insulating tube 50r located between the horn 50b and the piezoelectric element 50d is made of Teflon (registered trademark), polyamide, or the like to electrically insulate an anode and a cathode of the piezoelectric element 50d.

Figure 34:
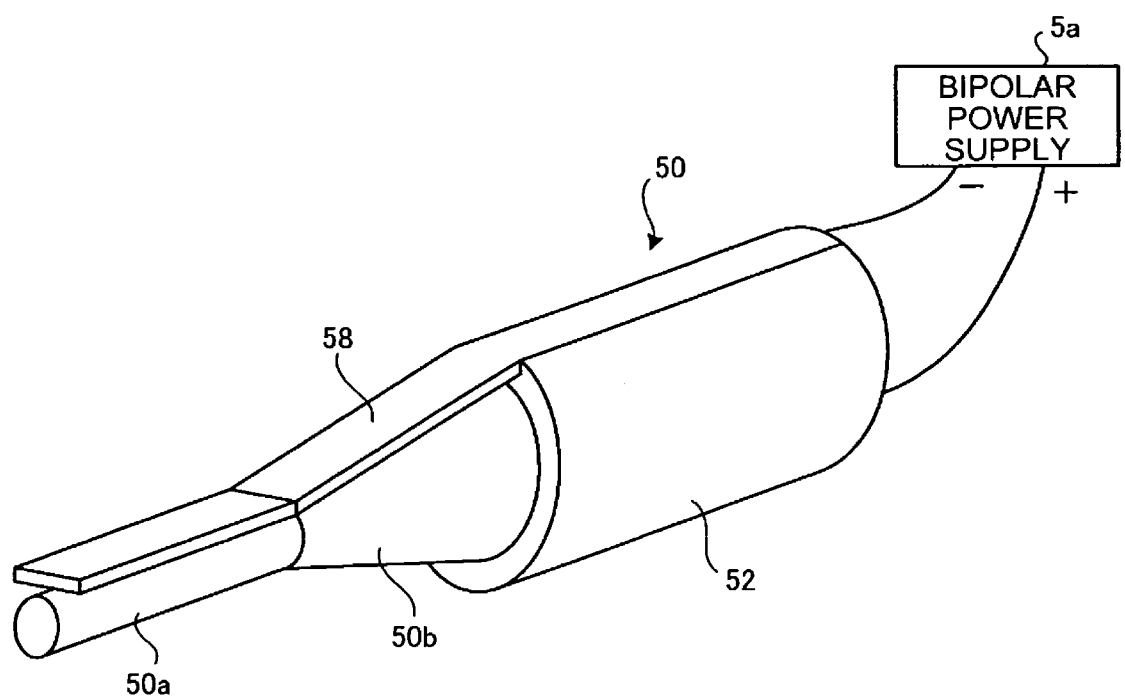
FIG. 34 is a perspective view of the ultrasonic treatment apparatus shown in FIG. 1 according to a sixth embodiment.
Figure 35:
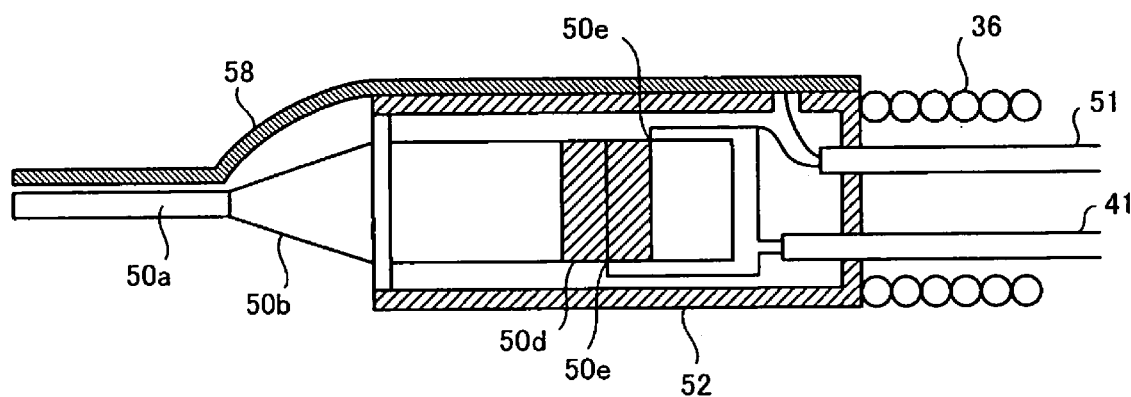
FIG. 35 is a sectional side view of the ultrasonic treatment apparatus of FIG. 34.

A sixth embodiment of the present invention will be described below. FIG. 34 is a perspective view of the ultrasonic treatment apparatus shown in FIG. 1 according to the sixth embodiment. FIG. 35 is a sectional side view of the ultrasonic treatment apparatus of FIG. 34. The flat plate 58 is provided in the sixth embodiment. The flat plate 58 is fixed to the outer surface in the longitudinal direction of the cover 52, and the flat plate 58 is formed in the longitudinal direction of the ultrasonic transducer 50 while having a predetermined clearance with the distal-end treatment unit 50a and horn 50b. Similarly to the third embodiment, the clearance between the flat plate 58 and the distal-end treatment unit 50a is set such that the mucosa D can be sandwiched between the flat plate 58 and the distal-end treatment unit 50a.

The flat plate 58 has a function of the counter electrode plate (electrode) shown in FIG. 3, the flat plate 58 is connected to the electric current line 51 at the end portion on the side of the cover 52, and the flat plate 58 is made of an electrically conductive material such as metal. A bipolar power supply 5a is provided as the high-frequency driving apparatus connected to the flat plate 58 and the ultrasonic transducer 50 which is the treatment unit, and the ultrasonic treatment apparatus is used as a bipolar treatment tool.

Figure 36:
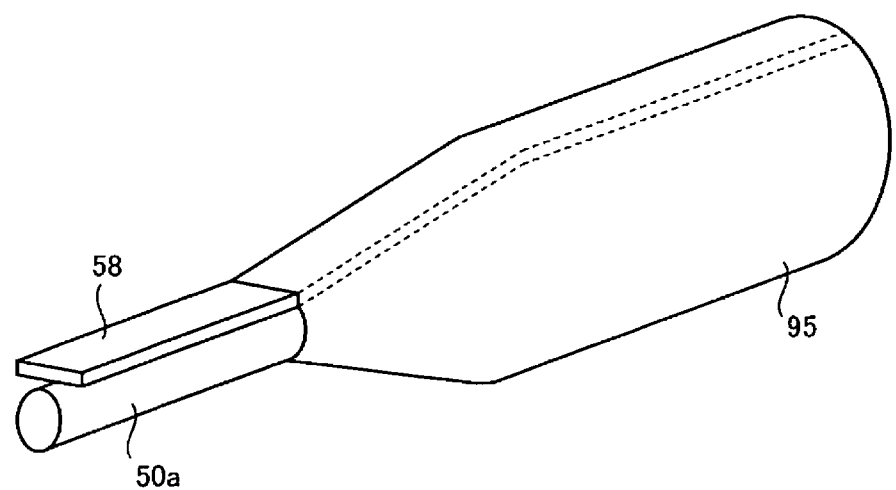
FIG. 36 is a perspective view of the ultrasonic treatment apparatus shown in FIG. 34, wherein the distal-end portion thereof is coated with an insulating heat-shrinkable tube.

Therefore, the cover 52 is made of an insulating material to prevent a short circuit between the electrode 50e and the flat plate 58, and the distal-end portion of the ultrasonic treatment apparatus except for the distal-end treatment unit 50a and a part of the flat plate 58 is coated with an insulating heat-shrinkable tube 95 in a insulating manner to prevent the short circuit from the channel as shown in FIG. 36.

Thus, in the sixth embodiment, the current can locally be passed through the human body because the current can be passed through the treated site such as the mucosa which is sandwiched between the distal-end treatment unit and the flat plate in the ultrasonic transducer, and the problem such as the short circuit can be prevented because the distal-end portion of the ultrasonic treatment apparatus is coated in the insulating manner.

Figure 37:
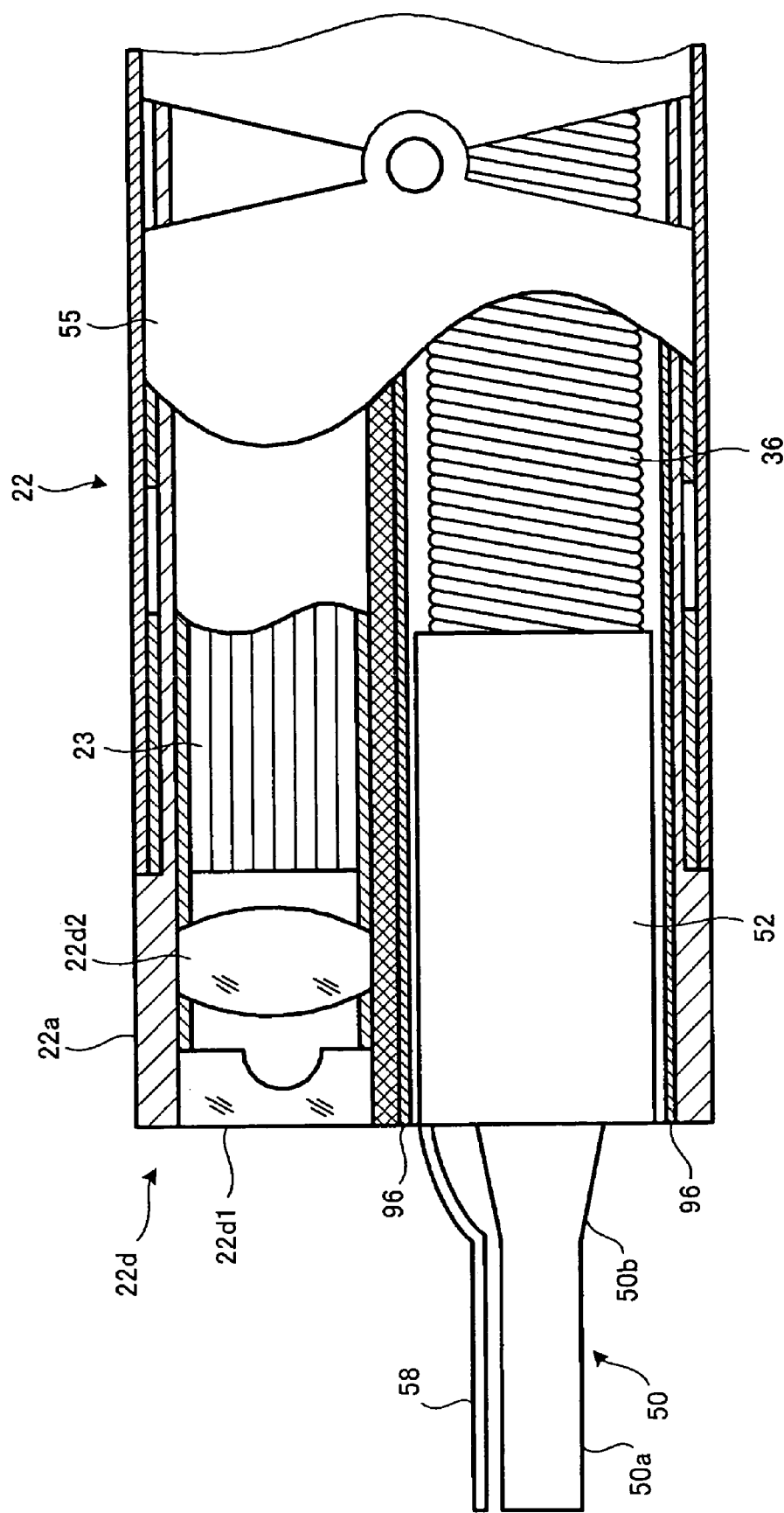
FIG. 37 is a perspective view of a distal end of the insertion unit whose inside channel is coated with an insulating member.

Although the distal-end portion of the ultrasonic treatment apparatus is coated in the insulating manner in the sixth embodiment, the present invention is not limited to the sixth embodiment. For example, as shown in FIG. 37, the inside of the channel of the insertion unit 22 can also be configured to be coated with an insulating member 96 to prevent the short circuit from the channel.

A seventh embodiment of the present invention will be described below. Because the ultrasonic treatment apparatus according to the present invention can use both the ultrasonic vibration function and the electric cautery function, sometimes the ultrasonic vibration and the electric signal of the electric cautery are mixed in the respective power supplies. There is a fear that the electric power cannot be supplied from each of the power supplies (ultrasonic driving apparatus 4 and high-frequency driving apparatus 5) unless the both functions are separated from each other. Therefore, a seventh embodiment provides an ultrasonic treatment apparatus which can insulate the both functions to stably drive the ultrasonic transducer even if the ultrasonic vibration and the electric signal of the electric cautery are outputted at the same time.

Figure 38:
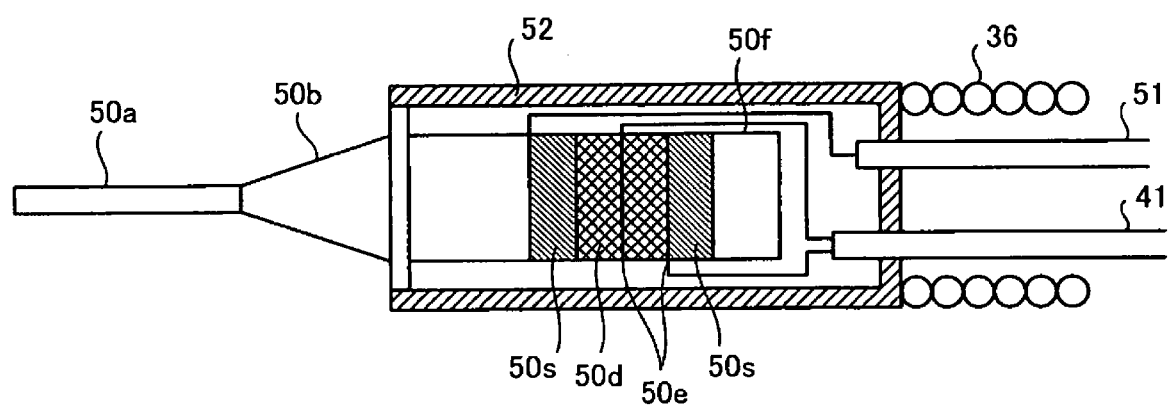
FIG. 38 is a sectional side view of a distal-end portion of an ultrasonic treatment apparatus according to a seventh embodiment.
Figure 39:
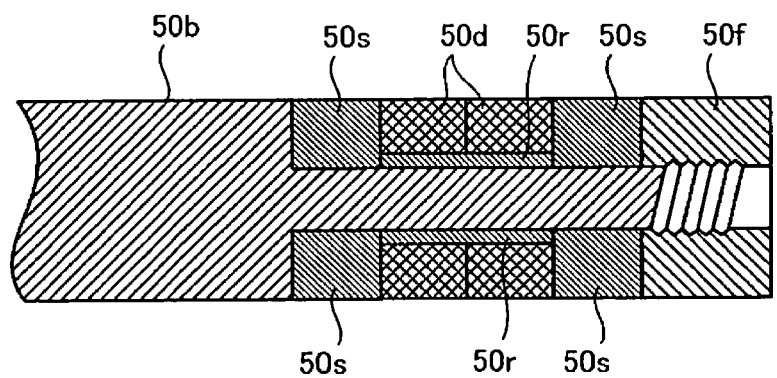
FIG. 39 is a sectional view of a part of the ultrasonic transducer shown in FIG. 38.

FIG. 38 is a sectional side view of a distal-end portion of an ultrasonic treatment apparatus according to the seventh embodiment. FIG. 39 is a sectional view of a part of the ultrasonic transducer shown in FIG. 38. In these drawings, in the seventh embodiment, insulating members 50s are provided so as to sandwich the piezoelectric element 50d. The insulating member is made of a material such as alumina. In the seventh embodiment, the electric power line 41 is connected to the electrode 50e of the piezoelectric element 50d, and the electric current line 51 is connected to the horn 50b located in front of the distal-end-side insulating member 50s. The insulating tube 50r is located between the horn 50b and the piezoelectric element 50d to enhance the insulating property.

Thus, in the seventh embodiment, because the electric power line and the electric current line are separately connected to the ultrasonic transducer through the insulating members, the ultrasonic vibration and the electric signal of the electric cautery are not mixed in the respective power supplies. Therefore, the both functions can stably be driven even if the ultrasonic vibration and the electric cautery are outputted at the same time.

Figure 40:
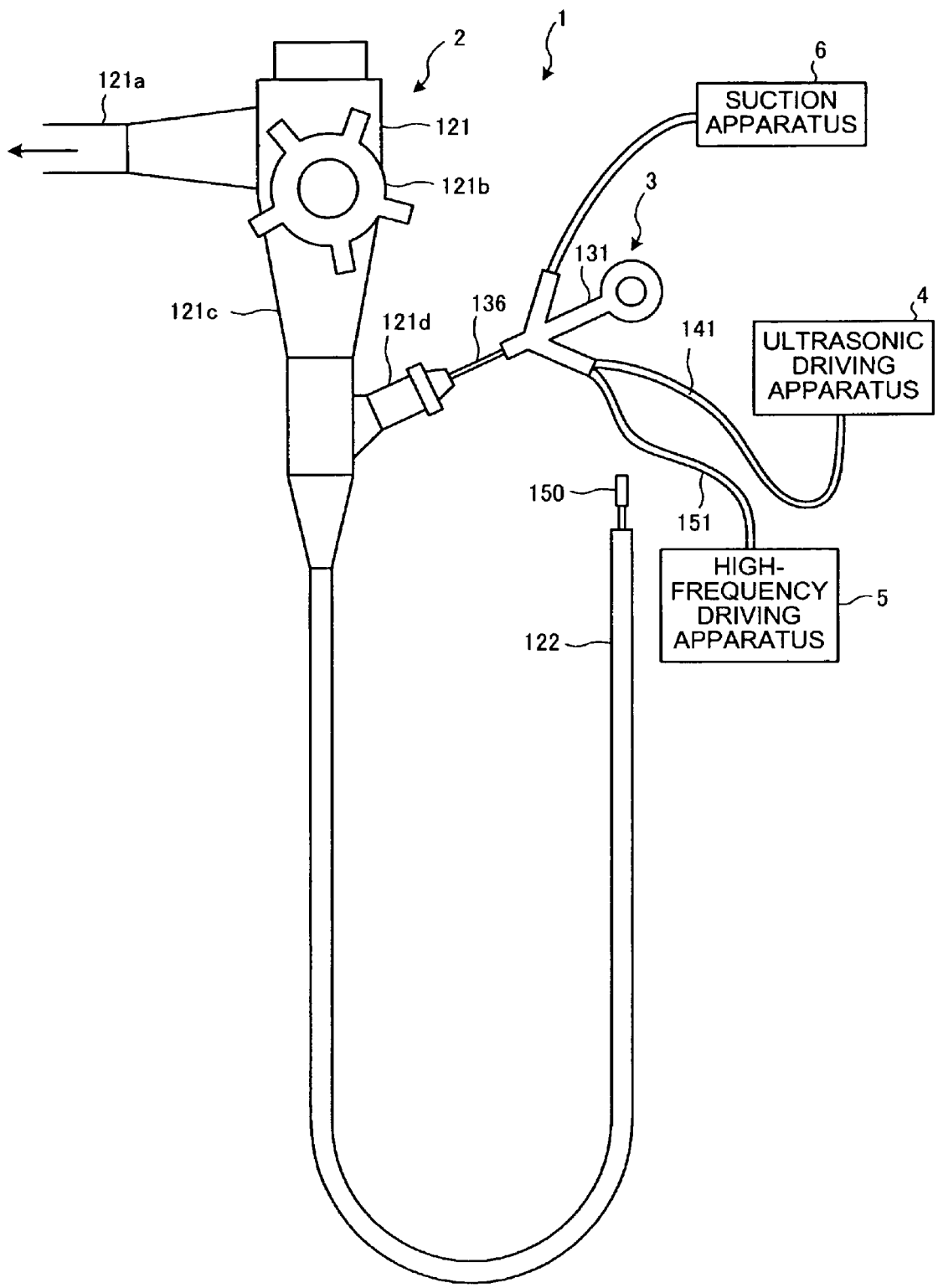
FIG. 40 is a schematic diagram of an endoscope apparatus which includes an ultrasonic treatment apparatus having a second exemplary configuration according to the present invention used in the endoscope apparatus.
Figure 41:
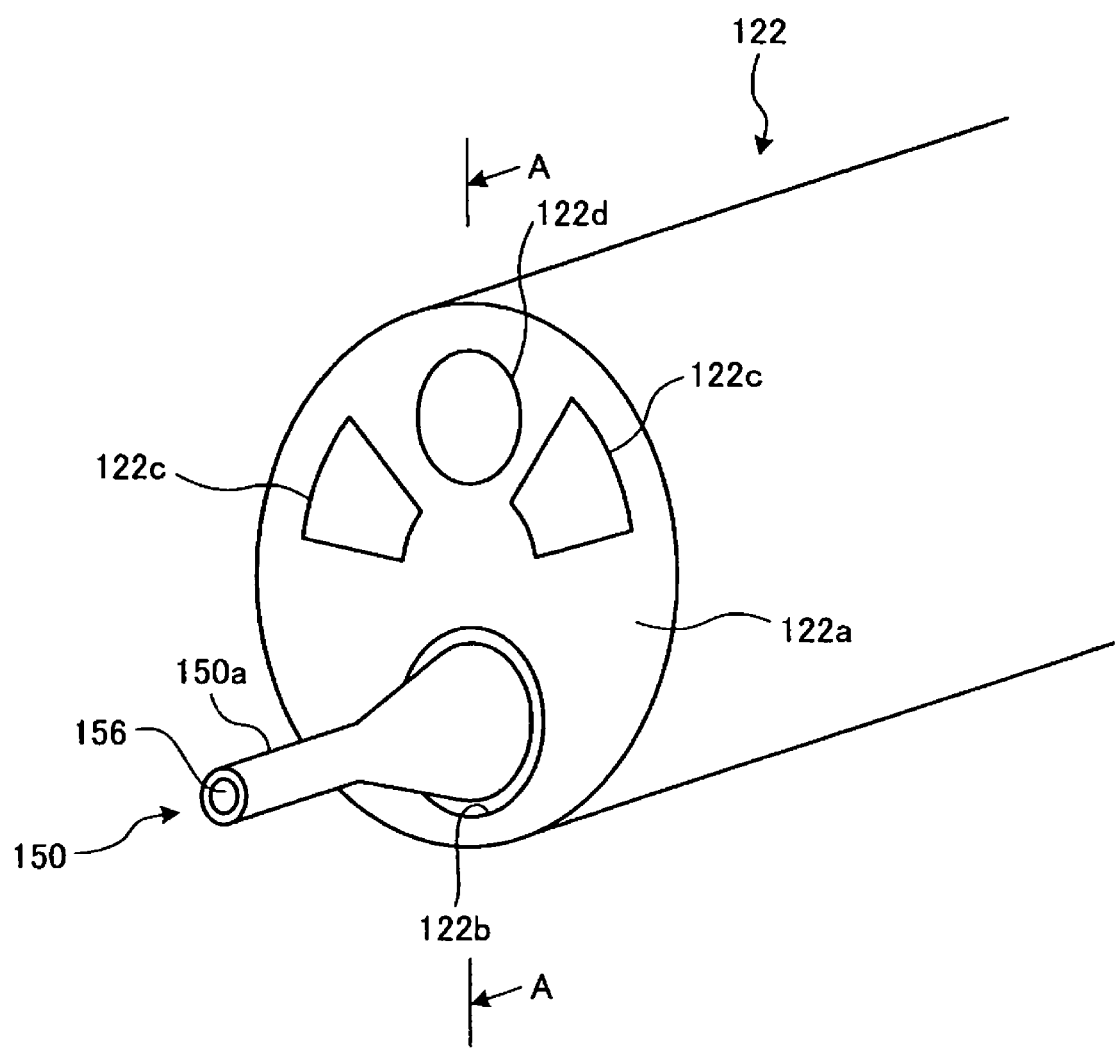
FIG. 41 is a perspective view of a distal-end portion of an insertion unit shown in FIG. 40 according to an eighth embodiment.
Figure 42:
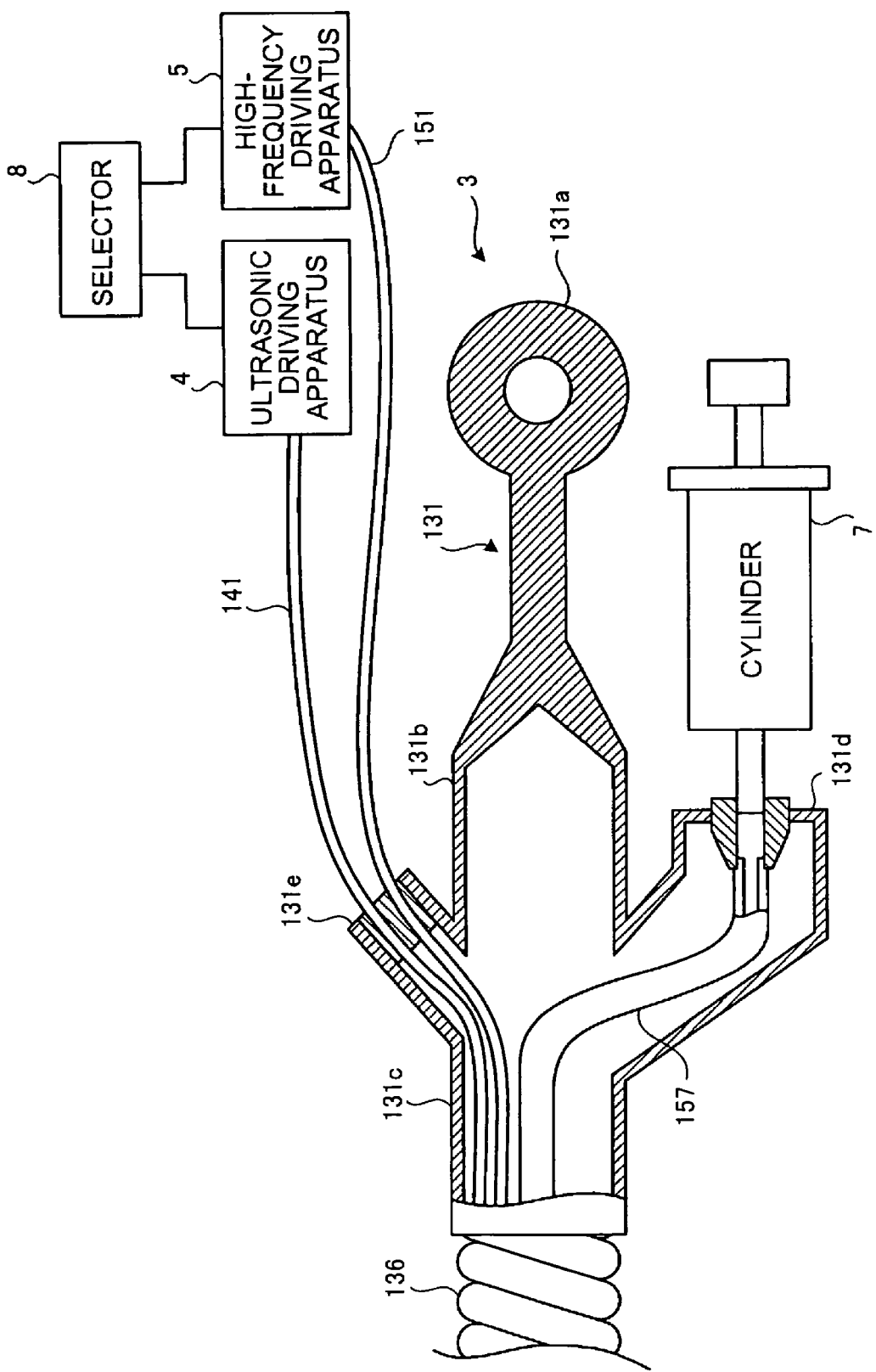
FIG. 42 is a sectional side view of an operating unit shown in FIG. 40.
Figure 43:
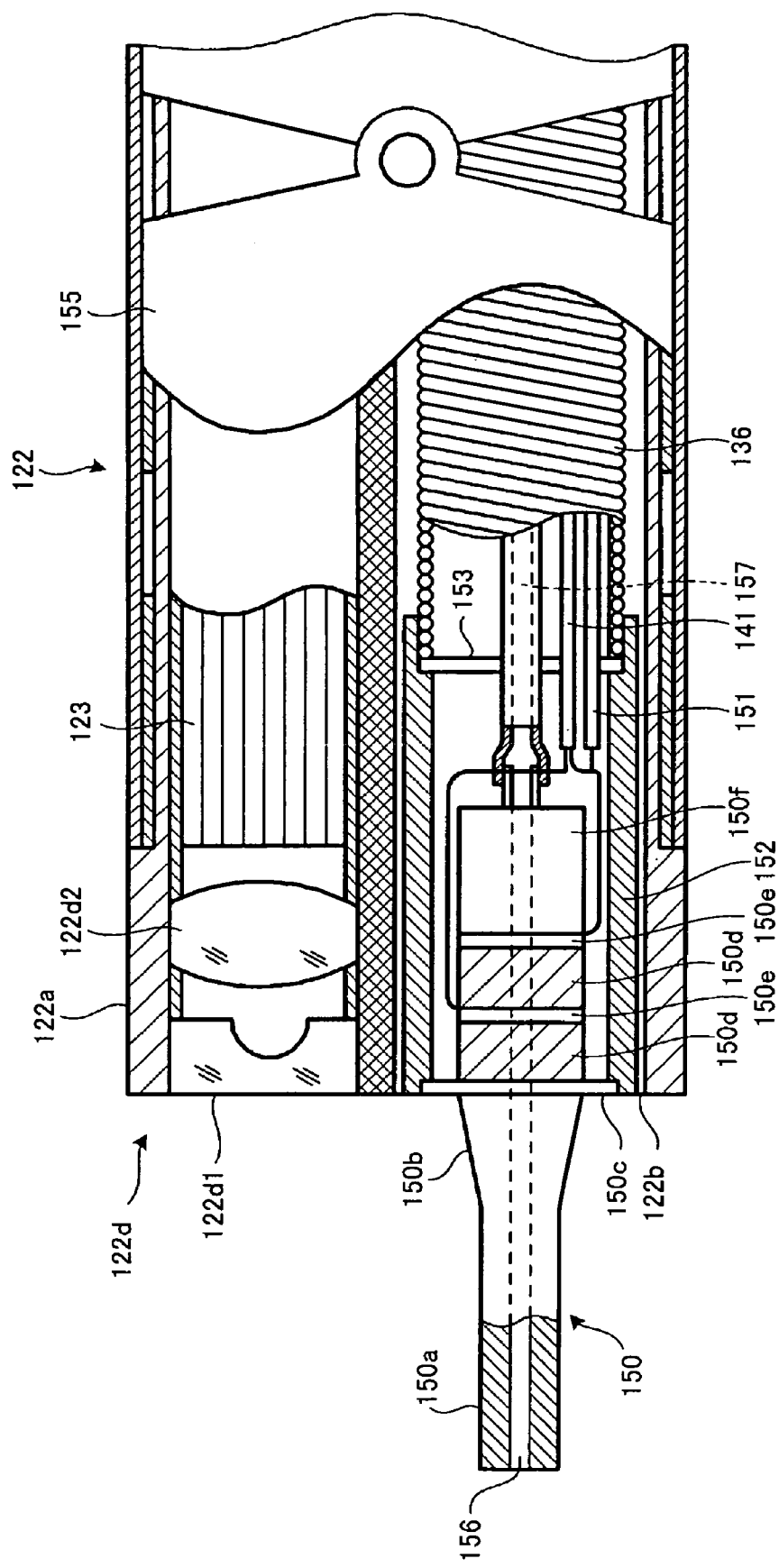
FIG. 43 is a sectional view of the insertion unit taken on line A-A of FIG. 41.

An eighth embodiment of the present invention will be described below. FIG. 40 is a schematic diagram of an endoscope apparatus which includes an ultrasonic treatment apparatus having a second exemplary configuration according to the present invention used in the endoscope apparatus. FIG. 41 is a perspective view of a distal-end portion of an insertion unit shown in FIG. 40 according to the eighth embodiment. FIG. 42 is a sectional side view of an operating unit shown in FIG. 40. FIG. 43 is a sectional view of the insertion unit taken on line A-A of FIG. 41. In these drawings, the endoscope apparatus 1 includes the videoscope 2 that is connected to the light source apparatus (not shown) and the display apparatus (not shown), the ultrasonic treatment apparatus 3, the ultrasonic driving apparatus 4 that is of the ultrasonic power supply unit which supplies the electric power to the ultrasonic treatment apparatus 3, the high-frequency driving apparatus 5 that is of the high-frequency power supply unit which supplies the current to the ultrasonic treatment apparatus 3, a suction apparatus 6 that is of a suction unit which can suck a substance from the outside through the tube in the sheath 136, and a cylinder 7 that is of a fluid supply unit which can supply a fluid to the tube. The ultrasonic treatment apparatus 3 and the ultrasonic driving apparatus 4 are connected to each other with an electric power line 141, and the ultrasonic treatment apparatus 3 and the high-frequency driving apparatus 5 are connected to each other with an electric current line 151. For example, the operator selects the suction apparatus 6 or the cylinder 7 and each of the suction apparatus 6 or the cylinder 7 is detachably provided in one tube.

The videoscope 2 includes a scope operating unit 121 provided on the proximal-end side of the insertion unit 122 and a thin cylindrical insertion unit 122 provided in the lower portion of the scope operating unit 121 and inserted into the subject. A flexible universal cord 121a is connected to the side face of the scope operating unit 121. The flexible universal cord 121a connects the scope operating unit 121 and the light source apparatus or display apparatus. A bending operation knob 121b is projected from the side face of the scope operating unit 121 at a different position from the position of the universal cord 121a. The bending operation knob 121b operates the bending action of the distal end of the insertion unit 122.

A grip unit 121c is provided in the scope operating unit 121. For example, an operator grips the grip unit 121c to hold and fix the videoscope 2. In the scope operating unit 121, a forceps insertion port 121d is projected on the side where the insertion unit 122 is attached. A pair of forceps which is of the ultrasonic treatment apparatus 3 according to the present invention is inserted into the forceps insertion port 121d. FIG. 40 shows a state in which the ultrasonic treatment apparatus 3 is inserted into the forceps insertion port 121d to project an operating unit 131, which operates the ultrasonic treatment apparatus 3, from the forceps insertion port 121d through a flexible sheath 136.

The insertion unit 122 inserted into the subject includes a distal-end portion 122a, a bending unit, and a flexible pipe. The distal-end portion 122a is provided at the distal end of the insertion unit 122, the bending unit is caused to perform the curving action by operating the scope operating unit 121, and the flexible pipe has flexibility. These units are configured to be aligned linearly. As shown in FIG. 41, a channel 122b is formed in the distal-end portion 122a of the insertion unit 122, and an ultrasonic transducer 150 of the ultrasonic treatment apparatus 3 is provided inside while being able to be projected. The distal-end portion 122a of the insertion unit 122 includes two lighting windows 122c, one observation window 122d, and an image guide fiber 123. The lighting window 122c includes a lighting system fixed to the distal end, the observation window 122d includes an observation system lens, and one end of the image guide fiber 123 is fixed to the observation window 122d. The lighting window 122c, the observation window 122d, and the image guide fiber 123 are of the component of the observation unit. The other end of the image guide fiber 123 provided in the insertion unit 122 is connected to the light source apparatus through the universal cord 121a.

One end of a lightguide fiber provided in the insertion unit 122 is provided in the lighting window 122c, and the other end is connected to the light source apparatus through the inside of the universal cord 121a. The outside, e.g., the treated site (living tissue) in the body cavity is illuminated with the illumination light emitted from the light source apparatus from the lighting window of the distal-end portion 122a through the lightguide fiber. The observation system lens includes, e.g., two lenses 122d1 and 122d2. The observation system lens takes in the light reflected from the treated site in the body cavity, and the observation system lens emits the light to an image guide fiber 123. The reflected light emitted from the observation system lens is sent through the image guide fiber 123 to the display apparatus located on the other end, the image of the treated site is displayed on the display apparatus to allow the operator to observe the treated site.

The ultrasonic treatment apparatus 3 includes an operating unit 131, the ultrasonic transducer 150, the electric power line 141, the electric current line 151, a cylindrical cover 152, a partition 153, and the flexible sheath 136. The operating unit 131 has a three-way configuration shown in FIG. 40. The ultrasonic transducer 150 is provided at the distal end as shown in the sectional view of FIG. 43. The electric power line 141 supplies the electric power to the ultrasonic transducer 150. The electric current line 151 supplies the electric current to the ultrasonic transducer 150. The cylindrical cover 152 fixes the ultrasonic transducer 150. The partition 153 keeps the watertight of the piezoelectric element and electrode of the ultrasonic transducer 150. The electric power line 141 and the electric current line 151 are inserted into the flexible sheath 136, and one end of the flexible sheath 136 is coupled to the cover 152 consisted of a rigid member. The partition 153 is arranged in a coupling portion between the cover 152 and the flexible sheath 136. One end of the flexible sheath 136, in which one piece of wire is wound in a spiral manner, is connected to the operating unit 131. The operator manually inserts or draws the flexible sheath 136 into or from the videoscope 2 to retractably move the flexible sheath 136 in the insertion unit 122. For example, the flexible sheath 136 is inserted into the videoscope 2 through the forceps insertion port 121d. The flexible sheath 136 is moved toward a direction of the distal-end portion 122a in the channel of the insertion unit 122, the ultrasonic transducer 150 and a part of the cover 152 are projected from the distal-end portion 122a, and the treatment is performed with the electric cautery in which the ultrasonic vibration or high-frequency current of the ultrasonic transducer 150 is utilized. The flexible sheath 136 is moved toward the direction of the operating unit 131 in the channel of the insertion unit 122 to store the ultrasonic transducer 150 and cover 152 in the distal-end portion 122a.

The ultrasonic transducer 150 is made of an electrically conductive material such as titanium. The ultrasonic transducer 150 includes a distal-end treatment unit 150a, a horn 150b, a flange 150c, a piezoelectric element 150d, an electrode 150e, and a backing plate 150f. The cylindrical distal-end treatment unit 150a has a hollow structure. The horn 150b transmits the ultrasonic vibration to the distal-end treatment unit 150a. The flange 150c fixes the ultrasonic transducer 150 to the cover 152. The piezoelectric element 150d generates the ultrasonic vibration. The electrode 150e is connected to the electric power line 141, and the electrode 150e supplies an electric signal to the piezoelectric element 150d. The ultrasonic driving apparatus 4 supplies an electric power signal to the piezoelectric element 150d through the electric power line 141 and the operating unit 131. The piezoelectric element 150d receives the electric power signal to generate the ultrasonic vibration having a frequency of 100 kHz. The generated ultrasonic vibration passes through the horn 150b having the drawn shape to enlarge the vibration amplitude, and the ultrasonic vibration is transmitted to the distal-end treatment unit 150a. The flange 150c is provided at the node position of the vibration, and the flange 150c is fixed to the end portion of the cover 152.

The electric current line 151 is connected to the electrode 150e. The current signal is supplied from the high-frequency driving apparatus 5 through the electric current line 151, the operating unit 131, and a driving port 131e of the operating unit 131, which enables the ultrasonic treatment apparatus 3 to function as the electric cautery having, e.g., a frequency of 350 kHz. The ultrasonic treatment apparatus 3 includes the selector 8. The operator can select the treatments with the electric cautery, in which the ultrasonic vibration or high-frequency current is utilized, by the selector 8. The selector 8 is connected to the ultrasonic driving apparatus 4 and high-frequency driving apparatus 5 to enable the selection of the supply of the electric power and/or the supply of the electric current. Hereinafter the electric power signal and the current signal are collectively referred to as electric signal, and the electric power line and the electric current line are collectively referred to as electric signal line. In the eighth embodiment, the frequency of the ultrasonic vibration is set at 100 kHz, and the frequency of the electric cautery is set at 350 kHz. However, the present invention is not limited to the eighth embodiment. For example, the frequencies may be selected from a range where resonance is not generated between the frequencies of the ultrasonic vibration and electric cautery.

In the ultrasonic transducer 150, a hollow treatment pipe 156 is formed in a central axis in the longitudinal direction of the distal-end treatment unit 150a, and a treatment tube 157 is connected to the rear end of the treatment pipe 156. The other end of the treatment tube 157 pierces through the partition 153, and the other end is connected to the suction apparatus 6 or the cylinder 7 at a solution injection port 131d through the inside of the flexible sheath 136 and the operating unit 131. In the above configuration, the emulsified or crushed living tissue or unnecessary body fluid, which flows in from the treatment pipe 156, can be caused to pass through the tube 157 to be discharged outside the ultrasonic treatment apparatus 3 by the suction action of the suction apparatus 6. The physiological salt solution or chemicals which flow into the tube 157 by the cylinder 7 are dispersed to the outside from the distal end of the treatment pipe 156.

As shown in FIG. 42, the operating unit 131 includes a substantially cylindrical operating unit main body 131a, a ring unit 131b, and a three-way joint unit 131c. The ring unit 131b is provided at one end of the operating unit main body 131a. The three-way joint unit 131c is provided at the other end of the operating unit main body 131a, and the three-way joint unit 131c inserts the tube 157 into the flexible sheath 136. The tube 157 is connected to the electric signal lines 141 and 151 run from the pieces of driving apparatus 4 and 5 and also to the cylinder 7. The operating unit 131 can also includes an instruction button which is of the selector 8 for providing an instruction of selecting the supply of the electric power and/or the supply of the electric current from the driving apparatus 4 or 5.

As described above, the electric signal lines 141 and 151 are inserted from the driving port 131e, the electric signal lines 141 and 151 are bent in the joint unit 131c, and the electric signal lines 141 and 151 are connected through the inside of the flexible sheath 136 to the ultrasonic transducer 150 provided at the distal end of the insertion unit 122. This enables the electric signal to be supplied to the ultrasonic transducer 150. As described above, the suction apparatus 6 and the cylinder 7 are connected to each other using the tube 157 and the solution injection port 131d. The tube 157 is bent inside the joint unit 131c, and the suction apparatus 6 and the cylinder 7 are connected through the inside of the flexible sheath 136 to the treatment pipe 156 of the ultrasonic transducer 150 provided at the distal end of the insertion unit 122. This enables the fluid to be sucked or dispersed from the treatment pipe 156.

The endoscope apparatus 1 includes a bending block 155 in the insertion unit 122 near the distal-end portion 122a. The bending block 155 is connected to the bending operation knob 121b, and the bending operation knob 121b is operated to enables the distal end of the insertion unit 122 of the endoscope apparatus 1 to be bent. For example, the endoscope apparatus 1 is consisted of a compact soft endoscope in which the insertion unit 122 has the flexibility.

Figure 44:
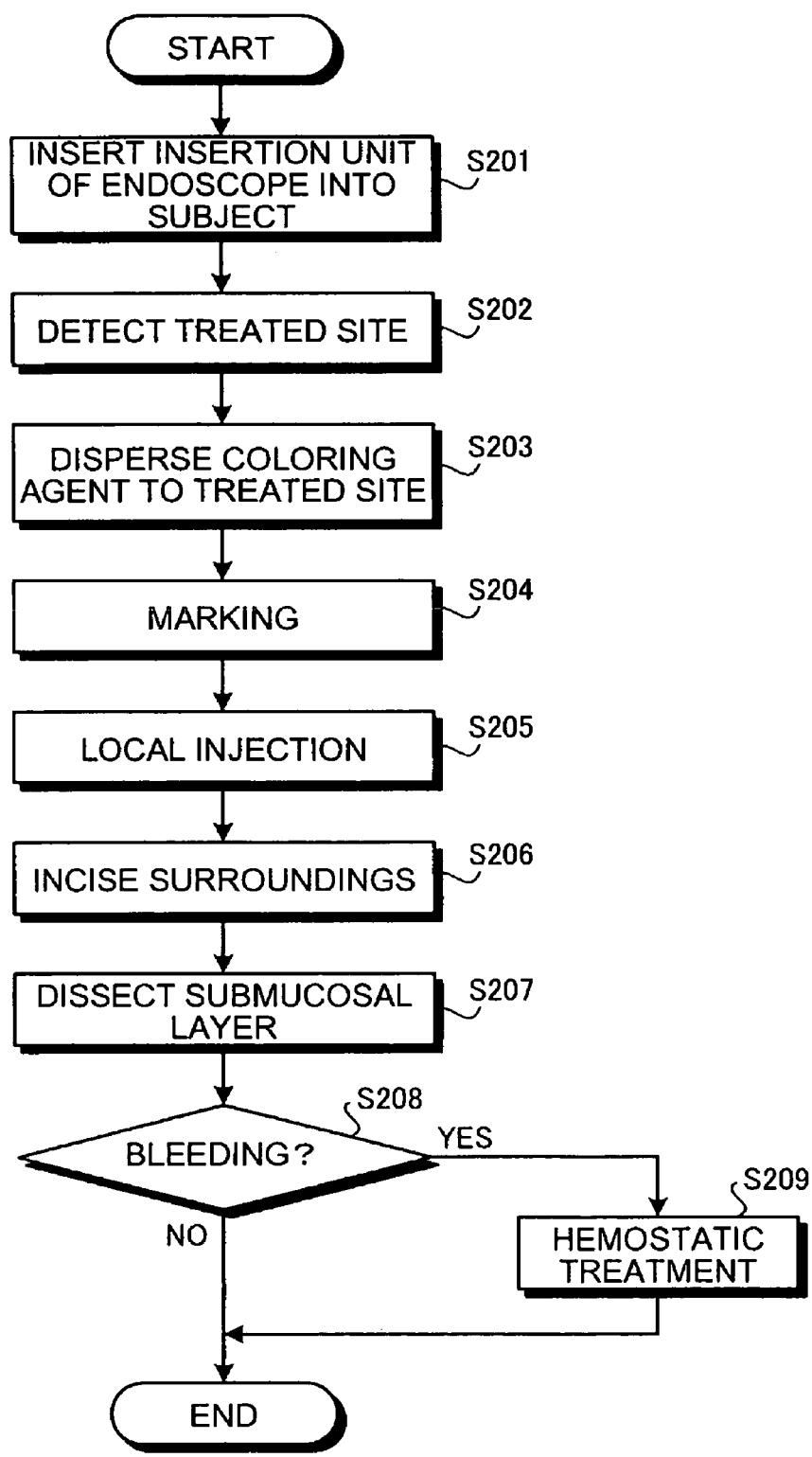
FIG. 44 is a flowchart of a treatment procedure of the ultrasonic treatment apparatus shown in FIG. 40.

The treatment action of the ultrasonic treatment apparatus will be described with reference to FIG. 44 to FIG. 56. In this configuration, FIG. 44 is a flowchart of the treatment procedure of the ultrasonic treatment apparatus, and FIG. 45 to FIG. 56 show respective processes of the treatment procedure in the incision operation.

Figure 45:
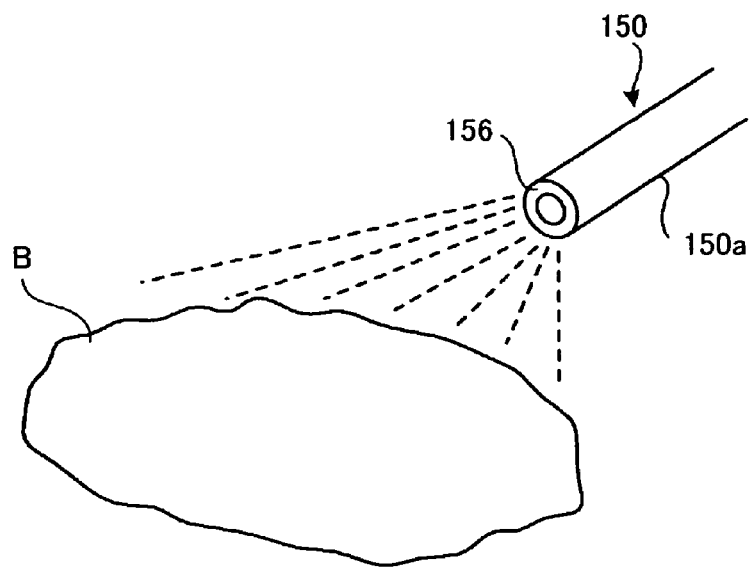
FIG. 45 shows how a coloring agent is spread from the distal-end portion shown in FIG. 41.

In these drawings, the insertion unit 122 of the endoscope apparatus 1 is inserted into the subject (Step 201), and a treated site to be treated is arranged within the visual field and detected by the observation unit (Step 202). Nextly, when the treated site is detected, the distal-end portion 122a of the insertion unit 122 is brought close to the treated site, the cylinder 7 in which the coloring agent is injected is attached to the solution injection port 131d, and the coloring agent is dispersed to the treated site B from the treatment pipe 156 of the ultrasonic transducer 150 through the tube 157 as shown in FIG. 45. The treatment pipe 156 is attached to the distal end of the insertion unit 122 (Step 203). In dispersing the coloring agent, the ultrasonic driving apparatus 4 supplies the electric power signal to the ultrasonic transducer 150 to generate the ultrasonic vibration, and the coloring agent is preferably sprayed on the treated site.

Figure 46:
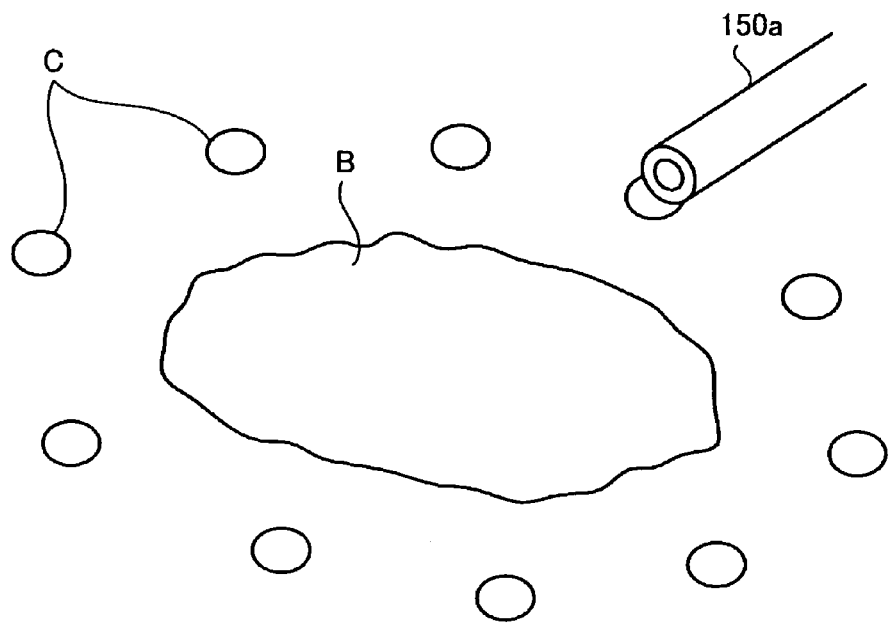
FIG. 46 shows how a marking is performed by the distal-end portion shown in FIG. 41.

Then, the current signal is supplied from the high-frequency driving apparatus 5 to the electrode 150e of the ultrasonic transducer 150 through the electric current line 151. This enables the distal-end treatment unit 150a to function as the electric cautery. As shown in FIG. 46, the recognizable markings C are formed by cauterizing the living tissue around the coloring treated site B using the distal-end treatment unit 150a having the function of the electric cautery (Step 204).

Figure 47:
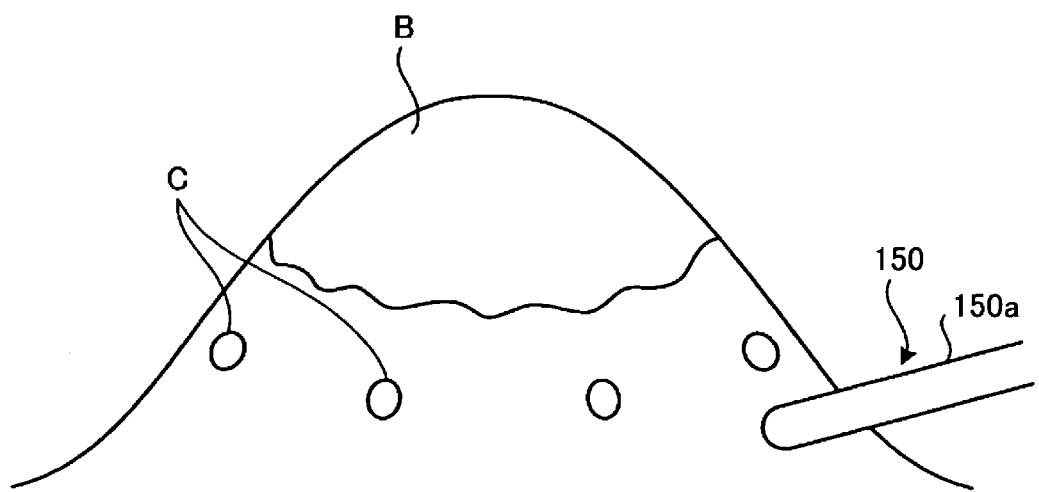
FIG. 47 shows how a local injection is performed by the distal-end portion shown in FIG. 41.

Then, the cylinder 7 is attached to the solution injection port 131d. The local injection solution (such as the physiological salt solution or Glyceol) is injected in the cylinder 7. As shown in FIG. 47, the distal end of the distal-end treatment unit 150a is inserted into the lower portion of the treated site B from the outside of the markings C, the local injection solution is injected from the treatment pipe 156 of the ultrasonic transducer 150, and the living tissue including the treated site B is raised (Step 205). In this process, for example, the lower portion of the treated site B may be cut through using a tool in which the distal end of the distal-end treatment unit 150a is formed in a injection needle shape, or the ultrasonic vibration may be generated to cut through the lower portion of the treated site B with distal end of the distal-end treatment unit 150a.

Figure 48:
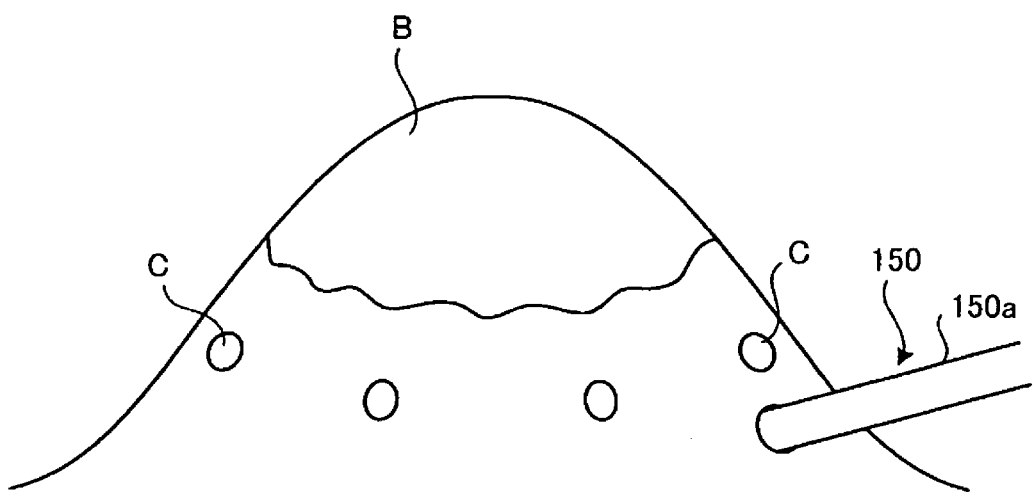
FIG. 48 shows how a periphery of a living tissue is incised by the distal-end portion shown in FIG. 41.
Figure 49:
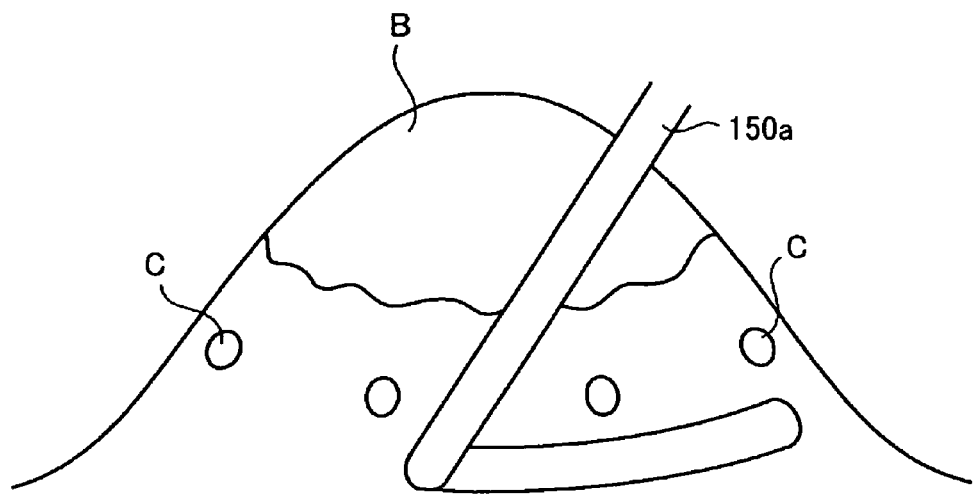
FIG. 49 shows how a periphery of a living tissue is incised by the distal-end portion shown in FIG. 41.
Figure 50:
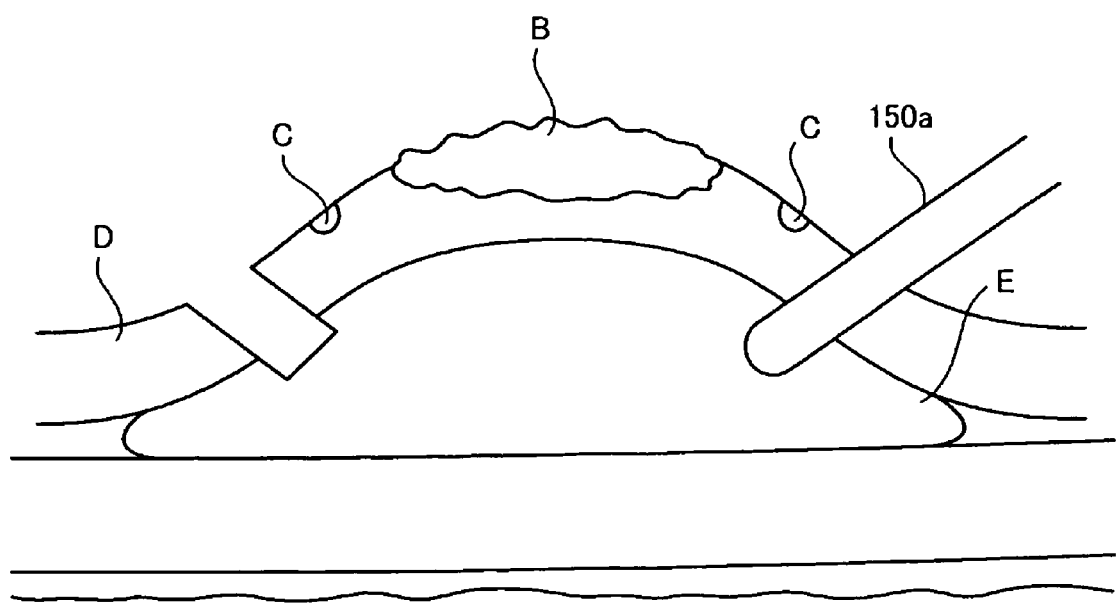
FIG. 50 shows how a periphery of a living tissue is incised by the distal-end portion shown in FIG. 41.
Figure 51:
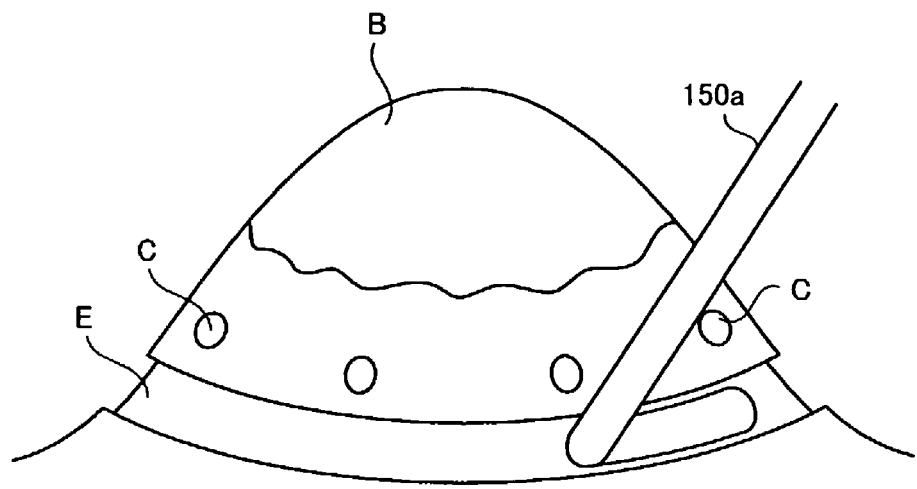
FIG. 51 shows how a submucosal tissue is ablated by the distal-end portion shown in FIG. 41.
Figure 52:
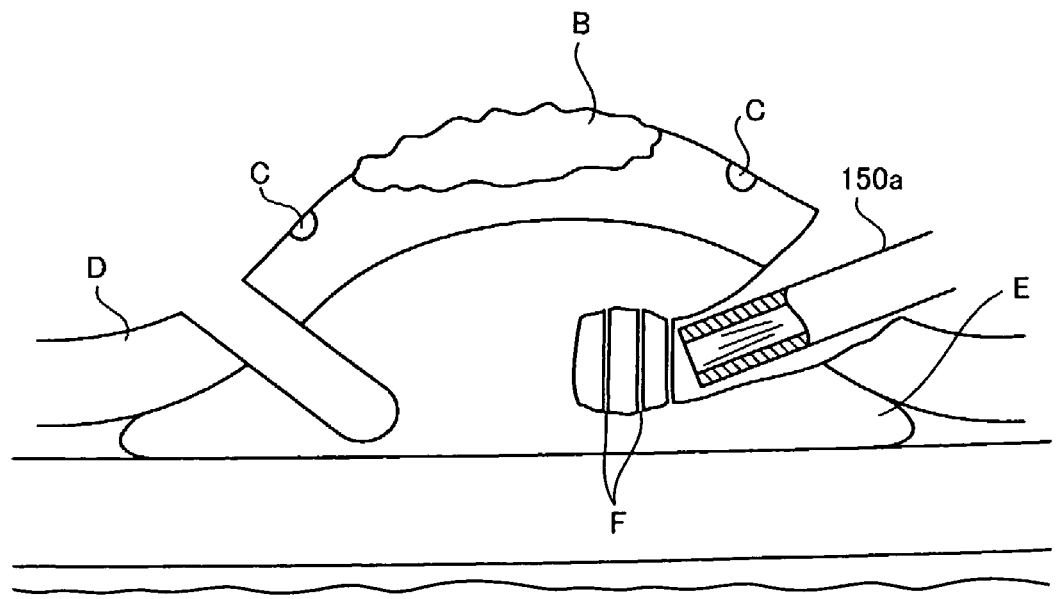
FIG. 52 shows how a submucosal tissue is ablated by the distal-end portion shown in FIG. 41.
Figure 53:
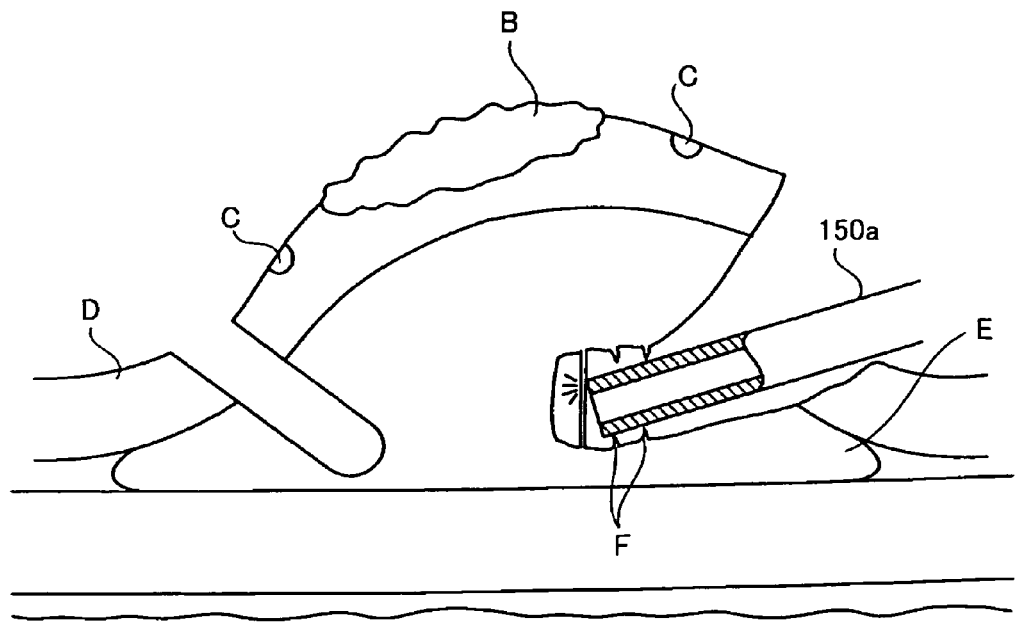
FIG. 53 shows how a submucosal tissue is ablated by the distal-end portion shown in FIG. 41.

Then, the ultrasonic vibration is generated, the surroundings of the living tissue (mucosa D) raised by the distal-end treatment unit 50a are incised as shown in FIG. 48 to FIG. 50, and the mucosa D is incised over all circumferences (Step 206). Further, in the eighth embodiment, the submucosal layer E existing below the mucosa D is peeled off as shown in FIG. 51 (Step 207). In this case, the suction apparatus 6 is connected to the solution injection port 131d, and the submucosal layer E crushed into the jelly-like substance by the ultrasonic treatment is sucked and discharged to the outside as shown in FIG. 52. For the fiber F and the blood vessel shown in FIG. 52 and FIG. 53, the tissue having high rigidity is easily cut while the hemostasis is performed by selecting the electric cautery function to cauterize and cut the fiber F and the blood vessel.

Figure 54:
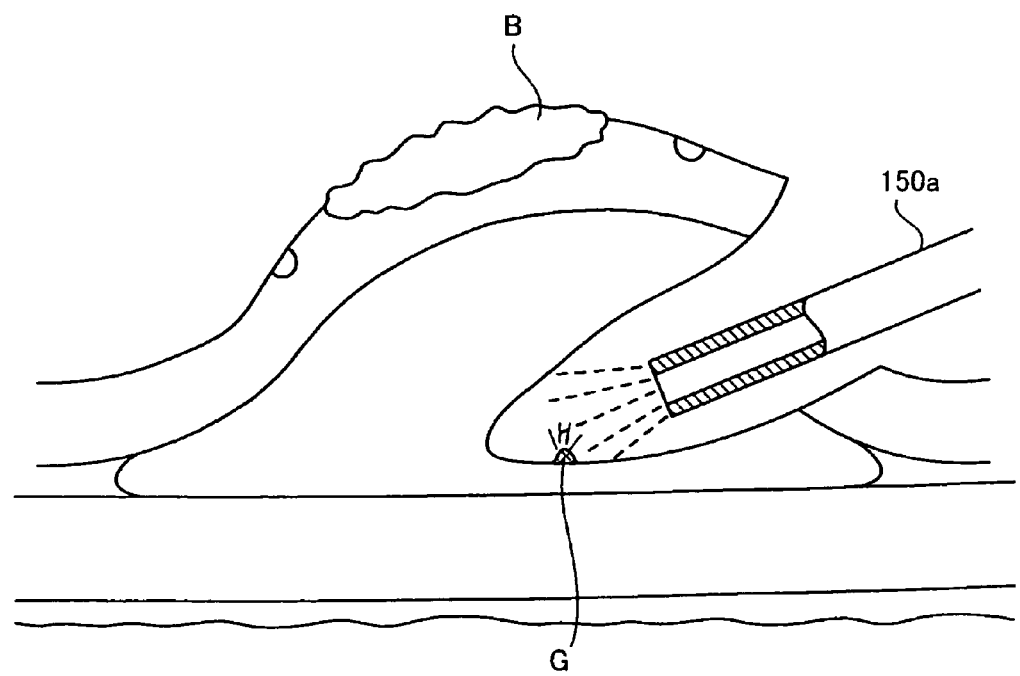
FIG. 54 shows how homeostasis is performed by the distal-end portion shown in FIG. 41.
Figure 55:
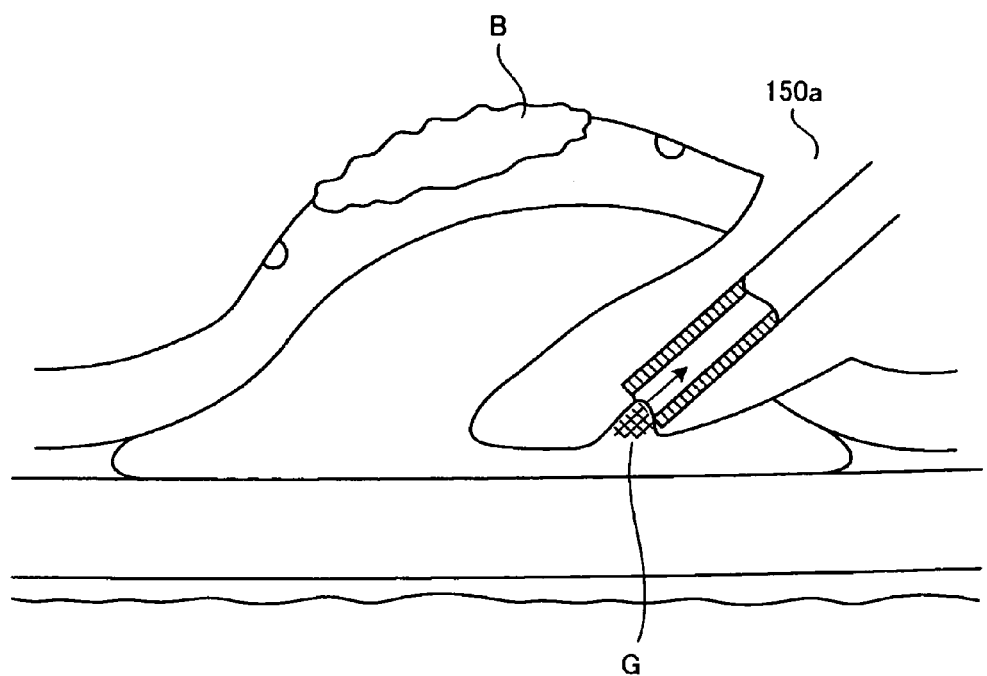
FIG. 55 shows how homeostasis is performed by the distal-end portion shown in FIG. 41.
Figure 56:
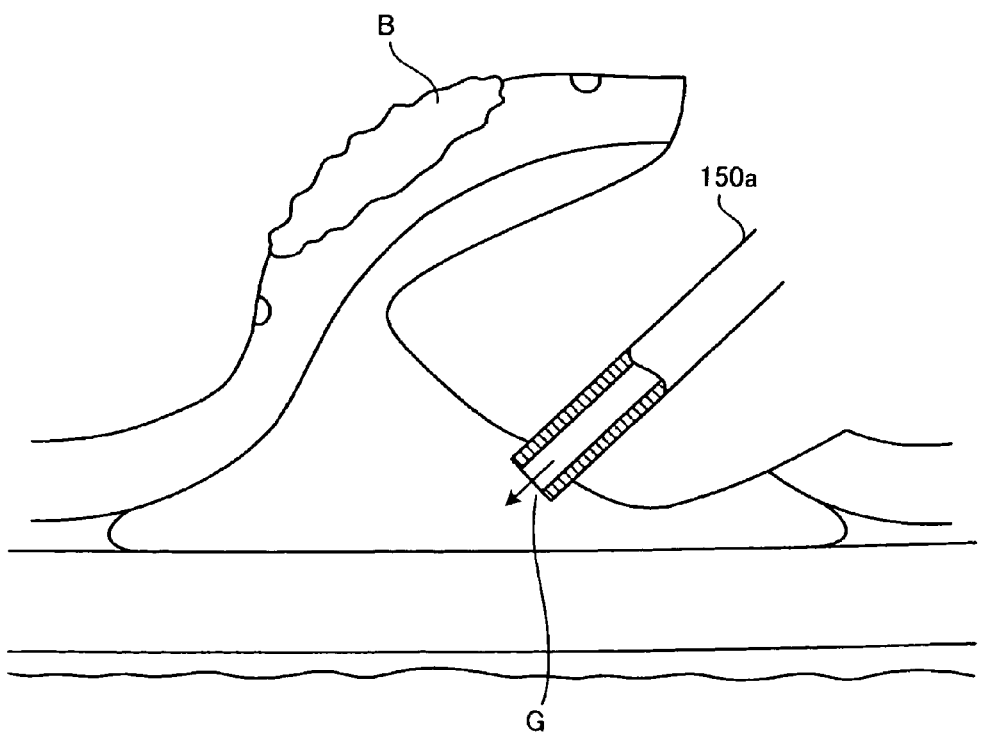
FIG. 56 shows how homeostasis is performed by the distal-end portion shown in FIG. 41.

In the case where the bleeding exists (Step 208), the hemostastic treatment is performed using the electric cautery function (Step 209). In the hemostastic treatment, for example, the hemostastic treatment of a bleeding region G is performed by the high-frequency current while the physiological salt solution is supplied from the cylinder 7 as shown in FIG. 54, which allows the treatment to be performed with a good visual field. As shown in FIG. 55, instead of the cylinder 7, the suction apparatus 6 may be attached to the solution injection port 131d to suck the bleeding blood from the bleeding region G, or the ultrasonic treatment may be performed while the bleeding blood is sucked. The cylinder in which the hemostatic is injected is attached to the solution injection port 131d, and the hemostatic treatment may be performed by cutting through the bleeding region G with the distal end of the distal-end treatment unit 150a to inject the hemostatic as shown in FIG. 56. In order to recover the cut tissue specimen, instead of the ultrasonic treatment apparatus 3, for example a pair of grip forceps (not shown) is inserted from the forceps insertion port 121d into the channel 122b of the distal-end portion 122a, and the tissue specimen can be taken out while being gripped by the grip forceps.

Although the ultrasonic vibration function and the electric cautery function are individually driven in the eighth embodiment, the present invention is not limited to the first embodiment. For example, in the process of dissecting the submucosal layer, either or both of the ultrasonic vibration function and the electric cautery function may simultaneously be driven according to the treatment process.

Thus, in the first embodiment, the ultrasonic treatment apparatus includes the treatment unit having both the ultrasonic vibration function and the electric cautery function, the surroundings of the living tissue are incised to crush the living tissue by the ultrasonic vibration, and other incisions are performed by selecting any of the functions. Therefore, the heat damage of the tissue specimen to be cut off is prevented to obtain the proper tissue specimen, so that the work necessary to cut the surroundings can be decreased as compared with the conventional art.

In the first embodiment, the treatment unit of the ultrasonic transducer has the hollow shaped portion, and the chemicals dispersing process and the local injection process are performed through the hollow shaped portion. Accordingly, it is not necessary that the ultrasonic transducer be changed to, e.g., the treatment tool with injection needle or the dispersing tube in each process, and the treatment necessary for the incision of the living tissue can be simplified.

The eighth embodiment includes the treatment unit which can be used for both the ultrasonic treatment and the high-frequency treatment. Therefore, it is not necessary to change the treatment tools to select the ultrasonic treatment or the high-frequency treatment, and the incision operation can be performed simply and rapidly.

A ninth embodiment of the present invention will be described below. Generally, for the electric cautery function, it is desirable that the current density be concentrated on one point to increase resistance. Therefore, the electric cautery is brought into point contact with the treated site, and the treated site is incised by the generated heat. In the eighth embodiment, since the distal-end treatment unit 150a of the ultrasonic transducer 150 is formed in the cylindrical hollow structure, an area is considerably small in the distal-end portion of the distal-end treatment unit 150a, and the ultrasonic treatment apparatus can function as the electric cautery while functioning as the ultrasonic vibration, even when the distal-end portion is caused to abut against the treated site. However, sometimes it is necessary that the further effects be obtained as the ultrasonic vibration and the electric cautery.

Figure 57:
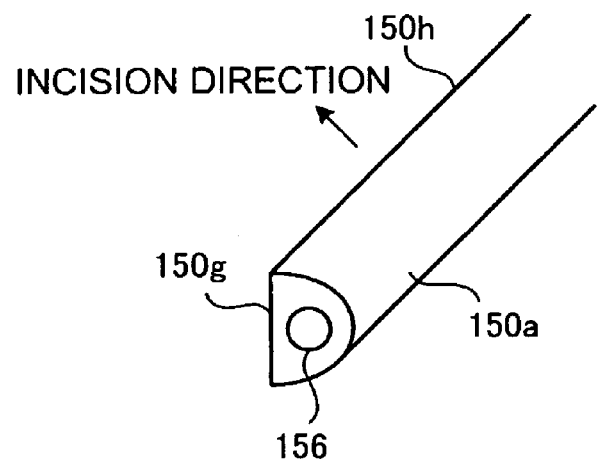
FIG. 57 is a perspective view of the distal-end portion of the insertion unit shown in FIG. 40 having a first exemplary configuration according to a ninth embodiment.

Therefore, in the ninth embodiment, as shown in a first exemplary configuration of the distal-end portion of the insertion unit shown in FIG. 57, a sharp unit 150h having the sharp angle is formed at the tangential line between the outer periphery of the distal-end treatment unit 150a and a cut unit 150g by providing a part of the distal-end treatment unit 150a is cut in the longitudinal direction. In the ninth embodiment, the treated site is incised by utilizing the sharp unit 150h. That is, when the sharp unit 150h is orientated toward the incision direction to incise the mucosa D or submucosal layer E (for example, see FIG. 50) which is of the treated site using the electric cautery function, the sharp unit 150h having the high current density comes into contact linearly with the treated site, and the treated site can be well incised by the generated heat.

In the case where the ultrasonic vibration function is used, similarly, when the sharp unit 150h is orientated toward the incision direction to incise the treated site by the ultrasonic vibration, the ultrasonically vibrating sharp unit 150h comes into contact with the treated site, and the treated site can be well incised. Therefore, in addition to the effects of the first embodiment, usability of the ultrasonic treatment apparatus can be improved.

Figure 58:
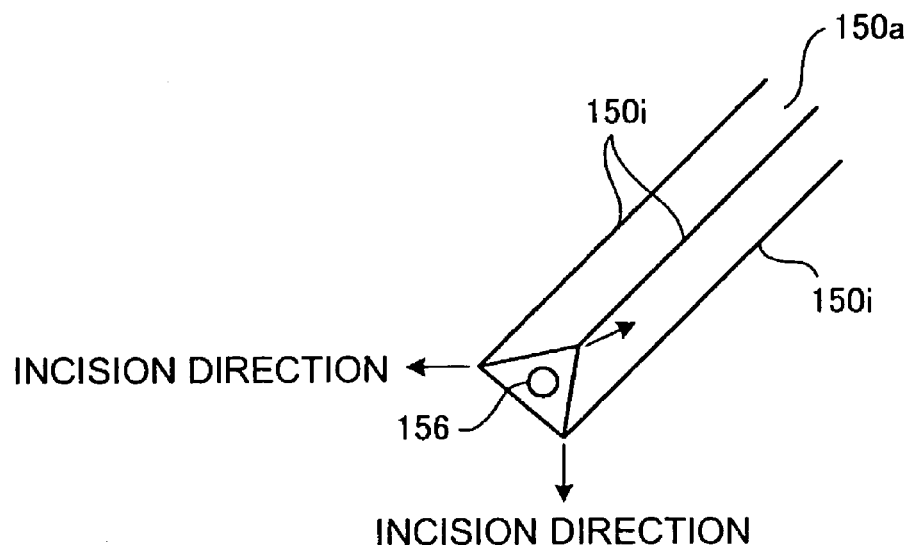
FIG. 58 is a perspective view of the distal-end portion of the insertion unit shown in FIG. 40 having a second exemplary configuration according to the ninth embodiment.

FIG. 58 is a perspective view of the distal-end portion of the insertion unit shown in FIG. 40 having a second exemplary configuration according to the ninth embodiment. In FIG. 58, the distal-end treatment unit 150a of the ultrasonic transducer 150 is formed by the triangle pole having the hollow structure, and three sharp units 150i having angles sharper than that of the sharp unit 150h are formed in the tangential lines between sides. In the ninth embodiment, the incision can be performed with the sharp units 150i orientated toward the three directions using the ultrasonic vibration function and the electric cautery function, and the usability of the ultrasonic treatment apparatus can be further improved as compared with the first example.

In the ninth embodiment, since the incision is performed with the sharp units 150i having angles sharper than that of the sharp unit 150h, the treated site can be incised more rapidly and securely.

Figure 59:
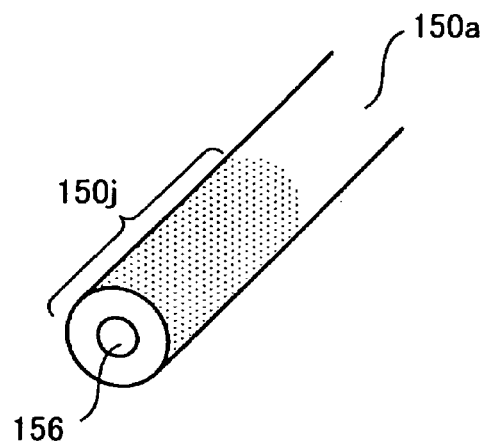
FIG. 59 is a perspective view of the distal-end portion of the insertion unit shown in FIG. 40 having a third exemplary configuration according to the ninth embodiment.

FIG. 59 is a perspective view of the distal-end portion of the insertion unit shown in FIG. 40 having a third exemplary configuration according to the ninth embodiment. In FIG. 59, similarly to the eighth embodiment, the distal-end treatment unit 150a of the ultrasonic transducer 150 is formed in the cylindrical hollow structure. However, the third example differs from the eighth embodiment in that a roughened surface portion 150j which is formed in the roughened shape is provided in the outer peripheral surface.

An average interval between concavity and convexity in the roughened surface portion 150j is determined by the vibration amplitude of the ultrasonic transducer 150. For example, in the normal ultrasonic transducer, the vibration amplitude depends on a size thereof, the vibration amplitude is about 0.3 mm at the maximum, and the vibration amplitude is about 0.003 mm at the minimum. Therefore, in the second embodiment, the average interval between concavity and convexity in the roughened surface portion 150j is preferably set slightly smaller than the vibration amplitude, e.g., in the range of 0.002 mm to 0.2 mm.

Accordingly, in the second embodiment, when the roughened surface portion 150j is brought into contact with the treated site to perform the incision by the ultrasonic vibration, the vibration is transmitted to the distal-end treatment unit 150a to enhance friction between the roughened surface portion 150j and the treated site, which allows the treated site to be incised more favorably as compared with the eighth embodiment.

Figure 60:
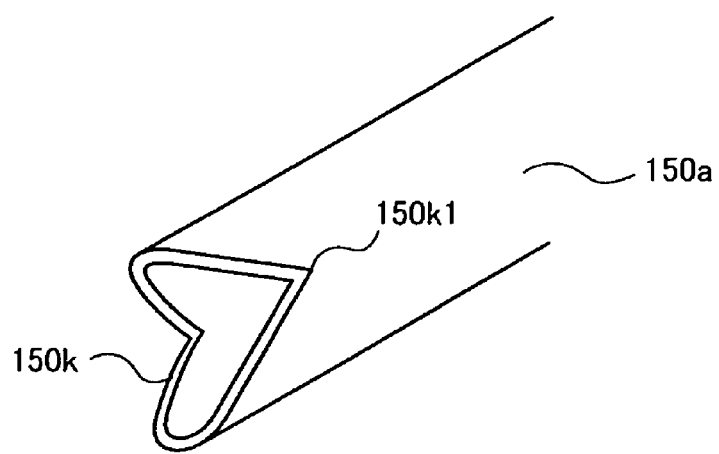
FIG. 60 is a perspective view of the distal-end portion of the insertion unit shown in FIG. 40 having a fourth exemplary configuration according to the ninth embodiment.
Figure 61:
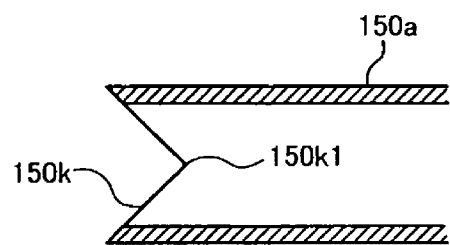
FIG. 61 is a sectional view of the distal-end portion of FIG. 60.

FIG. 60 is a perspective view of the distal-end portion of the insertion unit shown in FIG. 40 having a fourth exemplary configuration according to the ninth embodiment. FIG. 61 is a sectional view of the distal-end portion of FIG. 60. In the drawings, similarly to the eighth embodiment, the distal-end treatment unit 150a of the ultrasonic transducer 150 is formed in the cylindrical hollow structure. However, the fourth example differs from the eighth embodiment in that a mouth-shaped opening 150k having a mouth angle 150k1 is provided at the distal end of the distal-end treatment unit 150a.

In the ninth embodiment, when the mucosa D or submucosal layer E (for example, see FIG. 50) which is of the treated site is hooked by the mouth angle 150k1 to perform the ultrasonic vibration function or the electric cautery function, the treated site can be incised more favorably as compared with the eighth embodiment. In the ninth embodiment, when the suction apparatus 6 is simultaneously used to suck the incised treated site, the treated site can be incised more favorably.

Figure 62:
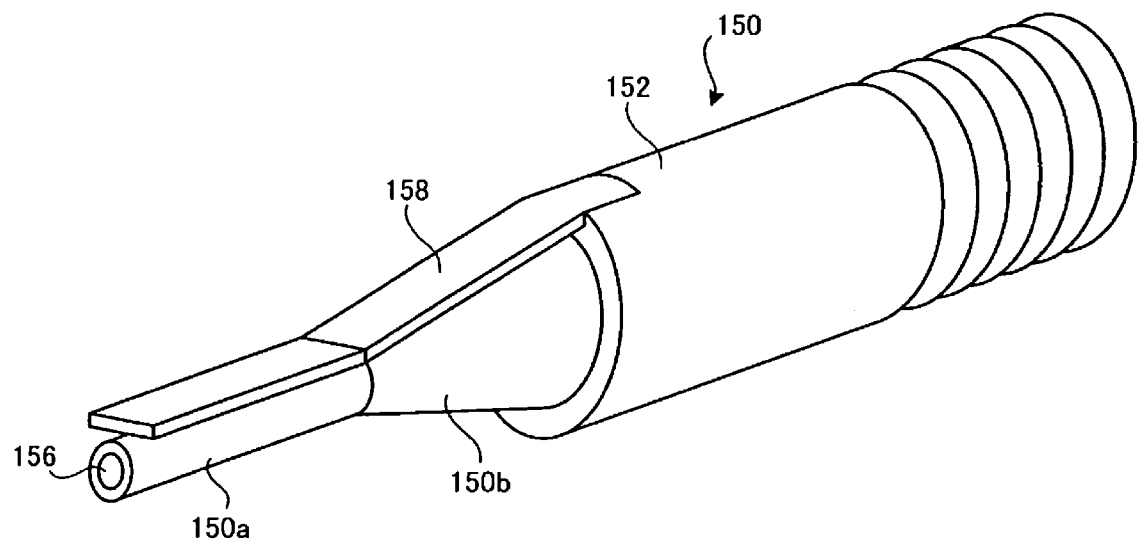
FIG. 62 is a perspective view of the distal-end portion of the insertion unit shown in FIG. 40 according to a tenth embodiment.

A tenth embodiment of the present invention will be described below. FIG. 62 is a perspective view of a first example of a configuration according to the tenth embodiment in the distal-end portion of the insertion unit shown in FIG. 40. A flat plate 158 is provided in the tenth embodiment. The flat plate 158 is fixed to the end portion of the cover 152, and the flat plate 158 is formed in the longitudinal direction of the ultrasonic transducer 150 while having a predetermined clearance with the distal-end treatment unit 150a and horn 150b. For example, the flat plate 158 is made of a Teflon (registered trademark) material. For example, the clearance between the flat plate 158 and the distal-end treatment unit 150a is set such that the mucosa D can be sandwiched between the flat plate 158 and the distal-end treatment unit 150a and flat plate 158.

Figure 63:
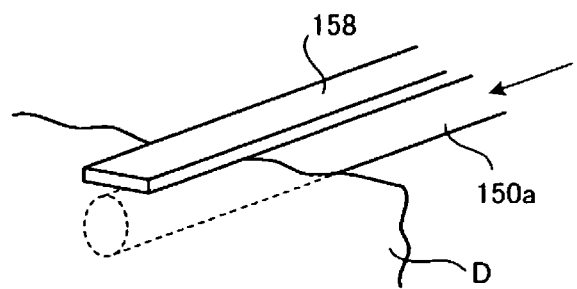
FIG. 63 is a perspective view for explaining a usage condition of the distal-end portion shown in FIG. 62.
Figure 64:
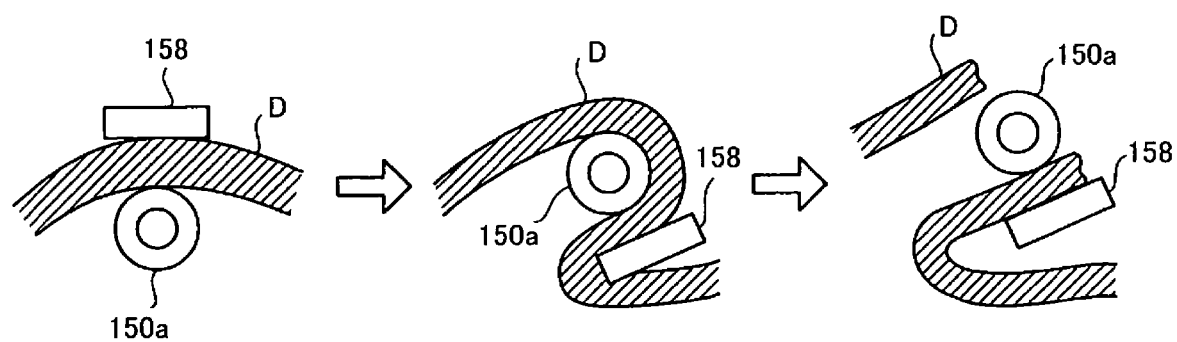
FIG. 64 is a front view for explaining the usage condition of the distal-end portion shown in FIG. 62.

In the ninth embodiment, the mucosa D is sandwiched between the distal-end treatment unit 150a and the flat plate 158 as shown in a perspective view of FIG. 63, and the ultrasonic treatment apparatus is twisted in the circumferential direction of the distal-end treatment unit 150a while the ultrasonic vibration is applied as shown in FIG. 64. Therefore, the mucosa D is entangled with the distal-end treatment unit 150a and flat plate 158 to apply the tension to the mucosa D, which allows the mucosa D to be cut.

In the ninth embodiment, the mucosa D sandwiched between the distal-end treatment unit 150a and the flat plate 158 is cut by twisting the mucosa. Therefore, in addition to the effects of the eighth embodiment, the mucosa can be incised more easily.

Figure 65:
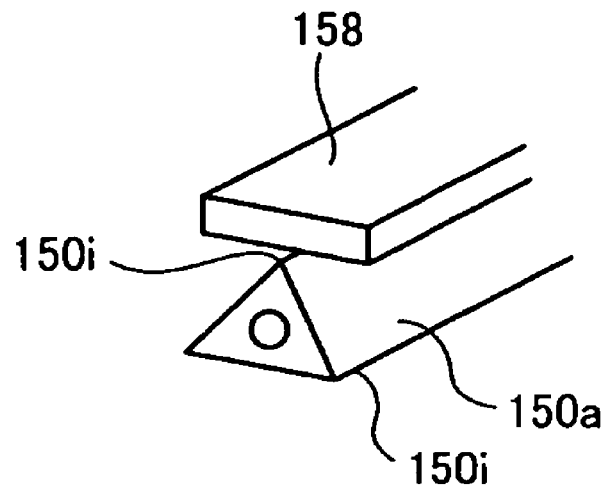
FIG. 65 is a perspective view of the distal-end portion of the insertion unit shown in FIG. 40 having a second exemplary configuration according to the tenth embodiment.
Figure 66:
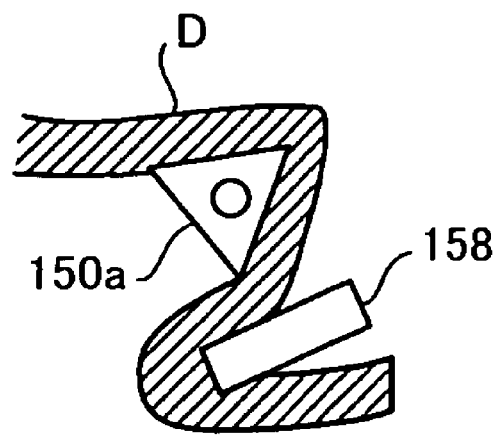
FIG. 66 is a front view for explaining a usage condition of the distal-end portion shown in FIG. 65.

FIG. 65 is a perspective view of the distal-end portion of the insertion unit shown in FIG. 40 having a second exemplary configuration according to the tenth embodiment. FIG. 66 is a front view showing the usage condition of the distal-end portion shown in FIG. 65. In the drawings, the distal-end treatment unit 150a formed by the triangle pole having the hollow structure shown in FIG. 58 and the flat plate 158 shown in FIG. 62 are combined in the tenth embodiment.

In the tenth embodiment, the mucosa D is sandwiched and twisted between the flat plate 158 and the distal-end treatment unit 150a in which the sharp units 150i are formed, and the tension is further applied to the mucosa D. Therefore, the mucosa D can be cut, and the mucosa can be incised still more easily as compared with the first example.

An eleventh embodiment of the present invention will be described below. Because the incision of the treated site has the directional property in the above embodiments, it is necessary that the flexible sheath 136 precisely transmit the torque. Therefore, the configuration of the flexible sheath 136 which precisely transmits the torque will be described in the eleventh embodiment.

Figure 67:
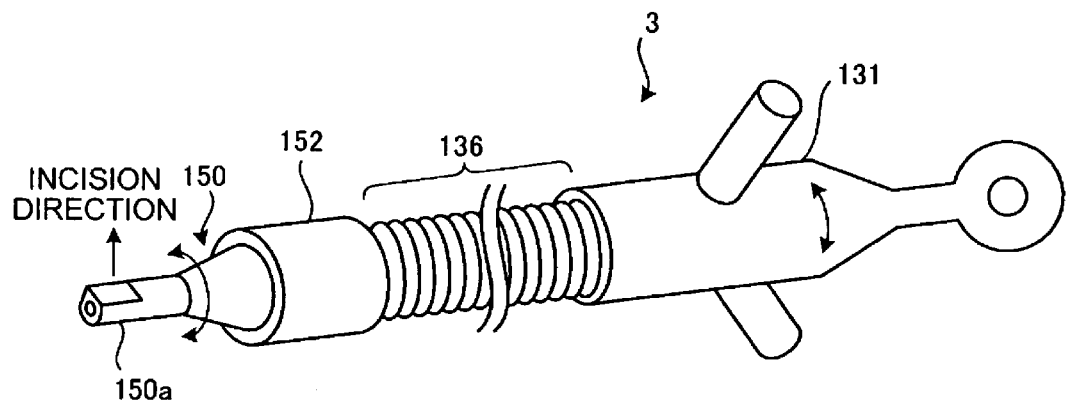
FIG. 67 is a perspective view of an ultrasonic treatment apparatus shown in FIG. 40 according to an eleventh embodiment.
Figure 68:
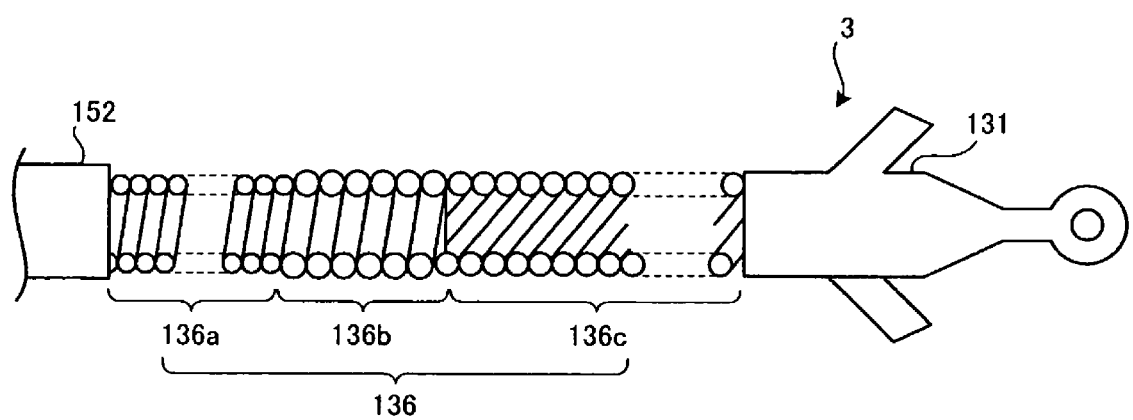
FIG. 68 is a sectional side view of a flexible sheath portion shown in FIG. 67.

FIG. 67 is a perspective side view showing a configuration according to the eleventh embodiment of the ultrasonic treatment apparatus 3 shown in FIG. 40, and FIG. 68 is a sectional view showing the side section of a portion of flexible sheath 136 shown in FIG. 67. In the drawings, in the eleventh embodiment, the flexible sheath 136 is formed by three components, and the components are connected to one another while working with one another. That is, the flexible sheath 136 includes a sheath 136a, a sheath 136b, and sheath 136c. The sheath 136a connected to the cover 152 is formed by one strip of coil. The sheath 136b is connected to the sheath 136a, and the sheath 136b is formed by one strip of coil whose element-wire diameter is larger than that of the sheath 136a. The sheath 136c is connected to the sheath 136b and the operating unit 131, and the sheath 136c is formed by one coil in the appearance in which plural strips, e.g., three to five strips of coils are collectively wound.

For example, the sheaths 136a and 136b are formed by the right-handed coils, and the sheath 136c is formed by the left-handed coil. The element-wire diameter of the coil of the sheath 136c is formed smaller than the element-wire diameter of the coil of the sheath 136a. Therefore, the spring force of the coil of the sheath 136c is strengthened to eliminate the clearance, and the transmission power of the torque is increased. The torque is transmitted to the sheath 136a having the smaller diameter through the sheath 136b having the larger diameter, and thereby the torque of the sheath 136c is precisely transmitted to the distal-end treatment unit 150a of the ultrasonic transducer 150.

Thus, the eleventh embodiment includes the three components, and the different sheaths are used while being combined. Therefore, the torque from the operating unit 131, e.g., the torque of clockwise rotation or the torque of counterclockwise rotation is precisely transmitted to the distal-end treatment unit 150a through the sheath, so that the treated site can be well incised rapidly.

Figure 70:
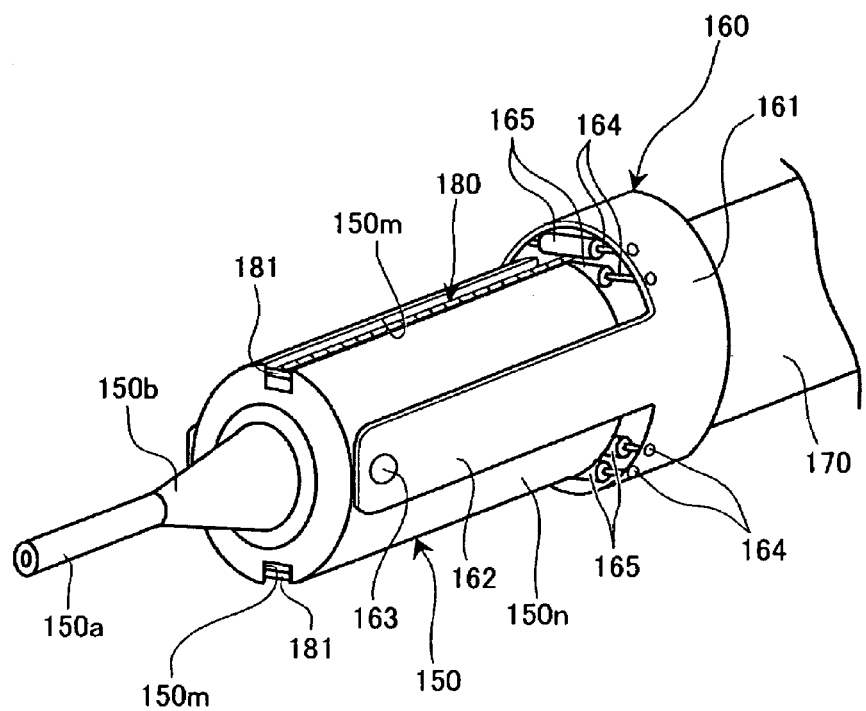
FIG. 70 is a perspective view of a distal-end portion of the ultrasonic treatment apparatus shown in FIG. 69.
Figure 71:
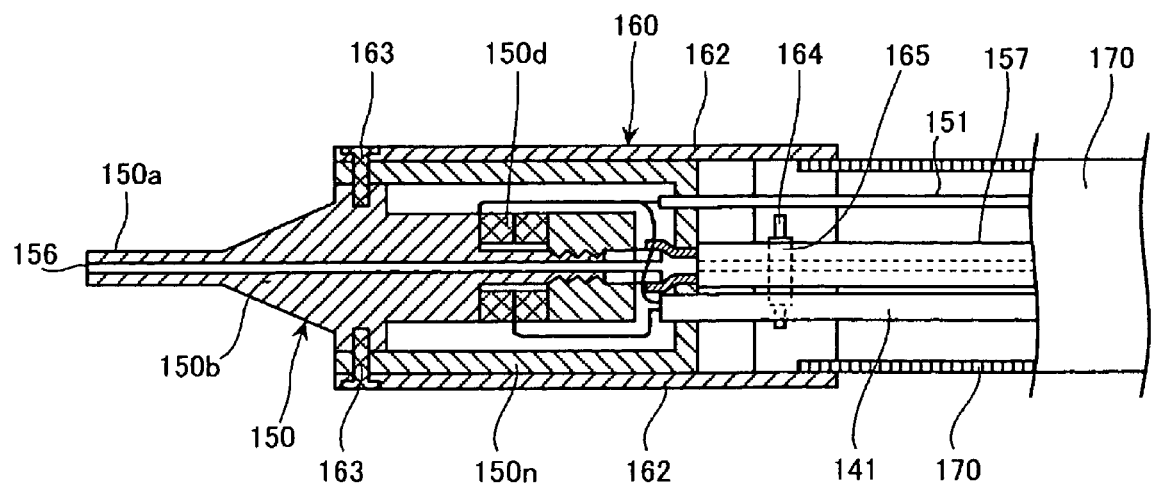
FIG. 71 is a sectional side of the distal-end portion of the ultrasonic treatment apparatus shown in FIG. 70.
Figure 72:
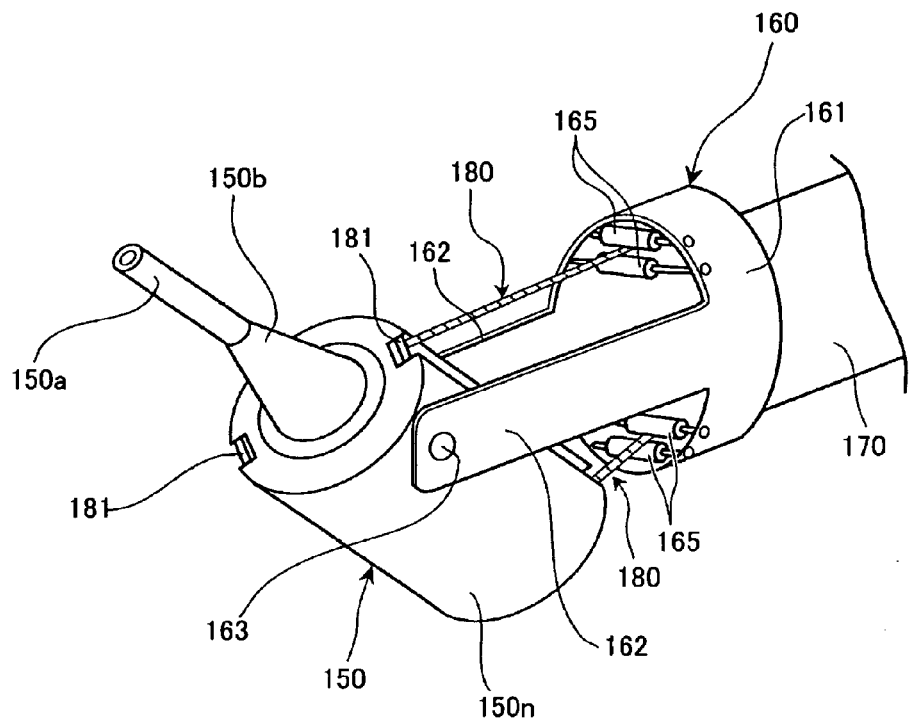
FIG. 72 is a perspective view of the ultrasonic transducer shown in FIG. 70 in an open state.

A twelfth embodiment of the present invention will be described below. FIG. 69 is a partial sectional side view showing a configuration of a fifth embodiment in which an ultrasonic transducer can be oscillated, FIG. 70 is a perspective view showing a configuration of the distal-end portion of the ultrasonic treatment apparatus shown in FIG. 69, FIG. 71 is sectional side view showing a configuration of the distal-end portion shown in FIG. 69, and FIG. 72 is a perspective view showing a state in which the ultrasonic transducer shown in FIG. 70 is opened. The oscillating mechanism of the ultrasonic transducer is substantially similar to that disclosed in JP-A No. 2004-122868, and the oscillating mechanism will be described below.

In these drawings, the ultrasonic treatment apparatus 3 includes the ultrasonic transducer 150, a support cover 160, the electric power line 141 and electric current line 151, a sheath 170, and an operating wire 180.

The ultrasonic transducer 150 is arranged at the distal end of the ultrasonic treatment apparatus 3, the piezoelectric element 150d is provided at the back of the horn 150b, and the distal-end treatment unit 150a having the hollow structure is provided in front of the horn 150b. The ultrasonic transducer 150 includes a cylinder 150n at the back of the horn 150b, and the cylinder 150n accommodates the piezoelectric element 150d. In FIG. 69, in the ultrasonic transducer 150, wire grooves 150m are formed along the longitudinal direction while being located at the upper and lower portions of the cylinder 150n respectively.

The support cover 160 is attached to the end portion of the sheath 170. As shown in FIG. 70, two support arms 162 extending in a forward direction of a cylindrical unit 161 are provided in the support cover 160, and the distal end of the support arm 162 is attached to the cylinder 150n by a support pin 163. The cylindrical unit 161 is formed by guide means for guiding an operating wire 180, and each pair of wire guides 165 supported by pins 164 is provided in each of the upper and lower portions of the cylindrical unit 161.

At this point, the support pin 163 is attached to the cylinder 150n between the two wire grooves 150m of the outer periphery of the cylinder 150n while being located at the node position of the ultrasonic vibration. Therefore, the support cover 160 suppresses the influence of the ultrasonic vibration to the minimum, and the support cover 160 supports the ultrasonic transducer 150 while the ultrasonic transducer 150 can be rotatably supported about the support pin 163. As shown in FIG. 40, the two pairs of wire guides 165 provided in the upper and lower portions respectively are provided at the positions shifted toward the side of the support arm 162 with respect to the extending direction of the wire groove 150m. Therefore, the ultrasonic transducer 150 can effectively be rotated by the tension of the operating wire 180. The support pin 163 may be placed while piecing through the horn 150b. Instead of the support pin 163, two protrusions are provided at the node position of the ultrasonic vibration in the horn 150b, and the support cover 160 may support the ultrasonic transducer 150 using the protrusions.

As shown in FIG. 69, the electric signal lines 141 and 151 extend from the cylinder 150n, the electric signal lines 141 and 151 are guided to the outside from a leading port 177 of an operating unit 171 through the inside of the sheath 170, and end portions of the electric signal lines 141 and 151 are connected to the ultrasonic driving apparatus and high-frequency driving apparatus (not shown) respectively. As shown in FIG. 69, the treatment tube 157 extends from the cylinder 150n, the treatment tube 157 is fixed to a leading port 172 of the operating unit 171 through the inside of the sheath 170. One end of the treatment tube 157 is configured to be connectable to the suction apparatus (not shown) or the cylinder (not shown).

As shown in FIG. 69, in the sheath 170, the operating unit 171 is provided at one end, and the support cover 160 is attached at the other end. The end portion of the sheath 170 is fixed to the support cover 160 or the operating unit 171 by the laser welding or the bonding agent.

The operating unit 171 is a portion which the operator manually grips to operate the ultrasonic treatment apparatus 3. As shown in FIG. 69, in the operating unit 171, the leading ports 172 and 177 of the electric signal lines 141 and 151 is provided near the coupling portion with the sheath 170. An operating dial 173 is provided at the substantially intermediate position of the outer surface in the operating unit 171, and a pulley 174 coaxial with the operating dial 173 is provided inside the operating unit 171. The operating dial 173 is rotated clockwise or counterclockwise to move the operating wire 180 along the longitudinal direction, which allows the ultrasonic transducer 150 to rotate about a support pin 163. The operating dial 173 includes a knob (not shown) which fixes the operating dial 173 to the operating unit 171 to hold the ultrasonic transducer 150 in a desired rotation position. When the knob is rotated in one direction, the knob loosens to release the fixation of the operating dial 173 to the operating unit 171. Therefore, the ultrasonic transducer 150 can freely be rotated with respect to the support cover 160. When the knob is rotated in the other direction, the knob tightens to fix the operating dial 173 to the operating unit 171. Therefore, the ultrasonic transducer 150 is held so as not to rotate with respect to the support cover 160. Guide rollers 176 are provided at appropriate positions inside the operating unit 171. The guide roller 176 guides the movement of the operating wire 180 along the longitudinal direction in association with the rotation of the operating dial 173.

In the operating wire 180, relaxation removers 190 are provided near the pulley 174 of the operating unit 171. The operating wire 180 is entrained about the pulley 174 at the midpoint thereof, both ends of the operating wire 180 are coupled to the outside of the ultrasonic transducer 150, and the operating wire 180 is arranged along the longitudinal direction in the sheath 170. At this point, the both ends of the operating wire 180 are arranged in the wire grooves 150m formed in the cylinder 150n, and the both ends are coupled to the node positions in the ultrasonic vibration outside the cylinder 150n by wire pins 181. Therefore, the ultrasonic vibration generated by the ultrasonic transducer 150 is never transmitted to the operating wire 180, and thus the energy loss of ultrasonic transducer 150 is suppressed.

The relaxation remover 190 is one which absorbs relaxation or tension of the operating wire 180 when the operating dial 173 is rotated. In the relaxation remover 190, a latching unit 192 having the large diameter is accommodated in a case 191. The latching unit 192 latches the end portion of the operating wire 180. For example, in FIG. 69, when the operating dial 173 is rotated clockwise, the upper-side operating wire 180 is pulled and tensed by the pulley 174 while the lower-side operating wire 180 is relaxed in the operating unit 171. Therefore, assuming that the state shown in FIG. 69 is set at a reference, in the ultrasonic transducer 150, as shown in FIG. 72, the distal end of the distal-end treatment unit 150a is orientated obliquely upward, and the rear portion of the cylinder 150n is lowered. When the operating dial 173 is rotated, the relaxation remover 190 absorbs the relaxation or the tension of the operating wire 180 so as not to entangle the operating wire 180, and thereby the ultrasonic transducer 150 is smoothly rotated counterclockwise. When the operating dial 173 is rotated counterclockwise, the lower-side operating wire 180 is pulled and tensed by the pulley 174 while the upper-side operating wire 180 is relaxed in the operating unit 171. Therefore, contrary to the state shown in FIG. 72, the distal end of the distal-end treatment unit 150a is orientated obliquely downward, and the rear portion of the cylinder 150n is lifted.

Figure 73:
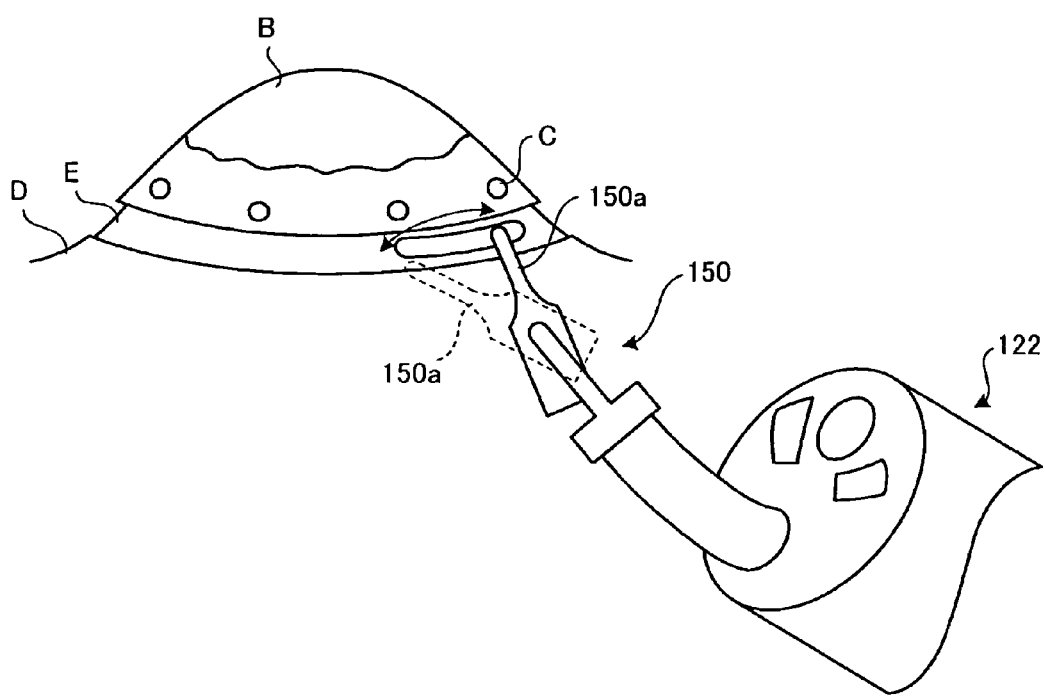
FIG. 73 shows how the incision is performed by the ultrasonic treatment apparatus shown in FIG. 69.

When the ultrasonic treatment apparatus 3 having the above configuration is used for the incision of the treated site, e.g., the submucosal layer E, the same effects as the eighth embodiment are obtained, and the ultrasonic transducer 150 can perform the oscillating action as shown in FIG. 73 to perform the incision operation simply and rapidly. Further, the incision can be performed while the jelly-like substance is sucked, so that the unnecessary substances hardly adhere to the cut tissue specimen. Therefore, the tissue specimen can be extracted while kept more cleaned.

Figure 74:
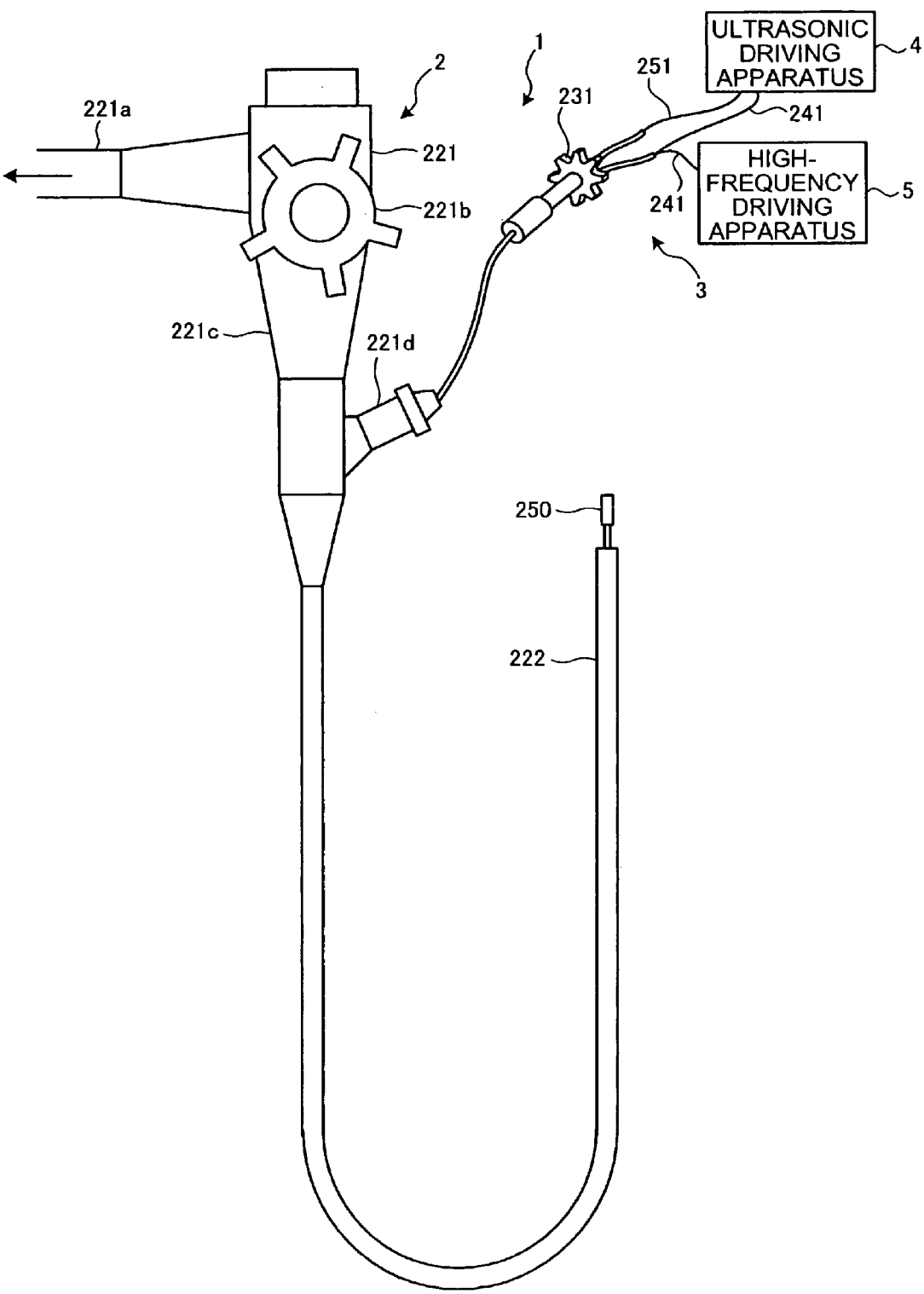
FIG. 74 is a schematic diagram of an endoscope apparatus which includes an ultrasonic treatment apparatus having a third exemplary configuration according to the present invention.
Figure 75:
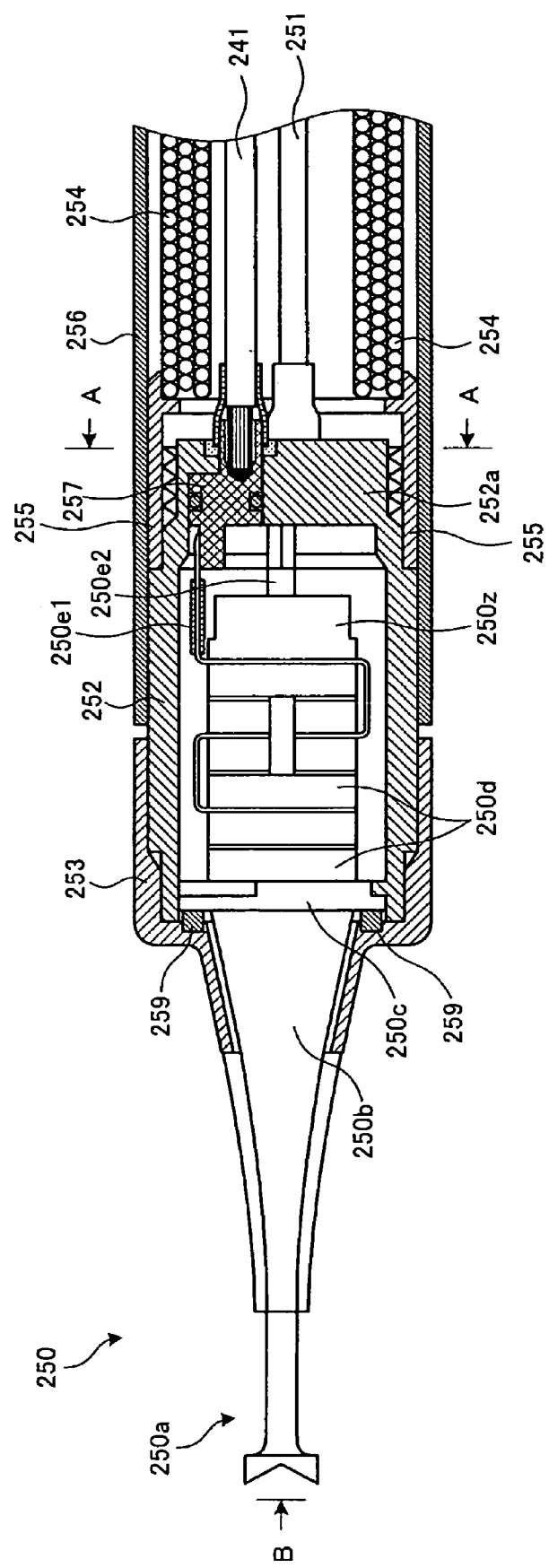
FIG. 75 is a sectional side view of a distal-end portion of an ultrasonic treatment apparatus according to a thirteenth embodiment.
Figure 76:
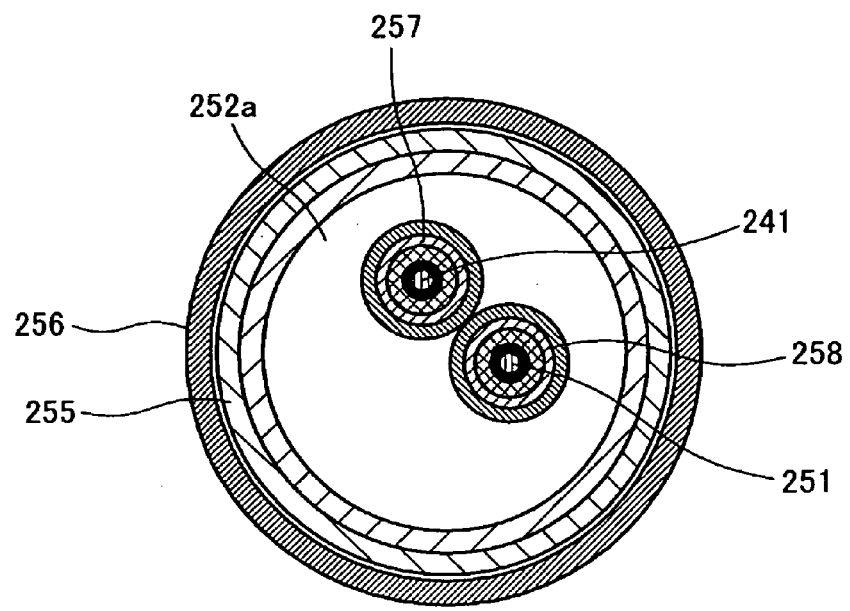
FIG. 76 is a sectional view of the ultrasonic treatment apparatus taken on line A-A of FIG. 75.
Figure 77:
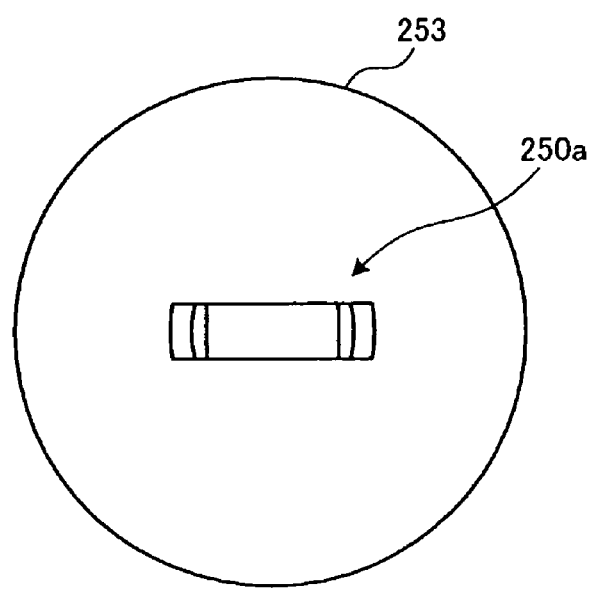
FIG. 77 is a front view of the distal-end portion when viewed from an arrow B of FIG. 75.
Figure 78:
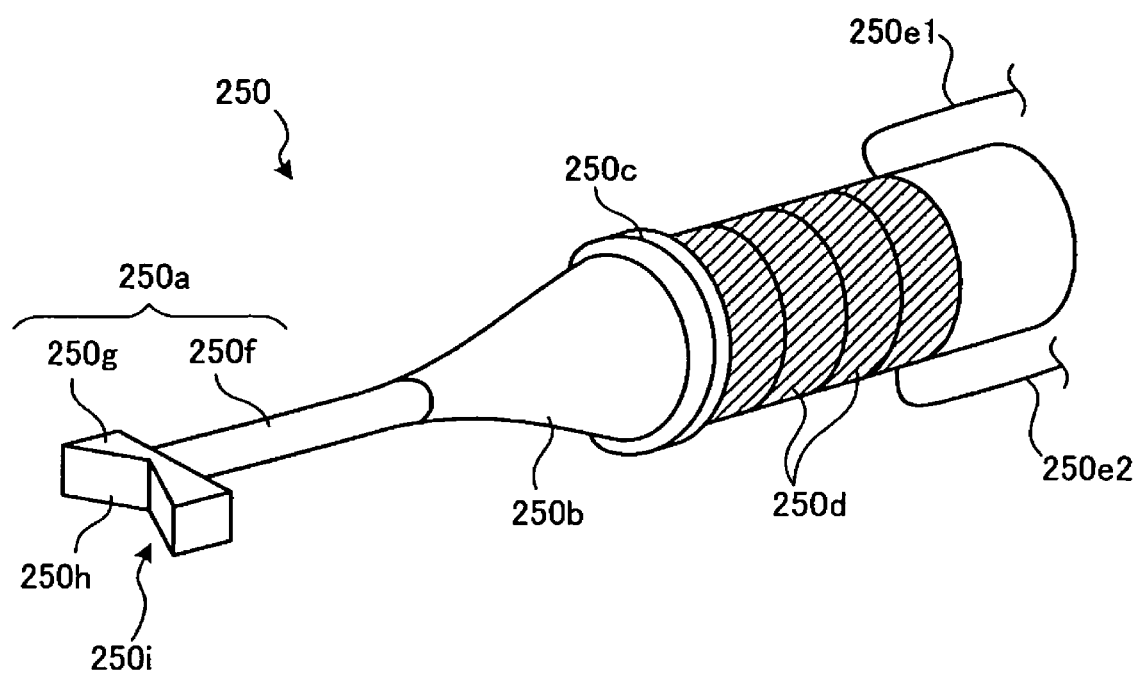
FIG. 78 is a perspective view of an ultrasonic transducer shown in FIG. 74.

A thirteenth embodiment will be described below. FIG. 74 is a schematic diagram showing a third example of a configuration of an ultrasonic treatment apparatus according to the present invention used in the endoscope apparatus 1, FIG. 75 is a sectional side view showing a configuration of a distal-end portion of an ultrasonic treatment apparatus according to a thirteenth embodiment, FIG. 76 is a sectional view taken on line A-A of FIG. 75, FIG. 77 is a view showing the distal-end portion when viewed from an arrow B of FIG. 75, and FIG. 78 is a perspective view of an ultrasonic transducer shown in FIG. 74. In these drawings, the endoscope apparatus 1 includes a videoscope 2, an ultrasonic treatment apparatus 3, an ultrasonic driving apparatus 4, and a high-frequency driving apparatus 5. The videoscope 2 is connected to a light source apparatus (not shown) and a display apparatus (not shown). The ultrasonic driving apparatus 4 is of an ultrasonic power supply unit which supplies electric power to the ultrasonic treatment apparatus 3. The high-frequency driving apparatus 5 is of a high-frequency power supply unit which supplies the current to the ultrasonic treatment apparatus 3. The ultrasonic treatment apparatus 3 and the ultrasonic driving apparatus 4 are connected to each other with a negative interconnection 241 and a positive interconnection 251, and the ultrasonic treatment apparatus 3 and the high-frequency driving apparatus 5 are connected to each other with the negative interconnection 241.

The videoscope 2 includes a scope operating unit 221 and a thin, cylindrical insertion unit 222. The scope operating unit 221 is provided on the proximal-end side of the insertion unit 222. The insertion unit 222 is provided in the lower portion of the scope operating unit 221, and the insertion unit 222 is inserted into the subject. A flexible universal cord 221a is connected to the side face of the scope operating unit 221. The flexible universal cord 221a connects the scope operating unit 221 and the light source apparatus or display apparatus. A bending operation knob 221b is projected from the side face of the scope operating unit 221 while being located at a position different from the universal cord 221a. The bending operation knob 221b operates a curving action of a distal end of the insertion unit 222.

A grip unit 221c is provided in the scope operating unit 221. For example, an operator grips the grip unit 221c to hold and fix the videoscope 2. In the scope operating unit 221, a forceps insertion port 221d is projected on the side where the insertion unit 222 is attached. A pair of forceps which is of the ultrasonic treatment apparatus 3 according to the present invention is inserted into the forceps insertion port 221d. FIG. 74 shows a state in which the ultrasonic treatment apparatus 3 is inserted into the forceps insertion port 221d to project an operating unit 231, which operates the ultrasonic treatment apparatus 3, from the forceps insertion port 221d through a flexible sheath 236.

The insertion unit 222 inserted into the subject includes a distal-end portion 222a, a bending unit, and a flexible pipe. The distal-end portion 222a is provided at the distal end of the insertion unit 222, the bending unit is caused to perform the curving action by operating the scope operating unit 221, and the flexible pipe has flexibility. The same channel as the channel 22b shown in FIG. 2 of the first embodiment is formed in the distal-end portion of the insertion unit 222, and an ultrasonic transducer 250 of the ultrasonic treatment apparatus 3 is provided inside while being able to be projected. Similarly to the first embodiment, the distal-end portion of the insertion unit 222 includes two lighting windows, one observation window, and an image guide fiber. The lighting window includes a lighting system fixed to the distal end, the observation window includes an observation system lens, and the other end of the image guide fiber is fixed to the observation window. The lighting window, the observation window, and the image guide fiber are of the component of the observation unit (not shown). The other end of the image guide fiber provided in the insertion unit 222 is connected to the light source apparatus through the universal cord 221a.

The ultrasonic treatment apparatus 3 includes the operating unit 231, the ultrasonic transducer 250, the negative interconnection 241, the positive interconnection 251, a distal-end cover 252, a horn cover 253, a coil shaft 254, a cover pressing unit 255, and a flexible sheath 256. The operating unit 231 has a cylindrical shape shown in FIG. 74. The ultrasonic transducer 250 is provided at the distal end as shown in the sectional view of FIG. 75. The negative interconnection 241 and the positive interconnection 251 supply the electric power and current to the ultrasonic transducer 250. The cylindrical distal-end cover 252 fixes the ultrasonic transducer 250. The horn cover 253 surrounds a horn 250b. The coil shaft 254 couples the operating unit 231 and the distal-end cover 252. The cover pressing unit 255 couples the distal-end cover 252 and the coil shaft 254. The negative interconnection 241, the positive interconnection 251, and the coil shaft 254 are inserted into the flexible sheath 256.

The distal-end cover 252 is made of an insulating resin, and the distal-end cover 252 formed in the cylindrical shape has a bottom unit 252a. The horn cover 253 and the cover pressing unit 255 are screwed on the distal-end cover 252 respectively. As shown in FIG. 76 which is of a sectional view taken on line A-A of FIG. 75, the negative interconnection 241 and the positive interconnection 251 are soldered to metal plates 257 and 258 provided in the bottom unit 252a, and the negative interconnection 241 and the positive interconnection 251 are connected to the ultrasonic transducer 250 through the metal plates 257 and 258.

The horn cover 253 is made of an insulating resin, and the horn 250b is covered with the horn cover 253 such that a slight clearance is formed between the horn 250b and the horn cover 253. Therefore, the short circuit is prevented in the larger diameter portion of the horn 250b in the case where the ultrasonic treatment apparatus 3 is used as the electric cautery, and the damage of the channel of the endoscope apparatus 1 is prevented in the case where the ultrasonic vibration is generated. The clearance between the horn 250b and the horn cover 253 is provided such that the horn 250b is not brought into contact with the horn cover 253 in the oscillation. The cover pressing unit 255 is brazed to the distal end of the coil shaft 254 while being screwed on the rear end of the distal-end cover 252, which couples the distal-end cover 252 and the coil shaft 254.

The coil shaft 254 is formed in a multi-layer structure, i.e., the coil shaft 254 is formed in a three-layer structure in the thirteenth embodiment. For example, an inner layer is formed by the left-handed coil, an intermediate layer is formed by the right-handed coil, and an outer layer is formed by the left-handed coil. Therefore, a rotation follow-up property from the proximal-end side of the operating unit 231 to the distal-end side of the ultrasonic transducer 250 is improved by alternately winding the coils of the three-layer structure. The outer diameter of the coil shaft 254 is slightly smaller than the inner diameter of the flexible sheath 256. For example, the outer diameter of the coil shaft 254 is formed smaller than the inner diameter of the flexible sheath 256 by about 2 mm. The coil shaft having the smaller outer diameter may be used to improve the operability of the treatment tool. In the present invention, the coil shaft 254 is not limited to the three-layer structure. However, in the multi-layer structure of at least two layers, the coils of the layers can be alternately wound, and thereby the rotation follow-up property can be realized. Accordingly, when the coil shaft 254 is rotated clockwise or counterclockwise on the side of the operating unit 231, the ultrasonic transducer 250 fixed to the distal-end cover 252 is rotated clockwise or counterclockwise by following the rotation of the coil shaft 254.

The flexible sheath 256 is formed by a flexible insulating tube made of polyurethane, Teflon, or the like. One end of the flexible sheath 256 is provided on the outer periphery of the distal-end cover 252, and one end of the flexible sheath 256 is latched by the horn cover 253 so as not to drop off onto the side of the distal-end cover 252. The other end of the flexible sheath 256 reaches onto the side of the operating unit 231. The operator manually inserts or draws the flexible sheath 256 into or from the videoscope 2 to retractably move the flexible sheath 256 in the insertion unit 222 along with the coil shaft 254 connected to the operating unit 231. For example, the flexible sheath 256 is moved toward the direction of the distal-end portion in the channel of the insertion unit 222, the ultrasonic transducer 250 and a part of the distal-end cover 252 are projected from the distal-end portion, and the treatment is performed with the electric cautery in which the ultrasonic vibration or high-frequency current of the ultrasonic transducer 250 is utilized. The flexible sheath 256 is moved toward the direction of the operating unit 231 in the channel of the insertion unit 222 to store the ultrasonic transducer 250 and distal-end cover 252 in the distal-end portion of the insertion portion 222.

Figure 79A:
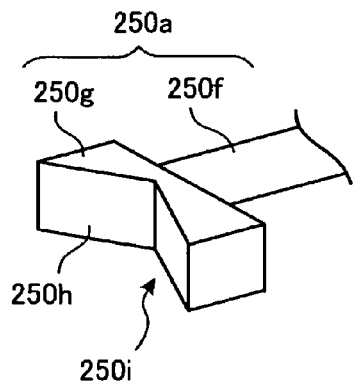
FIG. 79A is a perspective view of the distal-end treatment unit shown in FIG. 78.
Figure 79B:
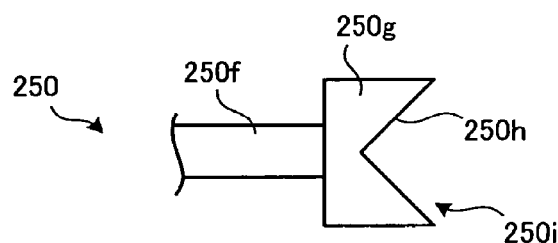
FIG. 79B is a top view of the distal-end treatment unit shown in FIG. 78.
Figure 79C:
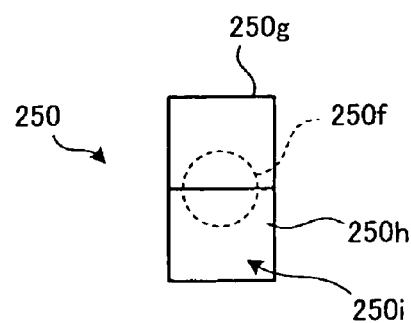
FIG. 79C is a front view of the distal-end treatment unit shown in FIG. 78.

The configuration of the ultrasonic transducer 250 will be described below. FIG. 77 is a view showing the distal-end portion when viewed from an arrow B of FIG. 75, FIG. 78 is a perspective view showing the configuration of the ultrasonic transducer of the present invention, FIG. 79A is a perspective view showing the configuration of the distal-end treatment unit shown in FIG. 78, FIG. 79B is a top view of the distal-end treatment unit shown in FIG. 78, and FIG. 79C is a front view of the distal-end treatment unit shown in FIG. 78. In the drawings, the ultrasonic transducer 250 is made of an electrically conductive material such as titanium. The ultrasonic transducer 250 includes a distal-end treatment unit 250a, a horn 250b, a flange 250c, a piezoelectric element 250d, a negative electrode 250e1, a positive electrode 250e2, and a backing plate 250z. The cylindrical distal-end treatment unit 250a has a hollow structure. The horn 250b transmits the ultrasonic vibration to the distal-end treatment unit 250a. The flange 250c fixes the ultrasonic transducer 250 to the cover 252. The piezoelectric element 250d generates the ultrasonic vibration. The negative electrode 250e1 and the positive electrode 250e2 are connected to the negative interconnection 241 and the positive interconnection 251 respectively, and the negative electrode 250e1 and the positive electrode 250e2 supply the electric signal to the piezoelectric element 250d. The ultrasonic driving apparatus 4 supplies the electric power signal to the piezoelectric element 250d through the negative interconnection 241, the positive interconnection 251 and the operating unit 231. The piezoelectric element 250d receives the electric power signal to generate the ultrasonic vibration having, e.g., a frequency of 100 kHz. The generated ultrasonic vibration passes through the horn 250b having the drawn shape to enlarge the vibration amplitude, and the ultrasonic vibration is transmitted to the distal-end treatment unit 250a. The flange 250c is provided at the node position of the vibration, and the flange 250c is fixed to the end portion of the distal-end cover 252. A cylindrical rubber 259 is provided between the flange 250c and the horn cover 253 to form the watertight structure of the inside of the distal-end cover 252. The outer diameter of the rubber 259 is substantially similar to that of the flange 250c.

The distal-end treatment unit 250a extends from the proximal-end side to the distal-end side, and the distal-end treatment unit 250a includes a small-diameter unit 250f having a longitudinal axis. A larger-diameter unit 250g is coupled to the distal-end portion of the smaller-diameter unit 250f. The outer diameter of at least a part of a cross section perpendicular to the longitudinal axis of the larger-diameter unit 250g is larger than that of at least a part of a cross section perpendicular to the longitudinal axis of the smaller-diameter unit 250f.

The distal-end treatment unit 250a will be described in detail. As shown in FIG. 78 to FIG. 79C, in the thirteenth embodiment, the proximal-end portion of the substantially cylindrical smaller-diameter unit 250f is coupled to the distal-end portion of an output end (horn 250b) of the ultrasonic transducer 250. The larger-diameter unit 250g having a substantially rectangular solid shape is coupled to the distal-end surface of the smaller-diameter unit 250f such that the proximal-end surface of the larger-diameter unit 250g is substantially perpendicular to the center axis of the smaller-diameter unit 250f. The cross section perpendicular to the center axis of the larger-diameter unit 250g has a substantially rectangular shape. At least a long side of the rectangular shape is larger than the diameter of the smaller-diameter unit 250f. A concave portion 250h which is of a holding unit is formed in the whole of the distal-end surface of the larger-diameter unit 250g. In the cross section parallel to the long sides, the concave portion 250h has a triangular shape which is opened toward the distal-end side. The concave portion 250h constitutes a distal-end surface portion 250i which is of an end face of the distal end.

Then, the working of the ultrasonic treatment apparatus 3 of the thirteenth embodiment will be described. The case, where a tissue in which fibers are mixed is crushed by cavitation to perform the treatment such that a liver is excised or the mucosa of a gaster or a large intestine is peeled off, will be described below. The ultrasonic vibration is generated by the ultrasonic transducer 250, the ultrasonic vibration is transmitted through a probe by the distal-end treatment unit 250a, longitudinal vibration is generated in the larger-diameter unit 250g of the distal-end treatment unit 250a, and the larger-diameter unit 250g is rotated toward the desired direction. Then, the larger-diameter unit 250g in the vibrating state is pressed against the tissue. As a result, the fibers of the tissue are concentrated in the concave portion 250h, the fibers are crushed by the cavitation generated by the distal-end surface portion 250i. At the same time, the larger-diameter unit 250g sinks into the tissue, and the fibers are caught in the proximal-end surface of the larger-diameter unit 250g, which also allows the fibers to be crushed by the cavitation generated by the proximal-end surface of the larger-diameter unit 250g.

Accordingly, the ultrasonic treatment apparatus 3 of the thirteenth embodiment has the following effect. In the distal-end treatment unit 250a of the thirteenth embodiment, the outer diameter of the larger-diameter unit 250g provided in the distal-end portion of the smaller-diameter unit 250f is larger than that of the smaller-diameter unit 250f. In the case where the liver is excised or the mucosa of the gaster or large intestine is peeled off, the larger-diameter unit 250g is rotated toward the desired direction by the operating unit, and the cavitation can be generated by the larger-diameter unit 250g. Therefore, treatment performance of the ultrasonic treatment apparatus 3 is improved.

The negative interconnection 241 is connected to the negative electrode 250e1, and a counter electrode plate (similar to the counter electrode plate 9 of FIG. 3) is connected to the high-frequency driving apparatus 5. The counter electrode plate is of a counterpart of the electrode 250e. The current signal supplied from the high-frequency driving apparatus 5 is passed between the distal-end treatment unit 250a and the counter electrode plate through the human body, which allows the ultrasonic treatment apparatus 3 to function as the electric cautery having, e.g., a frequency of 350 kHz. The ultrasonic treatment apparatus 3 includes a selector (similar to the selector 8 of FIG. 3). The operator can select the treatments with the electric cautery, in which the ultrasonic vibration or high-frequency current is utilized, by the selector. The selector is connected to the ultrasonic driving apparatus 4 and high-frequency driving apparatus 5 to enable the selection of the supply of the electric power and/or the supply of the electric current to the ultrasonic transducer 250. Hereinafter the electric power signal and the current signal are collectively referred to as electric signal, and the negative interconnection 241 and the positive interconnection 251 are collectively referred to as electric signal line. In the thirteenth embodiment, the frequency of the ultrasonic vibration is set at 100 kHz, and the frequency of the electric cautery is set at 350 kHz. However, the present invention is not limited to the thirteenth embodiment. For example, the frequencies may be selected from a range where resonance is not generated between the frequencies of the ultrasonic vibration and electric cautery.

Figure 80:
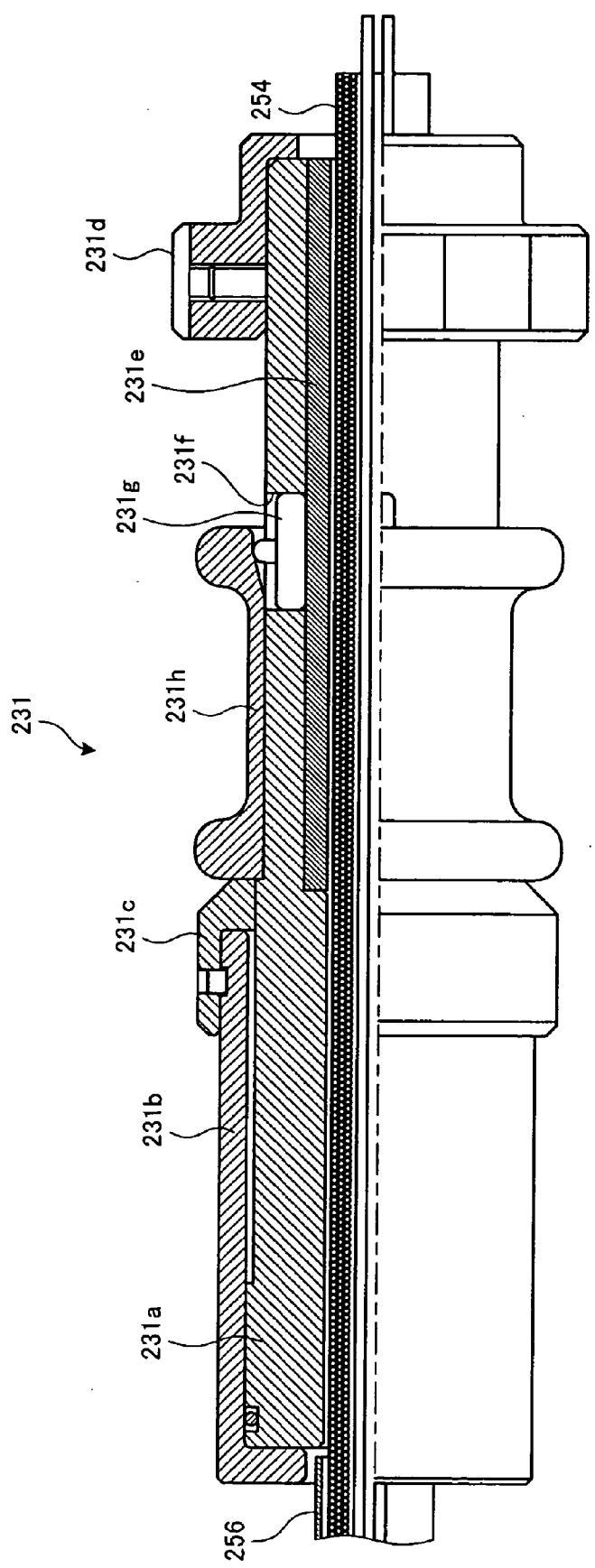
FIG. 80 is a sectional side view of the operating unit shown in FIG. 74 having a first exemplary configuration.

As shown in FIG. 80, the operating unit 231 includes a substantially cylindrical operating unit main body 231a, a base 231b, a pressing unit 231c, a handle 231d, a tube 231e, an opening 231f, a T-lock 231g, and a slider 231h. The substantially cylindrical housing 231a surrounds the coil shaft 254 projected from the flexible sheath 256. The proximal-end side of the housing 231a is covered with the base 231b. The housing 231a is fitted in the pressing unit 231c, and the pressing unit 231c is screwed on the base 231b. The distal-end side of the housing 231a is covered with the handle 231d, and the handle 231d is screwed on the housing 231a. The tube 231e is provided between the housing 231a and the coil shaft 254. The opening 231f is opened toward the outer peripheral surface and inner peripheral surface of the housing 231a. The T-shaped T-lock 231g is provided in the opening 231f, and the T-lock 231g is configured to be able to press the coil shaft 254 against the inner peripheral surface of the housing 231a. The slider 231h slidably engages the outer peripheral surface of the housing 231a. In the sliding, the slider 231h abuts against any of the T-lock 231g to move the T-lock 231g toward the inner peripheral direction of the housing 231a. The T-lock 231g is moved toward the inner peripheral direction to press the coil shaft 254 against the inner peripheral surface of the housing 231a, which fixes the coil shaft 254 to the housing 231a. In this state of things, when the handle 231d is rotated clockwise or counterclockwise, while the flexible sheath 256 is kept as it is, the ultrasonic transducer 250 fixed to the distal-end cover 252 is rotated clockwise or counterclockwise by following the rotation of the handle 231d, which enables the larger-diameter unit 250 of the distal-end treatment unit 250a to rotate to the desired position (angle) with respect to the treated site.

The endoscope apparatus 1 includes a bending block (similar to the bending block 55 of FIG. 4) in the insertion unit 222 near the distal-end portion. The bending block is connected to the bending operation knob 221b, and the bending operation knob 221b is operated to enables the distal end of the insertion unit 222 of the endoscope apparatus 1 to be bent. For example, the endoscope apparatus 1 includes a compact soft endoscope in which the insertion unit 222 has the flexibility.

Figure 81:
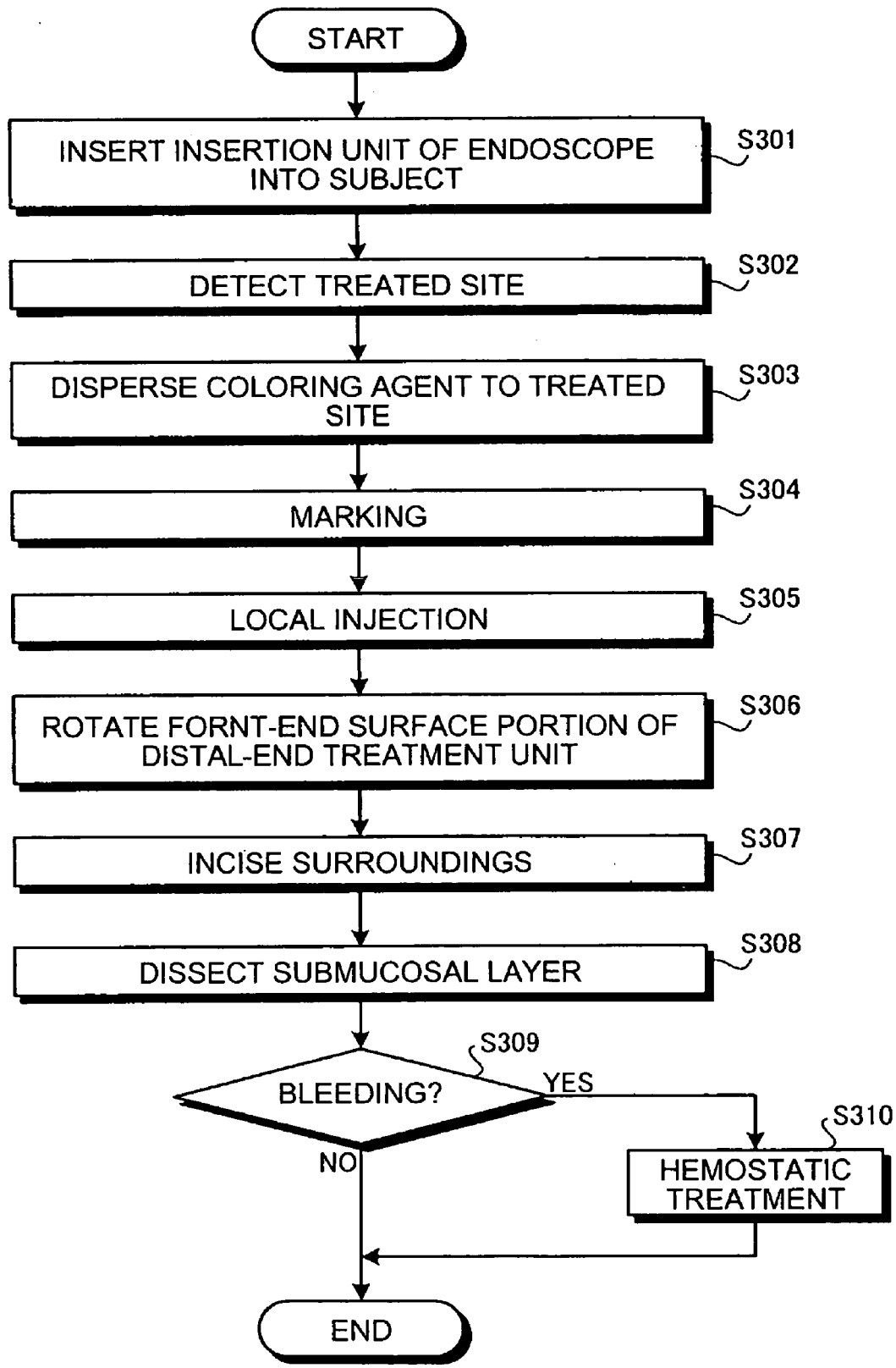
FIG. 81 is a flowchart of a treatment procedure of the ultrasonic treatment apparatus shown in FIG. 74.

The treatment action of the ultrasonic treatment apparatus will be described with reference to FIG. 81 to FIG. 90. FIG. 81 is a flowchart for explaining the treatment procedure of the ultrasonic treatment apparatus, and FIG. 82 to FIG. 90 show respective processes of the treatment procedure in the incision operation.

In these drawings, the insertion unit 222 of the endoscope apparatus 1 is inserted into the subject (Step 301), and the treated site B to be treated is arranged within the visual field and detected by the observation unit (Step 302). In the initial state, instead of the ultrasonic treatment apparatus 3, the tube 10 is inserted into the insertion unit 222 from the forceps insertion port 221d. The cylinder (not shown) in which the coloring agent is injected is attached to the tube 10, and the inserted tube 10 is provided while being projected to the outside from the distal end of the insertion unit 222.

Figure 82:
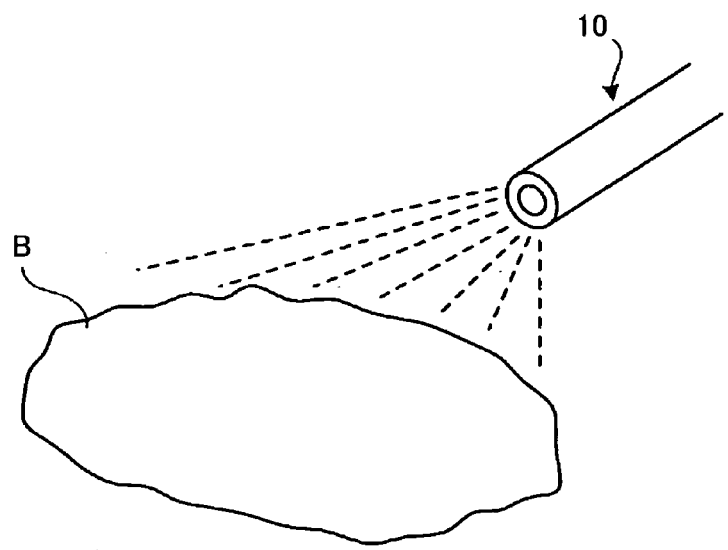
FIG. 82 shows how a coloring agent is spread from the distal-end portion shown in FIG. 75.

When the treated site is detected, while the distal-end portion of the insertion unit 222 is brought close to the treated site, the coloring agent injected in the cylinder is dispersed to the treated site B from the distal end of the tube 10 projected from the distal end of the insertion unit 222 as shown in FIG. 82 (Step 303).

Figure 83:
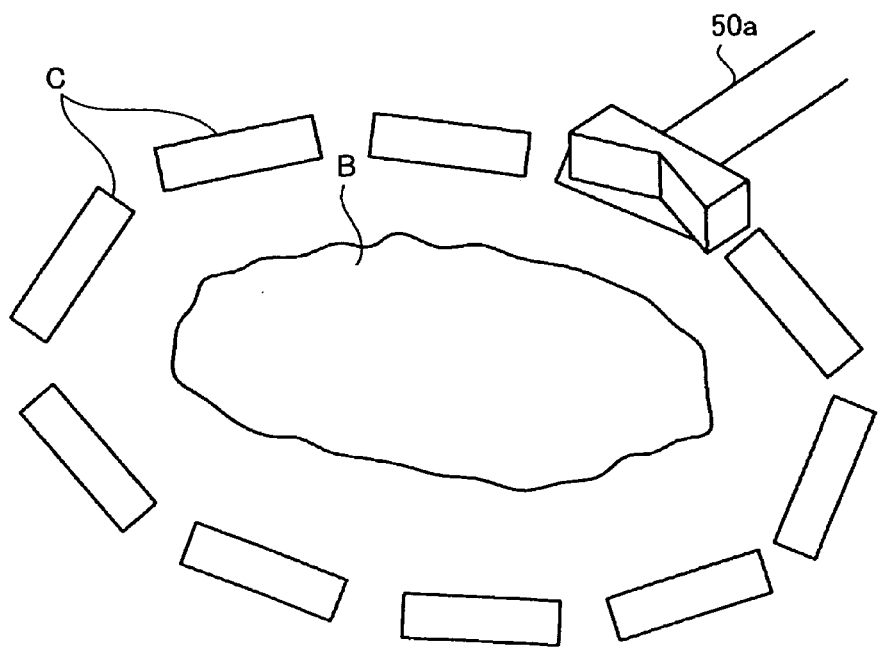
FIG. 83 shows how a marking is performed by the distal-end portion shown in FIG. 75.

Then, the tube 10 is taken out from the insertion unit 222 of the endoscope apparatus 1, instead the ultrasonic treatment apparatus 3 is inserted into the insertion unit 222 from the forceps insertion port 221d, and the current signal is supplied from the high-frequency driving apparatus 5 to the negative electrode 250e1 of the ultrasonic transducer 250 through the negative interconnection 241. This enables the distal-end treatment unit 250a to function as the electric cautery. As shown in FIG. 83, the recognizable markings C are formed by cauterizing the living tissue around the coloring treated site B using the distal-end treatment unit 250a having the function of the electric cautery (Step 304).

Figure 84:
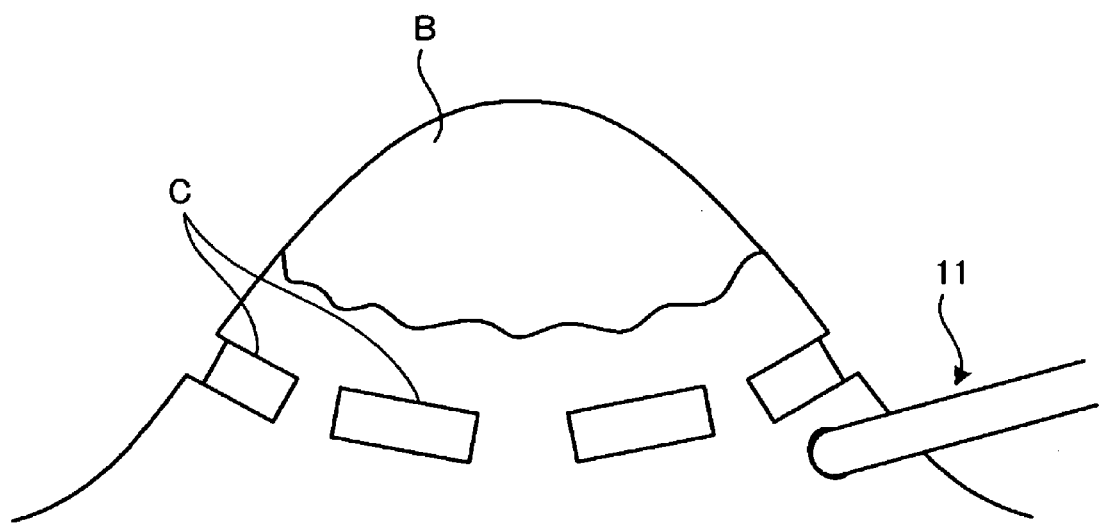
FIG. 84 shows how a local injection is performed by the distal-end portion shown in FIG. 75.

Then, the ultrasonic treatment apparatus 3 is taken out again from the insertion unit 222 of the endoscope apparatus 1, and instead the tube and a injection needle 11 attached at the distal end thereof are inserted into the insertion unit 222 from the forceps insertion port 221d. The cylinder (not shown) is attached to the tube, and the local injection solution (such as the physiological salt solution or Glyceol) is injected in the cylinder. As shown in FIG. 84, the distal end of the distal-end treatment unit 250a is inserted into the lower portion of the treated site B from the outside of the markings C, the local injection solution is injected from the tube, and the living tissue including the treated site B is raised (Step 305).

Then, the tube 10 is taken out from the insertion unit 222 of the endoscope apparatus 1, instead the ultrasonic treatment apparatus 3 is inserted into the insertion unit 222 from the forceps insertion port 221d, and the coil shaft 254 is locked by the operating unit 231. The distal-end treatment unit 250a is rotated to set the distal-end treatment unit 250a at the desired angle with respect to the treated site B by the rotation of the handle 231d. In the thirteenth embodiment, the distal-end treatment unit 250a is rotated such that the longitudinal direction of the distal-end surface portion 250i of the distal-end treatment unit 250a becomes horizontal with respect to the raised treated site B (Step 306).

Figure 85:
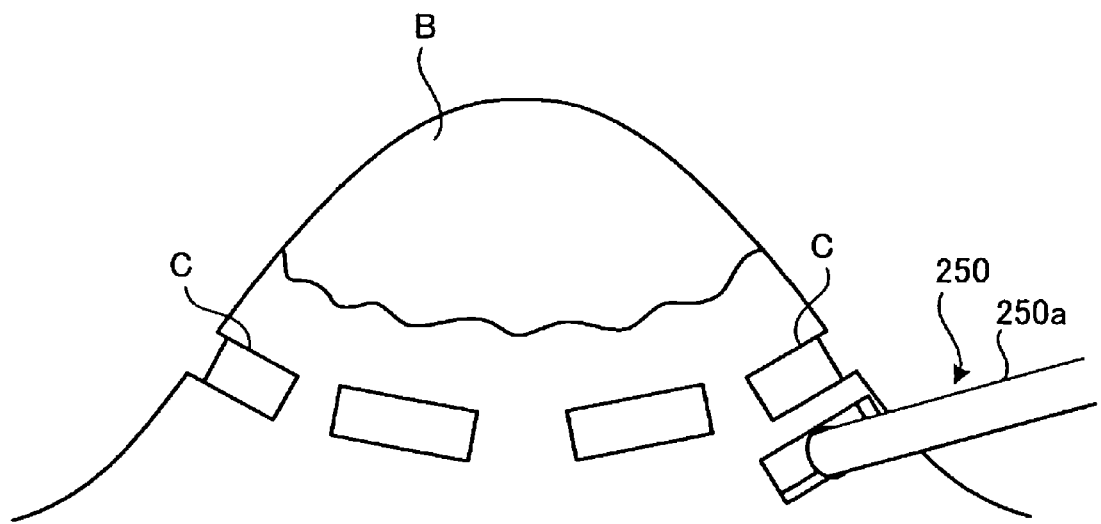
FIG. 85 shows how a periphery of a living tissue is incised by the distal-end portion shown in FIG. 75.
Figure 86:
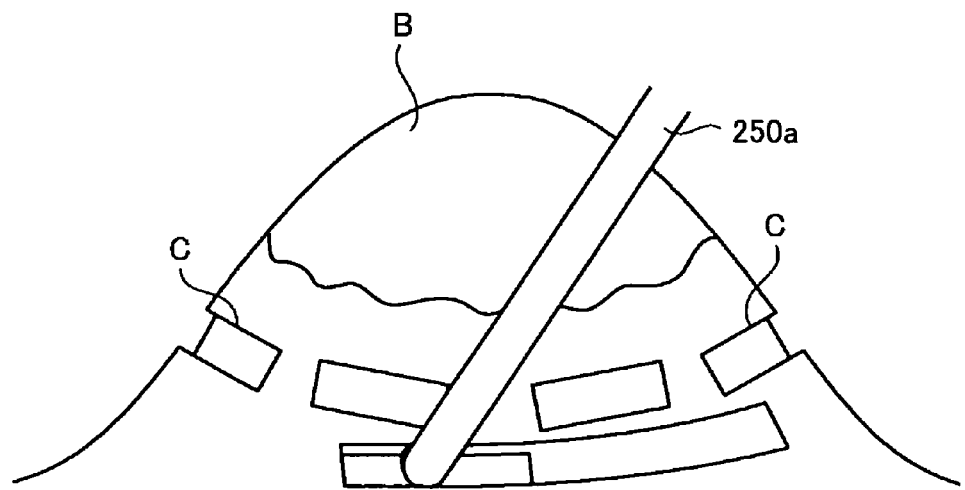
FIG. 86 shows how a periphery of a living tissue is incised by the distal-end portion shown in FIG. 75.
Figure 87:
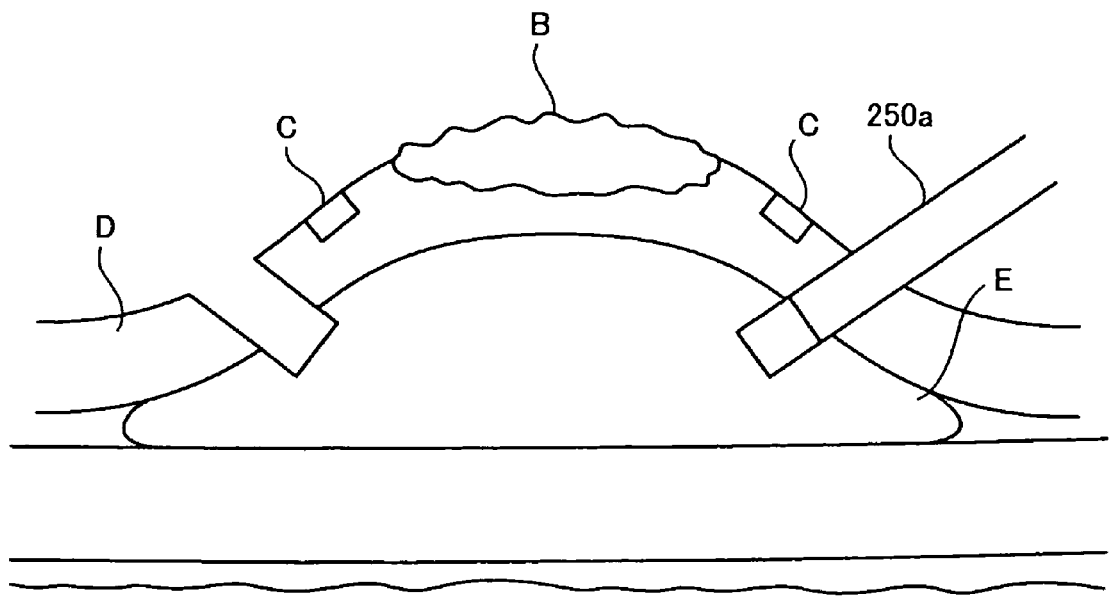
FIG. 87 shows how a periphery of a living tissue is incised by the distal-end portion shown in FIG. 75.
Figure 88:
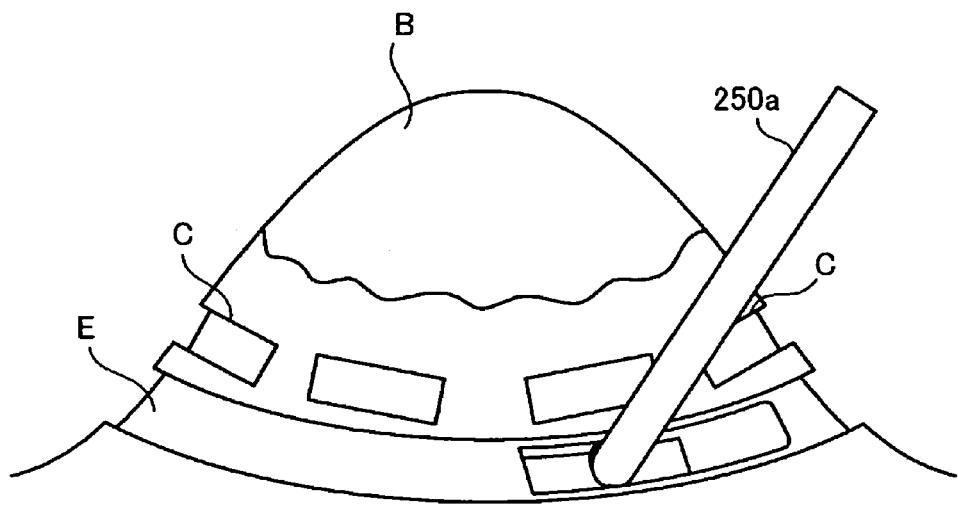
FIG. 88 shows how a submucosal tissue is ablated by the distal-end portion shown in FIG. 75.
Figure 89:
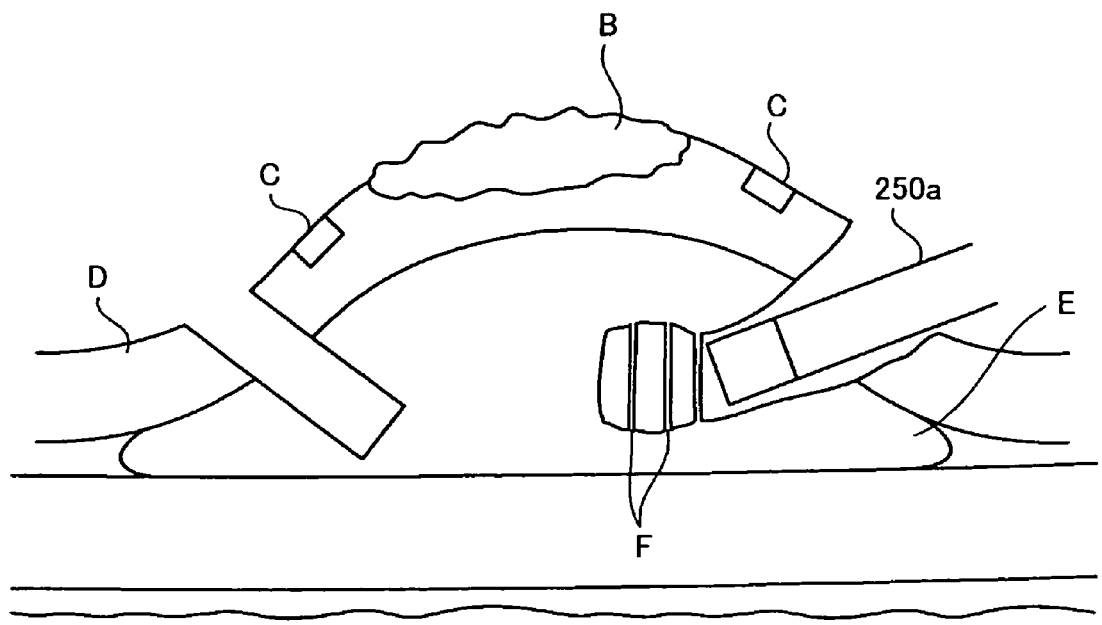
FIG. 89 shows how a submucosal tissue is ablated by the distal-end portion shown in FIG. 75.
Figure 90:
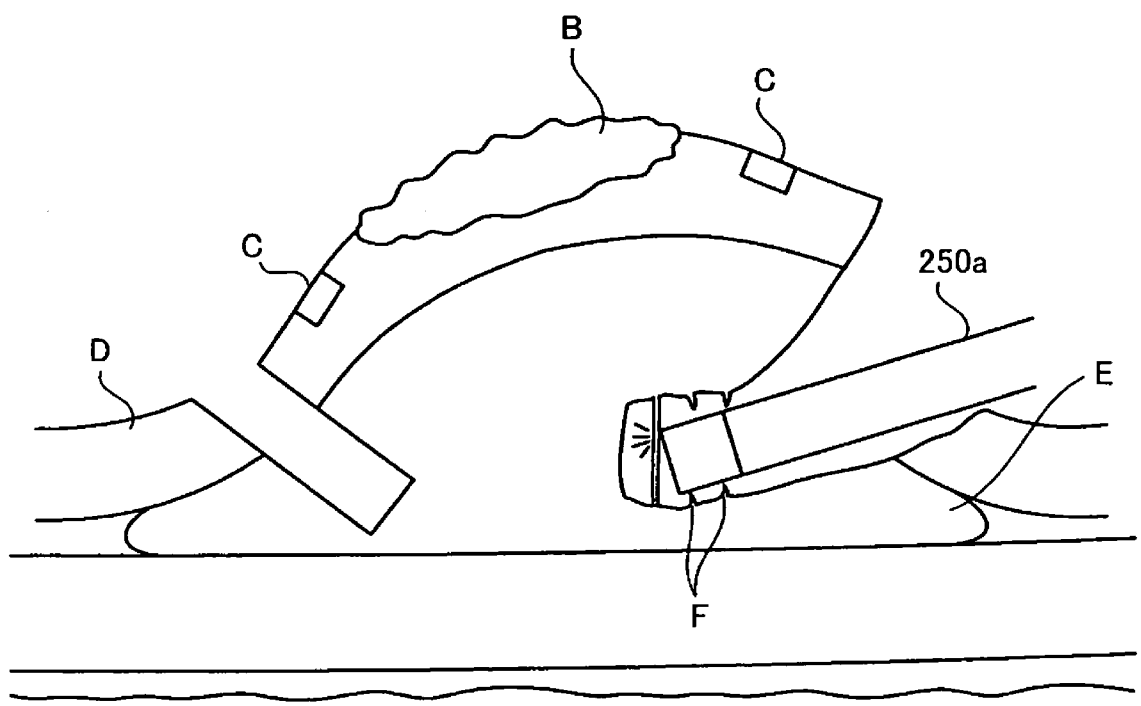
FIG. 90 shows how a submucosal tissue is ablated by the distal-end portion shown in FIG. 75.

Then, the ultrasonic vibration is generated, the surroundings of the living tissue (mucosa D) raised by the distal-end treatment unit 250a are incised as shown in FIG. 85 to FIG. 87, and the mucosa D is incised over all the circumferences (Step 307). At this point, the surroundings are sequentially incised while the distal-end treatment unit 250a is moved only by a length in the longitudinal direction of the distal-end surface portion 250i. Further, in the thirteenth embodiment, the submucosal layer E existing below the mucosa D is peeled off as shown in FIG. 88 (Step 308). In this case, as shown in FIG. 89, the submucosal layer E is crushed into the jelly-like substance by the ultrasonic treatment. For the fiber F and the blood vessel shown in FIG. 89 and FIG. 90, the tissue having high elasticity is easily cut while the hemostasis is performed by selecting the electric cautery function to cauterize and cut the fiber F and the blood vessel.

In the case where the bleeding exists (Step 309), the hemostatic treatment is performed using the electric cautery function (Step 310). In order to recover the cut tissue specimen, instead of the ultrasonic treatment apparatus 3, for example a pair of grip forceps (not shown) is inserted from the forceps insertion port 221d into the channel of the distal-end portion, and the tissue specimen can be taken out while being gripped by the grip forceps. In the thirteenth embodiment, even in the marking process, the distal-end treatment unit 250a can be rotated to perform the marking at the desired position.

Although the ultrasonic vibration function and the electric cautery function are individually driven in the thirteenth embodiment, the present invention is not limited to the thirteenth embodiment. For example, in the process of dissecting the submucosal layer, either or both of the ultrasonic vibration function and the electric cautery function may simultaneously be driven according to the treatment process.

Thus, in the thirteenth embodiment, the treatment unit including the distal-end surface portion having the directional movement in which the treated site can be treated in at least two directions is rotated by the operating unit and the coil shaft having the rotation follow-up property, and the distal-end surface portion can be set with respect to the treated site such that the treatment can be performed at the desired angle. Therefore, the improvement of the treatment performance can be achieved in the ultrasonic treatment apparatus.

In the thirteenth embodiment, the ultrasonic treatment apparatus includes the treatment unit having both the ultrasonic vibration function and the electric cautery function, the surroundings of the living tissue are incised to crush the living tissue by the ultrasonic vibration, and other incisions are performed by selecting any of the functions. Therefore, the heat damage of the tissue specimen to be cut off is prevented to obtain the proper tissue specimen, and the simplification of the treatment can be achieved. Accordingly, the work necessary to cut the surroundings can be decreased as compared with the conventional art.

Figure 91:
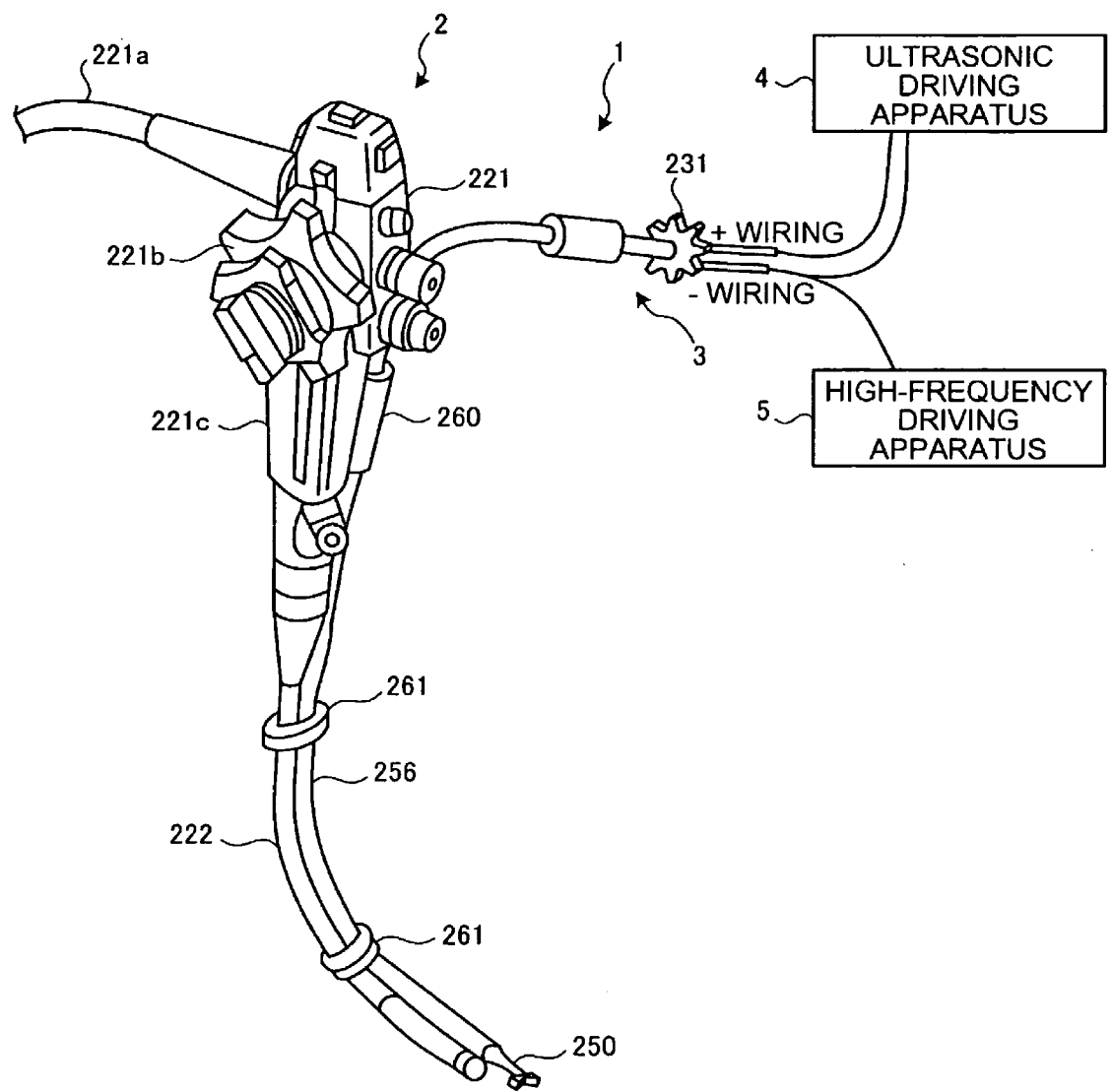
FIG. 91 is a schematic perspective view of the endoscope apparatus shown in FIG. 74 which includes a modification of the ultrasonic treatment apparatus having the third exemplary configuration according to the present invention.

Although the ultrasonic treatment apparatus 3 is inserted into the insertion unit 222 of the videoscope 2 in the thirteenth embodiment, the present invention is not limited to the thirteenth embodiment. For example, as shown in a modification of FIG. 91, the ultrasonic treatment apparatus 3 can also externally be attached with an endoscope clamping jig 260 fixed to the grip portion 221c by videoscope 2 and a holding member 261, which are fixed to the grip unit 221c of the videoscope 2. In this case, the flexible sheath 256 is caused to pass through the cylindrical endoscope clamping jig 260, the flexible sheath 256 is held so as to be arranged along the insertion unit 222 of the videoscope 2 by the plural holding members 261. Therefore, the ultrasonic treatment apparatus 3 can externally be attached to the videoscope 2 to treat the treated site.

Figure 92:
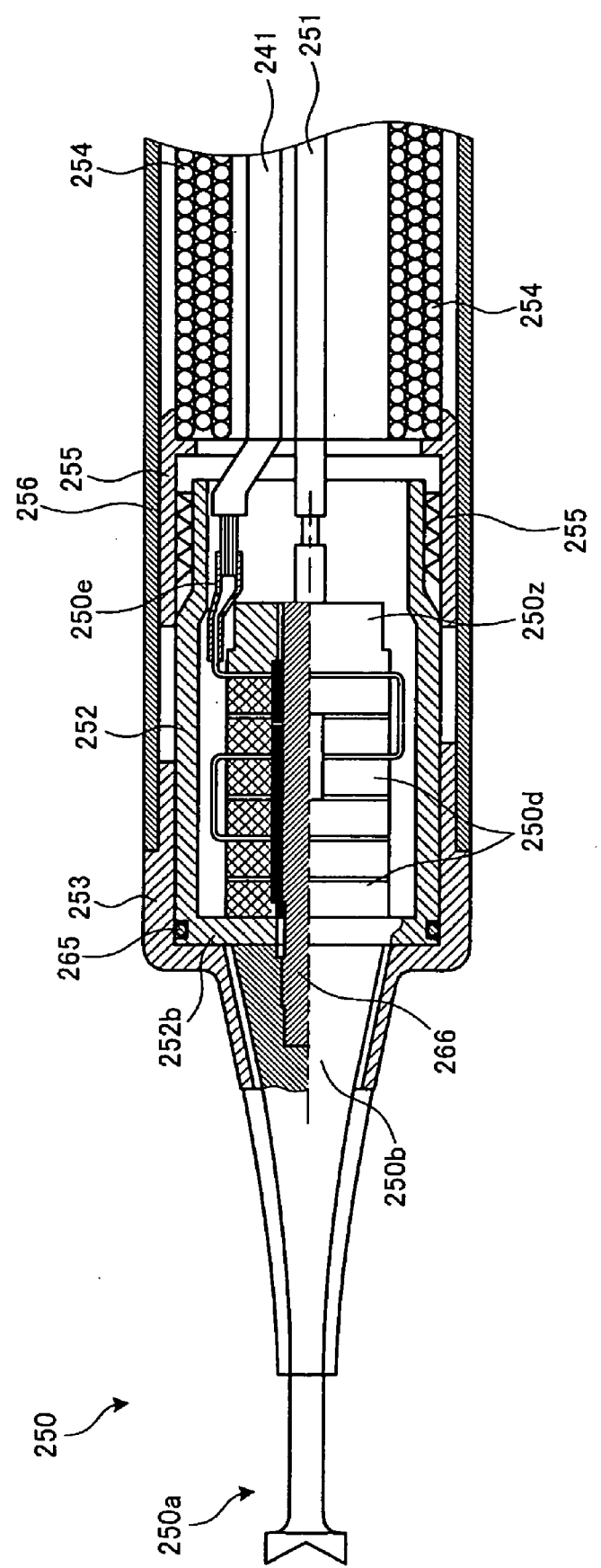
FIG. 92 is a sectional side view of a distal-end portion of an ultrasonic treatment apparatus according to a fourteenth embodiment.

A fourteenth embodiment of the present invention will be described below. FIG. 92 is a sectional side view showing a configuration of a distal-end portion of an ultrasonic treatment apparatus according to the fourteenth embodiment. The fourteenth embodiment prevents the invasion of a liquid into the flexible sheath 256. That is, in the fourteenth embodiment, the horn cover 253 and the flexible sheath 256 are integrally formed by bonding the horn cover 253 and the flexible sheath 256 with a bonding agent or the like. According to the configuration of the fourteenth embodiment, in order not to rotate both the horn cover 253 and the flexible sheath 256 by the operating the operating unit, an O-ring 265 is arranged between the horn cover 253 and the distal-end cover 252 having the U-shape cross section in FIG. 92. Therefore, the watertight is kept in the distal-end cover 252 and the coil shaft 254, and a slidable property of the rotation is secured. The proximal-end side of the distal-end cover 252 is opened, and, similarly to the thirteenth embodiment, this opening and the coil shaft 254 are coupled to each other with the cover pressing unit 255.

The ultrasonic transducer 250 is screwed to both the horn 250b and the backing plate 250z with a bolt 266 to sandwich the cylindrical piezoelectric element 250d, which assembles the whole components. In the fourteenth embodiment, instead of the flange 250c of the thirteenth embodiment, a side wall 252b of the distal-end cover 252 is sandwiched between the horn 250b and the piezoelectric element 250d and screwed with a bolt, and thereby the side wall 252b is integrally assembled with the ultrasonic transducer 250. The distal-end cover 252 may be made of an insulating material such as alumina and PEEK, or the distal-end cover 252 may be made of stainless steel whose the inner surface is coated with an insulating material.

Figure 93:
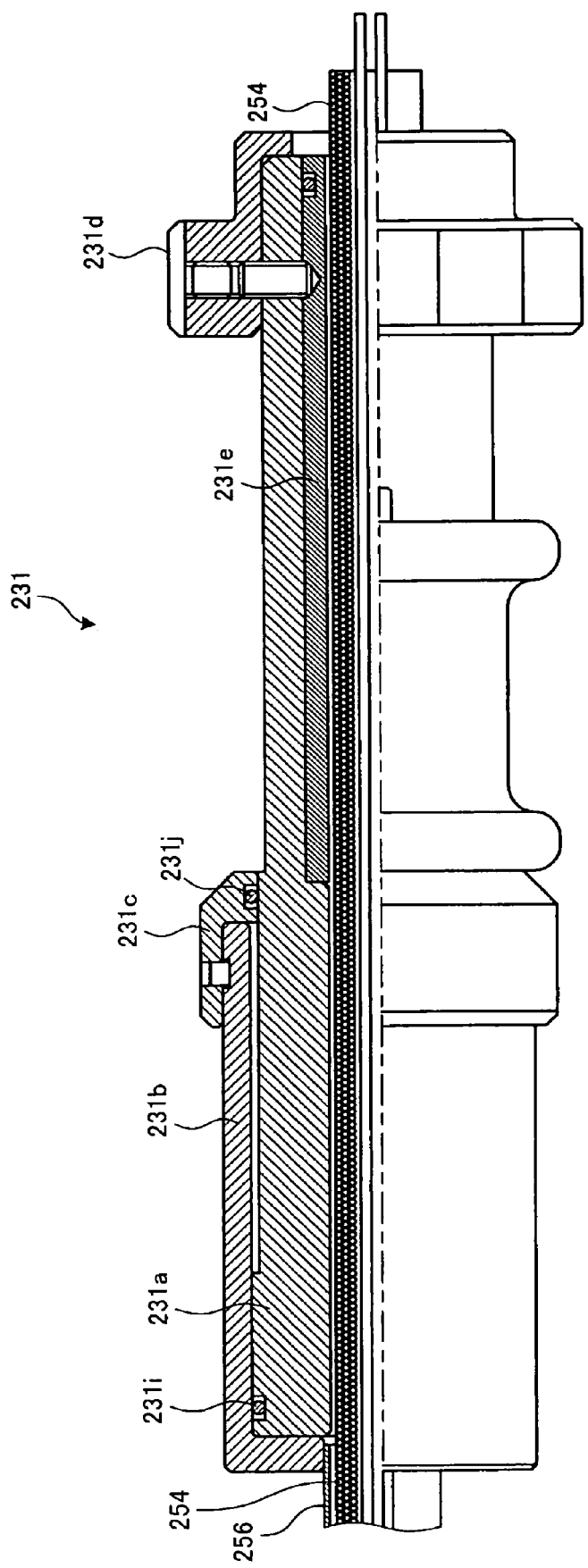
FIG. 93 is a sectional view of the operating unit shown in FIG. 74 having a second exemplary configuration.

As shown in FIG. 93, in the operating unit 231, the base 231b and the flexible sheath 256 are integrated with the bonding agent or the like, the O-ring 231i is fitted between the housing 231a and the base 231b to keep the watertight of the flexible sheath 256. An O-ring 231j is also fitted between the housing 231a and pressing unit 231c.

The tube 231e is made of stainless steel, and the tube 231e is screwed to the coil shaft 254 while being brazed, the watertight of the flexible sheath 256 is kept, and the rotary property is also secured. The screw is made of a resin material.

When the handle 231d is rotated, the base 231b, the pressing unit 231c, and the flexible sheath 256 are not rotated, but the housing 231a, the tube 231e, and the coil shaft 254 are simultaneously rotated. Therefore, and the distal-end surface portion of the distal-end surface portion can be rotated by following the rotations of the housing 231a, the tube 231e, and the coil shaft 254.

In the fourteenth embodiment, the same effect as the thirteenth embodiment is obtained, and the watertight structure of the flexible sheath can be formed on both the distal-end cover side and the operating unit side, so that a water content can be prevented from invading the inside of the flexible sheath.

Figure 94:
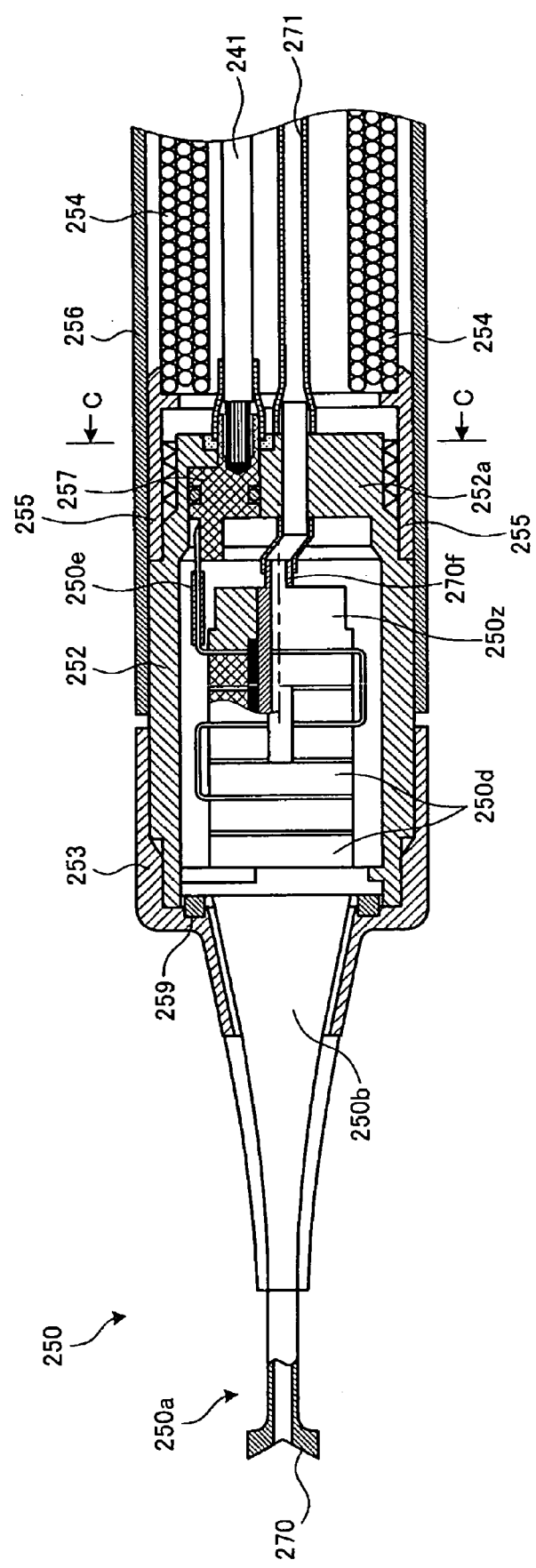
FIG. 94 is a sectional side view of a distal-end portion of an ultrasonic treatment apparatus according to a fifteenth embodiment.
Figure 95:
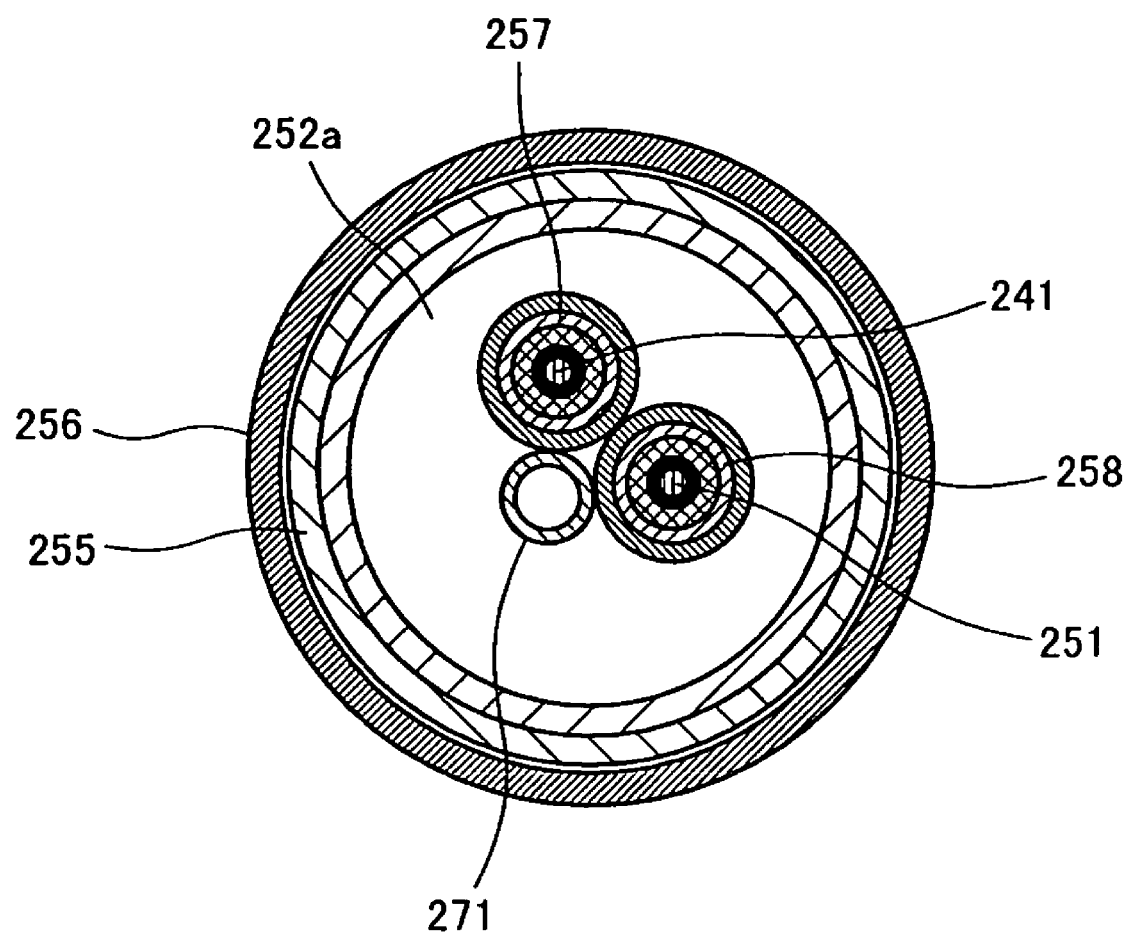
FIG. 95 is a sectional view of the distal-end portion taken on line C-C of FIG. 94.

A fifteenth embodiment will be described below. FIG. 94 is a sectional side view showing a distal-end portion of an ultrasonic treatment apparatus according to the fifteenth embodiment, and FIG. 95 is a sectional view taken on line C-C of FIG. 94. In the drawings, the fifteenth embodiment differs from the thirteenth embodiment in that, in the ultrasonic transducer 250, a hollow treatment pipe 270 is formed in the center axis in the longitudinal direction of the distal-end treatment unit 250a and a treatment tube 271 is connected to the rear end of the treatment pipe 270. The other end of the tube 271 is connected to a suction apparatus (similar to the suction apparatus 6 of FIG. 40) or a cylinder (similar to the cylinder 7 of FIG. 42) through the inside of coil shaft 254 and the operating unit 231. In the above configuration, the emulsified or crushed living tissue or unnecessary body fluid, which flows in from the treatment pipe 270, can be caused to pass through the tube 271 to be discharged outside the ultrasonic treatment apparatus 3 by the suction action of the suction apparatus. The physiological salt solution or chemicals which flow into the tube 271 by the cylinder are dispersed to the outside from the distal end of the treatment pipe 270.

The treatment action of the ultrasonic treatment apparatus will be described with reference to FIG. 81 and FIG. 96 to FIG. 107. In this case, because the treatment procedure with the ultrasonic treatment apparatus is similar to that of the thirteenth embodiment, the treatment procedure will be described with reference to the flowchart of FIG. 81. FIGS. 96 to 107 show respective process of the treatment procedure in the incision operation.

Figure 96:
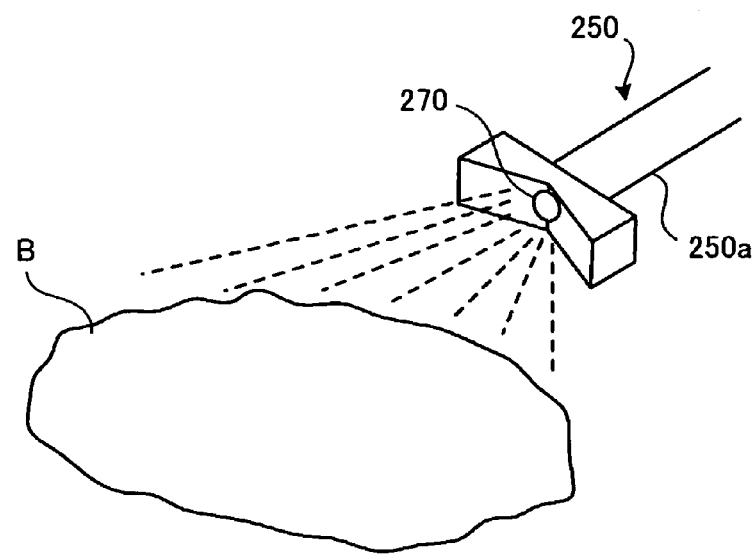
FIG. 96 shows how a coloring agent is spread by the distal-end portion shown in FIG. 94.

In these drawings, the insertion unit 222 of the endoscope apparatus 1 is inserted into the subject (Step 301), and a treated site to be treated is arranged within the visual field and detected by the observation unit (Step 302). When the treated site is detected, the distal-end portion of the insertion unit 222 is brought close to the treated site, the cylinder in which the coloring agent is injected is attached to the tube 271, and the coloring agent is dispersed to the treated site B from the treatment pipe 270 of the ultrasonic transducer 250 through the tube 271 as shown in FIG. 96. The treatment pipe 270 is attached to the distal end of the insertion unit 222 (Step 303). In dispersing the coloring agent, the ultrasonic driving apparatus 4 supplies the electric power signal to the ultrasonic transducer 250 to generate the ultrasonic vibration, and the coloring agent is preferably sprayed on the treated site.

Figure 97:
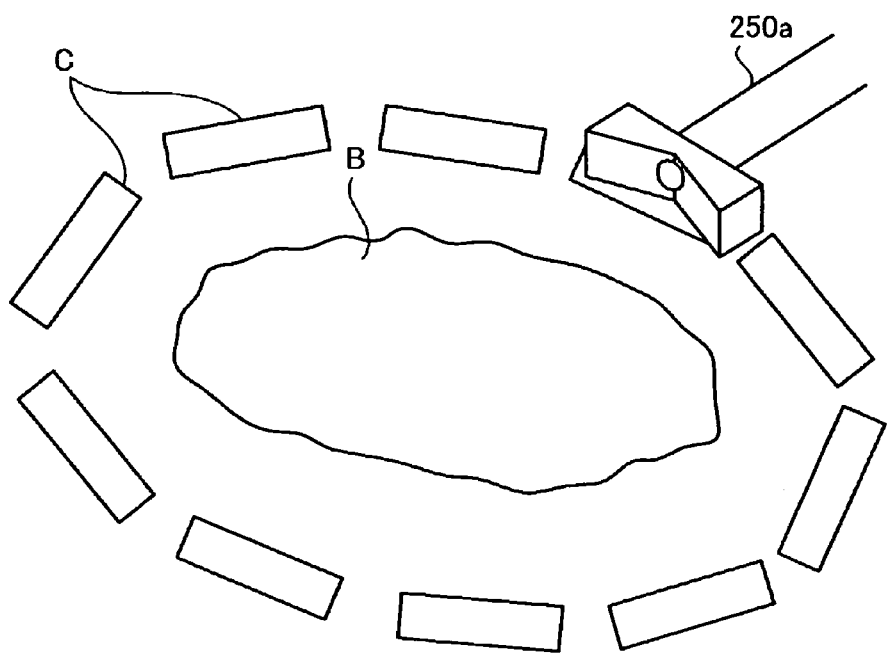
FIG. 97 shows how a marking is performed by the distal-end portion shown in FIG. 94.

Then, the current signal is supplied from the high-frequency driving apparatus 5 to the electrode 250e of the ultrasonic transducer 250 through the negative interconnection 251. This enables the distal-end treatment unit 250a to function as the electric cautery. As shown in FIG. 97, the recognizable markings C are formed by cauterizing the living tissue around the coloring treated site B using the distal-end treatment unit 250a having the function of the electric cautery (Step 304).

Figure 98:
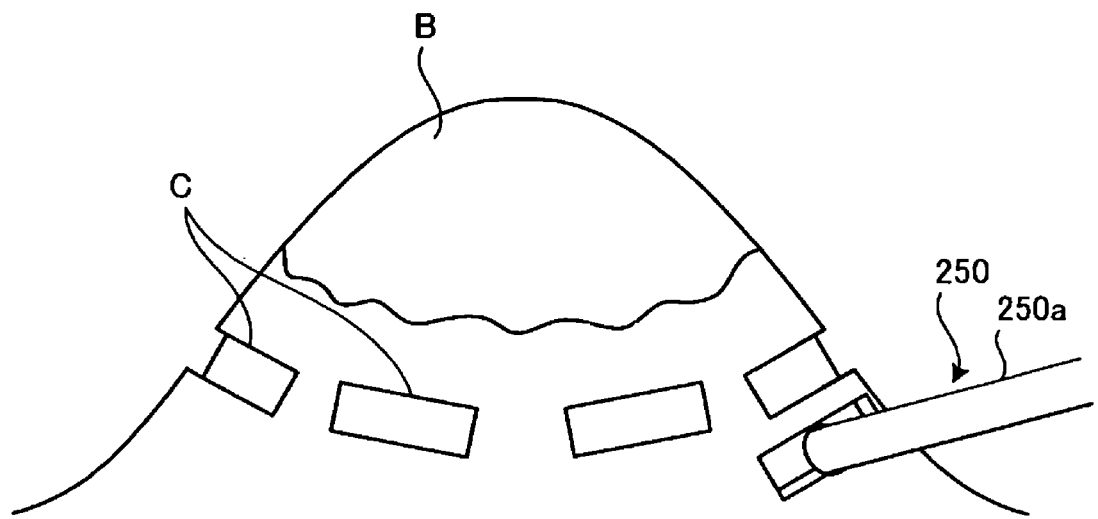
FIG. 98 shows how a local injection is performed by the distal-end portion shown in FIG. 94.

Then, the cylinder is attached to the tube 271. The local injection solution (such as the physiological salt solution or Glyceol) is injected in the cylinder. As shown in FIG. 98, the distal end of the distal-end treatment unit 250a is inserted into the lower portion of the treated site B from the outside of the markings C, the local injection solution is injected from the treatment pipe 270 of the ultrasonic transducer 250, and the living tissue including the treated site B is raised (Step 305).

Then, the distal-end treatment unit 250a is rotated to set the distal-end treatment unit 250a at the desired angle with respect to the treated site B by the rotation of the handle 231d. In the fifteenth embodiment, the distal-end treatment unit 250a is rotated such that the longitudinal direction of the distal-end surface portion 250i of the distal-end treatment unit 250a becomes horizontal with respect to the raised treated site B (Step 306).

Figure 99:
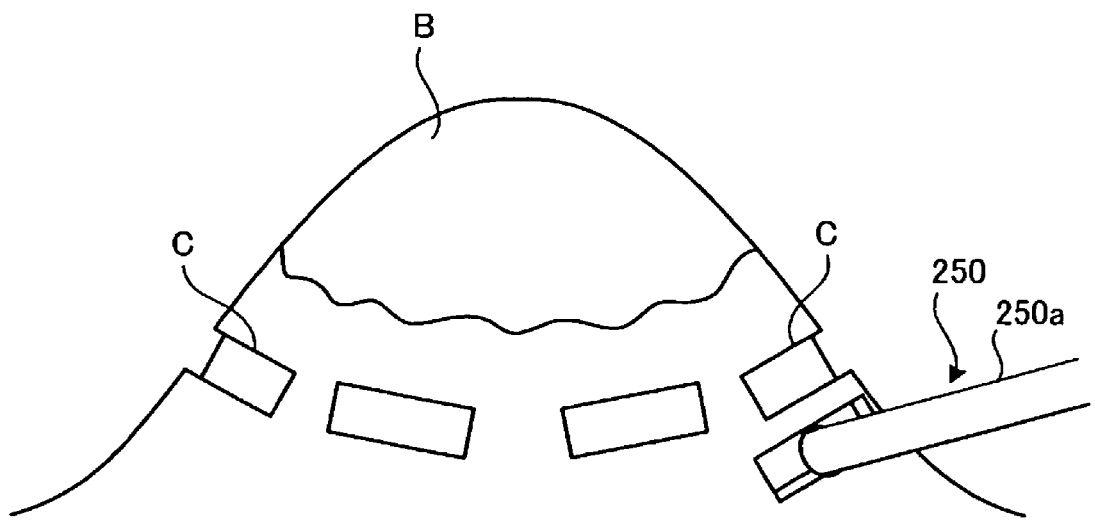
FIG. 99 shows how a periphery is incised by the distal-end portion shown in FIG. 94.
Figure 100:
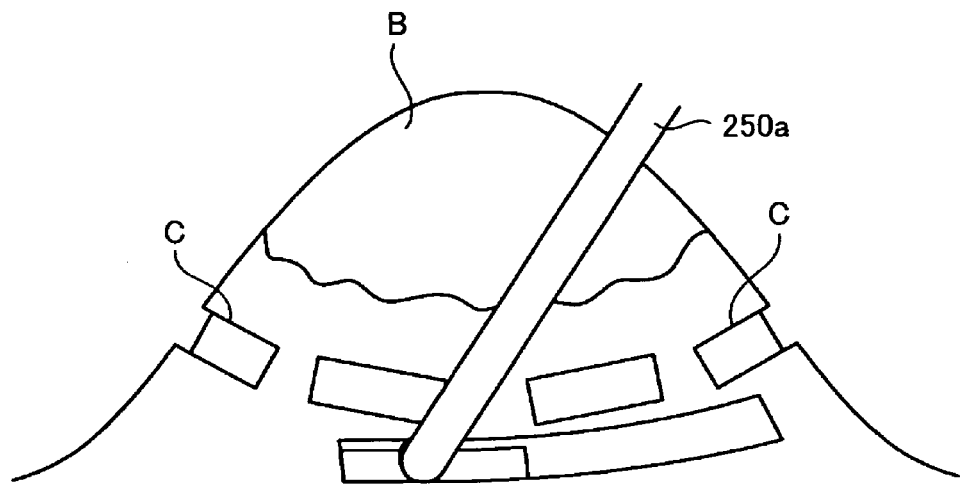
FIG. 100 shows how a periphery is incised by the distal-end portion shown in FIG. 94.
Figure 101:
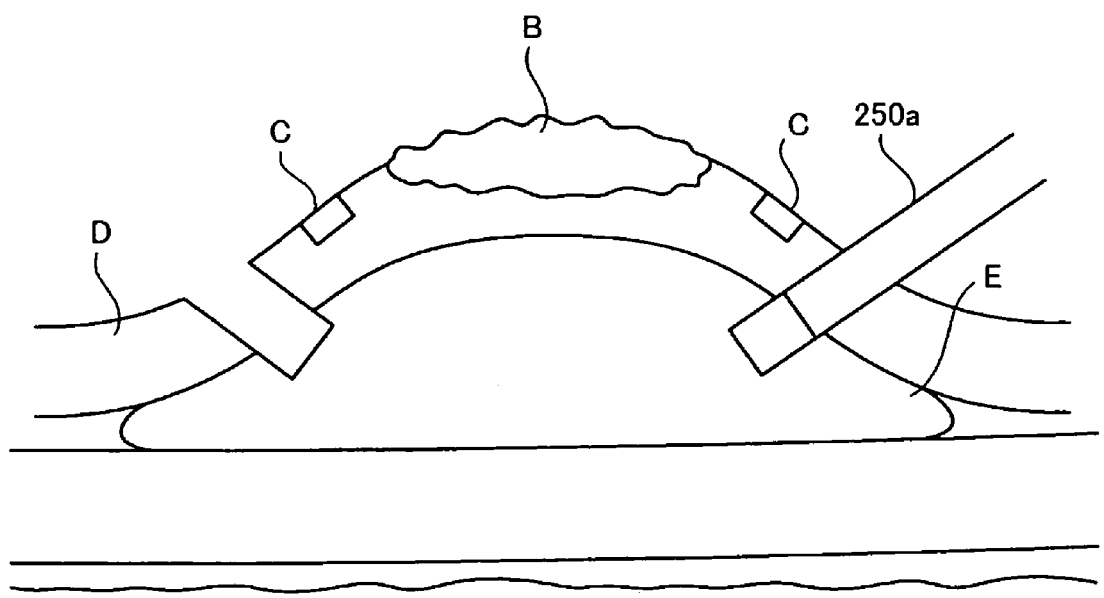
FIG. 101 shows how a periphery is incised by the distal-end portion shown in FIG. 94.
Figure 102:
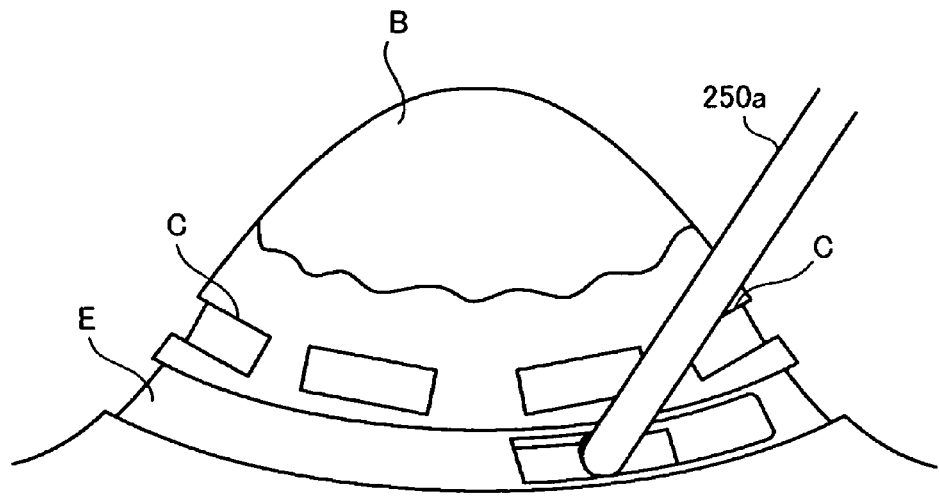
FIG. 102 shows how a submucosal tissue is ablated by the distal-end portion shown in FIG. 94.
Figure 103:
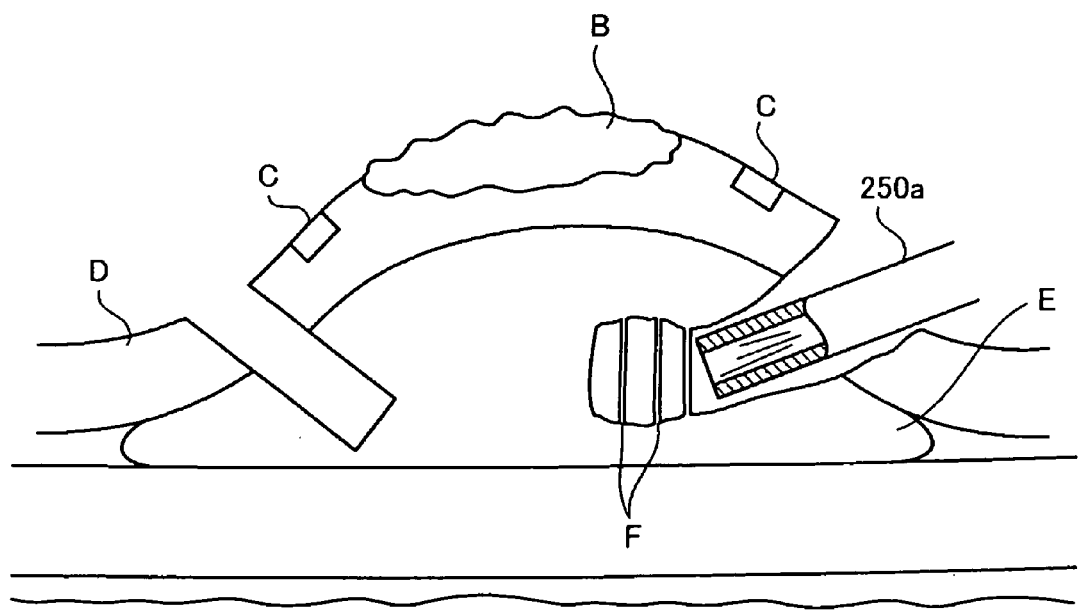
FIG. 103 shows how a submucosal tissue is ablated by the distal-end portion shown in FIG. 94.
Figure 104:
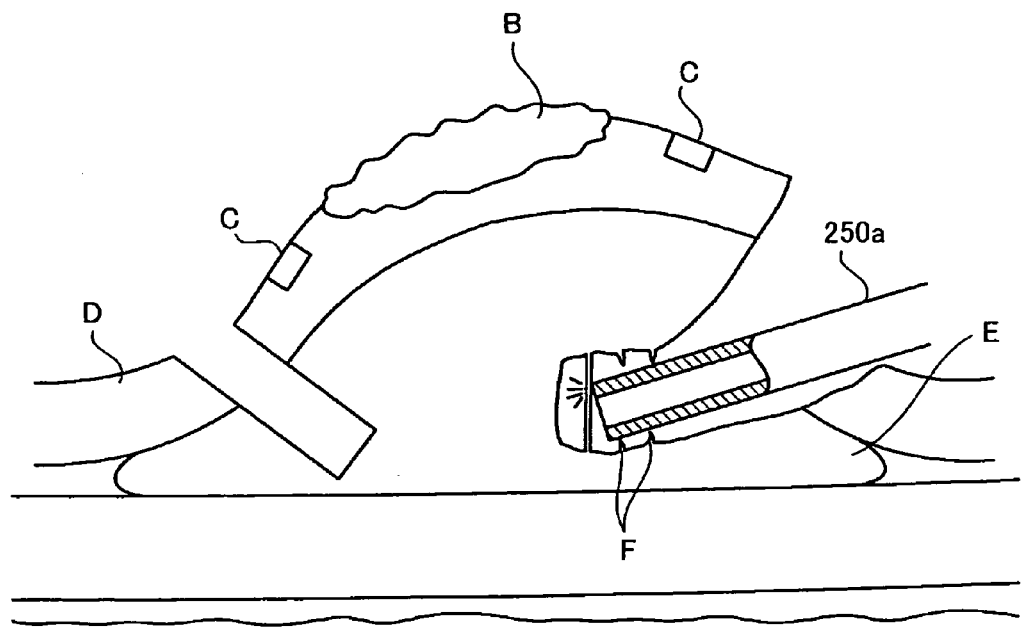
FIG. 104 shows how a submucosal tissue is ablated by the distal-end portion shown in FIG. 94.

Then, the ultrasonic vibration is generated, the surroundings of the living tissue (mucosa D) raised by the distal-end treatment unit 250a are incised as shown in FIG. 99 to FIG. 101, and the mucosa D is incised over all the circumferences (Step 307). Further, in the fifteenth embodiment, the submucosal layer E existing below the mucosa D is peed off as shown in FIG. 102 (Step 308). At this point, the surroundings are sequentially incised while the distal-end treatment unit 250a is moved by a length in the longitudinal direction of the distal-end surface portion 250i. In this case, as shown in FIG. 103, the submucosal layer E crushed into the jelly-like substance by the ultrasonic treatment is sucked and discharged to the outside. For the fiber F, the blood vessel, and the like shown in FIG. 103 and FIG. 104, the tissue having high elasticity is easily cut while the hemostasis is performed by selecting the electric cautery function to cauterize and cut the fiber F and the blood vessel.

Figure 105:
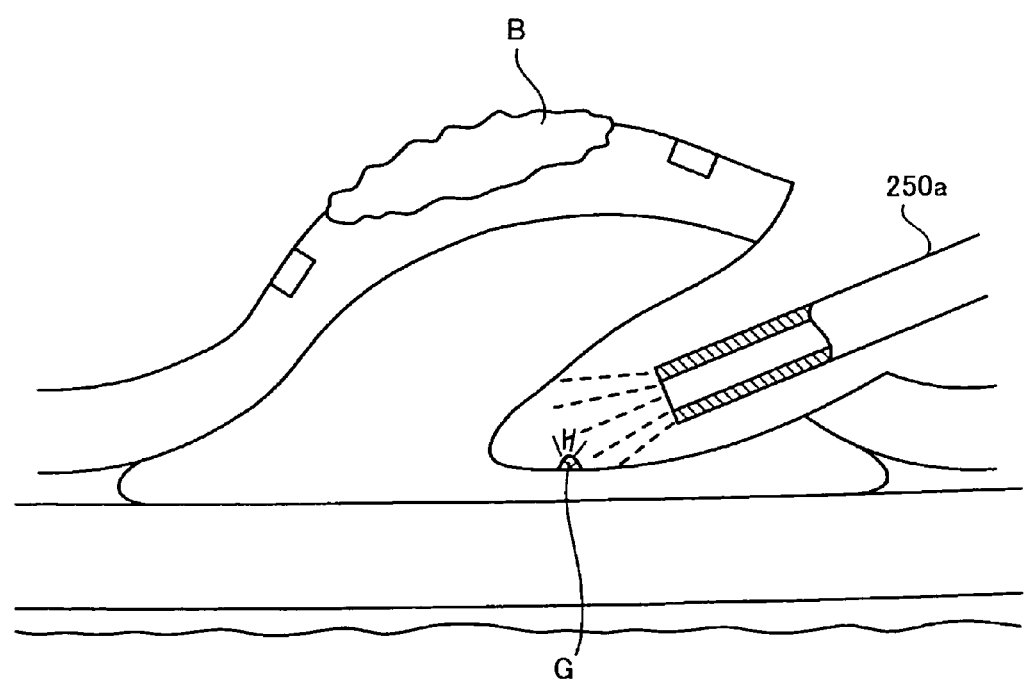
FIG. 105 shows how homeostasis is performed by the distal-end portion shown in FIG. 94.
Figure 106:
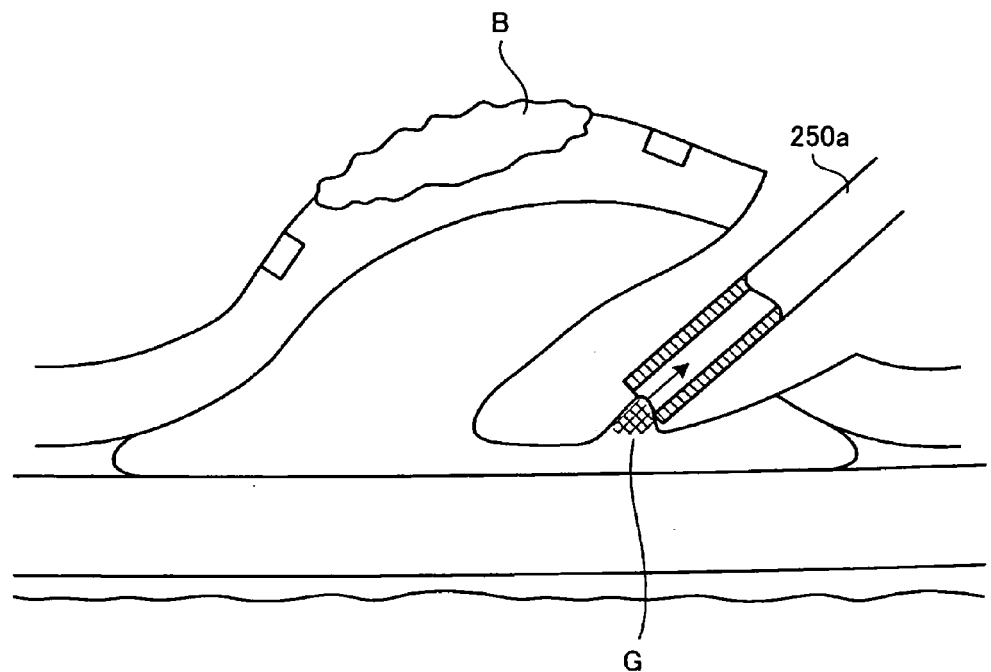
FIG. 106 shows how homeostasis is performed by the distal-end portion shown in FIG. 94.
Figure 107:
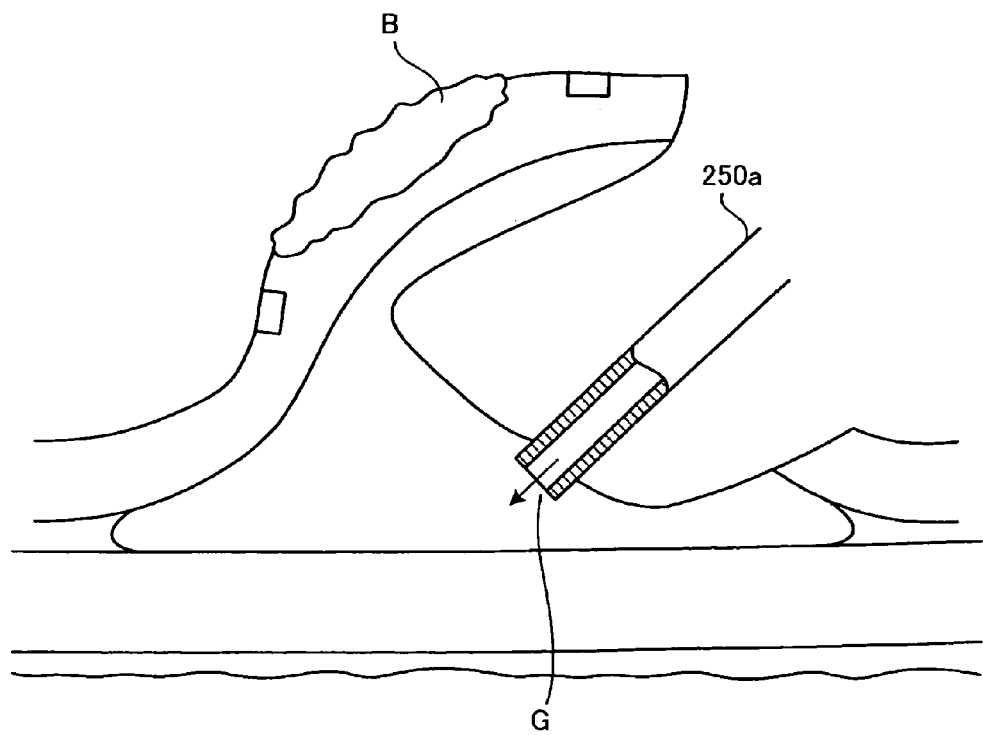
FIG. 107 shows how homeostasis is performed by the distal-end portion shown in FIG. 94.

In the case where the bleeding exists (Step 309), the hemostastic treatment is performed using the electric cautery function (Step 310). In the hemostastic treatment, for example, the hemostastic treatment of the bleeding region G is performed by the high-frequency current while the physiological salt solution is supplied from the cylinder 7 as shown in FIG. 105, which allows the treatment to be performed with a good visual field. As shown in FIG. 106, instead of the cylinder, the suction apparatus may be attached to the tube 271 to suck the bleeding blood from the bleeding region G, or the ultrasonic treatment may be performed while the bleeding blood is sucked. The cylinder in which the hemostatic is injected is attached to the tube 271, and the hemostatic treatment may be performed by cutting through the bleeding region G with the distal end of the distal-end treatment unit 250a to inject the hemostatic as shown in FIG. 107. In order to recover the cut tissue specimen, instead of the ultrasonic treatment apparatus 3, for example a pair of grip forceps (not shown) is inserted from the forceps insertion port 221d into the channel of the distal-end portion, and the tissue specimen can be taken out while being gripped by the grip forceps.

Although the ultrasonic vibration function and the electric cautery function are individually driven in the fifteenth embodiment, the present invention is not limited to the first embodiment. For example, in the process of dissecting the submucosal layer, either or both of the ultrasonic vibration function and the electric cautery function may simultaneously be driven according to the treatment process.

Thus, in the fifteenth embodiment, the treatment unit including the distal-end surface portion having the directional movement in which the treated site can be treated in at least two directions is rotated by the operating unit and the coil shaft having the rotation follow-up property, and the distal-end surface portion can be set with respect to the treated site such that the treatment can be performed at the desired angle (direction). Therefore, the improvement of the treatment performance can be achieved in the ultrasonic treatment apparatus.

In the fifteenth embodiment, the ultrasonic treatment apparatus includes the treatment unit having both the ultrasonic vibration function and the electric cautery function, the surroundings of the living tissue are incised to crush the living tissue by the ultrasonic vibration, and other incisions are performed by selecting any of the functions. Therefore, the heat damage of the tissue specimen to be cut off is prevented to obtain the proper tissue specimen, and the simplification of the treatment can be achieved. Accordingly, the work necessary to cut the surroundings can be decreased as compared with the conventional art.

In the fifteenth embodiment, the treatment unit of the ultrasonic transducer has the hollow shaped portion, and the chemicals dispersing process and the local injection process are performed through the hollow shaped portion. Accordingly, it is not necessary that the ultrasonic transducer be changed to, e.g., the treatment tool with injection needle or the dispersing tube in each process, and the treatment necessary for the incision of the living tissue can be simplified.

The fifteenth embodiment includes the treatment unit which can be used for both the ultrasonic treatment and the high-frequency treatment. Therefore, it is not necessary to change the treatment tools to select the ultrasonic treatment or the high-frequency treatment, and the incision operation can be performed simply and rapidly.

The configuration of the distal-end treatment unit is not limited to the configurations of the embodiments, but various modifications can be made. The configurations of modifications will be described below.

FIG. 108A to FIG. 130 show modifications of the thirteenth embodiment of the present invention. The component having the same function as the first embodiment is designated by the same reference numeral, and the description will be omitted. These modifications provide the optimum treatment unit according to the treatment or the treatment target.

Figure 108A:
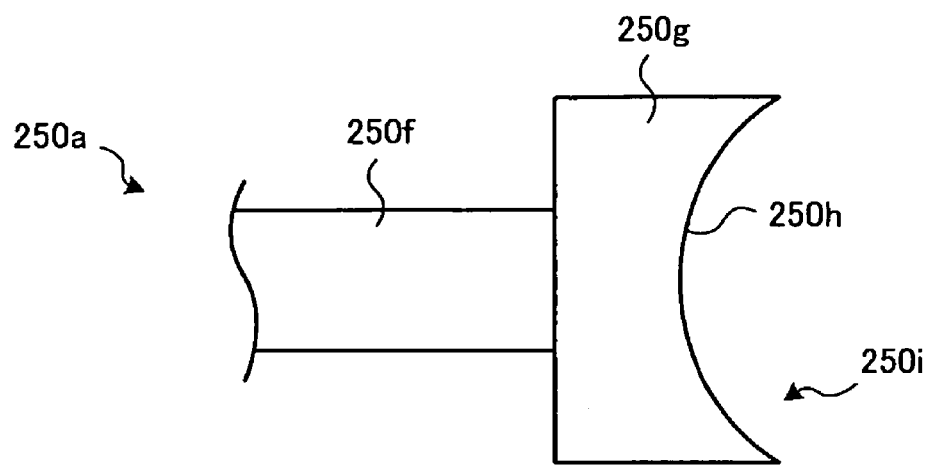
FIG. 108A is a top view of a distal-end treatment unit of a first modification of the thirteenth embodiment of the present invention.
Figure 108B:
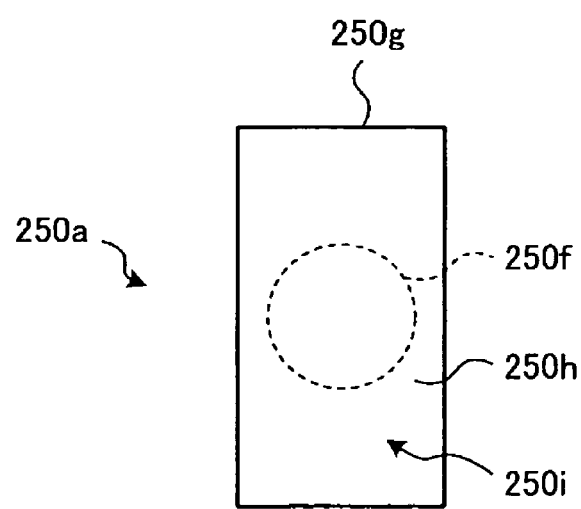
FIG. 108B is a front elevational view of the distal-end treatment unit of the first modification of the thirteenth embodiment of the present invention.

As shown in FIG. 108A and FIG. 108B, in the larger-diameter unit 250g of a first modification, similarly to the thirteenth embodiment, the concave portion 250h which is of the holding unit is formed in the whole of the distal-end surface, and the concave portion 250h is formed in a semicircular shape which is opened toward the distal-end side in the cross section parallel to both sides of the distal-end surface.

Figure 109A:
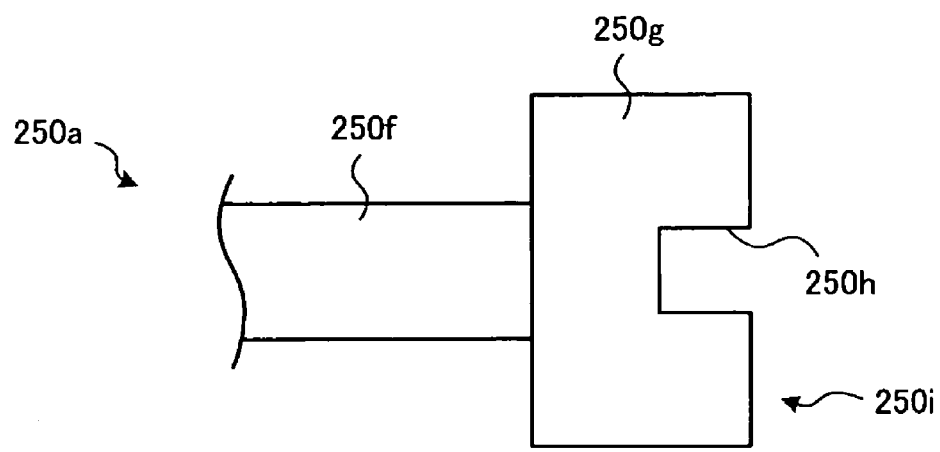
FIG. 109A is a top view of a distal-end treatment unit of a second modification of the thirteenth embodiment of the present invention.
Figure 109B:
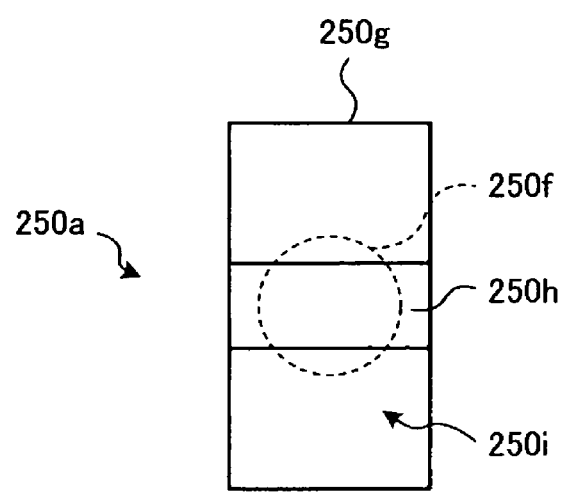
FIG. 109B is a front elevational view of the distal-end treatment unit of the second modification of the thirteenth embodiment of the present invention.

As shown in FIG. 109A and FIG. 109B, in the distal-end surface of the larger-diameter unit 250g of a second modification, the concave portion 250h having a groove shape is provided in the substantial center of the distal-end surface in parallel with the short side of the distal-end surface. In the concave portion 250h having the groove shape, the cross section perpendicular to the longitudinal direction is formed in a substantially square shape.

Figure 110A:
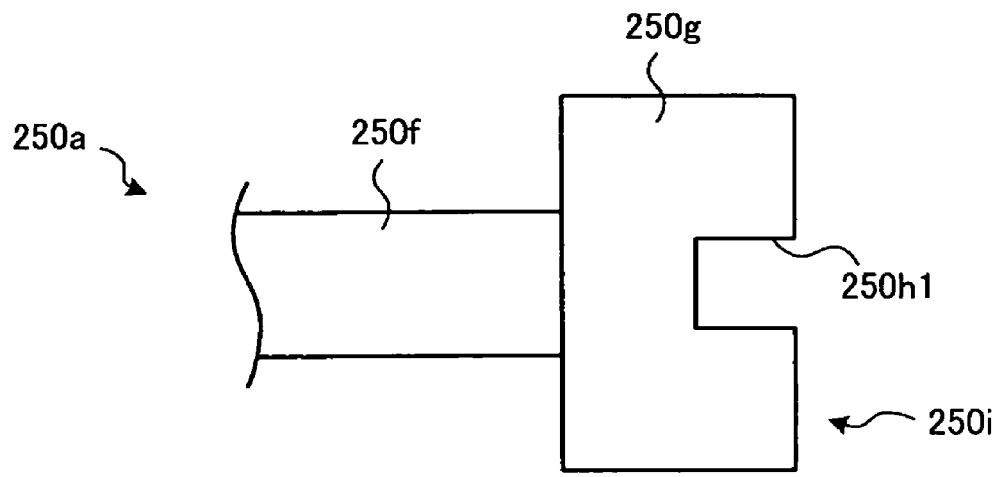
FIG. 110A is a top view of a distal-end treatment unit of a third modification of the thirteenth embodiment of the present invention.
Figure 110B:
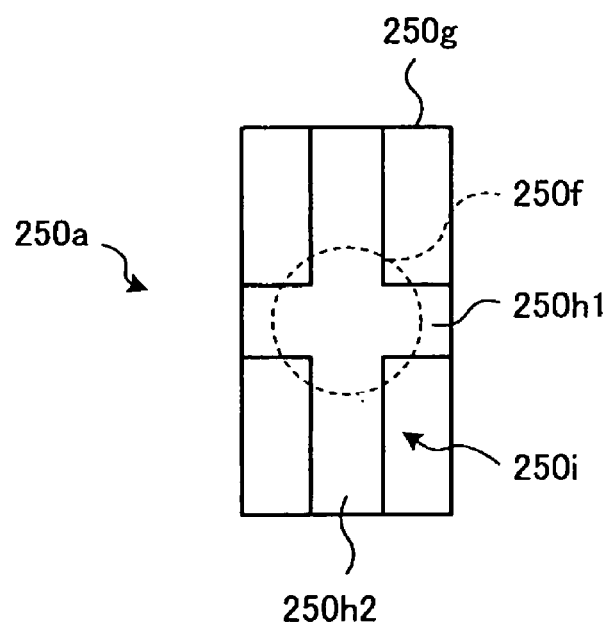
FIG. 110B is a front elevational view of the distal-end treatment unit of the third modification of the thirteenth embodiment of the present invention.

As shown in FIG. 110A and FIG. 110B, in the distal-end surface of the larger-diameter unit 250g of a third modification, first and second concave portions 250h1 and 250h2 having the grove shapes are formed in a cross shape. That is, the grove-shape second concave portions 250h1 and 250h2 are arranged in the substantial center of the distal-end surface while being in parallel with the short side and the long side of the distal-end surface respectively. In the first and second concave portions 250h1 and 250h2 having the groove shapes, the cross section perpendicular to the longitudinal direction is formed in the substantially square shape.

Figure 111A:
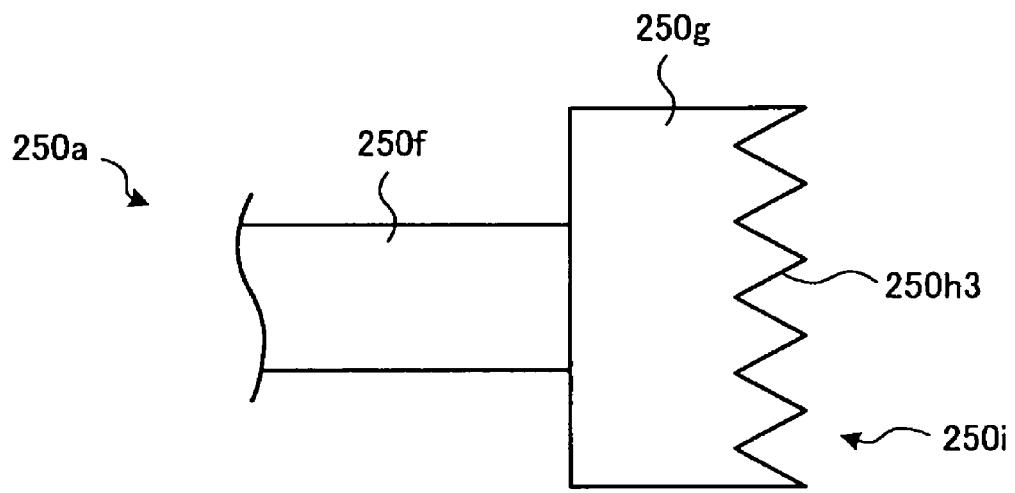
FIG. 111A is a top view of a distal-end treatment unit of a fourth modification of the thirteenth embodiment of the present invention.
Figure 111B:
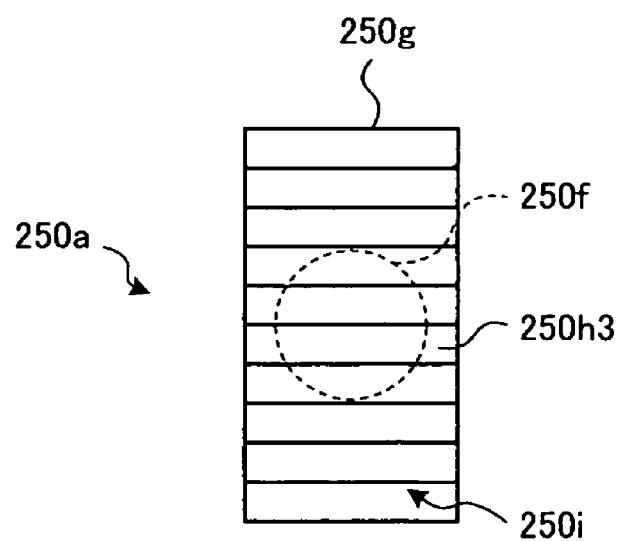
FIG. 111B is a front elevational view of the distal-end treatment unit of the fourth modification of the thirteenth embodiment of the present invention.

As shown in FIG. 111A and FIG. 111B, in the distal-end surface of the larger-diameter unit 250g of a fourth modification, plural concave portions 250h3 having the groove shapes are arranged with no clearance in substantially parallel with the short side of the distal-end surface. In the plural concave portions 250h3 having the groove shapes, the cross section perpendicular to the longitudinal direction is formed in a substantially triangular shape which is opened toward the distal-end side.

Figure 112A:
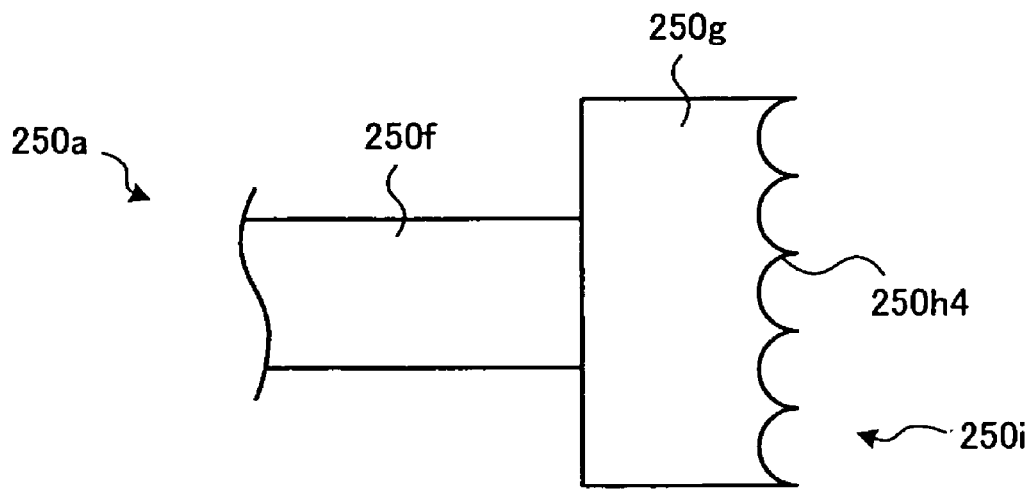
FIG. 112A is a top view of a distal-end treatment unit of a fifth modification of the thirteenth embodiment of the present invention.
Figure 112B:
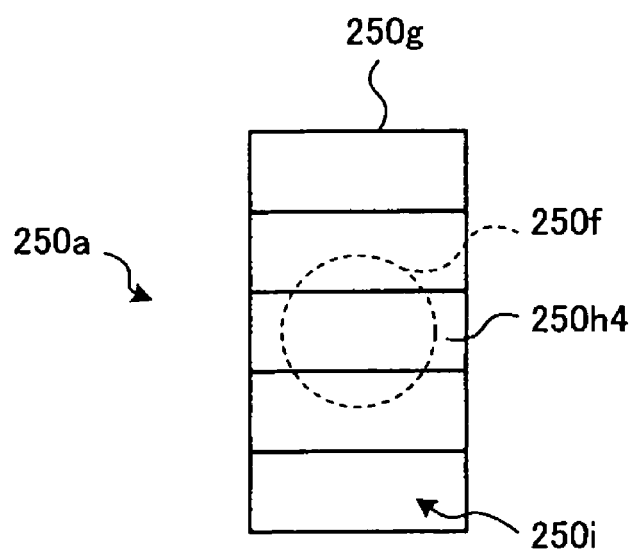
FIG. 112B is a front elevational view of the distal-end treatment unit of the fifth modification of the thirteenth embodiment of the present invention.

As shown in FIG. 112A and FIG. 112B, in the distal-end surface of the larger-diameter unit 250g of a fifth modification, similarly to the fourth modification, plural concave portions 250h4 having the groove shapes are arranged with no clearance in substantially parallel with the short side of the distal-end surface. In the plural concave portions 250h4 having the groove shapes, the cross section perpendicular to the longitudinal direction is formed in a substantially semi-circular shape which is opened toward the distal-end side.

Figure 113A:
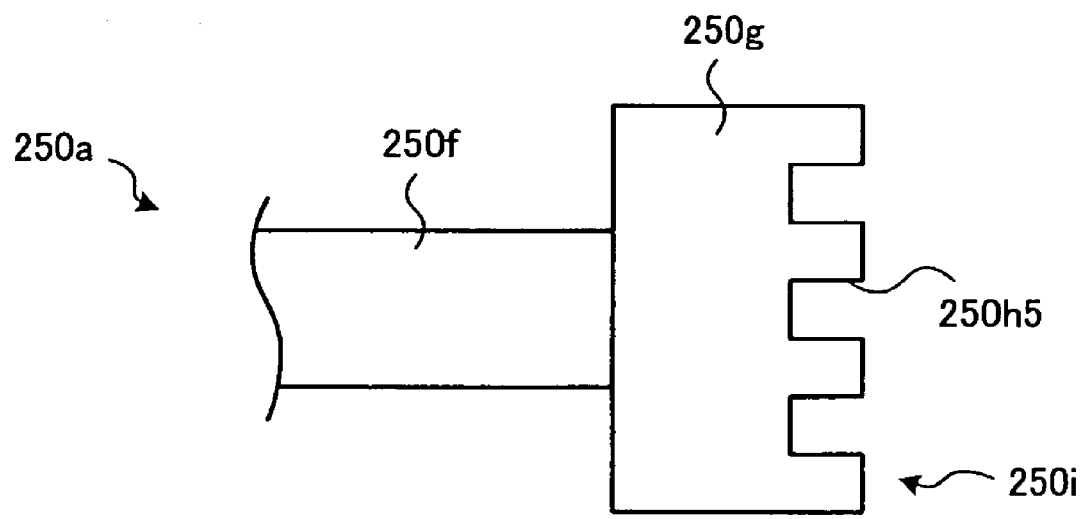
Figure 113B:
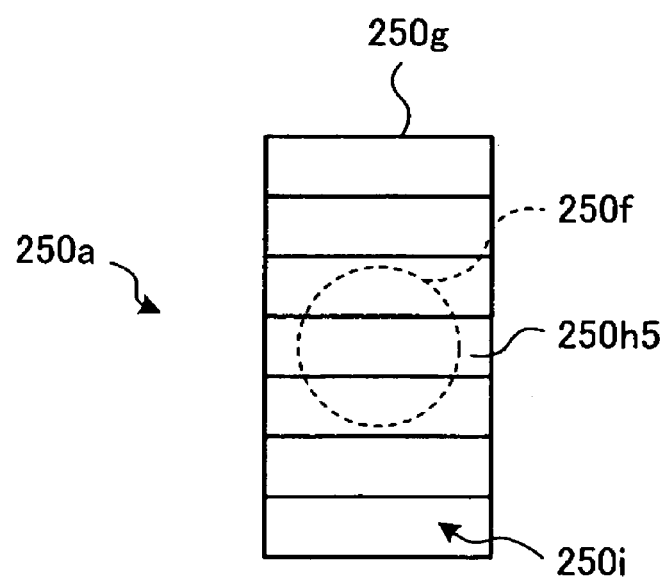

As shown in FIG. 113A and FIG. 113B, in the distal-end surface of the larger-diameter unit 250g of a sixth modification, plural concave portions 250h5 having the groove shapes are arranged in substantially parallel with the short side of the distal-end surface while being insulated from one another at predetermined intervals. In the plural concave portions 250h5 having the groove shapes, the cross section perpendicular to the longitudinal direction is formed in the substantially square shape.

Figure 114A:
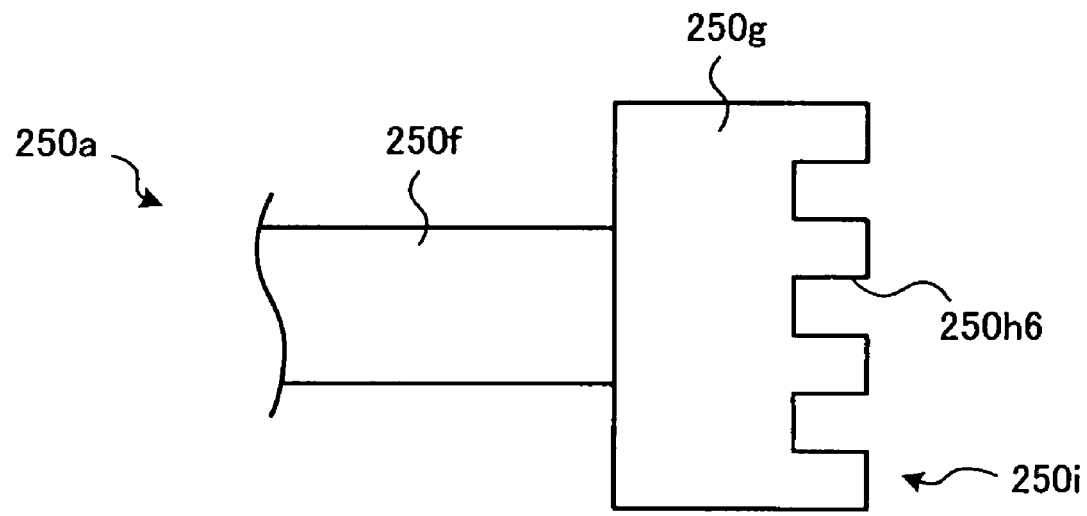
Figure 114B:
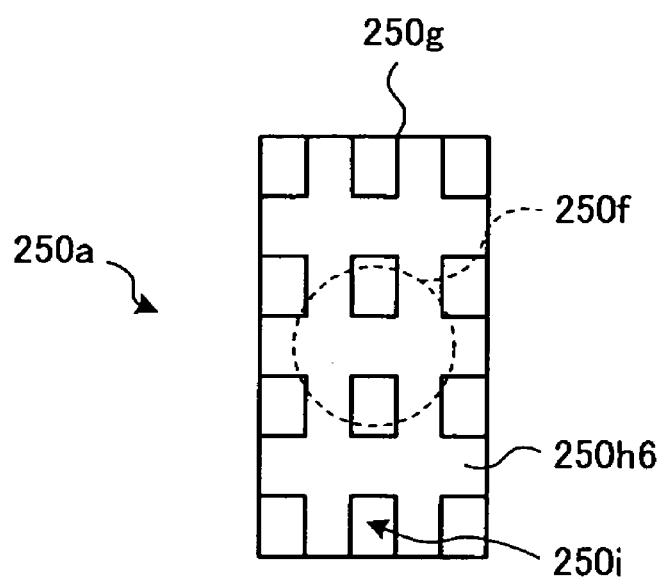

As shown in FIG. 114A and FIG. 114B, in the distal-end surface of the larger-diameter unit 250g of a seventh modification, plural concave portions 250h6 having the groove shapes are arranged in a lattice shape. That is, the plural concave portions 250h6 having the groove shapes are arranged while being separated from one another at predetermined intervals, the plural concave portions 250h6 are arranged in the short-side direction of the distal-end surface while being separated from one another at predetermined intervals, and the plural concave portions 250h6 are arranged in substantially parallel with the long side of the distal-end surface. In the plural concave portions 250h6 having the groove shapes, the cross section perpendicular to the longitudinal direction is formed in the substantially square shape.

Figure 115A:
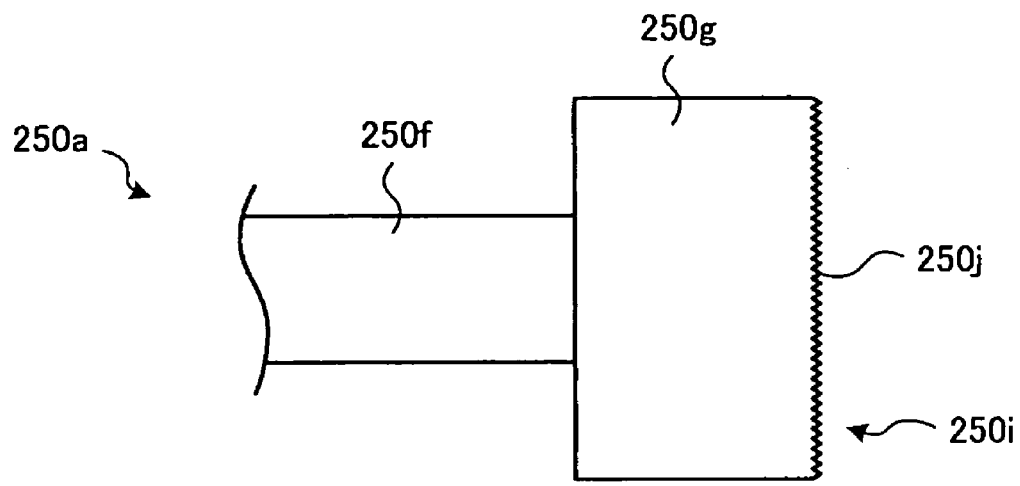
Figure 115B:
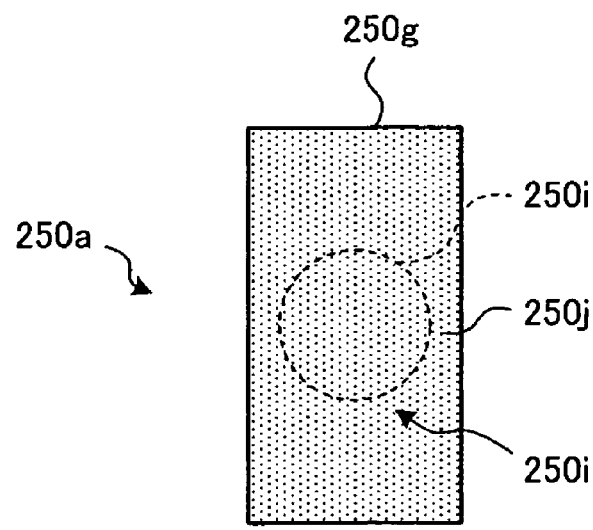

As shown in FIG. 115A and FIG. 115B, in an eighth modification, a roughened surface roughened surface portion 250j which is of the holding unit is provided in the distal-end surface portion 250j.

Figure 116A:
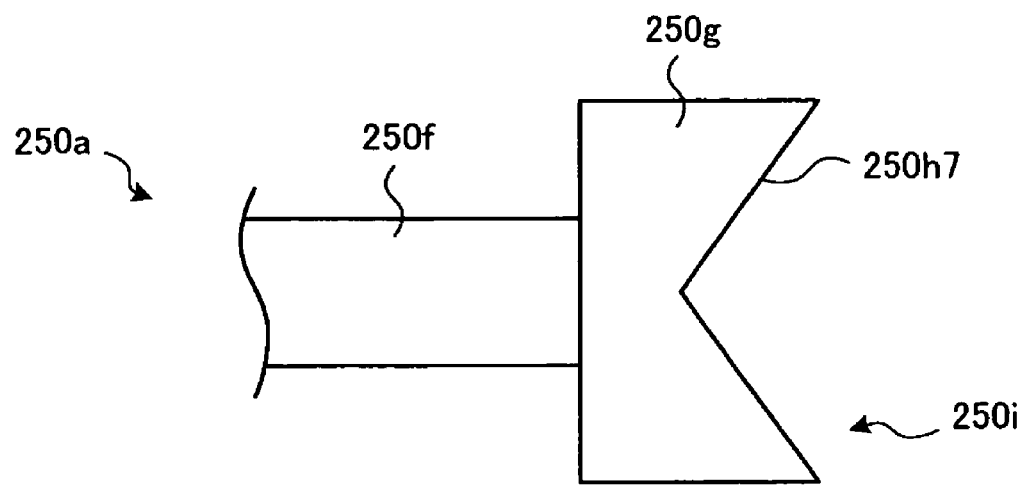
Figure 116B:
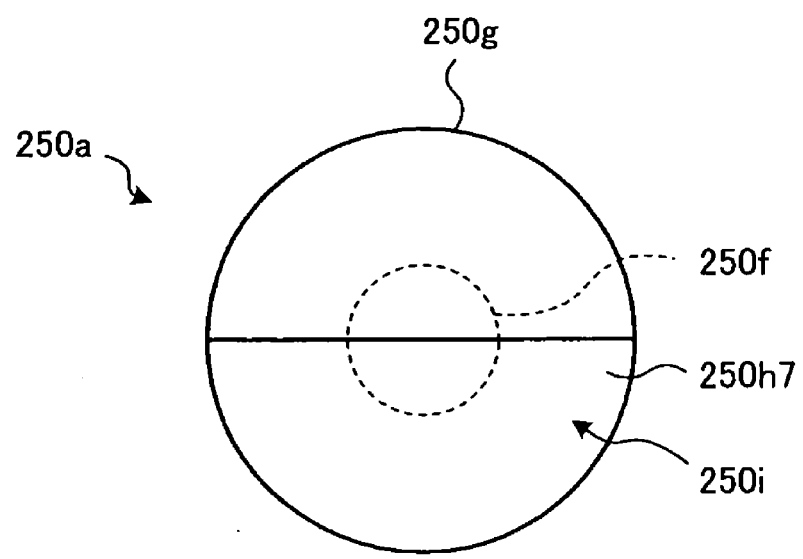

As shown in FIG. 116A and FIG. 116B, the larger-diameter unit 250g of a ninth modification is formed in a substantially short cylinder shape which is coaxial with the smaller-diameter unit 250f. A concave portion 250h7, which is of the holding unit, is formed in the whole of the distal-end surface of the larger-diameter unit 250g, and the concave portion 250h7 has a substantially linear bottom portion which is substantially orthogonal to the center axis of the smaller-diameter unit 250f. In the cross section perpendicular to the bottom portion of the concave portion 250h7, the concave portion 250h7 has the substantially triangular shape which is opened toward the distal-end side.

Figure 117A:
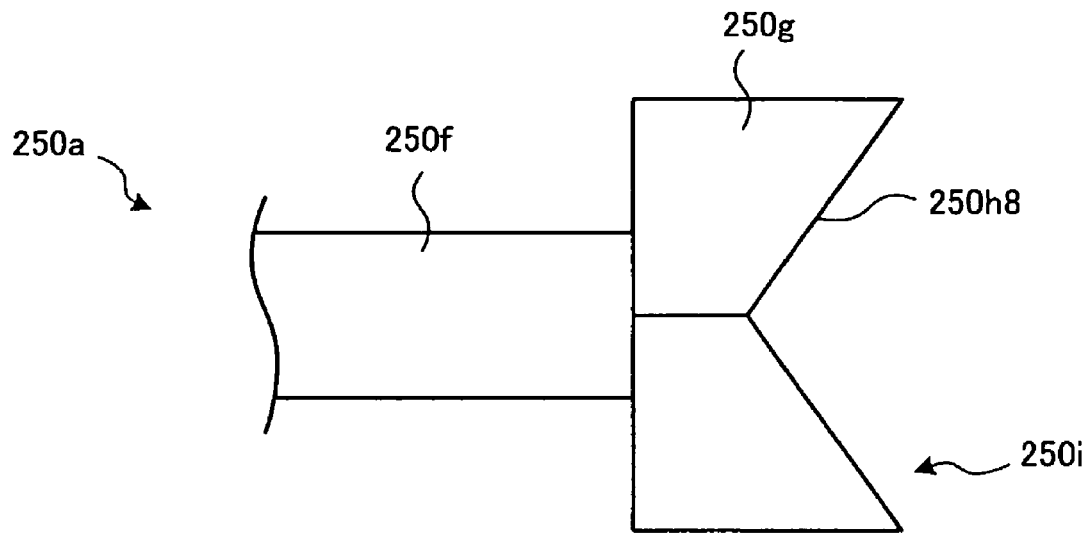
Figure 117B:
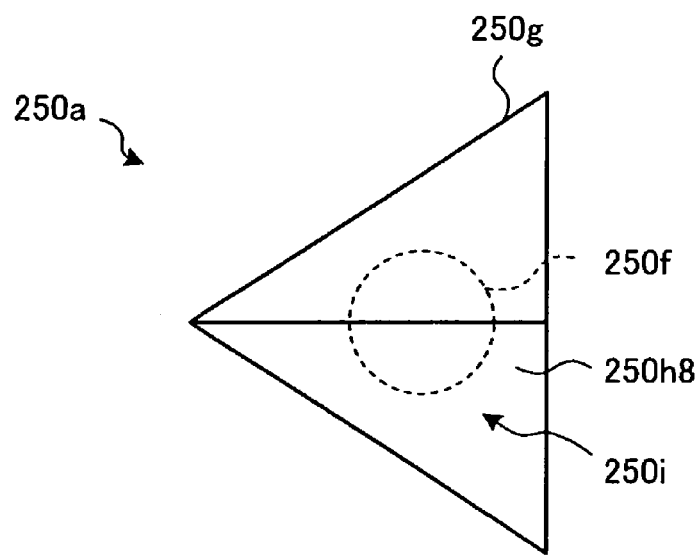

As shown in FIG. 117A and FIG. 117B, the larger-diameter unit 250g of a tenth modification is formed in a substantially short triangular shape which is coaxial with the smaller-diameter unit 250f. A concave portion 250h8 is formed in the whole of the distal-end surface of the larger-diameter unit 250*g*, and the concave portion 250*h*8 has the substantially linear bottom portion. The bottom portion is substantially orthogonal to the center axis of the smaller-diameter unit 250*f*, and the bottom portion passes through a vertex angle portion of the substantially triangular shape. In the cross section perpendicular to the bottom portion of the concave portion 250*h*8, the concave portion 250*h*8 has the substantially triangular shape which is opened toward the distal-end side.

Figure 118A:
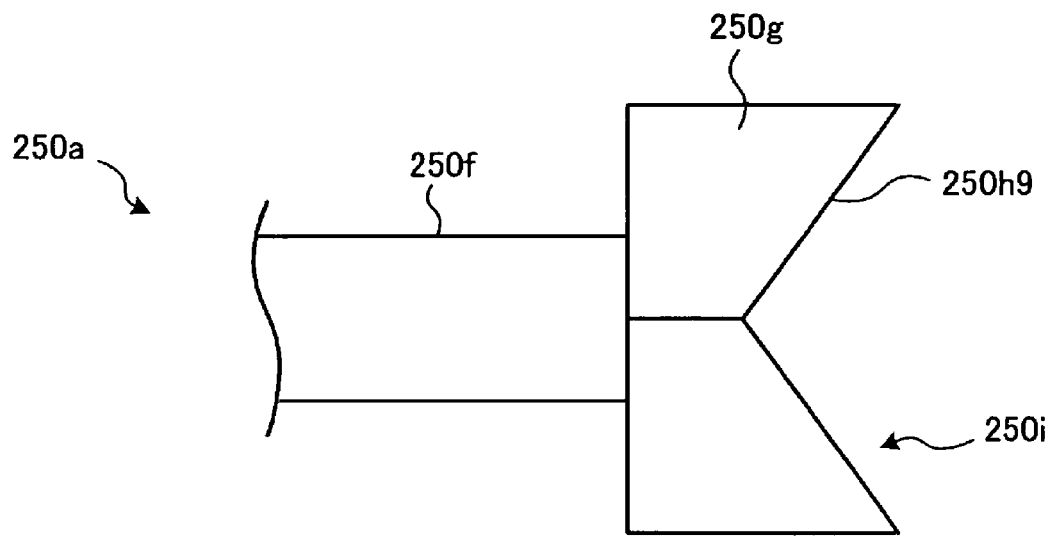
Figure 118B:
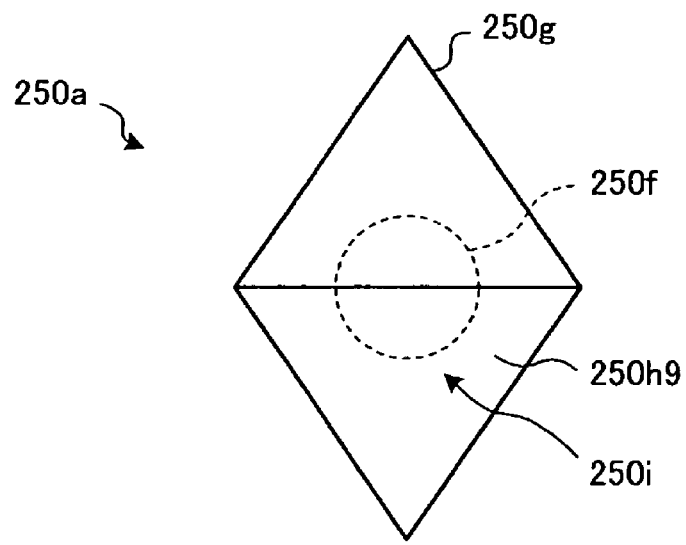

As shown in FIG. 118A and FIG. 118B, the larger-diameter unit 250*g* of an eleventh modification is formed in a substantially short rhombic prism which is coaxial with the smaller-diameter unit 250*f*. A concave portion 250*h*9 is formed in the whole of the distal-end surface of the larger-diameter unit 250*g*, and the concave portion 250*h*9 has a substantially linear bottom portion. The bottom portion is substantially orthogonal to the center axis of the smaller-diameter unit 250*f*, and the bottom portion passes through vertex angle portions facing each other in the substantially triangular shape. In the cross section perpendicular to the bottom portion of the concave portion 250*h*9, the concave portion 250*h*9 has the substantially triangular shape which is opened toward the distal-end side.

As shown in FIG. 119A to FIG. 119C, in the larger-diameter unit 250*g* of a twelfth modification, the length of the substantially rectangular shape short side in the cross section perpendicular to the center axis of the smaller-diameter unit 250*f* is continuously changed such that the length of short side is longer than the diameter of the smaller-diameter unit 250*f* in the proximal-end surface while being shorter than the diameter of the smaller-diameter unit 250*f* in the distal-end surface.

As shown in FIG. 120A to FIG. 120C, in the larger-diameter unit 250*g* of a twelfth modification, the length of the substantially rectangular shape short side in the cross section perpendicular to the center axis of the smaller-diameter unit 250*f* is decreased shorter than the diameter of the smaller-diameter unit 250*f*.

As shown in FIG. 121, in a fourteenth modification, R-chamfering or C-chamfering is performed in a connection portion between the smaller-diameter unit 250*f* and the larger-diameter unit 250*g* to increase the strength.

FIG. 122A and FIG. 122B show a fifteenth modification in which a knife-shape edge unit 250*k* extends toward the longitudinal direction of the smaller-diameter unit 250*f* in the connection portion between the smaller-diameter unit 250*f* and the larger-diameter unit 250*g*. In the case where the incision treatment is performed to the treatment target, the ultrasonic vibration is generated in the distal-end treatment unit 250*a* to longitudinally vibrate the edge unit 250*k* in the extending direction, and the incision treatment is performed to the treatment target with the edge unit 250*k*, which improves incision efficiency.

FIG. 123A to FIG. 124C show sixteenth and seventeenth modifications. As shown in FIG. 123A to FIG. 123C, in the smaller-diameter unit 250*f* of the sixteenth modification, the cross section perpendicular to the center axis of the smaller-diameter unit 250*f* is formed in the substantially rhombic shape. In the smaller-diameter unit 250*f*, first to fourth edge units 250*k* extend in the axial direction of the smaller-diameter unit 250*f* corresponding to vertexes of the rhombic shape. As shown in FIG. 124A to FIG. 124C, in the smaller-diameter unit 250*f* of the seventeenth modification, the cross section perpendicular to the center axis of the smaller-diameter unit 250*f* is formed in the substantially triangular shape. In the smaller-diameter unit 250*f*, first to third edge units 250*k* extend in the axial direction of the smaller-diameter unit 250*f* corresponding to vertexes of the triangular shape. In the case where the incision treatment is performed to the treatment target with the ultrasonic treatment apparatus of the sixteenth or seventeenth modification, the ultrasonic vibration is generated in the distal-end treatment unit 250*a* to longitudinally vibrate the edge unit 250*k* in the extending direction, the edge unit 250*k* is rotated so as to be set at the desired position with respect to the treatment target, the incision treatment is performed by pressing the edge unit 250*k* against the living tissue.

FIG. 125 shows an eighteenth modification. In the eighteenth modification, the distal-end treatment unit 250*a* is formed in the cylindrical shape, and the circular distal-end surface portion 250*i* is included at the distal end of the distal-end treatment unit 250*a*. First and second groove-shape concave portions 250*h*10 and 250*h*11 extending in the radial direction are formed in the distal-end surface portion 250*i*. The first and second concave portions 250*h*10 and 250*h*11 form the holding units which hold the living tissues respectively. The first and second concave portions 250*h*10 and 250*h*11 are substantially orthogonal to each other.

FIG. 126 shows a nineteenth modification. The component having the same function as the eighteenth modification is designated by the same reference numeral, and the description will be omitted. In the nineteenth modification, the width of the first concave portion 250*h*10 is larger than that of the second concave portion 250*h*11. In the living tissue, there are points where thin raised portions having various widths are formed such as the point where plural blood vessels having different diameters run therethrough. In the case where the treatment is performed to such points, the living tissue is held with the first concave portion 250*h*10 for the wide raised portion, and the living tissue is held with the second concave portion 250*h*11 for the narrow raised portion. Thus, in the nineteenth embodiment, the wide first concave portion 250*h*10 and the narrow second concave portion 250*h*11 are selectively used according to the width of the thin raised portion of the living tissue. Therefore, a situation where the living tissue cannot sufficiently be held because the width of the raised portion, which is excessively large or small with respect to the widths of the concave portions 250*h*10 and 250*h*11, can be avoided.

FIG. 127 shows a twentieth modification. In the twentieth modification, a convex portion 250*m* which is of the holding unit is formed in the distal-end surface portion 250*i* of the distal-end treatment unit 250*a*. A first pressing surface 250*n* is formed by a top surface of the convex portion 250*m*, and a second pressing surface 250*p* is generated by a portion where the convex portion 250*m* of the distal-end surface portion 250*i* is not formed. A step 250*q* is formed between the first pressing surface 250*n* and the second pressing surface 250*p* by a side face portion of the convex portion 250*m*. In the twentieth modification, the step 250*q* is arranged across the distal-end surface portion 250*i*, and the first pressing surface 250*n* is smaller than the second pressing surface 250*p*.

FIG. 128 shows a twenty-first modification. In the twenty-first modification, the distal-end treatment unit 250*a* has indexes 250*r* and 250*s* which exhibit the characteristics of the holding unit. That is, the configuration of the distal-end treatment unit 250*a* is substantially similar to the configuration of the distal-end treatment unit 250*a* of the eighteenth modification shown in FIG. 125. However, the first and second indexes 250*r* and 250*s* for indicating the first and second concave portions 250*h*10 and 250*h*11 are arranged in the distal-end surface portion 250*i* of the distal-end treatment unit 250*a*. The first and second indexes 250*r* and 250*s* are formed in elliptical shapes, and the first and second indexes 250r and 250s are aligned with end portions of the first and second groove-shape concave portions 250h10 and 250h11 with respect to the axial direction of the ultrasonic transducer 250. The operator can guess the arrangement of the first and second concave portions 250h10 and 250h11 by the first and second indexes 250r and 250s.

FIG. 129 shows a twenty-second modification. In the twenty-second modification, a rectangular index 250t is used according to a kind of a concave portion 250h12. Therefore, the kind of the concave portion and the rotating direction of the concave portion can be recognized by visually recognizing the index 250t.

FIG. 130 shows a twenty-third modification. In the distal-end treatment unit 250a of the twenty-third modification, first and second indexes 250u and 250v for indicating the arrangements and kinds of the first and second concave portions 250h10 and 250h11 are arranged in the distal-end surface portion 250i of the distal-end treatment unit 250a. The first index 250u is formed in the elliptical shape, and the first index 250u is aligned with one end portion of the wide groove-shape first concave portion 250h10 with respect to the axial direction of the ultrasonic transducer 250. On the other hand, the second index 250v is formed in the elliptical shape smaller than that of the first index 250u, and the second index 250v is aligned with one end portion of the narrow groove-shape second concave portion 250h11 with respect to the axial direction of the ultrasonic transducer 250. The operator can guess the arrangement of the first and second concave portions 250h10 and 250h11 by the first and second indexes 250u and 250v, and the operator can distinguish the kind of the wide first concave portion 250h10 from the narrow second concave portion 250h11 by a difference in size between the first index 250u and the second index 250v.

In the present invention, the distal-end surface portion is rotated so as to be set at the desired direction by following the rotation of the coil shaft using the above various modifications of the distal-end treatment unit, which allows the improvement of the treatment performance of the ultrasonic treatment apparatus.

In above embodiments, the small soft endoscope in which the insertion unit has the flexibility is described by way of example. However, the present invention is not limited to the above embodiments, but the ultrasonic treatment apparatus according to the present invention can be used in pieces of endoscope apparatus in general. In this case, the same effects as the above embodiments can be obtained.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment method comprising:
   an insertion process of inserting an insertion unit of an endoscope apparatus into a subject, the endoscope apparatus including:
      an ultrasonic treatment apparatus including;
         a sheath which has an opening at a distal end thereof,
         an ultrasonic transducer which is connected to the sheath, the ultrasonic transducer being able to generate ultrasonic vibration which is of treatment energy,
         an ultrasonic power supply unit which supplies electric power for driving the ultrasonic transducer,
         a treatment unit which is connected to the ultrasonic transducer, the treatment unit transmitting the ultrasonic vibration to a living tissue, and
         a flat plate which extends substantially parallel to the treatment unit with a predetermined clearance therebetween;
      the flexible insertion unit in which the sheath can be arranged; and
      an observation unit which is provided inside the insertion unit, the observation unit being able to observe an outside from a distal end of the insertion unit;
   an arrangement process of arranging a treated site of a subject in a visual field of the observation unit;
   a marking process of performing marking of surrounding tissue of the treated site;
   an injection process of injecting a local injection solution into a lower portion of the treated site through an inside channel of the insertion unit;
   an incision and dissection process of incising and dissecting a living tissue including the treated site with the ultrasonic treatment apparatus, the living tissue being raised by the injection of the local injection solution; and
   a hemostatic process of performing hemostasis with the ultrasonic treatment apparatus when bleeding is generated in the incision and dissection process,
   wherein the incision and dissection process includes sandwiching the living tissue between the treatment unit and the flat plate, applying ultrasonic vibration, and twisting the treatment unit in a circumferential direction.

2. The treatment method according to claim 1, wherein in the marking process, a high-frequency current which is of the treatment energy is supplied to the treatment unit, and the marking is performed with the treatment unit.

3. The treatment method according to claim 1, wherein in the incision and dissection process, the incision and the dissection are performed using at least one method of a method of transmitting the ultrasonic vibration which is of the treatment energy from the treatment unit to the living tissue including the treated site and a method of supplying the high-frequency current which is of the treatment energy to the treatment unit.

4. A treatment method comprising:
   an insertion process of inserting an insertion unit of an endoscope apparatus into a subject, the endoscope apparatus including:
      an ultrasonic treatment apparatus including;
         a sheath which has an opening at a distal end thereof,
         an ultrasonic transducer which is connected to the sheath, the ultrasonic transducer being able to generate ultrasonic vibration which is of treatment energy,
         a treatment unit which is connected to the ultrasonic transducer, the treatment unit transmitting the ultrasonic vibration to a living tissue, and
         a flat plate which extends substantially parallel to the treatment unit with a predetermined clearance there between;
      the flexible insertion unit in which the sheath can be arranged; and
      an observation unit which is provided inside the insertion unit, the observation unit being able to observe an outside from a distal end of the insertion unit;
   an arrangement process of arranging a treated site of a subject in a visual field of the observation unit;
   a marking process of performing marking of surrounding tissue of the treated site;
   an injection process of injecting a local injection solution into a lower portion of the treated site through an inside channel of the insertion unit;
   an incision and dissection process of incising and dissecting the living tissue including the treated site with the ultrasonic treatment apparatus, the living tissue being raised by the injection of the local injection solution; and a hemostatic process of performing hemostasis with the ultrasonic treatment apparatus when bleeding is generated in the incision and dissection process, wherein the incision and dissection process includes sandwiching the living tissue between the treatment unit and flat plate, applying ultrasonic vibration, and twisting the treatment unit in a circumferential direction.

* * * * *